(12) United States Patent
McKenna et al.

(10) Patent No.: US 9,217,747 B2
(45) Date of Patent: Dec. 22, 2015

(54) PROTEIN AND LIPID BIOMARKERS PROVIDING CONSISTENT IMPROVEMENT TO THE PREDICTION OF TYPE 2 DIABETES

(75) Inventors: Michael P. McKenna, Branford, CT (US); Steve M. Watkins, Sacramento, CA (US)

(73) Assignee: Health Diagnostic Laboratory, Inc., Richmond, VA (US)

(*) Notice: Subject to any disclaimer, the term of this patent is extended or adjusted under 35 U.S.C. 154(b) by 322 days.

(21) Appl. No.: 13/504,720

(22) PCT Filed: Oct. 28, 2010

(86) PCT No.: PCT/US2010/054398
§ 371 (c)(1),
(2), (4) Date: Sep. 17, 2012

(87) PCT Pub. No.: WO2011/059721
PCT Pub. Date: May 19, 2011

(65) Prior Publication Data
US 2012/0328594 A1    Dec. 27, 2012

Related U.S. Application Data

(60) Provisional application No. 61/256,302, filed on Oct. 29, 2009.

(51) Int. Cl.
G01N 31/00 (2006.01)
G01N 33/53 (2006.01)
G01N 33/68 (2006.01)
G01N 33/66 (2006.01)
G01N 33/92 (2006.01)

(52) U.S. Cl.
CPC ............ *G01N 33/6893* (2013.01); *G01N 33/66* (2013.01); *G01N 33/92* (2013.01); *G01N 2800/042* (2013.01)

(58) Field of Classification Search
CPC ................. G01N 33/48714; G01N 2800/42; G01N 2800/52; C12Q 1/6883; A61K 31/155
See application file for complete search history.

(56) References Cited

U.S. PATENT DOCUMENTS

| | | | |
|---|---|---|---|
| 4,230,797 A | 10/1980 | Boguslaski et al. | |
| 4,233,402 A | 11/1980 | Maggio et al. | |
| 4,275,149 A | 6/1981 | Litman et al. | |
| 4,376,110 A | 3/1983 | David et al. | |
| 4,659,678 A | 4/1987 | Forrest et al. | |
| 4,727,022 A | 2/1988 | Skold et al. | |
| 5,018,067 A | 5/1991 | Mohlenbrock et al. | |
| 5,744,305 A | 4/1998 | Fodor et al. | |
| 7,723,050 B2 * | 5/2010 | Urdea et al. | 435/7.1 |
| 8,119,358 B2 | 2/2012 | Urdea et al. | |
| 8,409,816 B2 | 4/2013 | Urdea et al. | |
| 2002/0038227 A1 | 3/2002 | Fey et al. | |
| 2003/0100486 A1 | 5/2003 | Ridker et al. | |
| 2004/0122296 A1 | 6/2004 | Hatlestad et al. | |
| 2004/0122297 A1 | 6/2004 | Stahmann et al. | |
| 2006/0084129 A1 | 4/2006 | Watkins | |
| 2009/0271124 A1 | 10/2009 | Urdea et al. | |
| 2010/0197028 A1 * | 8/2010 | Watkins et al. | 436/67 |
| 2012/0309030 A1 | 12/2012 | McKenna et al. | |

FOREIGN PATENT DOCUMENTS

| WO | WO-2004/056456 A1 | 7/2004 |
|---|---|---|
| WO | WO-2004/088309 A2 | 10/2004 |
| WO | WO-2007/044860 A2 | 4/2007 |
| WO | WO-2008/106054 A2 | 9/2008 |
| WO | WO-2008/131224 A2 | 10/2008 |

OTHER PUBLICATIONS

Urdea et al. Journal of Diabetes Science and Technology, Jul. 2009, vol. 3., No. 4, pp. 748-755.*
Amato et al., The evaluation of metabolic parameters and insulin sensitivity for a more robust diagnosis of the polycystic ovary syndrome, Clin. Endocrinol. (Oxf.), 69(1):52-60 (2008).
Aoyagi et al., Performance of a conventional enzyme immunoassay for hepatitis C virus core antigen in the early phases of hepatitis C infection, Clin. Lab., 47(3-4):1 19-27 (2001).
Badiou et al., Determination of plasma amino acids by fluorescent derivatization and reversed-phase liquid chromatographic separation, Clin. Lab., 50(3-4):153-8 (2004).
Bayer et al., Evaluation of a new enzyme-linked immunosorbent assay for the determination of neopterin, Clin. Lab., 51(9-10):495-504 (2005).
Boettcher et al., Precision and comparability of Abuscreen OnLine assays for drugs of abuse screening in urine on Hitachi 917 with other immunochemical tests and with GC/MS, Clin. Lab., 46(1-2):49-52 (2000).
Bottcher et al., Evaluation of buprenorphine CEDIA assay versus GC-MS and ELISA using urine samples from patients in substitution treatment, J. Anal. Toxicol., 29(8):769-76 (2005).
Breiman, Classification and Regression Trees. Boca Raton: Chapman & Hall/CRC (1984).
Breiman, Random Forests (Jan. 2001).
Brunelli et al., Comparison of three methods for total homocysteine plasma determination, Clin. Lab., 47(7-8):393-7 (2001).
Burke et al., Rapid rise in the incidence of type 2 diabetes from 1987 to 1996: results from the San Antonio Heart Study, Arch. Intern. Med., 159(13):1450-6 (1999).
Burke et al., Reversion from type 2 diabetes to nondiabetic status. Influence of the 1997 American Diabetes Association criteria, Diabetes Care, 21(8):1266-70 (1998).

(Continued)

*Primary Examiner* — Lisa Cook
(74) *Attorney, Agent, or Firm* — Finnegan, Henderson, Farrabow, Garrett & Dunner LLP

(57) ABSTRACT

The invention relates to biomarkers associated with Diabetes, including protein and lipid metabolite biomarkers, methods of using the biomarkers to determine the risk that an individual will develop Diabetes, and methods of screening a population to identify persons at risk for developing Diabetes and other pre-diabetic conditions.

20 Claims, 144 Drawing Sheets

(56) References Cited

OTHER PUBLICATIONS

Cook, Use and misuse of the receiver operating characteristic curve in risk prediction, Circulation, 115(7):928-35 (2007).
Cyr et al., A GC/MS validated method for the nanomolar range determination of succinylacetone in amniotic fluid and plasma: an analytical tool for tyrosinemia type I, J. Chromatogr. B Analyt. Technol. Biomed. Life Sci., 832(1):24-9 (2006).
D'Agostino et al., Validation of the Framingham coronary heart disease prediction scores: results of a multiple ethnic groups investigation, JAMA, 286(2):180-7 (2001).
Definition, Diagnosis and Classification of Diabetes Mellitus and its Complications, Part I, World Health Organization (1999).
Dupuy et al., Protein biochip systems for the clinical laboratory, Clin. Chem. Lab. Med., 43(12):1291-302 (2005).
Eddy et al., Archimedes: a trial-validated model of diabetes, Diabetes Care, 26(11):3093-101 (2003).
Eddy et al., Validation of the archimedes diabetes model, Diabetes Care, 26(11):3102-10 (2003).
Fouassier et al., Determination of serotonin release from platelets by HPLC and ELISA in the diagnosis of heparin-induced thrombocytopenia: comparison with reference method by [C]-serotonin release assay, J. Thromb. Haemost., 4(5):1136-9 (2006).
Gao et al., Rapid detection of *Staphylococcus aureus* by a combination of monoclonal antibody-coated latex and capillary electrophoresis, Electrophoresis, 27(9):1784-9 (2006).
Griffin et al., Diabetes risk score: towards earlier detection of type 2 diabetes in general practice, Diabetes Metab. Res. Rev., 16(3):164-71 (2000).
Groche et al., Standardization of two immunological HbA1c routine assays according to the new IFCC reference method, Clin. Lab., 49(11-12):657-61 (2003).
Haller et al., Comparison of an automated and point-of-care immunoassay to GC-MS for urine oxycodone testing in the clinical laboratory, J. Anal. Toxicol., 30(2):106-11 (2006).
Haukeland et al., Abnormal glucose tolerance is a predictor of steatohepatitis and fibrosis in patients with non-alcoholic fatty liver disease, Scand J. Gastroenterol., 40(12):1469-77 (2005).
Herrmann et al., Enzymatically-generated fluorescent detection in micro-channels with internal magnetic mixing for the development of parallel microfluidic ELISA, Lab Chip, 6(4):555-60 (2006).
Hubl et al., A multi-center quality control study of different CA15-3 immunoassays, Clin. Lab., 51(11-12):641-5 (2005).
Ivan et al., Applicability of recently established reference values for serum insulin-like growth factor 1: A comparison of two assays—an (automated) chemiluminescence immunoassay and an enzyme-linked immunosorbent assay, Clin. Lab., 51(7-8):381-7 (2005).
Jabeen et al., Capillary electrophoresis and the clinical laboratory, Electrophoresis, 27:2413-38 (2006).
Johannsessen et al., A suspended membrane nanocalorimeter for ultralow volume bioanalysis, IEEE Trans Nanobioscience, 1(1):29-36 (2002).
Jorgensen et al., A randomized non-pharmacological intervention study for prevention of ischaemic heart disease: baseline results Inter99, Eur. J. Cardiovasc. Prev. Rehabil., 10(5):377-86 (2003).
Julak, Chromatographic analysis in bacteriologic diagnostics of blood cultures, exudates, and bronchoalveolar lavages, Prague Med. Rep., 106(2):175-94 (2005).
Kannel et al., A general cardiovascular risk profile: the Framingham Study, Am. J. Cardiol., 38(1):46-51 (1976).
Khalil et al., Validation and application of a high-performance liquid chromatographic-based assay for determination of the inosine 5'-monophosphate dehydrogenase activity in erythrocytes, J. Chromatogr. B Analyt. Technol. Biomed. Life Sci., 842(1):1-7 (2006).
Kisner, Product development: the making of the Abbott ARCHITECT, Clin. Lab Manage Rev., 11(6):419-21 (1997).

Kolberg et al., Development of a type 2 diabetes risk model from a panel of serum biomarkers from the Inter99 cohort, Diabetes Care, 32(7):1207-12 (2009).
Kramer et al., Automated spectrophotometric analysis of mitochondrial respiratory chain complex enzyme activities in cultured skin fibroblasts, Clin. Chem., 51(11):2110-6 (2005).
Lapolla et al., Early detection of insulin sensitivity and beta-cell function with simple tests indicates future derangements in late pregnancy, J. Clin. Endocrinol. Metab., 93(3):876-80 (2008).
Lifestyle Intervention in a General Population for Prevention of Ischaemic Heart Disease, Clinical Trial NCT00289237 (Oct. 2012).
Lin et al., Impaired glucose tolerance and impaired fasting glucose share similar underlying pathophysiologies, Tohoku J. Exp. Med., 212(4):349-57 (2007).
Lyssenko et al., Predictors of and longitudinal changes in insulin sensitivity and secretion preceding onset of type 2 diabetes, Diabetes, 54(1):166-74 (2005).
Maggio, Enzyme-Immunoassay, Boca Raton: CRC Press (1980).
Pepe et al., Limitations of the odds ratio in gauging the performance of a diagnostic, prognostic, or screening marker, Am. J. Epidemiol., 159(9):882-90 (2004).
Sartorio et al., Predictors of non-alcoholic fatty liver disease in obese children, Eur. J. Clin. Nutr., 61(7):877-83 (2007).
Schultz, Clinical interpretation of laboratory procedures, chapter 14 pp. 192-199, In: Burtis et al. (eds.), Teitz,Fundamentals of Clinical Chemistry, 4th ed., W.B. Saunders (1996).
Shen et al., Eigengene-based linear discriminant model for tumor classification using gene expression microarray data, Bioinformatics, 22(21):2635-42 (2006).
Stern et al., Predicting diabetes. Moving beyond impaired glucose tolerance, Diabetes, 42(5):706-14 (1993).
Stern et al., Predicting future cardiovascular disease: do we need the oral glucose tolerance test?, Diabetes, Care, 25(10):1851-6 (2002).
Stern et al., Sex difference in the effects of sociocultural status on diabetes and cardiovascular risk factors in Mexican Americans. The San Antonio Heart Study, Am. J. Epidemiol., 120(6):834-51 (1984).
Stone et al., Lipopenia and skin barrier abnormalities in DGAT2-deficient mice, J. Biol. Chem., 279(12):11767-76 (2004).
Urdea et al., Validation of a multimarker model for assessing risk of type 2 diabetes from a five-year prospective study of 6784 Danish people (Inter99), J. Diabetes Sci. Technol., 3(4):748-55 (2009).
Vasan, Biomarkers of cardiovascular disease: molecular basis and practical considerations, Circulation, 113(19):2335-62 (2006).
Venables et al., Modern Applied Statistics with S, 4th ed., Springer (2002).
Vogeser, Liquid chromatography-tandem mass spectrometry—application in the clinical laboratory, Clin. Chem. Lab Med., 41(2):117-26 (2003).
Westermann et al., Simple, rapid and sensitive determination of epinephrine and norepinephrine in urine and plasma by non-competitive enzyme immunoassay, compared with HPLC method, Clin. Lab., 48(1-2):61-71 (2002).
Wilson et al., Clinical Chemistry Analyzer Sub-System Level Performance, American Association for Clinical Chemistry Annual Meeting, Chicago, Illinois, Jul. 23-27, 2008.
Wirth et al., Post-transitional modification detection using metastable ions in reflector matrix-assisted laser desoption/ionization-time of flight mass spectrometry, Proteomics, 2:1445-51 (2002).
Wolf, History of diagnostic enzymology: a review of significant investigations, Clin. Chim. Acta, 369(2):144-7 (2006).
Yang et al., Blood plasma separation in microfluidic channels using flow rate control, ASAIO J., 51(5):585-90 (2005).
Zinellu et al., Assay for the simultaneous determination of guanidinoacetic acid, creatinine and creatine in plasma and urine by capillary electrophoresis UV-detection, J. Sep. Sci., 29(5):704-8 (2006).
Zweig et al., ROC curve analysis: an example showing the relationships among serum lipid and apolipoprotein concentrations in identifying subjects with coronary artery disease, Clin. Chem., 38(8):1425-8 (1992).

* cited by examiner

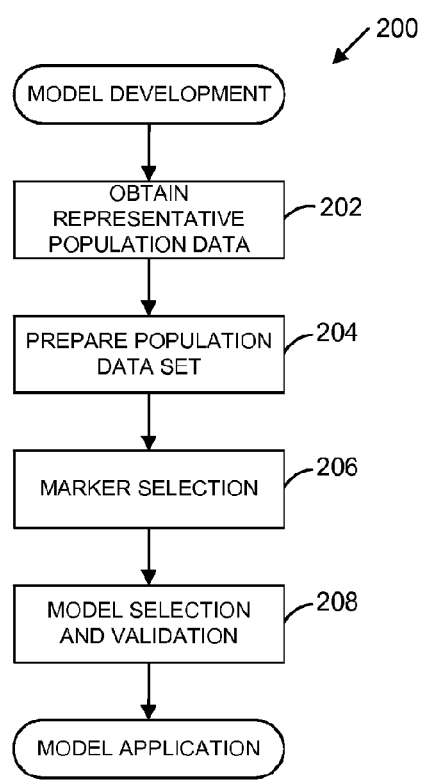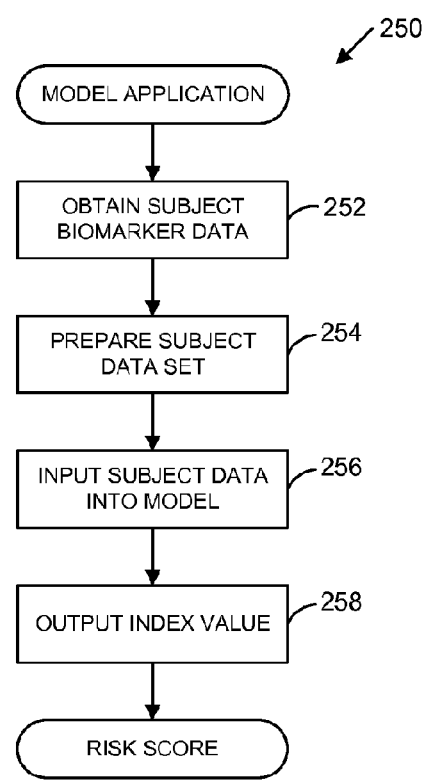

FIGURE 9

| Position 1 | Position 2 | Position 3 |
|---|---|---|
| ACE | CRP | GLUCOSE |
| ADIPOQ | CRP | GLUCOSE |
| AGE | CRP | GLUCOSE |
| AGER | CRP | GLUCOSE |
| AHSG | CRP | GLUCOSE |
| ANG | CRP | GLUCOSE |
| APOA1 | CRP | GLUCOSE |
| APOB | CRP | GLUCOSE |
| APOE | CRP | GLUCOSE |
| BAX | CRP | GLUCOSE |
| BCL2 | CRP | GLUCOSE |
| BMI | CRP | GLUCOSE |
| C3 | CRP | GLUCOSE |
| CCL2 | CRP | GLUCOSE |
| CD14 | CRP | GLUCOSE |
| CD40 | CRP | GLUCOSE |
| CDK5 | CRP | GLUCOSE |
| CHOL | CRP | GLUCOSE |
| CRP | CTSB | GLUCOSE |
| CRP | DBP | GLUCOSE |
| CRP | DPP4 | GLUCOSE |
| CRP | EGF | GLUCOSE |
| CRP | ENG | GLUCOSE |
| CRP | FAS | GLUCOSE |
| CRP | FGA | GLUCOSE |
| CRP | FHx1 | GLUCOSE |
| CRP | FHx2 | GLUCOSE |
| CRP | FTH1 | GLUCOSE |
| CRP | GH1 | GLUCOSE |
| CRP | GLUCOSE | GPT |
| CRP | GLUCOSE | HBA1C |
| CRP | GLUCOSE | HDL |
| CRP | GLUCOSE | HEIGHT |
| CRP | GLUCOSE | HGF |
| CRP | GLUCOSE | HIP |
| CRP | GLUCOSE | HP |
| CRP | GLUCOSE | HSPA1B |
| CRP | GLUCOSE | ICAM1 |
| CRP | GLUCOSE | IGF1 |

FIGURE 9 (continued)

| Position 1 | Position 2 | Position 3 |
|---|---|---|
| CRP | GLUCOSE | IGF1R |
| CRP | GLUCOSE | IGFBP1 |
| CRP | GLUCOSE | IGFBP2 |
| CRP | GLUCOSE | IGFBP3 |
| CRP | GLUCOSE | IL18 |
| CRP | GLUCOSE | IL2RA |
| CRP | GLUCOSE | IL2RB |
| CRP | GLUCOSE | IL6 |
| CRP | GLUCOSE | IL6R |
| CRP | GLUCOSE | IL6ST |
| CRP | GLUCOSE | IL8 |
| CRP | GLUCOSE | INHBA |
| CRP | GLUCOSE | INSULIN-M |
| CRP | GLUCOSE | LDL |
| CRP | GLUCOSE | LEP |
| CRP | GLUCOSE | PLAT |
| CRP | GLUCOSE | POMC |
| CRP | GLUCOSE | Proinsulin |
| CRP | GLUCOSE | RETN |
| CRP | GLUCOSE | SBP |
| CRP | GLUCOSE | SCp |
| CRP | GLUCOSE | SELE |
| CRP | GLUCOSE | SELP |
| CRP | GLUCOSE | SERPINE1 |
| CRP | GLUCOSE | SEX |
| CRP | GLUCOSE | SGK |
| CRP | GLUCOSE | SHBG |
| CRP | GLUCOSE | TGFB1 |
| CRP | GLUCOSE | TIMP2 |
| CRP | GLUCOSE | TNFRSF1B |
| CRP | GLUCOSE | TRIG |
| CRP | GLUCOSE | VCAM1 |
| CRP | GLUCOSE | VEGF |
| CRP | GLUCOSE | VWF |
| CRP | GLUCOSE | WAIST |
| CRP | GLUCOSE | WEIGHT |
| CRP | GLUCOSE | WHr |
| GLUCOSE | HBA1C | INSULIN-M |

FIGURE 10A

| Panel No. | Marker 1 | Marker 2 | Marker 3 |
|---|---|---|---|
| 3.1 | ADIPOQ | CRP | GLUCOSE |
| 3.2 | CRP | GLUCOSE | GPT |
| 3.3 | CRP | GLUCOSE | HBA1C |
| 3.4 | CRP | GLUCOSE | IGFBP2 |
| 3.5 | CRP | GLUCOSE | INSULIN-M |
| 3.6 | CRP | GLUCOSE | TRIG |
| 3.7 | GLUCOSE | HBA1C | INSULIN-M |

FIGURE 10B

| Panel No. | Marker 1 | Marker 2 | Marker 3 | Marker 4 |
|---|---|---|---|---|
| 4.1 | ADIPOQ | CRP | GLUCOSE | LEP |
| 4.2 | ADIPOQ | CRP | GLUCOSE | GPT |
| 4.3 | ADIPOQ | CRP | GLUCOSE | HBA1C |
| 4.4 | ADIPOQ | CRP | GLUCOSE | IGFBP2 |
| 4.5 | ADIPOQ | CRP | GLUCOSE | INSULIN-M |
| 4.6 | ADIPOQ | GLUCOSE | HSPA1B | LEP |
| 4.7 | CRP | GLUCOSE | GPT | HBA1C |
| 4.8 | CRP | GLUCOSE | GPT | HSPA1B |
| 4.9 | CRP | GLUCOSE | GPT | IGFBP2 |
| 4.10 | CRP | GLUCOSE | HBA1C | IGFBP2 |
| 4.11 | CRP | GLUCOSE | HBA1C | INSULIN-M |
| 4.12 | CRP | GLUCOSE | HBA1C | INSULIN-M |
| 4.13 | CRP | GLUCOSE | HBA1C | INSULIN-M |
| 4.14 | CRP | GLUCOSE | HBA1C | LEP |
| 4.15 | CRP | GLUCOSE | HSPA1B | LEP |
| 4.16 | CRP | GLUCOSE | IGFBP1 | LEP |
| 4.17 | CRP | GLUCOSE | IGFBP2 | TRIG |
| 4.18 | CRP | GLUCOSE | INSULIN-M | TRIG |
| 4.19 | CRP | GLUCOSE | INSULIN-M | TRIG |
| 4.20 | CRP | GLUCOSE | LEP | TRIG |
| 4.21 | CRP | GPT | HBA1C | INSULIN-M |
| 4.22 | CRP | HBA1C | INSULIN-M | TRIG |
| 4.23 | GLUCOSE | GPT | HBA1C | INSULIN-M |
| 4.24 | GLUCOSE | HBA1C | INSULIN-M | LEP |
| 4.25 | GLUCOSE | HBA1C | LEP | TRIG |

FIGURE 10C

| Panel No. | Marker 1 | Marker 2 | Marker 3 | Marker 4 | Marker 5 |
|---|---|---|---|---|---|
| 5.1 | ADIPOQ | CRP | GLUCOSE | GPT | HBA1C |
| 5.2 | ADIPOQ | CRP | GLUCOSE | GPT | HSPA1B |
| 5.3 | ADIPOQ | CRP | GLUCOSE | GPT | INSULIN-M |
| 5.4 | ADIPOQ | CRP | GLUCOSE | GPT | LEP |
| 5.5 | ADIPOQ | CRP | GLUCOSE | GPT | TRIG |
| 5.6 | ADIPOQ | CRP | GLUCOSE | HBA1C | HSPA1B |
| 5.7 | ADIPOQ | CRP | GLUCOSE | HBA1C | IGFBP1 |
| 5.8 | ADIPOQ | CRP | GLUCOSE | HBA1C | INSULIN-M |
| 5.9 | ADIPOQ | CRP | GLUCOSE | HBA1C | LEP |
| 5.10 | ADIPOQ | CRP | GLUCOSE | HBA1C | TRIG |
| 5.11 | ADIPOQ | CRP | GLUCOSE | HSPA1B | IGFBP1 |
| 5.12 | ADIPOQ | CRP | GLUCOSE | HSPA1B | INSULIN-M |
| 5.13 | ADIPOQ | CRP | GLUCOSE | HSPA1B | LEP |
| 5.14 | ADIPOQ | CRP | GLUCOSE | HSPA1B | TRIG |
| 5.15 | ADIPOQ | CRP | GLUCOSE | IGFBP1 | IGFBP2 |
| 5.16 | ADIPOQ | CRP | GLUCOSE | IGFBP1 | INSULIN-M |
| 5.17 | ADIPOQ | CRP | GLUCOSE | IGFBP1 | LEP |
| 5.18 | ADIPOQ | CRP | GLUCOSE | IGFBP1 | TRIG |
| 5.19 | ADIPOQ | CRP | GLUCOSE | IGFBP2 | LEP |
| 5.20 | ADIPOQ | CRP | GLUCOSE | INSULIN-M | LEP |
| 5.21 | ADIPOQ | CRP | GLUCOSE | INSULIN-M | TRIG |
| 5.22 | ADIPOQ | CRP | GLUCOSE | LEP | TRIG |
| 5.23 | ADIPOQ | CRP | GPT | HBA1C | INSULIN-M |
| 5.24 | ADIPOQ | GLUCOSE | GPT | HBA1C | INSULIN-M |
| 5.25 | ADIPOQ | GLUCOSE | GPT | HBA1C | LEP |
| 5.26 | ADIPOQ | GLUCOSE | GPT | INSULIN-M | LEP |
| 5.27 | ADIPOQ | GLUCOSE | HBA1C | IGFBP2 | LEP |
| 5.28 | ADIPOQ | GLUCOSE | HSPA1B | LEP | TRIG |
| 5.29 | CRP | GLUCOSE | GPT | HBA1C | HSPA1B |
| 5.30 | CRP | GLUCOSE | GPT | HBA1C | IGFBP1 |
| 5.31 | CRP | GLUCOSE | GPT | HBA1C | IGFBP2 |
| 5.32 | CRP | GLUCOSE | GPT | HBA1C | INSULIN-M |
| 5.33 | CRP | GLUCOSE | GPT | HBA1C | TRIG |
| 5.34 | CRP | GLUCOSE | GPT | HSPA1B | LEP |
| 5.35 | CRP | GLUCOSE | GPT | HSPA1B | TRIG |
| 5.36 | CRP | GLUCOSE | GPT | IGFBP1 | INSULIN-M |
| 5.37 | CRP | GLUCOSE | GPT | IGFBP2 | INSULIN-M |
| 5.38 | CRP | GLUCOSE | GPT | IGFBP2 | LEP |
| 5.39 | CRP | GLUCOSE | GPT | IGFBP2 | TRIG |
| 5.40 | CRP | GLUCOSE | GPT | INSULIN-M | LEP |

FIGURE 10C (continued)

| Panel No. | Marker 1 | Marker 2 | Marker 3 | Marker 4 | Marker 5 |
|---|---|---|---|---|---|
| 5.41 | CRP | GLUCOSE | GPT | INSULIN-M | TRIG |
| 5.42 | CRP | GLUCOSE | GPT | LEP | TRIG |
| 5.43 | CRP | GLUCOSE | HBA1C | HSPA1B | IGFBP1 |
| 5.44 | CRP | GLUCOSE | HBA1C | HSPA1B | IGFBP2 |
| 5.45 | CRP | GLUCOSE | HBA1C | HSPA1B | INSULIN-M |
| 5.46 | CRP | GLUCOSE | HBA1C | HSPA1B | TRIG |
| 5.47 | CRP | GLUCOSE | HBA1C | IGFBP1 | INSULIN-M |
| 5.48 | CRP | GLUCOSE | HBA1C | IGFBP1 | LEP |
| 5.49 | CRP | GLUCOSE | HBA1C | IGFBP1 | TRIG |
| 5.50 | CRP | GLUCOSE | HBA1C | INSULIN-M | LEP |
| 5.51 | CRP | GLUCOSE | HBA1C | INSULIN-M | TRIG |
| 5.52 | CRP | GLUCOSE | HSPA1B | IGFBP2 | INSULIN-M |
| 5.53 | CRP | GLUCOSE | HSPA1B | INSULIN-M | LEP |
| 5.54 | CRP | GLUCOSE | HSPA1B | INSULIN-M | TRIG |
| 5.55 | CRP | GLUCOSE | IGFBP1 | INSULIN-M | TRIG |
| 5.56 | CRP | GLUCOSE | IGFBP2 | INSULIN-M | TRIG |
| 5.57 | CRP | GLUCOSE | IGFBP2 | LEP | TRIG |
| 5.58 | CRP | HBA1C | HSPA1B | IGFBP1 | TRIG |
| 5.59 | GLUCOSE | GPT | HBA1C | HSPA1B | LEP |
| 5.60 | GLUCOSE | GPT | HBA1C | INSULIN-M | LEP |
| 5.61 | GLUCOSE | GPT | HBA1C | LEP | TRIG |
| 5.62 | GLUCOSE | GPT | HSPA1B | IGFBP2 | INSULIN-M |
| 5.63 | GLUCOSE | HBA1C | HSPA1B | IGFBP2 | INSULIN-M |
| 5.64 | GLUCOSE | HBA1C | HSPA1B | INSULIN-M | TRIG |
| 5.65 | GLUCOSE | HBA1C | HSPA1B | LEP | TRIG |

FIGURE 10D

| Panel No. | Marker 1 | Marker 2 | Marker 3 | Marker 4 | Marker 5 | Marker 6 |
|---|---|---|---|---|---|---|
| 6.1 | ADIPOQ | CRP | GLUCOSE | GPT | HBA1C | HSPA1B |
| 6.2 | ADIPOQ | CRP | GLUCOSE | GPT | HBA1C | IGFBP1 |
| 6.3 | ADIPOQ | CRP | GLUCOSE | GPT | HBA1C | IGFBP2 |
| 6.4 | ADIPOQ | CRP | GLUCOSE | GPT | HBA1C | INSULIN-M |
| 6.5 | ADIPOQ | CRP | GLUCOSE | GPT | HBA1C | LEP |
| 6.6 | ADIPOQ | CRP | GLUCOSE | GPT | HBA1C | TRIG |
| 6.7 | ADIPOQ | CRP | GLUCOSE | GPT | HSPA1B | INSULIN-M |
| 6.8 | ADIPOQ | CRP | GLUCOSE | GPT | HSPA1B | LEP |
| 6.9 | ADIPOQ | CRP | GLUCOSE | GPT | HSPA1B | TRIG |
| 6.10 | ADIPOQ | CRP | GLUCOSE | GPT | IGFBP1 | IGFBP2 |
| 6.11 | ADIPOQ | CRP | GLUCOSE | GPT | IGFBP1 | INSULIN-M |
| 6.12 | ADIPOQ | CRP | GLUCOSE | GPT | IGFBP1 | LEP |
| 6.13 | ADIPOQ | CRP | GLUCOSE | GPT | IGFBP2 | INSULIN-M |
| 6.14 | ADIPOQ | CRP | GLUCOSE | GPT | IGFBP2 | LEP |
| 6.15 | ADIPOQ | CRP | GLUCOSE | GPT | IGFBP2 | TRIG |
| 6.16 | ADIPOQ | CRP | GLUCOSE | GPT | INSULIN-M | LEP |
| 6.17 | ADIPOQ | CRP | GLUCOSE | GPT | INSULIN-M | TRIG |
| 6.18 | ADIPOQ | CRP | GLUCOSE | GPT | LEP | TRIG |
| 6.19 | ADIPOQ | CRP | GLUCOSE | HBA1C | HSPA1B | IGFBP1 |
| 6.20 | ADIPOQ | CRP | GLUCOSE | HBA1C | HSPA1B | IGFBP2 |
| 6.21 | ADIPOQ | CRP | GLUCOSE | HBA1C | HSPA1B | INSULIN-M |
| 6.22 | ADIPOQ | CRP | GLUCOSE | HBA1C | HSPA1B | LEP |
| 6.23 | ADIPOQ | CRP | GLUCOSE | HBA1C | HSPA1B | TRIG |
| 6.24 | ADIPOQ | CRP | GLUCOSE | HBA1C | IGFBP1 | IGFBP2 |
| 6.25 | ADIPOQ | CRP | GLUCOSE | HBA1C | IGFBP1 | INSULIN-M |
| 6.26 | ADIPOQ | CRP | GLUCOSE | HBA1C | IGFBP1 | LEP |
| 6.27 | ADIPOQ | CRP | GLUCOSE | HBA1C | IGFBP1 | TRIG |
| 6.28 | ADIPOQ | CRP | GLUCOSE | HBA1C | IGFBP2 | INSULIN-M |
| 6.29 | ADIPOQ | CRP | GLUCOSE | HBA1C | IGFBP2 | LEP |
| 6.30 | ADIPOQ | CRP | GLUCOSE | HBA1C | IGFBP2 | TRIG |
| 6.31 | ADIPOQ | CRP | GLUCOSE | HBA1C | INSULIN-M | LEP |
| 6.32 | ADIPOQ | CRP | GLUCOSE | HBA1C | INSULIN-M | TRIG |
| 6.33 | ADIPOQ | CRP | GLUCOSE | HBA1C | LEP | TRIG |
| 6.34 | ADIPOQ | CRP | GLUCOSE | HSPA1B | IGFBP1 | IGFBP2 |
| 6.35 | ADIPOQ | CRP | GLUCOSE | HSPA1B | IGFBP1 | INSULIN-M |
| 6.36 | ADIPOQ | CRP | GLUCOSE | HSPA1B | IGFBP1 | LEP |
| 6.37 | ADIPOQ | CRP | GLUCOSE | HSPA1B | IGFBP1 | TRIG |
| 6.38 | ADIPOQ | CRP | GLUCOSE | HSPA1B | IGFBP2 | INSULIN-M |
| 6.39 | ADIPOQ | CRP | GLUCOSE | HSPA1B | IGFBP2 | LEP |
| 6.40 | ADIPOQ | CRP | GLUCOSE | HSPA1B | INSULIN-M | LEP |

FIGURE 10D (continued)

| Panel No. | Marker 1 | Marker 2 | Marker 3 | Marker 4 | Marker 5 | Marker 6 |
|---|---|---|---|---|---|---|
| 6.41 | ADIPOQ | CRP | GLUCOSE | HSPA1B | INSULIN-M | TRIG |
| 6.42 | ADIPOQ | CRP | GLUCOSE | HSPA1B | LEP | TRIG |
| 6.43 | ADIPOQ | CRP | GLUCOSE | IGFBP1 | IGFBP2 | INSULIN-M |
| 6.44 | ADIPOQ | CRP | GLUCOSE | IGFBP1 | IGFBP2 | LEP |
| 6.45 | ADIPOQ | CRP | GLUCOSE | IGFBP1 | INSULIN-M | LEP |
| 6.46 | ADIPOQ | CRP | GLUCOSE | IGFBP1 | INSULIN-M | TRIG |
| 6.47 | ADIPOQ | CRP | GLUCOSE | IGFBP1 | LEP | TRIG |
| 6.48 | ADIPOQ | CRP | GLUCOSE | IGFBP2 | INSULIN-M | LEP |
| 6.49 | ADIPOQ | CRP | GLUCOSE | IGFBP2 | INSULIN-M | TRIG |
| 6.50 | ADIPOQ | CRP | GLUCOSE | IGFBP2 | LEP | TRIG |
| 6.51 | ADIPOQ | CRP | GLUCOSE | INSULIN-M | LEP | TRIG |
| 6.52 | ADIPOQ | CRP | GPT | HBA1C | HSPA1B | INSULIN-M |
| 6.53 | ADIPOQ | CRP | GPT | HBA1C | IGFBP2 | INSULIN-M |
| 6.54 | ADIPOQ | CRP | GPT | HBA1C | INSULIN-M | TRIG |
| 6.55 | ADIPOQ | GLUCOSE | GPT | HBA1C | HSPA1B | INSULIN-M |
| 6.56 | ADIPOQ | GLUCOSE | GPT | HBA1C | IGFBP2 | INSULIN-M |
| 6.57 | ADIPOQ | GLUCOSE | GPT | HBA1C | IGFBP2 | LEP |
| 6.58 | ADIPOQ | GLUCOSE | GPT | HBA1C | INSULIN-M | LEP |
| 6.59 | ADIPOQ | GLUCOSE | GPT | HBA1C | LEP | TRIG |
| 6.60 | ADIPOQ | GLUCOSE | GPT | HSPA1B | IGFBP2 | LEP |
| 6.61 | ADIPOQ | GLUCOSE | GPT | HSPA1B | INSULIN-M | LEP |
| 6.62 | ADIPOQ | GLUCOSE | GPT | HSPA1B | LEP | TRIG |
| 6.63 | ADIPOQ | GLUCOSE | GPT | IGFBP2 | LEP | TRIG |
| 6.64 | ADIPOQ | GLUCOSE | HBA1C | HSPA1B | IGFBP2 | INSULIN-M |
| 6.65 | ADIPOQ | GLUCOSE | HBA1C | HSPA1B | IGFBP2 | LEP |
| 6.66 | ADIPOQ | GLUCOSE | HBA1C | HSPA1B | INSULIN-M | LEP |
| 6.67 | ADIPOQ | GLUCOSE | HBA1C | HSPA1B | INSULIN-M | TRIG |
| 6.68 | ADIPOQ | GLUCOSE | HBA1C | HSPA1B | LEP | TRIG |
| 6.69 | ADIPOQ | GLUCOSE | HBA1C | IGFBP2 | LEP | TRIG |
| 6.70 | ADIPOQ | GLUCOSE | HBA1C | INSULIN-M | LEP | TRIG |
| 6.71 | ADIPOQ | GLUCOSE | HSPA1B | IGFBP1 | IGFBP2 | LEP |
| 6.72 | ADIPOQ | GLUCOSE | HSPA1B | IGFBP1 | LEP | TRIG |
| 6.73 | ADIPOQ | GLUCOSE | HSPA1B | IGFBP2 | INSULIN-M | LEP |
| 6.74 | ADIPOQ | GLUCOSE | HSPA1B | IGFBP2 | LEP | TRIG |
| 6.75 | ADIPOQ | GLUCOSE | HSPA1B | INSULIN-M | LEP | TRIG |
| 6.76 | CRP | GLUCOSE | GPT | HBA1C | HSPA1B | IGFBP1 |
| 6.77 | CRP | GLUCOSE | GPT | HBA1C | HSPA1B | IGFBP2 |
| 6.78 | CRP | GLUCOSE | GPT | HBA1C | HSPA1B | INSULIN-M |
| 6.79 | CRP | GLUCOSE | GPT | HBA1C | HSPA1B | LEP |
| 6.80 | CRP | GLUCOSE | GPT | HBA1C | HSPA1B | TRIG |

FIGURE 10D (continued)

| Panel No. | Marker 1 | Marker 2 | Marker 3 | Marker 4 | Marker 5 | Marker 6 |
|---|---|---|---|---|---|---|
| 6.81 | CRP | GLUCOSE | GPT | HBA1C | IGFBP1 | IGFBP2 |
| 6.82 | CRP | GLUCOSE | GPT | HBA1C | IGFBP1 | INSULIN-M |
| 6.83 | CRP | GLUCOSE | GPT | HBA1C | IGFBP1 | LEP |
| 6.84 | CRP | GLUCOSE | GPT | HBA1C | IGFBP1 | TRIG |
| 6.85 | CRP | GLUCOSE | GPT | HBA1C | IGFBP2 | INSULIN-M |
| 6.86 | CRP | GLUCOSE | GPT | HBA1C | INSULIN-M | LEP |
| 6.87 | CRP | GLUCOSE | GPT | HBA1C | INSULIN-M | TRIG |
| 6.88 | CRP | GLUCOSE | GPT | HBA1C | LEP | TRIG |
| 6.89 | CRP | GLUCOSE | GPT | HSPA1B | IGFBP2 | INSULIN-M |
| 6.90 | CRP | GLUCOSE | GPT | HSPA1B | IGFBP2 | LEP |
| 6.91 | CRP | GLUCOSE | GPT | HSPA1B | IGFBP2 | TRIG |
| 6.92 | CRP | GLUCOSE | GPT | HSPA1B | INSULIN-M | LEP |
| 6.93 | CRP | GLUCOSE | GPT | HSPA1B | INSULIN-M | TRIG |
| 6.94 | CRP | GLUCOSE | GPT | IGFBP1 | IGFBP2 | INSULIN-M |
| 6.95 | CRP | GLUCOSE | GPT | IGFBP1 | INSULIN-M | LEP |
| 6.96 | CRP | GLUCOSE | GPT | IGFBP1 | LEP | TRIG |
| 6.97 | CRP | GLUCOSE | GPT | IGFBP2 | INSULIN-M | TRIG |
| 6.98 | CRP | GLUCOSE | GPT | IGFBP2 | LEP | TRIG |
| 6.99 | CRP | GLUCOSE | GPT | INSULIN-M | LEP | TRIG |
| 6.100 | CRP | GLUCOSE | HBA1C | HSPA1B | IGFBP1 | INSULIN-M |
| 6.101 | CRP | GLUCOSE | HBA1C | HSPA1B | IGFBP1 | LEP |
| 6.102 | CRP | GLUCOSE | HBA1C | HSPA1B | IGFBP1 | TRIG |
| 6.103 | CRP | GLUCOSE | HBA1C | HSPA1B | IGFBP2 | INSULIN-M |
| 6.104 | CRP | GLUCOSE | HBA1C | HSPA1B | IGFBP2 | LEP |
| 6.105 | CRP | GLUCOSE | HBA1C | HSPA1B | INSULIN-M | LEP |
| 6.106 | CRP | GLUCOSE | HBA1C | HSPA1B | INSULIN-M | TRIG |
| 6.107 | CRP | GLUCOSE | HBA1C | HSPA1B | LEP | TRIG |
| 6.108 | CRP | GLUCOSE | HBA1C | IGFBP1 | IGFBP2 | INSULIN-M |
| 6.109 | CRP | GLUCOSE | HBA1C | IGFBP1 | IGFBP2 | TRIG |
| 6.110 | CRP | GLUCOSE | HBA1C | IGFBP1 | INSULIN-M | LEP |
| 6.111 | CRP | GLUCOSE | HBA1C | IGFBP1 | INSULIN-M | TRIG |
| 6.112 | CRP | GLUCOSE | HBA1C | IGFBP1 | LEP | TRIG |
| 6.113 | CRP | GLUCOSE | HBA1C | IGFBP2 | INSULIN-M | LEP |
| 6.114 | CRP | GLUCOSE | HBA1C | IGFBP2 | INSULIN-M | TRIG |
| 6.115 | CRP | GLUCOSE | HBA1C | IGFBP2 | LEP | TRIG |
| 6.116 | CRP | GLUCOSE | HBA1C | INSULIN-M | LEP | TRIG |
| 6.117 | CRP | GLUCOSE | HSPA1B | IGFBP1 | IGFBP2 | INSULIN-M |
| 6.118 | CRP | GLUCOSE | HSPA1B | IGFBP1 | LEP | TRIG |
| 6.119 | CRP | GLUCOSE | HSPA1B | IGFBP2 | INSULIN-M | LEP |
| 6.120 | CRP | GLUCOSE | HSPA1B | IGFBP2 | INSULIN-M | TRIG |

FIGURE 10D (continued)

| Panel No. | Marker 1 | Marker 2 | Marker 3 | Marker 4 | Marker 5 | Marker 6 |
|---|---|---|---|---|---|---|
| 6.121 | CRP | GLUCOSE | HSPA1B | IGFBP2 | LEP | TRIG |
| 6.122 | CRP | GLUCOSE | IGFBP1 | IGFBP2 | INSULIN-M | TRIG |
| 6.123 | CRP | GLUCOSE | IGFBP1 | INSULIN-M | LEP | TRIG |
| 6.124 | CRP | GLUCOSE | IGFBP2 | INSULIN-M | LEP | TRIG |
| 6.125 | CRP | GPT | HBA1C | HSPA1B | INSULIN-M | TRIG |
| 6.126 | GLUCOSE | GPT | HBA1C | HSPA1B | IGFBP2 | INSULIN-M |
| 6.127 | GLUCOSE | GPT | HBA1C | HSPA1B | IGFBP2 | LEP |
| 6.128 | GLUCOSE | GPT | HBA1C | IGFBP2 | INSULIN-M | LEP |
| 6.129 | GLUCOSE | GPT | HBA1C | INSULIN-M | LEP | TRIG |
| 6.130 | GLUCOSE | HBA1C | HSPA1B | IGFBP1 | IGFBP2 | INSULIN-M |
| 6.131 | GLUCOSE | HBA1C | HSPA1B | IGFBP2 | INSULIN-M | LEP |
| 6.132 | GLUCOSE | HBA1C | HSPA1B | IGFBP2 | INSULIN-M | TRIG |
| 6.133 | GLUCOSE | HBA1C | HSPA1B | IGFBP2 | LEP | TRIG |
| 6.134 | GLUCOSE | HBA1C | IGFBP1 | INSULIN-M | LEP | TRIG |

FIGURE 10E

| Panel No. | Marker 1 | Marker 2 | Marker 3 | Marker 4 | Marker 5 | Marker 6 | Marker 7 |
|---|---|---|---|---|---|---|---|
| 7.1 | ADIPOQ | CRP | GLUCOSE | GPT | HBA1C | HSPA1B | INSULIN-M |
| 7.2 | ADIPOQ | CRP | GLUCOSE | GPT | HBA1C | HSPA1B | LEP |
| 7.3 | ADIPOQ | CRP | GLUCOSE | GPT | HBA1C | HSPA1B | LEP |
| 7.4 | ADIPOQ | CRP | GLUCOSE | GPT | HBA1C | HSPA1B | LEP |
| 7.5 | ADIPOQ | CRP | GLUCOSE | GPT | HBA1C | HSPA1B | TRIG |
| 7.6 | ADIPOQ | CRP | GLUCOSE | GPT | HBA1C | IGFBP1 | LEP |
| 7.7 | ADIPOQ | CRP | GLUCOSE | GPT | HBA1C | IGFBP1 | LEP |
| 7.8 | ADIPOQ | CRP | GLUCOSE | GPT | HBA1C | IGFBP1 | LEP |
| 7.9 | ADIPOQ | CRP | GLUCOSE | GPT | HBA1C | IGFBP1 | TRIG |
| 7.10 | ADIPOQ | CRP | GLUCOSE | GPT | HBA1C | IGFBP2 | LEP |
| 7.11 | ADIPOQ | CRP | GLUCOSE | GPT | HBA1C | IGFBP2 | LEP |
| 7.12 | ADIPOQ | CRP | GLUCOSE | GPT | HBA1C | IGFBP2 | TRIG |
| 7.13 | ADIPOQ | CRP | GLUCOSE | GPT | HBA1C | INSULIN-M | LEP |
| 7.14 | ADIPOQ | CRP | GLUCOSE | GPT | HBA1C | INSULIN-M | TRIG |
| 7.15 | ADIPOQ | CRP | GLUCOSE | GPT | HBA1C | LEP | IGFBP2 |
| 7.16 | ADIPOQ | CRP | GLUCOSE | GPT | HSPA1B | IGFBP1 | INSULIN-M |
| 7.17 | ADIPOQ | CRP | GLUCOSE | GPT | HSPA1B | IGFBP1 | LEP |
| 7.18 | ADIPOQ | CRP | GLUCOSE | GPT | HSPA1B | IGFBP1 | TRIG |
| 7.19 | ADIPOQ | CRP | GLUCOSE | GPT | HSPA1B | IGFBP2 | LEP |
| 7.20 | ADIPOQ | CRP | GLUCOSE | GPT | HSPA1B | IGFBP2 | TRIG |
| 7.21 | ADIPOQ | CRP | GLUCOSE | GPT | HSPA1B | INSULIN-M | TRIG |
| 7.22 | ADIPOQ | CRP | GLUCOSE | GPT | HSPA1B | INSULIN-M | TRIG |
| 7.23 | ADIPOQ | CRP | GLUCOSE | GPT | HSPA1B | LEP | TRIG |
| 7.24 | ADIPOQ | CRP | GLUCOSE | GPT | IGFBP1 | IGFBP2 | LEP |
| 7.25 | ADIPOQ | CRP | GLUCOSE | GPT | IGFBP1 | IGFBP2 | TRIG |
| 7.26 | ADIPOQ | CRP | GLUCOSE | GPT | IGFBP1 | IGFBP2 | INSULIN-M |
| 7.27 | ADIPOQ | CRP | GLUCOSE | GPT | IGFBP1 | INSULIN-M | INSULIN-M |
| 7.28 | ADIPOQ | CRP | GLUCOSE | GPT | IGFBP1 | INSULIN-M | TRIG |
| 7.29 | ADIPOQ | CRP | GLUCOSE | GPT | IGFBP1 | LEP | INSULIN-M |
| 7.30 | ADIPOQ | CRP | GLUCOSE | GPT | IGFBP2 | INSULIN-M | LEP |
| 7.31 | ADIPOQ | CRP | GLUCOSE | GPT | IGFBP2 | INSULIN-M | TRIG |
| 7.32 | ADIPOQ | CRP | GLUCOSE | GPT | IGFBP2 | LEP | IGFBP2 |
| 7.33 | ADIPOQ | CRP | GLUCOSE | GPT | INSULIN-M | LEP | INSULIN-M |
| 7.34 | ADIPOQ | CRP | GLUCOSE | HBA1C | HSPA1B | IGFBP1 | IGFBP1 |
| 7.35 | ADIPOQ | CRP | GLUCOSE | HBA1C | HSPA1B | IGFBP1 | LEP |
| 7.36 | ADIPOQ | CRP | GLUCOSE | HBA1C | HSPA1B | IGFBP1 | TRIG |
| 7.37 | ADIPOQ | CRP | GLUCOSE | HBA1C | HSPA1B | IGFBP2 | LEP |
| 7.38 | ADIPOQ | CRP | GLUCOSE | HBA1C | HSPA1B | IGFBP2 | TRIG |
| 7.39 | ADIPOQ | CRP | GLUCOSE | HBA1C | HSPA1B | IGFBP2 | TRIG |
| 7.40 | ADIPOQ | CRP | GLUCOSE | HBA1C | HSPA1B | INSULIN-M | IGFBP2 |

FIGURE 10E (continued)

| Panel No. | Marker 1 | Marker 2 | Marker 3 | Marker 4 | Marker 5 | Marker 6 | Marker 7 |
|---|---|---|---|---|---|---|---|
| 7.41 | ADIPOQ | CRP | GLUCOSE | HBA1C | HSPA1B | INSULIN-M | TRIG |
| 7.42 | ADIPOQ | CRP | GLUCOSE | HBA1C | HSPA1B | LEP | LEP |
| 7.43 | ADIPOQ | CRP | GLUCOSE | HBA1C | IGFBP1 | IGFBP2 | LEP |
| 7.44 | ADIPOQ | CRP | GLUCOSE | HBA1C | IGFBP1 | IGFBP2 | TRIG |
| 7.45 | ADIPOQ | CRP | GLUCOSE | HBA1C | IGFBP1 | IGFBP2 | TRIG |
| 7.46 | ADIPOQ | CRP | GLUCOSE | HBA1C | IGFBP1 | INSULIN-M | TRIG |
| 7.47 | ADIPOQ | CRP | GLUCOSE | HBA1C | IGFBP1 | LEP | TRIG |
| 7.48 | ADIPOQ | CRP | GLUCOSE | HBA1C | IGFBP2 | INSULIN-M | INSULIN-M |
| 7.49 | ADIPOQ | CRP | GLUCOSE | HBA1C | IGFBP2 | INSULIN-M | TRIG |
| 7.50 | ADIPOQ | CRP | GLUCOSE | HBA1C | IGFBP2 | LEP | TRIG |
| 7.51 | ADIPOQ | CRP | GLUCOSE | HBA1C | INSULIN-M | LEP | TRIG |
| 7.52 | ADIPOQ | CRP | GLUCOSE | HSPA1B | IGFBP1 | IGFBP2 | INSULIN-M |
| 7.53 | ADIPOQ | CRP | GLUCOSE | HSPA1B | IGFBP1 | IGFBP2 | INSULIN-M |
| 7.54 | ADIPOQ | CRP | GLUCOSE | HSPA1B | IGFBP1 | IGFBP2 | TRIG |
| 7.55 | ADIPOQ | CRP | GLUCOSE | HSPA1B | IGFBP1 | INSULIN-M | TRIG |
| 7.56 | ADIPOQ | CRP | GLUCOSE | HSPA1B | IGFBP1 | LEP | TRIG |
| 7.57 | ADIPOQ | CRP | GLUCOSE | HSPA1B | IGFBP2 | INSULIN-M | LEP |
| 7.58 | ADIPOQ | CRP | GLUCOSE | HSPA1B | IGFBP2 | INSULIN-M | LEP |
| 7.59 | ADIPOQ | CRP | GLUCOSE | HSPA1B | IGFBP2 | LEP | TRIG |
| 7.60 | ADIPOQ | CRP | GLUCOSE | HSPA1B | INSULIN-M | LEP | LEP |
| 7.61 | ADIPOQ | CRP | GLUCOSE | IGFBP1 | IGFBP2 | INSULIN-M | TRIG |
| 7.62 | ADIPOQ | CRP | GLUCOSE | IGFBP1 | IGFBP2 | INSULIN-M | TRIG |
| 7.63 | ADIPOQ | CRP | GLUCOSE | IGFBP1 | IGFBP2 | LEP | TRIG |
| 7.64 | ADIPOQ | CRP | GLUCOSE | IGFBP2 | INSULIN-M | LEP | TRIG |
| 7.65 | ADIPOQ | CRP | GPT | HBA1C | HSPA1B | IGFBP2 | INSULIN-M |
| 7.66 | ADIPOQ | CRP | GPT | HBA1C | HSPA1B | IGFBP2 | TRIG |
| 7.67 | ADIPOQ | CRP | GPT | HBA1C | HSPA1B | INSULIN-M | TRIG |
| 7.68 | ADIPOQ | CRP | HBA1C | HSPA1B | IGFBP2 | INSULIN-M | LEP |
| 7.69 | ADIPOQ | CRP | HBA1C | HSPA1B | IGFBP2 | INSULIN-M | TRIG |
| 7.70 | ADIPOQ | CRP | HBA1C | HSPA1B | INSULIN-M | LEP | TRIG |
| 7.71 | ADIPOQ | GLUCOSE | GPT | HBA1C | HSPA1B | IGFBP1 | LEP |
| 7.72 | ADIPOQ | GLUCOSE | GPT | HBA1C | HSPA1B | IGFBP2 | LEP |
| 7.73 | ADIPOQ | GLUCOSE | GPT | HBA1C | HSPA1B | IGFBP2 | TRIG |
| 7.74 | ADIPOQ | GLUCOSE | GPT | HBA1C | HSPA1B | INSULIN-M | INSULIN-M |
| 7.75 | ADIPOQ | GLUCOSE | GPT | HBA1C | HSPA1B | INSULIN-M | LEP |

FIGURE 10E (continued)

| 7.76 | ADIPOQ | GLUCOSE | GPT | HBA1C | HSPA1B | LEP | TRIG |
|---|---|---|---|---|---|---|---|
| 7.77 | ADIPOQ | GLUCOSE | GPT | HBA1C | IGFBP1 | INSULIN-M | TRIG |
| 7.78 | ADIPOQ | GLUCOSE | GPT | HBA1C | IGFBP2 | INSULIN-M | LEP |
| 7.79 | ADIPOQ | GLUCOSE | GPT | HBA1C | IGFBP2 | LEP | INSULIN-M |
| 7.80 | ADIPOQ | GLUCOSE | GPT | HSPA1B | IGFBP1 | INSULIN-M | TRIG |

FIGURE 10E (continued)

| Panel No. | Marker 1 | Marker 2 | Marker 3 | Marker 4 | Marker 5 | Marker 6 | Marker 7 |
|---|---|---|---|---|---|---|---|
| 7.81 | ADIPOQ | GLUCOSE | GPT | HSPA1B | IGFBP2 | LEP | LEP |
| 7.82 | ADIPOQ | GLUCOSE | GPT | HSPA1B | INSULIN-M | LEP | LEP |
| 7.83 | ADIPOQ | GLUCOSE | GPT | IGFBP1 | IGFBP2 | INSULIN-M | TRIG |
| 7.84 | ADIPOQ | GLUCOSE | HBA1C | HSPA1B | IGFBP1 | IGFBP2 | LEP |
| 7.85 | ADIPOQ | GLUCOSE | HBA1C | HSPA1B | IGFBP1 | INSULIN-M | TRIG |
| 7.86 | ADIPOQ | GLUCOSE | HBA1C | HSPA1B | IGFBP1 | LEP | LEP |
| 7.87 | ADIPOQ | GLUCOSE | HBA1C | HSPA1B | IGFBP2 | INSULIN-M | INSULIN-M |
| 7.88 | ADIPOQ | GLUCOSE | HBA1C | HSPA1B | IGFBP2 | INSULIN-M | TRIG |
| 7.89 | ADIPOQ | GLUCOSE | HBA1C | HSPA1B | IGFBP2 | LEP | TRIG |
| 7.90 | ADIPOQ | GLUCOSE | HBA1C | HSPA1B | INSULIN-M | LEP | TRIG |
| 7.91 | ADIPOQ | GLUCOSE | HBA1C | IGFBP2 | INSULIN-M | LEP | TRIG |
| 7.92 | ADIPOQ | GLUCOSE | HSPA1B | IGFBP2 | INSULIN-M | LEP | TRIG |
| 7.93 | CRP | GLUCOSE | GPT | HBA1C | HSPA1B | IGFBP1 | INSULIN-M |
| 7.94 | CRP | GLUCOSE | GPT | HBA1C | HSPA1B | IGFBP1 | LEP |
| 7.95 | CRP | GLUCOSE | GPT | HBA1C | HSPA1B | IGFBP2 | INSULIN-M |
| 7.96 | CRP | GLUCOSE | GPT | HBA1C | HSPA1B | IGFBP2 | LEP |
| 7.97 | CRP | GLUCOSE | GPT | HBA1C | HSPA1B | IGFBP2 | TRIG |
| 7.98 | CRP | GLUCOSE | GPT | HBA1C | HSPA1B | INSULIN-M | TRIG |
| 7.99 | CRP | GLUCOSE | GPT | HBA1C | HSPA1B | INSULIN-M | TRIG |
| 7.100 | CRP | GLUCOSE | GPT | HBA1C | HSPA1B | LEP | TRIG |
| 7.101 | CRP | GLUCOSE | GPT | HBA1C | IGFBP1 | IGFBP2 | LEP |
| 7.102 | CRP | GLUCOSE | GPT | HBA1C | IGFBP1 | IGFBP2 | TRIG |
| 7.103 | CRP | GLUCOSE | GPT | HBA1C | IGFBP1 | IGFBP2 | TRIG |
| 7.104 | CRP | GLUCOSE | GPT | HBA1C | IGFBP1 | INSULIN-M | TRIG |
| 7.105 | CRP | GLUCOSE | GPT | HBA1C | IGFBP1 | INSULIN-M | TRIG |
| 7.106 | CRP | GLUCOSE | GPT | HBA1C | IGFBP1 | LEP | LEP |
| 7.107 | CRP | GLUCOSE | GPT | HBA1C | IGFBP2 | INSULIN-M | TRIG |
| 7.108 | CRP | GLUCOSE | GPT | HBA1C | IGFBP2 | INSULIN-M | TRIG |
| 7.109 | CRP | GLUCOSE | GPT | HBA1C | IGFBP2 | LEP | INSULIN-M |
| 7.110 | CRP | GLUCOSE | GPT | HBA1C | INSULIN-M | LEP | LEP |
| 7.111 | CRP | GLUCOSE | GPT | HSPA1B | IGFBP1 | IGFBP2 | INSULIN-M |
| 7.112 | CRP | GLUCOSE | GPT | HSPA1B | IGFBP1 | INSULIN-M | LEP |
| 7.113 | CRP | GLUCOSE | GPT | HSPA1B | IGFBP1 | LEP | TRIG |
| 7.114 | CRP | GLUCOSE | GPT | HSPA1B | IGFBP2 | INSULIN-M | LEP |
| 7.115 | CRP | GLUCOSE | GPT | HSPA1B | IGFBP2 | INSULIN-M | TRIG |
| 7.116 | CRP | GLUCOSE | GPT | HSPA1B | INSULIN-M | LEP | TRIG |
| 7.117 | CRP | GLUCOSE | GPT | IGFBP1 | IGFBP2 | INSULIN-M | TRIG |
| 7.118 | CRP | GLUCOSE | GPT | IGFBP1 | INSULIN-M | LEP | TRIG |
| 7.119 | CRP | GLUCOSE | HBA1C | HSPA1B | IGFBP1 | IGFBP2 | LEP |
| 7.120 | CRP | GLUCOSE | HBA1C | HSPA1B | IGFBP1 | IGFBP2 | TRIG |

FIGURE 10E (continued)

| Panel No. | Marker 1 | Marker 2 | Marker 3 | Marker 4 | Marker 5 | Marker 6 | Marker 7 |
|---|---|---|---|---|---|---|---|
| 7.121 | CRP | GLUCOSE | HBA1C | HSPA1B | IGFBP1 | IGFBP2 | TRIG |
| 7.122 | CRP | GLUCOSE | HBA1C | HSPA1B | IGFBP1 | INSULIN-M | INSULIN-M |
| 7.123 | CRP | GLUCOSE | HBA1C | HSPA1B | IGFBP1 | INSULIN-M | TRIG |
| 7.124 | CRP | GLUCOSE | HBA1C | HSPA1B | IGFBP1 | LEP | TRIG |
| 7.125 | CRP | GLUCOSE | HBA1C | HSPA1B | IGFBP2 | INSULIN-M | LEP |
| 7.126 | CRP | GLUCOSE | HBA1C | HSPA1B | IGFBP2 | INSULIN-M | LEP |
| 7.127 | CRP | GLUCOSE | HBA1C | HSPA1B | IGFBP2 | LEP | TRIG |
| 7.128 | CRP | GLUCOSE | HBA1C | HSPA1B | INSULIN-M | LEP | TRIG |
| 7.129 | CRP | GLUCOSE | HBA1C | IGFBP1 | IGFBP2 | INSULIN-M | TRIG |
| 7.130 | CRP | GLUCOSE | HBA1C | IGFBP1 | IGFBP2 | LEP | LEP |
| 7.131 | CRP | GLUCOSE | HBA1C | IGFBP1 | INSULIN-M | LEP | TRIG |
| 7.132 | CRP | GLUCOSE | HBA1C | IGFBP2 | INSULIN-M | LEP | TRIG |
| 7.133 | CRP | GLUCOSE | HSPA1B | IGFBP1 | IGFBP2 | LEP | TRIG |
| 7.134 | CRP | GLUCOSE | HSPA1B | IGFBP1 | INSULIN-M | LEP | TRIG |
| 7.135 | CRP | GLUCOSE | HSPA1B | IGFBP2 | INSULIN-M | LEP | TRIG |
| 7.136 | CRP | GLUCOSE | IGFBP1 | IGFBP2 | INSULIN-M | LEP | TRIG |
| 7.137 | CRP | GPT | HBA1C | HSPA1B | IGFBP1 | IGFBP2 | TRIG |
| 7.138 | GLUCOSE | GPT | HBA1C | HSPA1B | IGFBP1 | INSULIN-M | TRIG |
| 7.139 | GLUCOSE | GPT | HBA1C | HSPA1B | IGFBP1 | INSULIN-M | TRIG |
| 7.140 | GLUCOSE | GPT | HBA1C | HSPA1B | IGFBP2 | INSULIN-M | LEP |
| 7.141 | GLUCOSE | GPT | HBA1C | HSPA1B | IGFBP2 | INSULIN-M | TRIG |
| 7.142 | GLUCOSE | GPT | HBA1C | HSPA1B | IGFBP2 | LEP | LEP |
| 7.143 | GLUCOSE | GPT | HBA1C | HSPA1B | INSULIN-M | LEP | INSULIN-M |
| 7.144 | GLUCOSE | GPT | HBA1C | IGFBP2 | INSULIN-M | LEP | TRIG |
| 7.145 | GLUCOSE | GPT | HSPA1B | IGFBP1 | INSULIN-M | LEP | TRIG |
| 7.146 | GLUCOSE | GPT | HSPA1B | IGFBP2 | INSULIN-M | LEP | TRIG |
| 7.147 | GLUCOSE | HBA1C | HSPA1B | IGFBP1 | IGFBP2 | INSULIN-M | LEP |

FIGURE 10F

| Panel No. | Marker 1 | Marker 2 | Marker 3 | Marker 4 | Marker 5 | Marker 6 | Marker 7 | Marker 8 |
|---|---|---|---|---|---|---|---|---|
| 8.1 | ADIPOQ | CRP | GLUCOSE | GPT | HBA1C | HSPA1B | IGFBP2 | INSULIN-M |
| 8.2 | ADIPOQ | CRP | GLUCOSE | GPT | HBA1C | HSPA1B | IGFBP2 | LEP |
| 8.3 | ADIPOQ | CRP | GLUCOSE | GPT | HBA1C | HSPA1B | INSULIN-M | LEP |
| 8.4 | ADIPOQ | CRP | GLUCOSE | GPT | HBA1C | HSPA1B | INSULIN-M | LEP |
| 8.5 | ADIPOQ | CRP | GLUCOSE | GPT | HBA1C | HSPA1B | INSULIN-M | LEP |
| 8.6 | ADIPOQ | CRP | GLUCOSE | GPT | HBA1C | HSPA1B | INSULIN-M | LEP |
| 8.7 | ADIPOQ | CRP | GLUCOSE | GPT | HBA1C | HSPA1B | LEP | TRIG |
| 8.8 | ADIPOQ | CRP | GLUCOSE | GPT | HBA1C | HSPA1B | LEP | TRIG |
| 8.9 | ADIPOQ | CRP | GLUCOSE | GPT | HBA1C | HSPA1B | LEP | TRIG |
| 8.10 | ADIPOQ | CRP | GLUCOSE | GPT | HBA1C | IGFBP1 | IGFBP1 | IGFBP2 |
| 8.11 | ADIPOQ | CRP | GLUCOSE | GPT | HBA1C | IGFBP1 | IGFBP2 | INSULIN-M |
| 8.12 | ADIPOQ | CRP | GLUCOSE | GPT | HBA1C | IGFBP1 | INSULIN-M | LEP |
| 8.13 | ADIPOQ | CRP | GLUCOSE | GPT | HBA1C | IGFBP1 | INSULIN-M | TRIG |
| 8.14 | ADIPOQ | CRP | GLUCOSE | GPT | HBA1C | IGFBP1 | LEP | TRIG |
| 8.15 | ADIPOQ | CRP | GLUCOSE | GPT | HBA1C | IGFBP1 | LEP | TRIG |
| 8.16 | ADIPOQ | CRP | GLUCOSE | GPT | HBA1C | IGFBP2 | IGFBP2 | TRIG |
| 8.17 | ADIPOQ | CRP | GLUCOSE | GPT | HBA1C | IGFBP2 | INSULIN-M | TRIG |
| 8.18 | ADIPOQ | CRP | GLUCOSE | GPT | HBA1C | IGFBP2 | INSULIN-M | TRIG |
| 8.19 | ADIPOQ | CRP | GLUCOSE | GPT | HBA1C | INSULIN-M | LEP | TRIG |
| 8.20 | ADIPOQ | CRP | GLUCOSE | GPT | HSPA1B | IGFBP1 | IGFBP2 | LEP |
| 8.21 | ADIPOQ | CRP | GLUCOSE | GPT | HSPA1B | IGFBP1 | INSULIN-M | LEP |
| 8.22 | ADIPOQ | CRP | GLUCOSE | GPT | HSPA1B | IGFBP1 | INSULIN-M | LEP |
| 8.23 | ADIPOQ | CRP | GLUCOSE | GPT | HSPA1B | IGFBP1 | INSULIN-M | LEP |
| 8.24 | ADIPOQ | CRP | GLUCOSE | GPT | HSPA1B | IGFBP1 | LEP | TRIG |
| 8.25 | ADIPOQ | CRP | GLUCOSE | GPT | HSPA1B | IGFBP2 | INSULIN-M | TRIG |
| 8.26 | ADIPOQ | CRP | GLUCOSE | GPT | HSPA1B | IGFBP2 | LEP | TRIG |
| 8.27 | ADIPOQ | CRP | GLUCOSE | GPT | HSPA1B | IGFBP2 | LEP | TRIG |
| 8.28 | ADIPOQ | CRP | GLUCOSE | GPT | HSPA1B | INSULIN-M | IGFBP2 | LEP |
| 8.29 | ADIPOQ | CRP | GLUCOSE | GPT | IGFBP1 | IGFBP2 | IGFBP2 | INSULIN-M |
| 8.30 | ADIPOQ | CRP | GLUCOSE | GPT | IGFBP1 | IGFBP2 | INSULIN-M | LEP |
| 8.31 | ADIPOQ | CRP | GLUCOSE | GPT | IGFBP1 | IGFBP2 | LEP | TRIG |
| 8.32 | ADIPOQ | CRP | GLUCOSE | GPT | IGFBP1 | INSULIN-M | IGFBP1 | LEP |
| 8.33 | ADIPOQ | CRP | GLUCOSE | GPT | IGFBP2 | INSULIN-M | IGFBP1 | TRIG |
| 8.34 | ADIPOQ | CRP | GLUCOSE | HBA1C | HSPA1B | IGFBP1 | IGFBP1 | INSULIN-M |
| 8.35 | ADIPOQ | CRP | GLUCOSE | HBA1C | HSPA1B | IGFBP1 | INSULIN-M | TRIG |
| 8.36 | ADIPOQ | CRP | GLUCOSE | HBA1C | HSPA1B | IGFBP1 | LEP | TRIG |
| 8.37 | ADIPOQ | CRP | GLUCOSE | HBA1C | HSPA1B | IGFBP1 | LEP | TRIG |
| 8.38 | ADIPOQ | CRP | GLUCOSE | HBA1C | HSPA1B | IGFBP1 | LEP | TRIG |
| 8.39 | ADIPOQ | CRP | GLUCOSE | HBA1C | HSPA1B | IGFBP1 | LEP | TRIG |
| 8.40 | ADIPOQ | CRP | GLUCOSE | HBA1C | HSPA1B | IGFBP2 | IGFBP2 | TRIG |

FIGURE 10F (continued)

| Panel No. | Marker 1 | Marker 2 | Marker 3 | Marker 4 | Marker 5 | Marker 6 | Marker 7 | Marker 8 |
|---|---|---|---|---|---|---|---|---|
| 8.41 | ADIPOQ | CRP | GLUCOSE | HBA1C | HSPA1B | IGFBP2 | INSULIN-M | TRIG |
| 8.42 | ADIPOQ | CRP | GLUCOSE | HBA1C | HSPA1B | IGFBP2 | INSULIN-M | TRIG |
| 8.43 | ADIPOQ | CRP | GLUCOSE | HBA1C | HSPA1B | INSULIN-M | LEP | TRIG |
| 8.44 | ADIPOQ | CRP | GLUCOSE | HBA1C | IGFBP1 | IGFBP2 | INSULIN-M | TRIG |
| 8.45 | ADIPOQ | CRP | GLUCOSE | HBA1C | IGFBP1 | IGFBP2 | LEP | TRIG |
| 8.46 | ADIPOQ | CRP | GLUCOSE | HBA1C | IGFBP1 | IGFBP2 | LEP | TRIG |
| 8.47 | ADIPOQ | CRP | GLUCOSE | HBA1C | IGFBP1 | INSULIN-M | LEP | TRIG |
| 8.48 | ADIPOQ | CRP | GLUCOSE | HBA1C | IGFBP2 | INSULIN-M | LEP | TRIG |
| 8.49 | ADIPOQ | CRP | GLUCOSE | HSPA1B | IGFBP1 | IGFBP2 | IGFBP2 | INSULIN-M |
| 8.50 | ADIPOQ | CRP | GLUCOSE | HSPA1B | IGFBP1 | IGFBP2 | INSULIN-M | LEP |
| 8.51 | ADIPOQ | CRP | GLUCOSE | HSPA1B | IGFBP1 | INSULIN-M | LEP | TRIG |
| 8.52 | ADIPOQ | CRP | GLUCOSE | HSPA1B | IGFBP2 | INSULIN-M | IGFBP2 | LEP |
| 8.53 | ADIPOQ | CRP | GLUCOSE | IGFBP1 | IGFBP2 | INSULIN-M | INSULIN-M | TRIG |
| 8.54 | ADIPOQ | CRP | GPT | HBA1C | HSPA1B | IGFBP2 | INSULIN-M | LEP |
| 8.55 | ADIPOQ | CRP | GPT | HBA1C | HSPA1B | IGFBP2 | INSULIN-M | TRIG |
| 8.56 | ADIPOQ | GLUCOSE | GPT | HBA1C | HSPA1B | IGFBP1 | INSULIN-M | LEP |
| 8.57 | ADIPOQ | GLUCOSE | GPT | HBA1C | HSPA1B | IGFBP1 | LEP | TRIG |
| 8.58 | ADIPOQ | GLUCOSE | GPT | HBA1C | HSPA1B | IGFBP1 | LEP | TRIG |
| 8.59 | ADIPOQ | GLUCOSE | GPT | HBA1C | HSPA1B | IGFBP2 | IGFBP2 | LEP |
| 8.60 | ADIPOQ | GLUCOSE | GPT | HBA1C | HSPA1B | IGFBP2 | LEP | TRIG |
| 8.61 | ADIPOQ | GLUCOSE | GPT | HBA1C | HSPA1B | IGFBP2 | LEP | TRIG |
| 8.62 | ADIPOQ | GLUCOSE | GPT | HBA1C | HSPA1B | INSULIN-M | IGFBP2 | INSULIN-M |
| 8.63 | ADIPOQ | GLUCOSE | GPT | HBA1C | IGFBP1 | IGFBP2 | LEP | TRIG |
| 8.64 | ADIPOQ | GLUCOSE | GPT | HBA1C | IGFBP2 | INSULIN-M | INSULIN-M | LEP |
| 8.65 | ADIPOQ | GLUCOSE | GPT | HSPA1B | IGFBP1 | IGFBP2 | INSULIN-M | TRIG |
| 8.66 | ADIPOQ | GLUCOSE | GPT | HSPA1B | IGFBP1 | INSULIN-M | LEP | TRIG |
| 8.67 | ADIPOQ | GLUCOSE | GPT | HSPA1B | IGFBP2 | INSULIN-M | LEP | TRIG |
| 8.68 | ADIPOQ | GLUCOSE | HBA1C | HSPA1B | IGFBP1 | IGFBP2 | INSULIN-M | LEP |
| 8.69 | ADIPOQ | GLUCOSE | HBA1C | HSPA1B | IGFBP1 | IGFBP2 | LEP | TRIG |
| 8.70 | ADIPOQ | GLUCOSE | HBA1C | HSPA1B | IGFBP1 | IGFBP2 | LEP | TRIG |
| 8.71 | ADIPOQ | GLUCOSE | HBA1C | HSPA1B | IGFBP2 | INSULIN-M | INSULIN-M | TRIG |
| 8.72 | CRP | GLUCOSE | GPT | HBA1C | HSPA1B | IGFBP1 | IGFBP2 | TRIG |
| 8.73 | CRP | GLUCOSE | GPT | HBA1C | HSPA1B | IGFBP1 | INSULIN-M | LEP |
| 8.74 | CRP | GLUCOSE | GPT | HBA1C | HSPA1B | IGFBP1 | INSULIN-M | TRIG |
| 8.75 | CRP | GLUCOSE | GPT | HBA1C | HSPA1B | IGFBP1 | INSULIN-M | TRIG |
| 8.76 | CRP | GLUCOSE | GPT | HBA1C | HSPA1B | IGFBP1 | LEP | TRIG |
| 8.77 | CRP | GLUCOSE | GPT | HBA1C | HSPA1B | IGFBP1 | LEP | TRIG |
| 8.78 | CRP | GLUCOSE | GPT | HBA1C | HSPA1B | IGFBP2 | IGFBP2 | LEP |
| 8.79 | CRP | GLUCOSE | GPT | HBA1C | HSPA1B | IGFBP2 | LEP | TRIG |
| 8.80 | CRP | GLUCOSE | GPT | HBA1C | HSPA1B | IGFBP2 | LEP | TRIG |

FIGURE 10F (continued)

| Panel No. | Marker 1 | Marker 2 | Marker 3 | Marker 4 | Marker 5 | Marker 6 | Marker 7 | Marker 8 |
|---|---|---|---|---|---|---|---|---|
| 8.81 | CRP | GLUCOSE | GPT | HBA1C | HSPA1B | INSULIN-M | LEP | TRIG |
| 8.82 | CRP | GLUCOSE | GPT | HBA1C | IGFBP1 | IGFBP2 | INSULIN-M | LEP |
| 8.83 | CRP | GLUCOSE | GPT | HBA1C | IGFBP1 | IGFBP2 | LEP | TRIG |
| 8.84 | CRP | GLUCOSE | GPT | HBA1C | IGFBP1 | IGFBP2 | LEP | TRIG |
| 8.85 | CRP | GLUCOSE | GPT | HBA1C | IGFBP1 | INSULIN-M | INSULIN-M | TRIG |
| 8.86 | CRP | GLUCOSE | GPT | HBA1C | IGFBP2 | INSULIN-M | IGFBP2 | INSULIN-M |
| 8.87 | CRP | GLUCOSE | GPT | HSPA1B | IGFBP1 | IGFBP2 | INSULIN-M | LEP |
| 8.88 | CRP | GLUCOSE | GPT | HSPA1B | IGFBP1 | IGFBP2 | INSULIN-M | LEP |
| 8.89 | CRP | GLUCOSE | GPT | HSPA1B | IGFBP1 | IGFBP2 | INSULIN-M | TRIG |
| 8.90 | CRP | GLUCOSE | GPT | HSPA1B | IGFBP1 | INSULIN-M | LEP | TRIG |
| 8.91 | CRP | GLUCOSE | GPT | HSPA1B | IGFBP2 | INSULIN-M | LEP | TRIG |
| 8.92 | CRP | GLUCOSE | GPT | IGFBP1 | IGFBP2 | INSULIN-M | LEP | TRIG |
| 8.93 | CRP | GLUCOSE | HBA1C | HSPA1B | IGFBP1 | IGFBP2 | LEP | TRIG |
| 8.94 | CRP | GLUCOSE | HBA1C | HSPA1B | IGFBP1 | INSULIN-M | LEP | TRIG |
| 8.95 | CRP | GLUCOSE | HBA1C | HSPA1B | IGFBP2 | INSULIN-M | LEP | TRIG |
| 8.96 | CRP | GLUCOSE | HBA1C | IGFBP1 | IGFBP2 | INSULIN-M | LEP | TRIG |
| 8.97 | CRP | GPT | HBA1C | HSPA1B | IGFBP1 | IGFBP2 | INSULIN-M | TRIG |
| 8.98 | GLUCOSE | GPT | HBA1C | HSPA1B | IGFBP1 | IGFBP2 | INSULIN-M | LEP |
| 8.99 | GLUCOSE | GPT | HBA1C | HSPA1B | IGFBP1 | IGFBP2 | LEP | TRIG |
| 8.100 | GLUCOSE | GPT | HBA1C | HSPA1B | IGFBP2 | INSULIN-M | INSULIN-M | TRIG |

FIGURE 10G

| Panel No. | Marker 1 | Marker 2 | Marker 3 | Marker 4 | Marker 5 | Marker 6 | Marker 7 | Marker 8 | Marker 9 |
|---|---|---|---|---|---|---|---|---|---|
| 9.1 | ADIPOQ | CRP | GLUCOSE | GPT | HBA1C | HSPA1B | IGFBP1 | IGFBP2 | INSULIN-M |
| 9.2 | ADIPOQ | CRP | GLUCOSE | GPT | HBA1C | HSPA1B | IGFBP1 | IGFBP2 | LEP |
| 9.3 | ADIPOQ | CRP | GLUCOSE | GPT | HBA1C | HSPA1B | IGFBP1 | LEP | TRIG |
| 9.4 | ADIPOQ | CRP | GLUCOSE | GPT | HBA1C | HSPA1B | IGFBP2 | INSULIN-M | LEP |
| 9.5 | ADIPOQ | CRP | GLUCOSE | GPT | HBA1C | HSPA1B | IGFBP2 | INSULIN-M | TRIG |
| 9.6 | ADIPOQ | CRP | GLUCOSE | GPT | HBA1C | HSPA1B | IGFBP2 | INSULIN-M | TRIG |
| 9.7 | ADIPOQ | CRP | GLUCOSE | GPT | HBA1C | HSPA1B | IGFBP2 | LEP | TRIG |
| 9.8 | ADIPOQ | CRP | GLUCOSE | GPT | HBA1C | HSPA1B | IGFBP2 | LEP | TRIG |
| 9.9 | ADIPOQ | CRP | GLUCOSE | GPT | HBA1C | HSPA1B | INSULIN-M | LEP | TRIG |
| 9.10 | ADIPOQ | CRP | GLUCOSE | GPT | HBA1C | HSPA1B | INSULIN-M | LEP | TRIG |
| 9.11 | ADIPOQ | CRP | GLUCOSE | GPT | HBA1C | IGFBP1 | IGFBP2 | INSULIN-M | LEP |
| 9.12 | ADIPOQ | CRP | GLUCOSE | GPT | HBA1C | IGFBP1 | IGFBP2 | LEP | TRIG |
| 9.13 | ADIPOQ | CRP | GLUCOSE | GPT | HBA1C | IGFBP1 | IGFBP2 | LEP | TRIG |
| 9.14 | ADIPOQ | CRP | GLUCOSE | GPT | HBA1C | IGFBP1 | INSULIN-M | LEP | TRIG |
| 9.15 | ADIPOQ | CRP | GLUCOSE | GPT | HBA1C | IGFBP2 | INSULIN-M | LEP | TRIG |
| 9.16 | ADIPOQ | CRP | GLUCOSE | GPT | HSPA1B | IGFBP1 | IGFBP1 | INSULIN-M | LEP |
| 9.17 | ADIPOQ | CRP | GLUCOSE | GPT | HSPA1B | IGFBP1 | IGFBP2 | INSULIN-M | LEP |
| 9.18 | ADIPOQ | CRP | GLUCOSE | GPT | HSPA1B | IGFBP1 | IGFBP2 | INSULIN-M | LEP |
| 9.19 | ADIPOQ | CRP | GLUCOSE | GPT | HSPA1B | IGFBP2 | IGFBP1 | LEP | TRIG |
| 9.20 | ADIPOQ | CRP | GLUCOSE | GPT | IGFBP1 | IGFBP2 | INSULIN-M | LEP | TRIG |
| 9.21 | ADIPOQ | CRP | GLUCOSE | HBA1C | HSPA1B | IGFBP1 | IGFBP1 | INSULIN-M | TRIG |
| 9.22 | ADIPOQ | CRP | GLUCOSE | HBA1C | HSPA1B | IGFBP1 | INSULIN-M | LEP | TRIG |
| 9.23 | ADIPOQ | CRP | GLUCOSE | HBA1C | HSPA1B | IGFBP1 | INSULIN-M | LEP | TRIG |
| 9.24 | ADIPOQ | CRP | GLUCOSE | HBA1C | HSPA1B | IGFBP1 | INSULIN-M | LEP | TRIG |
| 9.25 | ADIPOQ | CRP | GLUCOSE | HBA1C | HSPA1B | IGFBP2 | IGFBP1 | IGFBP2 | TRIG |
| 9.26 | ADIPOQ | CRP | GLUCOSE | HBA1C | IGFBP1 | IGFBP2 | IGFBP2 | INSULIN-M | TRIG |
| 9.27 | ADIPOQ | CRP | GLUCOSE | HSPA1B | IGFBP1 | IGFBP2 | INSULIN-M | LEP | TRIG |
| 9.28 | ADIPOQ | CRP | GPT | HBA1C | HSPA1B | IGFBP1 | IGFBP2 | INSULIN-M | LEP |
| 9.29 | ADIPOQ | CRP | GPT | HBA1C | HSPA1B | IGFBP1 | IGFBP2 | INSULIN-M | TRIG |
| 9.30 | ADIPOQ | GLUCOSE | GPT | HBA1C | HSPA1B | IGFBP1 | IGFBP2 | INSULIN-M | LEP |
| 9.31 | ADIPOQ | GLUCOSE | GPT | HBA1C | HSPA1B | IGFBP1 | IGFBP2 | LEP | TRIG |
| 9.32 | ADIPOQ | GLUCOSE | GPT | HBA1C | HSPA1B | IGFBP1 | INSULIN-M | LEP | TRIG |
| 9.33 | ADIPOQ | GLUCOSE | GPT | HBA1C | HSPA1B | IGFBP1 | INSULIN-M | LEP | TRIG |
| 9.34 | ADIPOQ | GLUCOSE | GPT | HBA1C | HSPA1B | IGFBP2 | INSULIN-M | LEP | TRIG |
| 9.35 | ADIPOQ | GLUCOSE | GPT | HBA1C | IGFBP1 | IGFBP2 | IGFBP2 | INSULIN-M | TRIG |
| 9.36 | ADIPOQ | GLUCOSE | GPT | HSPA1B | IGFBP1 | IGFBP2 | INSULIN-M | LEP | TRIG |
| 9.37 | ADIPOQ | GLUCOSE | HBA1C | HSPA1B | IGFBP1 | IGFBP2 | INSULIN-M | LEP | TRIG |
| 9.38 | CRP | GLUCOSE | GPT | HSPA1B | IGFBP1 | IGFBP2 | INSULIN-M | LEP | TRIG |
| 9.39 | CRP | GLUCOSE | GPT | HBA1C | HSPA1B | IGFBP1 | IGFBP2 | INSULIN-M | LEP |
| 9.40 | CRP | GLUCOSE | GPT | HBA1C | HSPA1B | IGFBP1 | IGFBP2 | INSULIN-M | TRIG |
| 9.41 | CRP | GLUCOSE | GPT | HBA1C | HSPA1B | IGFBP1 | IGFBP2 | LEP | TRIG |
| 9.42 | CRP | GLUCOSE | GPT | HBA1C | HSPA1B | IGFBP1 | INSULIN-M | LEP | TRIG |
| 9.43 | CRP | GLUCOSE | GPT | HBA1C | HSPA1B | IGFBP2 | INSULIN-M | LEP | TRIG |
| 9.44 | CRP | GLUCOSE | GPT | HBA1C | IGFBP1 | IGFBP2 | INSULIN-M | LEP | TRIG |

FIGURE 10H

| Panel No. | Marker 1 | Marker 2 | Marker 3 | Marker 4 | Marker 5 | Marker 6 | Marker 7 | Marker 8 | Marker 9 | Marker 10 |
|---|---|---|---|---|---|---|---|---|---|---|
| 10.1 | ADIPOQ | CRP | GLUCOSE | GPT | HBA1C | HSPA1B | IGFBP1 | IGFBP2 | INSULIN-M | LEP |
| 10.2 | ADIPOQ | CRP | GLUCOSE | GPT | HBA1C | HSPA1B | IGFBP1 | IGFBP2 | INSULIN-M | TRIG |
| 10.3 | ADIPOQ | CRP | GLUCOSE | GPT | HBA1C | HSPA1B | IGFBP1 | IGFBP2 | LEP | TRIG |
| 10.4 | ADIPOQ | CRP | GLUCOSE | GPT | HBA1C | HSPA1B | IGFBP1 | INSULIN-M | LEP | TRIG |
| 10.5 | ADIPOQ | CRP | GLUCOSE | GPT | HBA1C | HSPA1B | IGFBP2 | INSULIN-M | LEP | TRIG |
| 10.6 | ADIPOQ | CRP | GLUCOSE | GPT | HBA1C | IGFBP1 | IGFBP2 | INSULIN-M | LEP | TRIG |
| 10.7 | ADIPOQ | CRP | GLUCOSE | GPT | HSPA1B | IGFBP1 | IGFBP2 | INSULIN-M | LEP | TRIG |
| 10.8 | ADIPOQ | CRP | GLUCOSE | HBA1C | HSPA1B | IGFBP1 | IGFBP2 | INSULIN-M | LEP | TRIG |
| 10.9 | ADIPOQ | CRP | GPT | HBA1C | HSPA1B | IGFBP1 | IGFBP2 | INSULIN-M | LEP | TRIG |
| 10.10 | ADIPOQ | GLUCOSE | GPT | HBA1C | HSPA1B | IGFBP1 | IGFBP2 | INSULIN-M | LEP | TRIG |
| 10.11 | CRP | GLUCOSE | GPT | HBA1C | HSPA1B | IGFBP1 | IGFBP2 | INSULIN-M | LEP | TRIG |

FIGURE 10I

| Panel No. | Marker 1 | Marker 2 | Marker 3 | Marker 4 | Marker 5 | Marker 6 | Marker 7 | Marker 8 |
|---|---|---|---|---|---|---|---|---|
| 11.1 | ADIPOQ | CRP | GLUCOSE | GPT | HBA1C | HSPA1B | IGFBP1 | IGFBP2 |

| Panel No. | Marker 9 | Marker 10 | Marker 11 |
|---|---|---|---|
| 11.1 continued | INSULIN-M | LEP | TRIG |

FIGURE 11A

| Panel No. | Marker 1 | Marker 2 | Marker 3 |
|---|---|---|---|
| 7.3.1 | ADIPOQ | CRP | GLUCOSE |
| 7.3.2 | CCL2 | CRP | GLUCOSE |
| 7.3.3 | CD40 | CRP | GLUCOSE |
| 7.3.4 | CRP | EGF | GLUCOSE |
| 7.3.5 | CRP | ENG | GLUCOSE |
| 7.3.6 | CRP | FGA | GLUCOSE |
| 7.3.7 | CRP | FTH1 | GLUCOSE |
| 7.3.8 | CRP | GLUCOSE | GPT |
| 7.3.9 | CRP | GLUCOSE | HBA1C |
| 7.3.10 | CRP | GLUCOSE | HP |
| 7.3.11 | CRP | GLUCOSE | HSPA1B |
| 7.3.12 | CRP | GLUCOSE | IGF1R |
| 7.3.13 | CRP | GLUCOSE | IGFBP1 |
| 7.3.14 | CRP | GLUCOSE | IGFBP2 |
| 7.3.15 | CRP | GLUCOSE | IL2RA |
| 7.3.16 | CRP | GLUCOSE | IL2RB |
| 7.3.17 | CRP | GLUCOSE | IL6R |
| 7.3.18 | CRP | GLUCOSE | INSULIN-M |
| 7.3.19 | CRP | GLUCOSE | LEP |
| 7.3.20 | CRP | GLUCOSE | SCp |
| 7.3.21 | CRP | GLUCOSE | SHBG |
| 7.3.22 | CRP | GLUCOSE | TIMP2 |
| 7.3.23 | CRP | GLUCOSE | TRIG |
| 7.3.24 | CRP | GLUCOSE | VWF |
| 7.3.25 | GLUCOSE | HBA1C | INSULIN-M |

FIGURE 11B

| Panel No. | Marker 1 | Marker 2 | Marker 3 | Marker 4 |
|---|---|---|---|---|
| 7.4.1 | ADIPOQ | CCL2 | CRP | GLUCOSE |
| 7.4.2 | ADIPOQ | CD40 | CRP | GLUCOSE |
| 7.4.3 | ADIPOQ | CRP | EGF | GLUCOSE |
| 7.4.4 | ADIPOQ | CRP | ENG | GLUCOSE |
| 7.4.5 | ADIPOQ | CRP | FGA | GLUCOSE |
| 7.4.6 | ADIPOQ | CRP | FTH1 | GLUCOSE |
| 7.4.7 | ADIPOQ | CRP | GLUCOSE | GPT |
| 7.4.8 | ADIPOQ | CRP | GLUCOSE | HBA1C |
| 7.4.9 | ADIPOQ | CRP | GLUCOSE | HP |
| 7.4.10 | ADIPOQ | CRP | GLUCOSE | HSPA1B |
| 7.4.11 | ADIPOQ | CRP | GLUCOSE | IGF1R |
| 7.4.12 | ADIPOQ | CRP | GLUCOSE | IGFBP1 |
| 7.4.13 | ADIPOQ | CRP | GLUCOSE | IGFBP2 |
| 7.4.14 | ADIPOQ | CRP | GLUCOSE | IL2RA |
| 7.4.15 | ADIPOQ | CRP | GLUCOSE | IL2RB |
| 7.4.16 | ADIPOQ | CRP | GLUCOSE | IL6R |
| 7.4.17 | ADIPOQ | CRP | GLUCOSE | INSULIN-M |
| 7.4.18 | ADIPOQ | CRP | GLUCOSE | LEP |
| 7.4.19 | ADIPOQ | CRP | GLUCOSE | SCp |
| 7.4.20 | ADIPOQ | CRP | GLUCOSE | SHBG |
| 7.4.21 | ADIPOQ | CRP | GLUCOSE | TIMP2 |
| 7.4.22 | ADIPOQ | CRP | GLUCOSE | TRIG |
| 7.4.23 | ADIPOQ | CRP | GLUCOSE | VWF |
| 7.4.24 | ADIPOQ | GLUCOSE | GPT | LEP |
| 7.4.25 | ADIPOQ | GLUCOSE | HBA1C | INSULIN-M |
| 7.4.26 | ADIPOQ | GLUCOSE | HBA1C | LEP |
| 7.4.27 | ADIPOQ | GLUCOSE | HSPA1B | LEP |
| 7.4.28 | ADIPOQ | GLUCOSE | IGFBP2 | LEP |
| 7.4.29 | ADIPOQ | GLUCOSE | INSULIN-M | LEP |
| 7.4.30 | ADIPOQ | GLUCOSE | LEP | TRIG |
| 7.4.31 | ADIPOQ | GLUCOSE | LEP | VWF |
| 7.4.32 | CCL2 | CD40 | CRP | GLUCOSE |
| 7.4.33 | CCL2 | CRP | EGF | GLUCOSE |
| 7.4.34 | CCL2 | CRP | ENG | GLUCOSE |
| 7.4.35 | CCL2 | CRP | FGA | GLUCOSE |
| 7.4.36 | CCL2 | CRP | FTH1 | GLUCOSE |
| 7.4.37 | CCL2 | CRP | GLUCOSE | GPT |
| 7.4.38 | CCL2 | CRP | GLUCOSE | HBA1C |
| 7.4.39 | CCL2 | CRP | GLUCOSE | HP |
| 7.4.40 | CCL2 | CRP | GLUCOSE | HSPA1B |

FIGURE 11B (continued)

| Panel No. | Marker 1 | Marker 2 | Marker 3 | Marker 4 |
|---|---|---|---|---|
| 7.4.41 | CCL2 | CRP | GLUCOSE | IGF1R |
| 7.4.42 | CCL2 | CRP | GLUCOSE | IGFBP1 |
| 7.4.43 | CCL2 | CRP | GLUCOSE | IGFBP2 |
| 7.4.44 | CCL2 | CRP | GLUCOSE | IL2RA |
| 7.4.45 | CCL2 | CRP | GLUCOSE | IL2RB |
| 7.4.46 | CCL2 | CRP | GLUCOSE | IL6R |
| 7.4.47 | CCL2 | CRP | GLUCOSE | INSULIN-M |
| 7.4.48 | CCL2 | CRP | GLUCOSE | LEP |
| 7.4.49 | CCL2 | CRP | GLUCOSE | SCp |
| 7.4.50 | CCL2 | CRP | GLUCOSE | SHBG |
| 7.4.51 | CCL2 | CRP | GLUCOSE | TIMP2 |
| 7.4.52 | CCL2 | CRP | GLUCOSE | TRIG |
| 7.4.53 | CCL2 | CRP | GLUCOSE | VWF |
| 7.4.54 | CCL2 | CRP | HBA1C | INSULIN-M |
| 7.4.55 | CCL2 | GLUCOSE | HBA1C | INSULIN-M |
| 7.4.56 | CCL2 | GLUCOSE | HBA1C | LEP |
| 7.4.57 | CCL2 | GLUCOSE | HSPA1B | INSULIN-M |
| 7.4.58 | CCL2 | GLUCOSE | LEP | TRIG |
| 7.4.59 | CD40 | CRP | EGF | GLUCOSE |
| 7.4.60 | CD40 | CRP | ENG | GLUCOSE |
| 7.4.61 | CD40 | CRP | FGA | GLUCOSE |
| 7.4.62 | CD40 | CRP | FTH1 | GLUCOSE |
| 7.4.63 | CD40 | CRP | GLUCOSE | GPT |
| 7.4.64 | CD40 | CRP | GLUCOSE | HBA1C |
| 7.4.65 | CD40 | CRP | GLUCOSE | HP |
| 7.4.66 | CD40 | CRP | GLUCOSE | HSPA1B |
| 7.4.67 | CD40 | CRP | GLUCOSE | IGF1R |
| 7.4.68 | CD40 | CRP | GLUCOSE | IGFBP1 |
| 7.4.69 | CD40 | CRP | GLUCOSE | IGFBP2 |
| 7.4.70 | CD40 | CRP | GLUCOSE | IL2RA |
| 7.4.71 | CD40 | CRP | GLUCOSE | IL2RB |
| 7.4.72 | CD40 | CRP | GLUCOSE | IL6R |
| 7.4.73 | CD40 | CRP | GLUCOSE | INSULIN-M |
| 7.4.74 | CD40 | CRP | GLUCOSE | LEP |
| 7.4.75 | CD40 | CRP | GLUCOSE | SCp |
| 7.4.76 | CD40 | CRP | GLUCOSE | SHBG |
| 7.4.77 | CD40 | CRP | GLUCOSE | TIMP2 |
| 7.4.78 | CD40 | CRP | GLUCOSE | TRIG |
| 7.4.79 | CD40 | CRP | GLUCOSE | VWF |
| 7.4.80 | CD40 | GLUCOSE | HBA1C | INSULIN-M |

FIGURE 11B (continued)

| Panel No. | Marker 1 | Marker 2 | Marker 3 | Marker 4 |
|---|---|---|---|---|
| 7.4.81 | CRP | EGF | ENG | GLUCOSE |
| 7.4.82 | CRP | EGF | FGA | GLUCOSE |
| 7.4.83 | CRP | EGF | FTH1 | GLUCOSE |
| 7.4.84 | CRP | EGF | GLUCOSE | GPT |
| 7.4.85 | CRP | EGF | GLUCOSE | HBA1C |
| 7.4.86 | CRP | EGF | GLUCOSE | HP |
| 7.4.87 | CRP | EGF | GLUCOSE | HSPA1B |
| 7.4.88 | CRP | EGF | GLUCOSE | IGF1R |
| 7.4.89 | CRP | EGF | GLUCOSE | IGFBP1 |
| 7.4.90 | CRP | EGF | GLUCOSE | IGFBP2 |
| 7.4.91 | CRP | EGF | GLUCOSE | IL2RA |
| 7.4.92 | CRP | EGF | GLUCOSE | IL2RB |
| 7.4.93 | CRP | EGF | GLUCOSE | IL6R |
| 7.4.94 | CRP | EGF | GLUCOSE | INSULIN-M |
| 7.4.95 | CRP | EGF | GLUCOSE | LEP |
| 7.4.96 | CRP | EGF | GLUCOSE | SCp |
| 7.4.97 | CRP | EGF | GLUCOSE | SHBG |
| 7.4.98 | CRP | EGF | GLUCOSE | TIMP2 |
| 7.4.99 | CRP | EGF | GLUCOSE | TRIG |
| 7.4.100 | CRP | EGF | GLUCOSE | VWF |
| 7.4.101 | CRP | EGF | HBA1C | INSULIN-M |
| 7.4.102 | CRP | EGF | HBA1C | TRIG |
| 7.4.103 | CRP | ENG | FGA | GLUCOSE |
| 7.4.104 | CRP | ENG | FTH1 | GLUCOSE |
| 7.4.105 | CRP | ENG | GLUCOSE | GPT |
| 7.4.106 | CRP | ENG | GLUCOSE | HBA1C |
| 7.4.107 | CRP | ENG | GLUCOSE | HP |
| 7.4.108 | CRP | ENG | GLUCOSE | HSPA1B |
| 7.4.109 | CRP | ENG | GLUCOSE | IGF1R |
| 7.4.110 | CRP | ENG | GLUCOSE | IGFBP1 |
| 7.4.111 | CRP | ENG | GLUCOSE | IGFBP2 |
| 7.4.112 | CRP | ENG | GLUCOSE | IL2RA |
| 7.4.113 | CRP | ENG | GLUCOSE | IL2RB |
| 7.4.114 | CRP | ENG | GLUCOSE | IL6R |
| 7.4.115 | CRP | ENG | GLUCOSE | INSULIN-M |
| 7.4.116 | CRP | ENG | GLUCOSE | LEP |
| 7.4.117 | CRP | ENG | GLUCOSE | SCp |
| 7.4.118 | CRP | ENG | GLUCOSE | SHBG |
| 7.4.119 | CRP | ENG | GLUCOSE | TIMP2 |
| 7.4.120 | CRP | ENG | GLUCOSE | TRIG |

FIGURE 11B (continued)

| Panel No. | Marker 1 | Marker 2 | Marker 3 | Marker 4 |
|---|---|---|---|---|
| 7.4.121 | CRP | ENG | GLUCOSE | VWF |
| 7.4.122 | CRP | ENG | HBA1C | INSULIN-M |
| 7.4.123 | CRP | ENG | HBA1C | TRIG |
| 7.4.124 | CRP | FGA | FTH1 | GLUCOSE |
| 7.4.125 | CRP | FGA | GLUCOSE | GPT |
| 7.4.126 | CRP | FGA | GLUCOSE | HBA1C |
| 7.4.127 | CRP | FGA | GLUCOSE | HP |
| 7.4.128 | CRP | FGA | GLUCOSE | HSPA1B |
| 7.4.129 | CRP | FGA | GLUCOSE | IGF1R |
| 7.4.130 | CRP | FGA | GLUCOSE | IGFBP1 |
| 7.4.131 | CRP | FGA | GLUCOSE | IGFBP2 |
| 7.4.132 | CRP | FGA | GLUCOSE | IL2RA |
| 7.4.133 | CRP | FGA | GLUCOSE | IL2RB |
| 7.4.134 | CRP | FGA | GLUCOSE | IL6R |
| 7.4.135 | CRP | FGA | GLUCOSE | INSULIN-M |
| 7.4.136 | CRP | FGA | GLUCOSE | LEP |
| 7.4.137 | CRP | FGA | GLUCOSE | SCp |
| 7.4.138 | CRP | FGA | GLUCOSE | SHBG |
| 7.4.139 | CRP | FGA | GLUCOSE | TIMP2 |
| 7.4.140 | CRP | FGA | GLUCOSE | TRIG |
| 7.4.141 | CRP | FGA | GLUCOSE | VWF |
| 7.4.142 | CRP | FTH1 | GLUCOSE | GPT |
| 7.4.143 | CRP | FTH1 | GLUCOSE | HBA1C |
| 7.4.144 | CRP | FTH1 | GLUCOSE | HP |
| 7.4.145 | CRP | FTH1 | GLUCOSE | HSPA1B |
| 7.4.146 | CRP | FTH1 | GLUCOSE | IGF1R |
| 7.4.147 | CRP | FTH1 | GLUCOSE | IGFBP1 |
| 7.4.148 | CRP | FTH1 | GLUCOSE | IGFBP2 |
| 7.4.149 | CRP | FTH1 | GLUCOSE | IL2RA |
| 7.4.150 | CRP | FTH1 | GLUCOSE | IL2RB |
| 7.4.151 | CRP | FTH1 | GLUCOSE | IL6R |
| 7.4.152 | CRP | FTH1 | GLUCOSE | INSULIN-M |
| 7.4.153 | CRP | FTH1 | GLUCOSE | LEP |
| 7.4.154 | CRP | FTH1 | GLUCOSE | SCp |
| 7.4.155 | CRP | FTH1 | GLUCOSE | SHBG |
| 7.4.156 | CRP | FTH1 | GLUCOSE | TIMP2 |
| 7.4.157 | CRP | FTH1 | GLUCOSE | TRIG |
| 7.4.158 | CRP | FTH1 | GLUCOSE | VWF |
| 7.4.159 | CRP | FTH1 | HBA1C | INSULIN-M |
| 7.4.160 | CRP | GLUCOSE | GPT | HBA1C |

FIGURE 11B (continued)

| Panel No. | Marker 1 | Marker 2 | Marker 3 | Marker 4 |
|---|---|---|---|---|
| 7.4.161 | CRP | GLUCOSE | GPT | HP |
| 7.4.162 | CRP | GLUCOSE | GPT | HSPA1B |
| 7.4.163 | CRP | GLUCOSE | GPT | IGF1R |
| 7.4.164 | CRP | GLUCOSE | GPT | IGFBP1 |
| 7.4.165 | CRP | GLUCOSE | GPT | IGFBP2 |
| 7.4.166 | CRP | GLUCOSE | GPT | IL2RA |
| 7.4.167 | CRP | GLUCOSE | GPT | IL2RB |
| 7.4.168 | CRP | GLUCOSE | GPT | IL6R |
| 7.4.169 | CRP | GLUCOSE | GPT | INSULIN-M |
| 7.4.170 | CRP | GLUCOSE | GPT | LEP |
| 7.4.171 | CRP | GLUCOSE | GPT | SCp |
| 7.4.172 | CRP | GLUCOSE | GPT | SHBG |
| 7.4.173 | CRP | GLUCOSE | GPT | TIMP2 |
| 7.4.174 | CRP | GLUCOSE | GPT | TRIG |
| 7.4.175 | CRP | GLUCOSE | GPT | VWF |
| 7.4.176 | CRP | GLUCOSE | HBA1C | HP |
| 7.4.177 | CRP | GLUCOSE | HBA1C | HSPA1B |
| 7.4.178 | CRP | GLUCOSE | HBA1C | IGF1R |
| 7.4.179 | CRP | GLUCOSE | HBA1C | IGFBP1 |
| 7.4.180 | CRP | GLUCOSE | HBA1C | IGFBP2 |
| 7.4.181 | CRP | GLUCOSE | HBA1C | IL2RA |
| 7.4.182 | CRP | GLUCOSE | HBA1C | IL2RB |
| 7.4.183 | CRP | GLUCOSE | HBA1C | IL6R |
| 7.4.184 | CRP | GLUCOSE | HBA1C | INSULIN-M |
| 7.4.185 | CRP | GLUCOSE | HBA1C | LEP |
| 7.4.186 | CRP | GLUCOSE | HBA1C | SCp |
| 7.4.187 | CRP | GLUCOSE | HBA1C | SHBG |
| 7.4.188 | CRP | GLUCOSE | HBA1C | TIMP2 |
| 7.4.189 | CRP | GLUCOSE | HBA1C | TRIG |
| 7.4.190 | CRP | GLUCOSE | HBA1C | VWF |
| 7.4.191 | CRP | GLUCOSE | HP | HSPA1B |
| 7.4.192 | CRP | GLUCOSE | HP | IGF1R |
| 7.4.193 | CRP | GLUCOSE | HP | IGFBP1 |
| 7.4.194 | CRP | GLUCOSE | HP | IGFBP2 |
| 7.4.195 | CRP | GLUCOSE | HP | IL2RA |
| 7.4.196 | CRP | GLUCOSE | HP | IL2RB |
| 7.4.197 | CRP | GLUCOSE | HP | IL6R |
| 7.4.198 | CRP | GLUCOSE | HP | INSULIN-M |
| 7.4.199 | CRP | GLUCOSE | HP | LEP |
| 7.4.200 | CRP | GLUCOSE | HP | SCp |

FIGURE 11B (continued)

| Panel No. | Marker 1 | Marker 2 | Marker 3 | Marker 4 |
|---|---|---|---|---|
| 7.4.201 | CRP | GLUCOSE | HP | SHBG |
| 7.4.202 | CRP | GLUCOSE | HP | TIMP2 |
| 7.4.203 | CRP | GLUCOSE | HP | TRIG |
| 7.4.204 | CRP | GLUCOSE | HP | VWF |
| 7.4.205 | CRP | GLUCOSE | HSPA1B | IGF1R |
| 7.4.206 | CRP | GLUCOSE | HSPA1B | IGFBP1 |
| 7.4.207 | CRP | GLUCOSE | HSPA1B | IGFBP2 |
| 7.4.208 | CRP | GLUCOSE | HSPA1B | IL2RA |
| 7.4.209 | CRP | GLUCOSE | HSPA1B | IL2RB |
| 7.4.210 | CRP | GLUCOSE | HSPA1B | IL6R |
| 7.4.211 | CRP | GLUCOSE | HSPA1B | INSULIN-M |
| 7.4.212 | CRP | GLUCOSE | HSPA1B | LEP |
| 7.4.213 | CRP | GLUCOSE | HSPA1B | SCp |
| 7.4.214 | CRP | GLUCOSE | HSPA1B | SHBG |
| 7.4.215 | CRP | GLUCOSE | HSPA1B | TIMP2 |
| 7.4.216 | CRP | GLUCOSE | HSPA1B | TRIG |
| 7.4.217 | CRP | GLUCOSE | HSPA1B | VWF |
| 7.4.218 | CRP | GLUCOSE | IGF1R | IGFBP1 |
| 7.4.219 | CRP | GLUCOSE | IGF1R | IGFBP2 |
| 7.4.220 | CRP | GLUCOSE | IGF1R | IL2RA |
| 7.4.221 | CRP | GLUCOSE | IGF1R | IL2RB |
| 7.4.222 | CRP | GLUCOSE | IGF1R | IL6R |
| 7.4.223 | CRP | GLUCOSE | IGF1R | INSULIN-M |
| 7.4.224 | CRP | GLUCOSE | IGF1R | LEP |
| 7.4.225 | CRP | GLUCOSE | IGF1R | SCp |
| 7.4.226 | CRP | GLUCOSE | IGF1R | SHBG |
| 7.4.227 | CRP | GLUCOSE | IGF1R | TIMP2 |
| 7.4.228 | CRP | GLUCOSE | IGF1R | TRIG |
| 7.4.229 | CRP | GLUCOSE | IGF1R | VWF |
| 7.4.230 | CRP | GLUCOSE | IGFBP1 | IGFBP2 |
| 7.4.231 | CRP | GLUCOSE | IGFBP1 | IL2RA |
| 7.4.232 | CRP | GLUCOSE | IGFBP1 | IL2RB |
| 7.4.233 | CRP | GLUCOSE | IGFBP1 | IL6R |
| 7.4.234 | CRP | GLUCOSE | IGFBP1 | INSULIN-M |
| 7.4.235 | CRP | GLUCOSE | IGFBP1 | LEP |
| 7.4.236 | CRP | GLUCOSE | IGFBP1 | SCp |
| 7.4.237 | CRP | GLUCOSE | IGFBP1 | SHBG |
| 7.4.238 | CRP | GLUCOSE | IGFBP1 | TIMP2 |
| 7.4.239 | CRP | GLUCOSE | IGFBP1 | TRIG |
| 7.4.240 | CRP | GLUCOSE | IGFBP1 | VWF |

FIGURE 11B (continued)

| Panel No. | Marker 1 | Marker 2 | Marker 3 | Marker 4 |
|---|---|---|---|---|
| 7.4.241 | CRP | GLUCOSE | IGFBP2 | IL2RA |
| 7.4.242 | CRP | GLUCOSE | IGFBP2 | IL2RB |
| 7.4.243 | CRP | GLUCOSE | IGFBP2 | IL6R |
| 7.4.244 | CRP | GLUCOSE | IGFBP2 | INSULIN-M |
| 7.4.245 | CRP | GLUCOSE | IGFBP2 | LEP |
| 7.4.246 | CRP | GLUCOSE | IGFBP2 | SCp |
| 7.4.247 | CRP | GLUCOSE | IGFBP2 | SHBG |
| 7.4.248 | CRP | GLUCOSE | IGFBP2 | TIMP2 |
| 7.4.249 | CRP | GLUCOSE | IGFBP2 | TRIG |
| 7.4.250 | CRP | GLUCOSE | IGFBP2 | VWF |
| 7.4.251 | CRP | GLUCOSE | IL2RA | IL2RB |
| 7.4.252 | CRP | GLUCOSE | IL2RA | IL6R |
| 7.4.253 | CRP | GLUCOSE | IL2RA | INSULIN-M |
| 7.4.254 | CRP | GLUCOSE | IL2RA | LEP |
| 7.4.255 | CRP | GLUCOSE | IL2RA | SCp |
| 7.4.256 | CRP | GLUCOSE | IL2RA | SHBG |
| 7.4.257 | CRP | GLUCOSE | IL2RA | TIMP2 |
| 7.4.258 | CRP | GLUCOSE | IL2RA | TRIG |
| 7.4.259 | CRP | GLUCOSE | IL2RA | VWF |
| 7.4.260 | CRP | GLUCOSE | IL2RB | IL6R |
| 7.4.261 | CRP | GLUCOSE | IL2RB | INSULIN-M |
| 7.4.262 | CRP | GLUCOSE | IL2RB | LEP |
| 7.4.263 | CRP | GLUCOSE | IL2RB | SCp |
| 7.4.264 | CRP | GLUCOSE | IL2RB | SHBG |
| 7.4.265 | CRP | GLUCOSE | IL2RB | TIMP2 |
| 7.4.266 | CRP | GLUCOSE | IL2RB | TRIG |
| 7.4.267 | CRP | GLUCOSE | IL2RB | VWF |
| 7.4.268 | CRP | GLUCOSE | IL6R | INSULIN-M |
| 7.4.269 | CRP | GLUCOSE | IL6R | LEP |
| 7.4.270 | CRP | GLUCOSE | IL6R | SCp |
| 7.4.271 | CRP | GLUCOSE | IL6R | SHBG |
| 7.4.272 | CRP | GLUCOSE | IL6R | TIMP2 |
| 7.4.273 | CRP | GLUCOSE | IL6R | TRIG |
| 7.4.274 | CRP | GLUCOSE | IL6R | VWF |
| 7.4.275 | CRP | GLUCOSE | INSULIN-M | LEP |
| 7.4.276 | CRP | GLUCOSE | INSULIN-M | SCp |
| 7.4.277 | CRP | GLUCOSE | INSULIN-M | SHBG |
| 7.4.278 | CRP | GLUCOSE | INSULIN-M | TIMP2 |
| 7.4.279 | CRP | GLUCOSE | INSULIN-M | TRIG |
| 7.4.280 | CRP | GLUCOSE | INSULIN-M | VWF |

FIGURE 11B (continued)

| Panel No. | Marker 1 | Marker 2 | Marker 3 | Marker 4 |
|---|---|---|---|---|
| 7.4.281 | CRP | GLUCOSE | LEP | SCp |
| 7.4.282 | CRP | GLUCOSE | LEP | SHBG |
| 7.4.283 | CRP | GLUCOSE | LEP | TIMP2 |
| 7.4.284 | CRP | GLUCOSE | LEP | TRIG |
| 7.4.285 | CRP | GLUCOSE | LEP | VWF |
| 7.4.286 | CRP | GLUCOSE | SCp | SHBG |
| 7.4.287 | CRP | GLUCOSE | SCp | TIMP2 |
| 7.4.288 | CRP | GLUCOSE | SCp | TRIG |
| 7.4.289 | CRP | GLUCOSE | SCp | VWF |
| 7.4.290 | CRP | GLUCOSE | SHBG | TIMP2 |
| 7.4.291 | CRP | GLUCOSE | SHBG | TRIG |
| 7.4.292 | CRP | GLUCOSE | SHBG | VWF |
| 7.4.293 | CRP | GLUCOSE | TIMP2 | TRIG |
| 7.4.294 | CRP | GLUCOSE | TIMP2 | VWF |
| 7.4.295 | CRP | GLUCOSE | TRIG | VWF |
| 7.4.296 | CRP | GPT | HBA1C | INSULIN-M |
| 7.4.297 | CRP | HBA1C | HP | INSULIN-M |
| 7.4.298 | CRP | HBA1C | HP | TRIG |
| 7.4.299 | CRP | HBA1C | HSPA1B | INSULIN-M |
| 7.4.300 | CRP | HBA1C | HSPA1B | TRIG |
| 7.4.301 | CRP | HBA1C | INSULIN-M | TRIG |
| 7.4.302 | CRP | HBA1C | TIMP2 | TRIG |
| 7.4.303 | EGF | GLUCOSE | HBA1C | INSULIN-M |
| 7.4.304 | EGF | GLUCOSE | HBA1C | LEP |
| 7.4.305 | ENG | GLUCOSE | HBA1C | INSULIN-M |
| 7.4.306 | ENG | GLUCOSE | HBA1C | LEP |
| 7.4.307 | ENG | GLUCOSE | HSPA1B | INSULIN-M |
| 7.4.308 | ENG | GLUCOSE | HSPA1B | LEP |
| 7.4.309 | ENG | GLUCOSE | LEP | TRIG |
| 7.4.310 | FGA | GLUCOSE | HBA1C | INSULIN-M |
| 7.4.311 | FTH1 | GLUCOSE | HBA1C | INSULIN-M |
| 7.4.312 | FTH1 | GLUCOSE | HBA1C | LEP |
| 7.4.313 | GLUCOSE | GPT | HBA1C | INSULIN-M |
| 7.4.314 | GLUCOSE | GPT | HBA1C | LEP |
| 7.4.315 | GLUCOSE | GPT | HSPA1B | LEP |
| 7.4.316 | GLUCOSE | GPT | INSULIN-M | LEP |
| 7.4.317 | GLUCOSE | GPT | LEP | TRIG |
| 7.4.318 | GLUCOSE | HBA1C | HP | INSULIN-M |
| 7.4.319 | GLUCOSE | HBA1C | HSPA1B | INSULIN-M |
| 7.4.320 | GLUCOSE | HBA1C | HSPA1B | LEP |

FIGURE 11B (continued)

| Panel No. | Marker 1 | Marker 2 | Marker 3 | Marker 4 |
|---|---|---|---|---|
| 7.4.321 | GLUCOSE | HBA1C | IGF1R | INSULIN-M |
| 7.4.322 | GLUCOSE | HBA1C | IGFBP1 | INSULIN-M |
| 7.4.323 | GLUCOSE | HBA1C | IGFBP2 | INSULIN-M |
| 7.4.324 | GLUCOSE | HBA1C | IL2RA | INSULIN-M |
| 7.4.325 | GLUCOSE | HBA1C | IL2RB | INSULIN-M |
| 7.4.326 | GLUCOSE | HBA1C | IL6R | INSULIN-M |
| 7.4.327 | GLUCOSE | HBA1C | INSULIN-M | LEP |
| 7.4.328 | GLUCOSE | HBA1C | INSULIN-M | SCp |
| 7.4.329 | GLUCOSE | HBA1C | INSULIN-M | SHBG |
| 7.4.330 | GLUCOSE | HBA1C | INSULIN-M | TIMP2 |
| 7.4.331 | GLUCOSE | HBA1C | INSULIN-M | TRIG |
| 7.4.332 | GLUCOSE | HBA1C | INSULIN-M | VWF |
| 7.4.333 | GLUCOSE | HBA1C | LEP | TRIG |
| 7.4.334 | GLUCOSE | HSPA1B | IGFBP2 | INSULIN-M |
| 7.4.335 | GLUCOSE | HSPA1B | IL2RA | INSULIN-M |
| 7.4.336 | GLUCOSE | HSPA1B | IL2RA | LEP |
| 7.4.337 | GLUCOSE | HSPA1B | INSULIN-M | LEP |
| 7.4.338 | GLUCOSE | HSPA1B | LEP | TRIG |

Figure 11C

| Panel No. | Marker 1 | Marker 2 | Marker 3 | Marker 4 | Marker 5 |
|---|---|---|---|---|---|
| 7.5.1 | ADIPOQ | CCL2 | CRP | EGF | GLUCOSE |
| 7.5.2 | ADIPOQ | CCL2 | CRP | ENG | GLUCOSE |
| 7.5.3 | ADIPOQ | CCL2 | CRP | GLUCOSE | GPT |
| 7.5.4 | ADIPOQ | CCL2 | CRP | GLUCOSE | HBA1C |
| 7.5.5 | ADIPOQ | CCL2 | CRP | GLUCOSE | HP |
| 7.5.6 | ADIPOQ | CCL2 | CRP | GLUCOSE | HSPA1B |
| 7.5.7 | ADIPOQ | CCL2 | CRP | GLUCOSE | IGFBP2 |
| 7.5.8 | ADIPOQ | CCL2 | CRP | GLUCOSE | IL2RA |
| 7.5.9 | ADIPOQ | CCL2 | CRP | GLUCOSE | INSULIN-M |
| 7.5.10 | ADIPOQ | CCL2 | CRP | GLUCOSE | LEP |
| 7.5.11 | ADIPOQ | CCL2 | CRP | GLUCOSE | TIMP2 |
| 7.5.12 | ADIPOQ | CCL2 | CRP | GLUCOSE | TRIG |
| 7.5.13 | ADIPOQ | CCL2 | CRP | GLUCOSE | VWF |
| 7.5.14 | ADIPOQ | CD40 | CRP | GLUCOSE | HBA1C |
| 7.5.15 | ADIPOQ | CD40 | CRP | GLUCOSE | INSULIN-M |
| 7.5.16 | ADIPOQ | CD40 | CRP | GLUCOSE | LEP |
| 7.5.17 | ADIPOQ | CRP | EGF | GLUCOSE | GPT |
| 7.5.18 | ADIPOQ | CRP | EGF | GLUCOSE | HBA1C |
| 7.5.19 | ADIPOQ | CRP | EGF | GLUCOSE | LEP |
| 7.5.20 | ADIPOQ | CRP | EGF | GLUCOSE | TRIG |
| 7.5.21 | ADIPOQ | CRP | ENG | GLUCOSE | GPT |
| 7.5.22 | ADIPOQ | CRP | ENG | GLUCOSE | HBA1C |
| 7.5.23 | ADIPOQ | CRP | ENG | GLUCOSE | HSPA1B |
| 7.5.24 | ADIPOQ | CRP | ENG | GLUCOSE | IL2RA |
| 7.5.25 | ADIPOQ | CRP | ENG | GLUCOSE | INSULIN-M |
| 7.5.26 | ADIPOQ | CRP | ENG | GLUCOSE | LEP |
| 7.5.27 | ADIPOQ | CRP | ENG | GLUCOSE | TIMP2 |
| 7.5.28 | ADIPOQ | CRP | ENG | GLUCOSE | TRIG |
| 7.5.29 | ADIPOQ | CRP | ENG | GLUCOSE | VWF |
| 7.5.30 | ADIPOQ | CRP | FGA | GLUCOSE | GPT |
| 7.5.31 | ADIPOQ | CRP | FGA | GLUCOSE | HBA1C |
| 7.5.32 | ADIPOQ | CRP | FGA | GLUCOSE | LEP |
| 7.5.33 | ADIPOQ | CRP | FTH1 | GLUCOSE | HBA1C |
| 7.5.34 | ADIPOQ | CRP | FTH1 | GLUCOSE | INSULIN-M |
| 7.5.35 | ADIPOQ | CRP | FTH1 | GLUCOSE | LEP |
| 7.5.36 | ADIPOQ | CRP | GLUCOSE | GPT | HBA1C |
| 7.5.37 | ADIPOQ | CRP | GLUCOSE | GPT | HP |
| 7.5.38 | ADIPOQ | CRP | GLUCOSE | GPT | HSPA1B |
| 7.5.39 | ADIPOQ | CRP | GLUCOSE | GPT | IGFBP2 |
| 7.5.40 | ADIPOQ | CRP | GLUCOSE | GPT | IL2RA |

FIGURE 11C (continued)

| Panel No. | Marker 1 | Marker 2 | Marker 3 | Marker 4 | Marker 5 |
|---|---|---|---|---|---|
| 7.5.41 | ADIPOQ | CRP | GLUCOSE | GPT | INSULIN-M |
| 7.5.42 | ADIPOQ | CRP | GLUCOSE | GPT | LEP |
| 7.5.43 | ADIPOQ | CRP | GLUCOSE | GPT | TIMP2 |
| 7.5.44 | ADIPOQ | CRP | GLUCOSE | GPT | TRIG |
| 7.5.45 | ADIPOQ | CRP | GLUCOSE | GPT | VWF |
| 7.5.46 | ADIPOQ | CRP | GLUCOSE | HBA1C | HP |
| 7.5.47 | ADIPOQ | CRP | GLUCOSE | HBA1C | HSPA1B |
| 7.5.48 | ADIPOQ | CRP | GLUCOSE | HBA1C | IGF1R |
| 7.5.49 | ADIPOQ | CRP | GLUCOSE | HBA1C | IGFBP1 |
| 7.5.50 | ADIPOQ | CRP | GLUCOSE | HBA1C | IGFBP2 |
| 7.5.51 | ADIPOQ | CRP | GLUCOSE | HBA1C | IL2RA |
| 7.5.52 | ADIPOQ | CRP | GLUCOSE | HBA1C | IL2RB |
| 7.5.53 | ADIPOQ | CRP | GLUCOSE | HBA1C | IL6R |
| 7.5.54 | ADIPOQ | CRP | GLUCOSE | HBA1C | INSULIN-M |
| 7.5.55 | ADIPOQ | CRP | GLUCOSE | HBA1C | LEP |
| 7.5.56 | ADIPOQ | CRP | GLUCOSE | HBA1C | SCp |
| 7.5.57 | ADIPOQ | CRP | GLUCOSE | HBA1C | SHBG |
| 7.5.58 | ADIPOQ | CRP | GLUCOSE | HBA1C | TIMP2 |
| 7.5.59 | ADIPOQ | CRP | GLUCOSE | HBA1C | TRIG |
| 7.5.60 | ADIPOQ | CRP | GLUCOSE | HBA1C | VWF |
| 7.5.61 | ADIPOQ | CRP | GLUCOSE | HP | HSPA1B |
| 7.5.62 | ADIPOQ | CRP | GLUCOSE | HP | INSULIN-M |
| 7.5.63 | ADIPOQ | CRP | GLUCOSE | HP | LEP |
| 7.5.64 | ADIPOQ | CRP | GLUCOSE | HP | TRIG |
| 7.5.65 | ADIPOQ | CRP | GLUCOSE | HSPA1B | IL2RA |
| 7.5.66 | ADIPOQ | CRP | GLUCOSE | HSPA1B | INSULIN-M |
| 7.5.67 | ADIPOQ | CRP | GLUCOSE | HSPA1B | LEP |
| 7.5.68 | ADIPOQ | CRP | GLUCOSE | HSPA1B | TIMP2 |
| 7.5.69 | ADIPOQ | CRP | GLUCOSE | HSPA1B | TRIG |
| 7.5.70 | ADIPOQ | CRP | GLUCOSE | IGF1R | LEP |
| 7.5.71 | ADIPOQ | CRP | GLUCOSE | IGFBP1 | LEP |
| 7.5.72 | ADIPOQ | CRP | GLUCOSE | IGFBP2 | INSULIN-M |
| 7.5.73 | ADIPOQ | CRP | GLUCOSE | IGFBP2 | LEP |
| 7.5.74 | ADIPOQ | CRP | GLUCOSE | IL2RA | LEP |
| 7.5.75 | ADIPOQ | CRP | GLUCOSE | IL2RB | LEP |
| 7.5.76 | ADIPOQ | CRP | GLUCOSE | IL2RB | TRIG |
| 7.5.77 | ADIPOQ | CRP | GLUCOSE | IL6R | LEP |
| 7.5.78 | ADIPOQ | CRP | GLUCOSE | INSULIN-M | LEP |
| 7.5.79 | ADIPOQ | CRP | GLUCOSE | INSULIN-M | SCp |
| 7.5.80 | ADIPOQ | CRP | GLUCOSE | INSULIN-M | SHBG |

FIGURE 11C (continued)

| Panel No. | Marker 1 | Marker 2 | Marker 3 | Marker 4 | Marker 5 |
|---|---|---|---|---|---|
| 7.5.81 | ADIPOQ | CRP | GLUCOSE | INSULIN-M | TIMP2 |
| 7.5.82 | ADIPOQ | CRP | GLUCOSE | INSULIN-M | TRIG |
| 7.5.83 | ADIPOQ | CRP | GLUCOSE | INSULIN-M | VWF |
| 7.5.84 | ADIPOQ | CRP | GLUCOSE | LEP | SCp |
| 7.5.85 | ADIPOQ | CRP | GLUCOSE | LEP | SHBG |
| 7.5.86 | ADIPOQ | CRP | GLUCOSE | LEP | TIMP2 |
| 7.5.87 | ADIPOQ | CRP | GLUCOSE | LEP | TRIG |
| 7.5.88 | ADIPOQ | CRP | GLUCOSE | LEP | VWF |
| 7.5.89 | ADIPOQ | CRP | GLUCOSE | TIMP2 | TRIG |
| 7.5.90 | ADIPOQ | CRP | GLUCOSE | TRIG | VWF |
| 7.5.91 | ADIPOQ | GLUCOSE | HBA1C | HSPA1B | LEP |
| 7.5.92 | CCL2 | CD40 | CRP | GLUCOSE | HBA1C |
| 7.5.93 | CCL2 | CD40 | CRP | GLUCOSE | INSULIN-M |
| 7.5.94 | CCL2 | CRP | EGF | GLUCOSE | HBA1C |
| 7.5.95 | CCL2 | CRP | EGF | GLUCOSE | INSULIN-M |
| 7.5.96 | CCL2 | CRP | EGF | GLUCOSE | TRIG |
| 7.5.97 | CCL2 | CRP | ENG | GLUCOSE | GPT |
| 7.5.98 | CCL2 | CRP | ENG | GLUCOSE | HBA1C |
| 7.5.99 | CCL2 | CRP | ENG | GLUCOSE | HP |
| 7.5.100 | CCL2 | CRP | ENG | GLUCOSE | HSPA1B |
| 7.5.101 | CCL2 | CRP | ENG | GLUCOSE | IL2RA |
| 7.5.102 | CCL2 | CRP | ENG | GLUCOSE | INSULIN-M |
| 7.5.103 | CCL2 | CRP | ENG | GLUCOSE | LEP |
| 7.5.104 | CCL2 | CRP | ENG | GLUCOSE | TRIG |
| 7.5.105 | CCL2 | CRP | FGA | GLUCOSE | HBA1C |
| 7.5.106 | CCL2 | CRP | FGA | GLUCOSE | INSULIN-M |
| 7.5.107 | CCL2 | CRP | FGA | GLUCOSE | TRIG |
| 7.5.108 | CCL2 | CRP | FTH1 | GLUCOSE | HBA1C |
| 7.5.109 | CCL2 | CRP | GLUCOSE | GPT | HBA1C |
| 7.5.110 | CCL2 | CRP | GLUCOSE | GPT | HP |
| 7.5.111 | CCL2 | CRP | GLUCOSE | GPT | IL2RA |
| 7.5.112 | CCL2 | CRP | GLUCOSE | GPT | INSULIN-M |
| 7.5.113 | CCL2 | CRP | GLUCOSE | GPT | LEP |
| 7.5.114 | CCL2 | CRP | GLUCOSE | GPT | TRIG |
| 7.5.115 | CCL2 | CRP | GLUCOSE | HBA1C | HP |
| 7.5.116 | CCL2 | CRP | GLUCOSE | HBA1C | HSPA1B |
| 7.5.117 | CCL2 | CRP | GLUCOSE | HBA1C | IGF1R |
| 7.5.118 | CCL2 | CRP | GLUCOSE | HBA1C | IGFBP1 |
| 7.5.119 | CCL2 | CRP | GLUCOSE | HBA1C | IGFBP2 |
| 7.5.120 | CCL2 | CRP | GLUCOSE | HBA1C | IL2RA |

FIGURE 11C (continued)

| Panel No. | Marker 1 | Marker 2 | Marker 3 | Marker 4 | Marker 5 |
|---|---|---|---|---|---|
| 7.5.121 | CCL2 | CRP | GLUCOSE | HBA1C | IL2RB |
| 7.5.122 | CCL2 | CRP | GLUCOSE | HBA1C | IL6R |
| 7.5.123 | CCL2 | CRP | GLUCOSE | HBA1C | INSULIN-M |
| 7.5.124 | CCL2 | CRP | GLUCOSE | HBA1C | LEP |
| 7.5.125 | CCL2 | CRP | GLUCOSE | HBA1C | SCp |
| 7.5.126 | CCL2 | CRP | GLUCOSE | HBA1C | SHBG |
| 7.5.127 | CCL2 | CRP | GLUCOSE | HBA1C | TIMP2 |
| 7.5.128 | CCL2 | CRP | GLUCOSE | HBA1C | TRIG |
| 7.5.129 | CCL2 | CRP | GLUCOSE | HBA1C | VWF |
| 7.5.130 | CCL2 | CRP | GLUCOSE | HP | HSPA1B |
| 7.5.131 | CCL2 | CRP | GLUCOSE | HP | IGFBP2 |
| 7.5.132 | CCL2 | CRP | GLUCOSE | HP | INSULIN-M |
| 7.5.133 | CCL2 | CRP | GLUCOSE | HP | LEP |
| 7.5.134 | CCL2 | CRP | GLUCOSE | HP | SHBG |
| 7.5.135 | CCL2 | CRP | GLUCOSE | HP | TIMP2 |
| 7.5.136 | CCL2 | CRP | GLUCOSE | HP | TRIG |
| 7.5.137 | CCL2 | CRP | GLUCOSE | HSPA1B | INSULIN-M |
| 7.5.138 | CCL2 | CRP | GLUCOSE | HSPA1B | LEP |
| 7.5.139 | CCL2 | CRP | GLUCOSE | HSPA1B | TRIG |
| 7.5.140 | CCL2 | CRP | GLUCOSE | IGF1R | INSULIN-M |
| 7.5.141 | CCL2 | CRP | GLUCOSE | IGFBP1 | INSULIN-M |
| 7.5.142 | CCL2 | CRP | GLUCOSE | IGFBP2 | INSULIN-M |
| 7.5.143 | CCL2 | CRP | GLUCOSE | IL2RA | INSULIN-M |
| 7.5.144 | CCL2 | CRP | GLUCOSE | IL2RA | TRIG |
| 7.5.145 | CCL2 | CRP | GLUCOSE | IL2RB | INSULIN-M |
| 7.5.146 | CCL2 | CRP | GLUCOSE | IL6R | INSULIN-M |
| 7.5.147 | CCL2 | CRP | GLUCOSE | INSULIN-M | LEP |
| 7.5.148 | CCL2 | CRP | GLUCOSE | INSULIN-M | SCp |
| 7.5.149 | CCL2 | CRP | GLUCOSE | INSULIN-M | SHBG |
| 7.5.150 | CCL2 | CRP | GLUCOSE | INSULIN-M | TIMP2 |
| 7.5.151 | CCL2 | CRP | GLUCOSE | INSULIN-M | TRIG |
| 7.5.152 | CCL2 | CRP | GLUCOSE | INSULIN-M | VWF |
| 7.5.153 | CCL2 | CRP | GLUCOSE | LEP | TRIG |
| 7.5.154 | CCL2 | CRP | GLUCOSE | TIMP2 | TRIG |
| 7.5.155 | CCL2 | GLUCOSE | GPT | HBA1C | INSULIN-M |
| 7.5.156 | CCL2 | GLUCOSE | HBA1C | HSPA1B | INSULIN-M |
| 7.5.157 | CD40 | CRP | ENG | GLUCOSE | INSULIN-M |
| 7.5.158 | CD40 | CRP | GLUCOSE | GPT | HBA1C |
| 7.5.159 | CD40 | CRP | GLUCOSE | GPT | INSULIN-M |
| 7.5.160 | CD40 | CRP | GLUCOSE | HBA1C | HP |

FIGURE 11C (continued)

| Panel No. | Marker 1 | Marker 2 | Marker 3 | Marker 4 | Marker 5 |
|---|---|---|---|---|---|
| 7.5.161 | CD40 | CRP | GLUCOSE | HBA1C | INSULIN-M |
| 7.5.162 | CD40 | CRP | GLUCOSE | HBA1C | TRIG |
| 7.5.163 | CD40 | CRP | GLUCOSE | HP | INSULIN-M |
| 7.5.164 | CRP | EGF | ENG | GLUCOSE | HBA1C |
| 7.5.165 | CRP | EGF | ENG | GLUCOSE | INSULIN-M |
| 7.5.166 | CRP | EGF | ENG | GLUCOSE | TRIG |
| 7.5.167 | CRP | EGF | FGA | GLUCOSE | HBA1C |
| 7.5.168 | CRP | EGF | FTH1 | GLUCOSE | HBA1C |
| 7.5.169 | CRP | EGF | GLUCOSE | GPT | HBA1C |
| 7.5.170 | CRP | EGF | GLUCOSE | GPT | IL2RA |
| 7.5.171 | CRP | EGF | GLUCOSE | GPT | INSULIN-M |
| 7.5.172 | CRP | EGF | GLUCOSE | GPT | LEP |
| 7.5.173 | CRP | EGF | GLUCOSE | GPT | TRIG |
| 7.5.174 | CRP | EGF | GLUCOSE | HBA1C | HP |
| 7.5.175 | CRP | EGF | GLUCOSE | HBA1C | HSPA1B |
| 7.5.176 | CRP | EGF | GLUCOSE | HBA1C | IGF1R |
| 7.5.177 | CRP | EGF | GLUCOSE | HBA1C | IGFBP2 |
| 7.5.178 | CRP | EGF | GLUCOSE | HBA1C | IL2RA |
| 7.5.179 | CRP | EGF | GLUCOSE | HBA1C | IL2RB |
| 7.5.180 | CRP | EGF | GLUCOSE | HBA1C | INSULIN-M |
| 7.5.181 | CRP | EGF | GLUCOSE | HBA1C | LEP |
| 7.5.182 | CRP | EGF | GLUCOSE | HBA1C | SHBG |
| 7.5.183 | CRP | EGF | GLUCOSE | HBA1C | TIMP2 |
| 7.5.184 | CRP | EGF | GLUCOSE | HBA1C | TRIG |
| 7.5.185 | CRP | EGF | GLUCOSE | HP | INSULIN-M |
| 7.5.186 | CRP | EGF | GLUCOSE | HSPA1B | IL2RA |
| 7.5.187 | CRP | EGF | GLUCOSE | HSPA1B | INSULIN-M |
| 7.5.188 | CRP | EGF | GLUCOSE | HSPA1B | TRIG |
| 7.5.189 | CRP | EGF | GLUCOSE | IGFBP2 | INSULIN-M |
| 7.5.190 | CRP | EGF | GLUCOSE | IL2RA | TRIG |
| 7.5.191 | CRP | EGF | GLUCOSE | INSULIN-M | SHBG |
| 7.5.192 | CRP | EGF | GLUCOSE | INSULIN-M | TRIG |
| 7.5.193 | CRP | EGF | GLUCOSE | LEP | TRIG |
| 7.5.194 | CRP | EGF | GLUCOSE | SHBG | TRIG |
| 7.5.195 | CRP | EGF | GLUCOSE | TIMP2 | TRIG |
| 7.5.196 | CRP | EGF | GLUCOSE | TRIG | VWF |
| 7.5.197 | CRP | ENG | FGA | GLUCOSE | INSULIN-M |
| 7.5.198 | CRP | ENG | FGA | GLUCOSE | TRIG |
| 7.5.199 | CRP | ENG | FTH1 | GLUCOSE | HBA1C |
| 7.5.200 | CRP | ENG | FTH1 | GLUCOSE | INSULIN-M |

FIGURE 11C (continued)

| Panel No. | Marker 1 | Marker 2 | Marker 3 | Marker 4 | Marker 5 |
|---|---|---|---|---|---|
| 7.5.201 | CRP | ENG | FTH1 | GLUCOSE | TRIG |
| 7.5.202 | CRP | ENG | GLUCOSE | GPT | HBA1C |
| 7.5.203 | CRP | ENG | GLUCOSE | GPT | IGFBP2 |
| 7.5.204 | CRP | ENG | GLUCOSE | GPT | IL2RA |
| 7.5.205 | CRP | ENG | GLUCOSE | GPT | IL2RB |
| 7.5.206 | CRP | ENG | GLUCOSE | GPT | INSULIN-M |
| 7.5.207 | CRP | ENG | GLUCOSE | GPT | LEP |
| 7.5.208 | CRP | ENG | GLUCOSE | GPT | TIMP2 |
| 7.5.209 | CRP | ENG | GLUCOSE | GPT | TRIG |
| 7.5.210 | CRP | ENG | GLUCOSE | HBA1C | HP |
| 7.5.211 | CRP | ENG | GLUCOSE | HBA1C | HSPA1B |
| 7.5.212 | CRP | ENG | GLUCOSE | HBA1C | IGF1R |
| 7.5.213 | CRP | ENG | GLUCOSE | HBA1C | IGFBP1 |
| 7.5.214 | CRP | ENG | GLUCOSE | HBA1C | IL2RA |
| 7.5.215 | CRP | ENG | GLUCOSE | HBA1C | IL2RB |
| 7.5.216 | CRP | ENG | GLUCOSE | HBA1C | INSULIN-M |
| 7.5.217 | CRP | ENG | GLUCOSE | HBA1C | LEP |
| 7.5.218 | CRP | ENG | GLUCOSE | HBA1C | SCp |
| 7.5.219 | CRP | ENG | GLUCOSE | HBA1C | SHBG |
| 7.5.220 | CRP | ENG | GLUCOSE | HBA1C | TIMP2 |
| 7.5.221 | CRP | ENG | GLUCOSE | HBA1C | TRIG |
| 7.5.222 | CRP | ENG | GLUCOSE | HBA1C | VWF |
| 7.5.223 | CRP | ENG | GLUCOSE | HP | INSULIN-M |
| 7.5.224 | CRP | ENG | GLUCOSE | HP | TRIG |
| 7.5.225 | CRP | ENG | GLUCOSE | HSPA1B | IL2RA |
| 7.5.226 | CRP | ENG | GLUCOSE | HSPA1B | INSULIN-M |
| 7.5.227 | CRP | ENG | GLUCOSE | HSPA1B | LEP |
| 7.5.228 | CRP | ENG | GLUCOSE | HSPA1B | TRIG |
| 7.5.229 | CRP | ENG | GLUCOSE | IGF1R | INSULIN-M |
| 7.5.230 | CRP | ENG | GLUCOSE | IGFBP1 | INSULIN-M |
| 7.5.231 | CRP | ENG | GLUCOSE | IGFBP1 | TRIG |
| 7.5.232 | CRP | ENG | GLUCOSE | IGFBP2 | INSULIN-M |
| 7.5.233 | CRP | ENG | GLUCOSE | IGFBP2 | TRIG |
| 7.5.234 | CRP | ENG | GLUCOSE | IL2RA | INSULIN-M |
| 7.5.235 | CRP | ENG | GLUCOSE | IL2RA | TRIG |
| 7.5.236 | CRP | ENG | GLUCOSE | IL2RB | INSULIN-M |
| 7.5.237 | CRP | ENG | GLUCOSE | IL2RB | TRIG |
| 7.5.238 | CRP | ENG | GLUCOSE | IL6R | INSULIN-M |
| 7.5.239 | CRP | ENG | GLUCOSE | IL6R | TRIG |
| 7.5.240 | CRP | ENG | GLUCOSE | INSULIN-M | LEP |

FIGURE 11C (continued)

| Panel No. | Marker 1 | Marker 2 | Marker 3 | Marker 4 | Marker 5 |
|---|---|---|---|---|---|
| 7.5.241 | CRP | ENG | GLUCOSE | INSULIN-M | SCp |
| 7.5.242 | CRP | ENG | GLUCOSE | INSULIN-M | SHBG |
| 7.5.243 | CRP | ENG | GLUCOSE | INSULIN-M | TIMP2 |
| 7.5.244 | CRP | ENG | GLUCOSE | INSULIN-M | TRIG |
| 7.5.245 | CRP | ENG | GLUCOSE | INSULIN-M | VWF |
| 7.5.246 | CRP | ENG | GLUCOSE | LEP | TRIG |
| 7.5.247 | CRP | ENG | GLUCOSE | SCp | TRIG |
| 7.5.248 | CRP | ENG | GLUCOSE | SHBG | TRIG |
| 7.5.249 | CRP | ENG | GLUCOSE | TIMP2 | TRIG |
| 7.5.250 | CRP | ENG | GLUCOSE | TRIG | VWF |
| 7.5.251 | CRP | FGA | GLUCOSE | GPT | HBA1C |
| 7.5.252 | CRP | FGA | GLUCOSE | GPT | IL2RA |
| 7.5.253 | CRP | FGA | GLUCOSE | GPT | INSULIN-M |
| 7.5.254 | CRP | FGA | GLUCOSE | GPT | LEP |
| 7.5.255 | CRP | FGA | GLUCOSE | HBA1C | HP |
| 7.5.256 | CRP | FGA | GLUCOSE | HBA1C | INSULIN-M |
| 7.5.257 | CRP | FGA | GLUCOSE | HBA1C | TRIG |
| 7.5.258 | CRP | FGA | GLUCOSE | HP | INSULIN-M |
| 7.5.259 | CRP | FGA | GLUCOSE | HSPA1B | INSULIN-M |
| 7.5.260 | CRP | FGA | GLUCOSE | INSULIN-M | TRIG |
| 7.5.261 | CRP | FTH1 | GLUCOSE | GPT | HBA1C |
| 7.5.262 | CRP | FTH1 | GLUCOSE | GPT | INSULIN-M |
| 7.5.263 | CRP | FTH1 | GLUCOSE | HBA1C | HP |
| 7.5.264 | CRP | FTH1 | GLUCOSE | HBA1C | INSULIN-M |
| 7.5.265 | CRP | FTH1 | GLUCOSE | HBA1C | LEP |
| 7.5.266 | CRP | FTH1 | GLUCOSE | HBA1C | TRIG |
| 7.5.267 | CRP | FTH1 | GLUCOSE | HP | INSULIN-M |
| 7.5.268 | CRP | FTH1 | GLUCOSE | INSULIN-M | TRIG |
| 7.5.269 | CRP | GLUCOSE | GPT | HBA1C | HP |
| 7.5.270 | CRP | GLUCOSE | GPT | HBA1C | HSPA1B |
| 7.5.271 | CRP | GLUCOSE | GPT | HBA1C | IGF1R |
| 7.5.272 | CRP | GLUCOSE | GPT | HBA1C | IGFBP1 |
| 7.5.273 | CRP | GLUCOSE | GPT | HBA1C | IGFBP2 |
| 7.5.274 | CRP | GLUCOSE | GPT | HBA1C | IL2RA |
| 7.5.275 | CRP | GLUCOSE | GPT | HBA1C | IL2RB |
| 7.5.276 | CRP | GLUCOSE | GPT | HBA1C | IL6R |
| 7.5.277 | CRP | GLUCOSE | GPT | HBA1C | INSULIN-M |
| 7.5.278 | CRP | GLUCOSE | GPT | HBA1C | LEP |
| 7.5.279 | CRP | GLUCOSE | GPT | HBA1C | SCp |
| 7.5.280 | CRP | GLUCOSE | GPT | HBA1C | SHBG |

FIGURE 11C (continued)

| Panel No. | Marker 1 | Marker 2 | Marker 3 | Marker 4 | Marker 5 |
|---|---|---|---|---|---|
| 7.5.281 | CRP | GLUCOSE | GPT | HBA1C | TIMP2 |
| 7.5.282 | CRP | GLUCOSE | GPT | HBA1C | TRIG |
| 7.5.283 | CRP | GLUCOSE | GPT | HBA1C | VWF |
| 7.5.284 | CRP | GLUCOSE | GPT | HP | IGFBP2 |
| 7.5.285 | CRP | GLUCOSE | GPT | HP | IL2RA |
| 7.5.286 | CRP | GLUCOSE | GPT | HP | IL2RB |
| 7.5.287 | CRP | GLUCOSE | GPT | HP | INSULIN-M |
| 7.5.288 | CRP | GLUCOSE | GPT | HP | LEP |
| 7.5.289 | CRP | GLUCOSE | GPT | HP | TRIG |
| 7.5.290 | CRP | GLUCOSE | GPT | HSPA1B | INSULIN-M |
| 7.5.291 | CRP | GLUCOSE | GPT | IGF1R | INSULIN-M |
| 7.5.292 | CRP | GLUCOSE | GPT | IGFBP1 | INSULIN-M |
| 7.5.293 | CRP | GLUCOSE | GPT | IGFBP2 | INSULIN-M |
| 7.5.294 | CRP | GLUCOSE | GPT | IL2RA | INSULIN-M |
| 7.5.295 | CRP | GLUCOSE | GPT | IL2RA | LEP |
| 7.5.296 | CRP | GLUCOSE | GPT | IL2RA | TRIG |
| 7.5.297 | CRP | GLUCOSE | GPT | IL2RB | INSULIN-M |
| 7.5.298 | CRP | GLUCOSE | GPT | IL2RB | LEP |
| 7.5.299 | CRP | GLUCOSE | GPT | IL2RB | TRIG |
| 7.5.300 | CRP | GLUCOSE | GPT | IL6R | INSULIN-M |
| 7.5.301 | CRP | GLUCOSE | GPT | INSULIN-M | LEP |
| 7.5.302 | CRP | GLUCOSE | GPT | INSULIN-M | SCp |
| 7.5.303 | CRP | GLUCOSE | GPT | INSULIN-M | SHBG |
| 7.5.304 | CRP | GLUCOSE | GPT | INSULIN-M | TIMP2 |
| 7.5.305 | CRP | GLUCOSE | GPT | INSULIN-M | TRIG |
| 7.5.306 | CRP | GLUCOSE | GPT | INSULIN-M | VWF |
| 7.5.307 | CRP | GLUCOSE | GPT | LEP | TRIG |
| 7.5.308 | CRP | GLUCOSE | GPT | TIMP2 | TRIG |
| 7.5.309 | CRP | GLUCOSE | HBA1C | HP | HSPA1B |
| 7.5.310 | CRP | GLUCOSE | HBA1C | HP | IGF1R |
| 7.5.311 | CRP | GLUCOSE | HBA1C | HP | IGFBP1 |
| 7.5.312 | CRP | GLUCOSE | HBA1C | HP | IGFBP2 |
| 7.5.313 | CRP | GLUCOSE | HBA1C | HP | IL2RA |
| 7.5.314 | CRP | GLUCOSE | HBA1C | HP | IL2RB |
| 7.5.315 | CRP | GLUCOSE | HBA1C | HP | IL6R |
| 7.5.316 | CRP | GLUCOSE | HBA1C | HP | INSULIN-M |
| 7.5.317 | CRP | GLUCOSE | HBA1C | HP | LEP |
| 7.5.318 | CRP | GLUCOSE | HBA1C | HP | SCp |
| 7.5.319 | CRP | GLUCOSE | HBA1C | HP | SHBG |
| 7.5.320 | CRP | GLUCOSE | HBA1C | HP | TIMP2 |

FIGURE 11C (continued)

| Panel No. | Marker 1 | Marker 2 | Marker 3 | Marker 4 | Marker 5 |
|---|---|---|---|---|---|
| 7.5.321 | CRP | GLUCOSE | HBA1C | HP | TRIG |
| 7.5.322 | CRP | GLUCOSE | HBA1C | HP | VWF |
| 7.5.323 | CRP | GLUCOSE | HBA1C | HSPA1B | IL2RA |
| 7.5.324 | CRP | GLUCOSE | HBA1C | HSPA1B | IL2RB |
| 7.5.325 | CRP | GLUCOSE | HBA1C | HSPA1B | INSULIN-M |
| 7.5.326 | CRP | GLUCOSE | HBA1C | HSPA1B | LEP |
| 7.5.327 | CRP | GLUCOSE | HBA1C | HSPA1B | TIMP2 |
| 7.5.328 | CRP | GLUCOSE | HBA1C | HSPA1B | TRIG |
| 7.5.329 | CRP | GLUCOSE | HBA1C | IGF1R | INSULIN-M |
| 7.5.330 | CRP | GLUCOSE | HBA1C | IGF1R | LEP |
| 7.5.331 | CRP | GLUCOSE | HBA1C | IGF1R | TRIG |
| 7.5.332 | CRP | GLUCOSE | HBA1C | IGFBP1 | INSULIN-M |
| 7.5.333 | CRP | GLUCOSE | HBA1C | IGFBP1 | TRIG |
| 7.5.334 | CRP | GLUCOSE | HBA1C | IGFBP2 | INSULIN-M |
| 7.5.335 | CRP | GLUCOSE | HBA1C | IGFBP2 | TRIG |
| 7.5.336 | CRP | GLUCOSE | HBA1C | IL2RA | INSULIN-M |
| 7.5.337 | CRP | GLUCOSE | HBA1C | IL2RA | TIMP2 |
| 7.5.338 | CRP | GLUCOSE | HBA1C | IL2RA | TRIG |
| 7.5.339 | CRP | GLUCOSE | HBA1C | IL2RB | INSULIN-M |
| 7.5.340 | CRP | GLUCOSE | HBA1C | IL2RB | LEP |
| 7.5.341 | CRP | GLUCOSE | HBA1C | IL2RB | TRIG |
| 7.5.342 | CRP | GLUCOSE | HBA1C | IL6R | INSULIN-M |
| 7.5.343 | CRP | GLUCOSE | HBA1C | IL6R | LEP |
| 7.5.344 | CRP | GLUCOSE | HBA1C | IL6R | TIMP2 |
| 7.5.345 | CRP | GLUCOSE | HBA1C | IL6R | TRIG |
| 7.5.346 | CRP | GLUCOSE | HBA1C | INSULIN-M | LEP |
| 7.5.347 | CRP | GLUCOSE | HBA1C | INSULIN-M | SCp |
| 7.5.348 | CRP | GLUCOSE | HBA1C | INSULIN-M | SHBG |
| 7.5.349 | CRP | GLUCOSE | HBA1C | INSULIN-M | TIMP2 |
| 7.5.350 | CRP | GLUCOSE | HBA1C | INSULIN-M | TRIG |
| 7.5.351 | CRP | GLUCOSE | HBA1C | INSULIN-M | VWF |
| 7.5.352 | CRP | GLUCOSE | HBA1C | LEP | TRIG |
| 7.5.353 | CRP | GLUCOSE | HBA1C | SCp | TRIG |
| 7.5.354 | CRP | GLUCOSE | HBA1C | SHBG | TRIG |
| 7.5.355 | CRP | GLUCOSE | HBA1C | TIMP2 | TRIG |
| 7.5.356 | CRP | GLUCOSE | HBA1C | TRIG | VWF |
| 7.5.357 | CRP | GLUCOSE | HP | HSPA1B | INSULIN-M |
| 7.5.358 | CRP | GLUCOSE | HP | HSPA1B | TRIG |
| 7.5.359 | CRP | GLUCOSE | HP | IGFBP2 | INSULIN-M |
| 7.5.360 | CRP | GLUCOSE | HP | IGFBP2 | TRIG |

FIGURE 11C (continued)

| Panel No. | Marker 1 | Marker 2 | Marker 3 | Marker 4 | Marker 5 |
|---|---|---|---|---|---|
| 7.5.361 | CRP | GLUCOSE | HP | IL2RA | INSULIN-M |
| 7.5.362 | CRP | GLUCOSE | HP | IL2RB | INSULIN-M |
| 7.5.363 | CRP | GLUCOSE | HP | IL2RB | TRIG |
| 7.5.364 | CRP | GLUCOSE | HP | IL6R | INSULIN-M |
| 7.5.365 | CRP | GLUCOSE | HP | INSULIN-M | LEP |
| 7.5.366 | CRP | GLUCOSE | HP | INSULIN-M | SCp |
| 7.5.367 | CRP | GLUCOSE | HP | INSULIN-M | SHBG |
| 7.5.368 | CRP | GLUCOSE | HP | INSULIN-M | TIMP2 |
| 7.5.369 | CRP | GLUCOSE | HP | INSULIN-M | TRIG |
| 7.5.370 | CRP | GLUCOSE | HP | INSULIN-M | VWF |
| 7.5.371 | CRP | GLUCOSE | HP | LEP | TRIG |
| 7.5.372 | CRP | GLUCOSE | HP | SHBG | TRIG |
| 7.5.373 | CRP | GLUCOSE | HP | TIMP2 | TRIG |
| 7.5.374 | CRP | GLUCOSE | HP | TRIG | VWF |
| 7.5.375 | CRP | GLUCOSE | HSPA1B | IGFBP2 | INSULIN-M |
| 7.5.376 | CRP | GLUCOSE | HSPA1B | IL2RA | INSULIN-M |
| 7.5.377 | CRP | GLUCOSE | HSPA1B | IL2RA | LEP |
| 7.5.378 | CRP | GLUCOSE | HSPA1B | IL2RA | TRIG |
| 7.5.379 | CRP | GLUCOSE | HSPA1B | IL2RB | INSULIN-M |
| 7.5.380 | CRP | GLUCOSE | HSPA1B | INSULIN-M | LEP |
| 7.5.381 | CRP | GLUCOSE | HSPA1B | INSULIN-M | TIMP2 |
| 7.5.382 | CRP | GLUCOSE | HSPA1B | INSULIN-M | TRIG |
| 7.5.383 | CRP | GLUCOSE | HSPA1B | LEP | TRIG |
| 7.5.384 | CRP | GLUCOSE | HSPA1B | TIMP2 | TRIG |
| 7.5.385 | CRP | GLUCOSE | IGFBP2 | INSULIN-M | TRIG |
| 7.5.386 | CRP | GLUCOSE | IGFBP2 | LEP | TRIG |
| 7.5.387 | CRP | GLUCOSE | IL2RA | INSULIN-M | TRIG |
| 7.5.388 | CRP | GLUCOSE | IL2RA | LEP | TRIG |
| 7.5.389 | CRP | GLUCOSE | IL2RA | TIMP2 | TRIG |
| 7.5.390 | CRP | GLUCOSE | IL2RB | LEP | TRIG |
| 7.5.391 | CRP | GLUCOSE | IL6R | INSULIN-M | TRIG |
| 7.5.392 | CRP | GLUCOSE | INSULIN-M | LEP | TRIG |
| 7.5.393 | CRP | GLUCOSE | INSULIN-M | SCp | TRIG |
| 7.5.394 | CRP | GLUCOSE | INSULIN-M | SHBG | TRIG |
| 7.5.395 | CRP | GLUCOSE | INSULIN-M | TIMP2 | TRIG |
| 7.5.396 | CRP | GLUCOSE | INSULIN-M | TRIG | VWF |
| 7.5.397 | CRP | GLUCOSE | LEP | TIMP2 | TRIG |
| 7.5.398 | GLUCOSE | GPT | HBA1C | INSULIN-M | LEP |
| 7.5.399 | GLUCOSE | HBA1C | HSPA1B | IGFBP2 | INSULIN-M |
| 7.5.400 | GLUCOSE | HBA1C | HSPA1B | INSULIN-M | LEP |

FIGURE 11D

| Panel No. | Marker 1 | Marker 2 | Marker 3 | Marker 4 | Marker 5 | Marker 6 |
|---|---|---|---|---|---|---|
| 7.6.1 | ADIPOQ | CCL2 | CRP | EGF | GLUCOSE | HBA1C |
| 7.6.2 | ADIPOQ | CCL2 | CRP | ENG | GLUCOSE | GPT |
| 7.6.3 | ADIPOQ | CCL2 | CRP | ENG | GLUCOSE | HBA1C |
| 7.6.4 | ADIPOQ | CCL2 | CRP | ENG | GLUCOSE | LEP |
| 7.6.5 | ADIPOQ | CCL2 | CRP | GLUCOSE | GPT | HBA1C |
| 7.6.6 | ADIPOQ | CCL2 | CRP | GLUCOSE | GPT | HP |
| 7.6.7 | ADIPOQ | CCL2 | CRP | GLUCOSE | GPT | INSULIN-M |
| 7.6.8 | ADIPOQ | CCL2 | CRP | GLUCOSE | GPT | LEP |
| 7.6.9 | ADIPOQ | CCL2 | CRP | GLUCOSE | HBA1C | HP |
| 7.6.10 | ADIPOQ | CCL2 | CRP | GLUCOSE | HBA1C | HSPA1B |
| 7.6.11 | ADIPOQ | CCL2 | CRP | GLUCOSE | HBA1C | INSULIN-M |
| 7.6.12 | ADIPOQ | CCL2 | CRP | GLUCOSE | HBA1C | LEP |
| 7.6.13 | ADIPOQ | CCL2 | CRP | GLUCOSE | HBA1C | TIMP2 |
| 7.6.14 | ADIPOQ | CCL2 | CRP | GLUCOSE | HBA1C | TRIG |
| 7.6.15 | ADIPOQ | CCL2 | CRP | GLUCOSE | HP | HSPA1B |
| 7.6.16 | ADIPOQ | CCL2 | CRP | GLUCOSE | HP | LEP |
| 7.6.17 | ADIPOQ | CCL2 | CRP | GLUCOSE | HSPA1B | INSULIN-M |
| 7.6.18 | ADIPOQ | CCL2 | CRP | GLUCOSE | HSPA1B | LEP |
| 7.6.19 | ADIPOQ | CD40 | CRP | GLUCOSE | GPT | LEP |
| 7.6.20 | ADIPOQ | CD40 | CRP | GLUCOSE | HBA1C | INSULIN-M |
| 7.6.21 | ADIPOQ | CD40 | CRP | GLUCOSE | HSPA1B | LEP |
| 7.6.22 | ADIPOQ | CRP | EGF | GLUCOSE | GPT | HBA1C |
| 7.6.23 | ADIPOQ | CRP | EGF | GLUCOSE | GPT | LEP |
| 7.6.24 | ADIPOQ | CRP | EGF | GLUCOSE | HBA1C | INSULIN-M |
| 7.6.25 | ADIPOQ | CRP | EGF | GLUCOSE | HBA1C | LEP |
| 7.6.26 | ADIPOQ | CRP | EGF | GLUCOSE | HBA1C | TRIG |
| 7.6.27 | ADIPOQ | CRP | EGF | GLUCOSE | HSPA1B | LEP |
| 7.6.28 | ADIPOQ | CRP | ENG | GLUCOSE | GPT | HBA1C |
| 7.6.29 | ADIPOQ | CRP | ENG | GLUCOSE | GPT | INSULIN-M |
| 7.6.30 | ADIPOQ | CRP | ENG | GLUCOSE | GPT | LEP |
| 7.6.31 | ADIPOQ | CRP | ENG | GLUCOSE | HBA1C | HP |
| 7.6.32 | ADIPOQ | CRP | ENG | GLUCOSE | HBA1C | INSULIN-M |
| 7.6.33 | ADIPOQ | CRP | ENG | GLUCOSE | HBA1C | LEP |
| 7.6.34 | ADIPOQ | CRP | ENG | GLUCOSE | HBA1C | TRIG |
| 7.6.35 | ADIPOQ | CRP | ENG | GLUCOSE | HSPA1B | INSULIN-M |
| 7.6.36 | ADIPOQ | CRP | ENG | GLUCOSE | HSPA1B | LEP |
| 7.6.37 | ADIPOQ | CRP | ENG | GLUCOSE | LEP | TRIG |
| 7.6.38 | ADIPOQ | CRP | FGA | GLUCOSE | GPT | LEP |
| 7.6.39 | ADIPOQ | CRP | FGA | GLUCOSE | HBA1C | INSULIN-M |
| 7.6.40 | ADIPOQ | CRP | FGA | GLUCOSE | HBA1C | LEP |

FIGURE 11D (continued)

| Panel No. | Marker 1 | Marker 2 | Marker 3 | Marker 4 | Marker 5 | Marker 6 |
|---|---|---|---|---|---|---|
| 7.6.41 | ADIPOQ | CRP | FGA | GLUCOSE | HSPA1B | LEP |
| 7.6.42 | ADIPOQ | CRP | FTH1 | GLUCOSE | GPT | LEP |
| 7.6.43 | ADIPOQ | CRP | FTH1 | GLUCOSE | HBA1C | INSULIN-M |
| 7.6.44 | ADIPOQ | CRP | FTH1 | GLUCOSE | HBA1C | LEP |
| 7.6.45 | ADIPOQ | CRP | FTH1 | GLUCOSE | HSPA1B | LEP |
| 7.6.46 | ADIPOQ | CRP | GLUCOSE | GPT | HBA1C | HP |
| 7.6.47 | ADIPOQ | CRP | GLUCOSE | GPT | HBA1C | HSPA1B |
| 7.6.48 | ADIPOQ | CRP | GLUCOSE | GPT | HBA1C | IGF1R |
| 7.6.49 | ADIPOQ | CRP | GLUCOSE | GPT | HBA1C | IGFBP2 |
| 7.6.50 | ADIPOQ | CRP | GLUCOSE | GPT | HBA1C | IL2RB |
| 7.6.51 | ADIPOQ | CRP | GLUCOSE | GPT | HBA1C | INSULIN-M |
| 7.6.52 | ADIPOQ | CRP | GLUCOSE | GPT | HBA1C | LEP |
| 7.6.53 | ADIPOQ | CRP | GLUCOSE | GPT | HBA1C | TIMP2 |
| 7.6.54 | ADIPOQ | CRP | GLUCOSE | GPT | HBA1C | TRIG |
| 7.6.55 | ADIPOQ | CRP | GLUCOSE | GPT | HP | IGFBP2 |
| 7.6.56 | ADIPOQ | CRP | GLUCOSE | GPT | HP | INSULIN-M |
| 7.6.57 | ADIPOQ | CRP | GLUCOSE | GPT | HP | LEP |
| 7.6.58 | ADIPOQ | CRP | GLUCOSE | GPT | HSPA1B | LEP |
| 7.6.59 | ADIPOQ | CRP | GLUCOSE | GPT | IGF1R | LEP |
| 7.6.60 | ADIPOQ | CRP | GLUCOSE | GPT | IGFBP1 | LEP |
| 7.6.61 | ADIPOQ | CRP | GLUCOSE | GPT | IGFBP2 | INSULIN-M |
| 7.6.62 | ADIPOQ | CRP | GLUCOSE | GPT | IGFBP2 | LEP |
| 7.6.63 | ADIPOQ | CRP | GLUCOSE | GPT | IL2RA | LEP |
| 7.6.64 | ADIPOQ | CRP | GLUCOSE | GPT | IL2RB | LEP |
| 7.6.65 | ADIPOQ | CRP | GLUCOSE | GPT | IL6R | LEP |
| 7.6.66 | ADIPOQ | CRP | GLUCOSE | GPT | INSULIN-M | LEP |
| 7.6.67 | ADIPOQ | CRP | GLUCOSE | GPT | LEP | SCp |
| 7.6.68 | ADIPOQ | CRP | GLUCOSE | GPT | LEP | SHBG |
| 7.6.69 | ADIPOQ | CRP | GLUCOSE | GPT | LEP | TIMP2 |
| 7.6.70 | ADIPOQ | CRP | GLUCOSE | GPT | LEP | TRIG |
| 7.6.71 | ADIPOQ | CRP | GLUCOSE | GPT | LEP | VWF |
| 7.6.72 | ADIPOQ | CRP | GLUCOSE | HBA1C | HP | HSPA1B |
| 7.6.73 | ADIPOQ | CRP | GLUCOSE | HBA1C | HP | IGFBP2 |
| 7.6.74 | ADIPOQ | CRP | GLUCOSE | HBA1C | HP | INSULIN-M |
| 7.6.75 | ADIPOQ | CRP | GLUCOSE | HBA1C | HP | LEP |
| 7.6.76 | ADIPOQ | CRP | GLUCOSE | HBA1C | HP | TIMP2 |
| 7.6.77 | ADIPOQ | CRP | GLUCOSE | HBA1C | HP | TRIG |
| 7.6.78 | ADIPOQ | CRP | GLUCOSE | HBA1C | HSPA1B | INSULIN-M |
| 7.6.79 | ADIPOQ | CRP | GLUCOSE | HBA1C | HSPA1B | LEP |
| 7.6.80 | ADIPOQ | CRP | GLUCOSE | HBA1C | HSPA1B | TRIG |

FIGURE 11D (continued)

| Panel No. | Marker 1 | Marker 2 | Marker 3 | Marker 4 | Marker 5 | Marker 6 |
|---|---|---|---|---|---|---|
| 7.6.81 | ADIPOQ | CRP | GLUCOSE | HBA1C | IGF1R | LEP |
| 7.6.82 | ADIPOQ | CRP | GLUCOSE | HBA1C | IGFBP1 | INSULIN-M |
| 7.6.83 | ADIPOQ | CRP | GLUCOSE | HBA1C | IGFBP2 | INSULIN-M |
| 7.6.84 | ADIPOQ | CRP | GLUCOSE | HBA1C | IGFBP2 | TIMP2 |
| 7.6.85 | ADIPOQ | CRP | GLUCOSE | HBA1C | IL2RB | INSULIN-M |
| 7.6.86 | ADIPOQ | CRP | GLUCOSE | HBA1C | IL6R | INSULIN-M |
| 7.6.87 | ADIPOQ | CRP | GLUCOSE | HBA1C | IL6R | LEP |
| 7.6.88 | ADIPOQ | CRP | GLUCOSE | HBA1C | INSULIN-M | LEP |
| 7.6.89 | ADIPOQ | CRP | GLUCOSE | HBA1C | INSULIN-M | SCp |
| 7.6.90 | ADIPOQ | CRP | GLUCOSE | HBA1C | INSULIN-M | SHBG |
| 7.6.91 | ADIPOQ | CRP | GLUCOSE | HBA1C | INSULIN-M | TIMP2 |
| 7.6.92 | ADIPOQ | CRP | GLUCOSE | HBA1C | INSULIN-M | TRIG |
| 7.6.93 | ADIPOQ | CRP | GLUCOSE | HBA1C | INSULIN-M | VWF |
| 7.6.94 | ADIPOQ | CRP | GLUCOSE | HBA1C | LEP | TIMP2 |
| 7.6.95 | ADIPOQ | CRP | GLUCOSE | HBA1C | LEP | TRIG |
| 7.6.96 | ADIPOQ | CRP | GLUCOSE | HBA1C | TIMP2 | TRIG |
| 7.6.97 | ADIPOQ | CRP | GLUCOSE | HP | HSPA1B | INSULIN-M |
| 7.6.98 | ADIPOQ | CRP | GLUCOSE | HP | HSPA1B | LEP |
| 7.6.99 | ADIPOQ | CRP | GLUCOSE | HP | LEP | TRIG |
| 7.6.100 | ADIPOQ | CRP | GLUCOSE | HSPA1B | IGF1R | LEP |
| 7.6.101 | ADIPOQ | CRP | GLUCOSE | HSPA1B | IGFBP1 | LEP |
| 7.6.102 | ADIPOQ | CRP | GLUCOSE | HSPA1B | IGFBP2 | LEP |
| 7.6.103 | ADIPOQ | CRP | GLUCOSE | HSPA1B | IL2RA | LEP |
| 7.6.104 | ADIPOQ | CRP | GLUCOSE | HSPA1B | IL2RB | LEP |
| 7.6.105 | ADIPOQ | CRP | GLUCOSE | HSPA1B | IL6R | LEP |
| 7.6.106 | ADIPOQ | CRP | GLUCOSE | HSPA1B | INSULIN-M | LEP |
| 7.6.107 | ADIPOQ | CRP | GLUCOSE | HSPA1B | LEP | SCp |
| 7.6.108 | ADIPOQ | CRP | GLUCOSE | HSPA1B | LEP | SHBG |
| 7.6.109 | ADIPOQ | CRP | GLUCOSE | HSPA1B | LEP | TIMP2 |
| 7.6.110 | ADIPOQ | CRP | GLUCOSE | HSPA1B | LEP | TRIG |
| 7.6.111 | ADIPOQ | CRP | GLUCOSE | HSPA1B | LEP | VWF |
| 7.6.112 | ADIPOQ | CRP | GLUCOSE | LEP | SCp | TRIG |
| 7.6.113 | ADIPOQ | CRP | GLUCOSE | LEP | TRIG | VWF |
| 7.6.114 | CCL2 | CD40 | CRP | GLUCOSE | HBA1C | HP |
| 7.6.115 | CCL2 | CD40 | CRP | GLUCOSE | HBA1C | INSULIN-M |
| 7.6.116 | CCL2 | CRP | EGF | GLUCOSE | GPT | HBA1C |
| 7.6.117 | CCL2 | CRP | EGF | GLUCOSE | HBA1C | HP |
| 7.6.118 | CCL2 | CRP | EGF | GLUCOSE | HBA1C | HSPA1B |
| 7.6.119 | CCL2 | CRP | EGF | GLUCOSE | HBA1C | INSULIN-M |
| 7.6.120 | CCL2 | CRP | EGF | GLUCOSE | HBA1C | TRIG |

FIGURE 11D (continued)

| Panel No. | Marker 1 | Marker 2 | Marker 3 | Marker 4 | Marker 5 | Marker 6 |
|---|---|---|---|---|---|---|
| 7.6.121 | CCL2 | CRP | EGF | GLUCOSE | HSPA1B | INSULIN-M |
| 7.6.122 | CCL2 | CRP | ENG | FTH1 | GLUCOSE | HBA1C |
| 7.6.123 | CCL2 | CRP | ENG | GLUCOSE | GPT | HBA1C |
| 7.6.124 | CCL2 | CRP | ENG | GLUCOSE | GPT | HP |
| 7.6.125 | CCL2 | CRP | ENG | GLUCOSE | GPT | INSULIN-M |
| 7.6.126 | CCL2 | CRP | ENG | GLUCOSE | HBA1C | HP |
| 7.6.127 | CCL2 | CRP | ENG | GLUCOSE | HBA1C | HSPA1B |
| 7.6.128 | CCL2 | CRP | ENG | GLUCOSE | HBA1C | INSULIN-M |
| 7.6.129 | CCL2 | CRP | ENG | GLUCOSE | HBA1C | LEP |
| 7.6.130 | CCL2 | CRP | ENG | GLUCOSE | HBA1C | TRIG |
| 7.6.131 | CCL2 | CRP | ENG | GLUCOSE | HSPA1B | INSULIN-M |
| 7.6.132 | CCL2 | CRP | FGA | GLUCOSE | GPT | HBA1C |
| 7.6.133 | CCL2 | CRP | FGA | GLUCOSE | HBA1C | HP |
| 7.6.134 | CCL2 | CRP | FGA | GLUCOSE | HBA1C | INSULIN-M |
| 7.6.135 | CCL2 | CRP | FGA | GLUCOSE | HBA1C | TRIG |
| 7.6.136 | CCL2 | CRP | FTH1 | GLUCOSE | GPT | HBA1C |
| 7.6.137 | CCL2 | CRP | FTH1 | GLUCOSE | HBA1C | HP |
| 7.6.138 | CCL2 | CRP | FTH1 | GLUCOSE | HBA1C | INSULIN-M |
| 7.6.139 | CCL2 | CRP | GLUCOSE | GPT | HBA1C | HP |
| 7.6.140 | CCL2 | CRP | GLUCOSE | GPT | HBA1C | IGFBP1 |
| 7.6.141 | CCL2 | CRP | GLUCOSE | GPT | HBA1C | IGFBP2 |
| 7.6.142 | CCL2 | CRP | GLUCOSE | GPT | HBA1C | IL2RB |
| 7.6.143 | CCL2 | CRP | GLUCOSE | GPT | HBA1C | IL6R |
| 7.6.144 | CCL2 | CRP | GLUCOSE | GPT | HBA1C | INSULIN-M |
| 7.6.145 | CCL2 | CRP | GLUCOSE | GPT | HBA1C | LEP |
| 7.6.146 | CCL2 | CRP | GLUCOSE | GPT | HBA1C | SHBG |
| 7.6.147 | CCL2 | CRP | GLUCOSE | GPT | HBA1C | TIMP2 |
| 7.6.148 | CCL2 | CRP | GLUCOSE | GPT | HBA1C | TRIG |
| 7.6.149 | CCL2 | CRP | GLUCOSE | GPT | HBA1C | VWF |
| 7.6.150 | CCL2 | CRP | GLUCOSE | GPT | HP | IL2RA |
| 7.6.151 | CCL2 | CRP | GLUCOSE | GPT | HP | INSULIN-M |
| 7.6.152 | CCL2 | CRP | GLUCOSE | GPT | HP | LEP |
| 7.6.153 | CCL2 | CRP | GLUCOSE | GPT | HP | SHBG |
| 7.6.154 | CCL2 | CRP | GLUCOSE | GPT | HP | TRIG |
| 7.6.155 | CCL2 | CRP | GLUCOSE | GPT | HSPA1B | INSULIN-M |
| 7.6.156 | CCL2 | CRP | GLUCOSE | GPT | IGFBP2 | INSULIN-M |
| 7.6.157 | CCL2 | CRP | GLUCOSE | HBA1C | HP | HSPA1B |
| 7.6.158 | CCL2 | CRP | GLUCOSE | HBA1C | HP | IGFBP1 |
| 7.6.159 | CCL2 | CRP | GLUCOSE | HBA1C | HP | IGFBP2 |
| 7.6.160 | CCL2 | CRP | GLUCOSE | HBA1C | HP | IL2RB |

FIGURE 11D (continued)

| Panel No. | Marker 1 | Marker 2 | Marker 3 | Marker 4 | Marker 5 | Marker 6 |
|---|---|---|---|---|---|---|
| 7.6.161 | CCL2 | CRP | GLUCOSE | HBA1C | HP | IL6R |
| 7.6.162 | CCL2 | CRP | GLUCOSE | HBA1C | HP | INSULIN-M |
| 7.6.163 | CCL2 | CRP | GLUCOSE | HBA1C | HP | LEP |
| 7.6.164 | CCL2 | CRP | GLUCOSE | HBA1C | HP | SCp |
| 7.6.165 | CCL2 | CRP | GLUCOSE | HBA1C | HP | SHBG |
| 7.6.166 | CCL2 | CRP | GLUCOSE | HBA1C | HP | TIMP2 |
| 7.6.167 | CCL2 | CRP | GLUCOSE | HBA1C | HP | TRIG |
| 7.6.168 | CCL2 | CRP | GLUCOSE | HBA1C | HSPA1B | INSULIN-M |
| 7.6.169 | CCL2 | CRP | GLUCOSE | HBA1C | HSPA1B | TRIG |
| 7.6.170 | CCL2 | CRP | GLUCOSE | HBA1C | IGF1R | INSULIN-M |
| 7.6.171 | CCL2 | CRP | GLUCOSE | HBA1C | IGFBP1 | INSULIN-M |
| 7.6.172 | CCL2 | CRP | GLUCOSE | HBA1C | IGFBP2 | INSULIN-M |
| 7.6.173 | CCL2 | CRP | GLUCOSE | HBA1C | IL2RA | INSULIN-M |
| 7.6.174 | CCL2 | CRP | GLUCOSE | HBA1C | IL2RB | INSULIN-M |
| 7.6.175 | CCL2 | CRP | GLUCOSE | HBA1C | IL2RB | TRIG |
| 7.6.176 | CCL2 | CRP | GLUCOSE | HBA1C | IL6R | INSULIN-M |
| 7.6.177 | CCL2 | CRP | GLUCOSE | HBA1C | IL6R | TRIG |
| 7.6.178 | CCL2 | CRP | GLUCOSE | HBA1C | INSULIN-M | LEP |
| 7.6.179 | CCL2 | CRP | GLUCOSE | HBA1C | INSULIN-M | SCp |
| 7.6.180 | CCL2 | CRP | GLUCOSE | HBA1C | INSULIN-M | SHBG |
| 7.6.181 | CCL2 | CRP | GLUCOSE | HBA1C | INSULIN-M | TIMP2 |
| 7.6.182 | CCL2 | CRP | GLUCOSE | HBA1C | INSULIN-M | TRIG |
| 7.6.183 | CCL2 | CRP | GLUCOSE | HBA1C | INSULIN-M | VWF |
| 7.6.184 | CCL2 | CRP | GLUCOSE | HBA1C | LEP | TRIG |
| 7.6.185 | CCL2 | CRP | GLUCOSE | HBA1C | TIMP2 | TRIG |
| 7.6.186 | CCL2 | CRP | GLUCOSE | HP | HSPA1B | INSULIN-M |
| 7.6.187 | CCL2 | CRP | GLUCOSE | HP | HSPA1B | LEP |
| 7.6.188 | CCL2 | CRP | GLUCOSE | HP | HSPA1B | TRIG |
| 7.6.189 | CCL2 | CRP | GLUCOSE | HP | IGFBP2 | INSULIN-M |
| 7.6.190 | CCL2 | CRP | GLUCOSE | HP | INSULIN-M | SCp |
| 7.6.191 | CCL2 | CRP | GLUCOSE | HP | INSULIN-M | SHBG |
| 7.6.192 | CCL2 | CRP | GLUCOSE | HP | INSULIN-M | TIMP2 |
| 7.6.193 | CCL2 | CRP | GLUCOSE | HSPA1B | IL2RA | INSULIN-M |
| 7.6.194 | CCL2 | CRP | GLUCOSE | HSPA1B | INSULIN-M | TIMP2 |
| 7.6.195 | CCL2 | CRP | GLUCOSE | HSPA1B | TIMP2 | TRIG |
| 7.6.196 | CD40 | CRP | ENG | GLUCOSE | GPT | INSULIN-M |
| 7.6.197 | CD40 | CRP | ENG | GLUCOSE | HBA1C | INSULIN-M |
| 7.6.198 | CD40 | CRP | ENG | GLUCOSE | HBA1C | TRIG |
| 7.6.199 | CD40 | CRP | GLUCOSE | GPT | HBA1C | HP |
| 7.6.200 | CD40 | CRP | GLUCOSE | GPT | HBA1C | INSULIN-M |

FIGURE 11D (continued)

| Panel No. | Marker 1 | Marker 2 | Marker 3 | Marker 4 | Marker 5 | Marker 6 |
|---|---|---|---|---|---|---|
| 7.6.201 | CD40 | CRP | GLUCOSE | GPT | HP | INSULIN-M |
| 7.6.202 | CD40 | CRP | GLUCOSE | HBA1C | HP | INSULIN-M |
| 7.6.203 | CD40 | CRP | GLUCOSE | HBA1C | HP | TRIG |
| 7.6.204 | CD40 | CRP | GLUCOSE | HBA1C | INSULIN-M | TRIG |
| 7.6.205 | CD40 | CRP | GLUCOSE | HBA1C | TIMP2 | TRIG |
| 7.6.206 | CRP | EGF | ENG | GLUCOSE | GPT | INSULIN-M |
| 7.6.207 | CRP | EGF | ENG | GLUCOSE | HBA1C | INSULIN-M |
| 7.6.208 | CRP | EGF | ENG | GLUCOSE | HBA1C | TRIG |
| 7.6.209 | CRP | EGF | FGA | GLUCOSE | HBA1C | INSULIN-M |
| 7.6.210 | CRP | EGF | FTH1 | GLUCOSE | HBA1C | INSULIN-M |
| 7.6.211 | CRP | EGF | GLUCOSE | GPT | HBA1C | HP |
| 7.6.212 | CRP | EGF | GLUCOSE | GPT | HBA1C | INSULIN-M |
| 7.6.213 | CRP | EGF | GLUCOSE | GPT | HBA1C | LEP |
| 7.6.214 | CRP | EGF | GLUCOSE | GPT | HBA1C | TRIG |
| 7.6.215 | CRP | EGF | GLUCOSE | HBA1C | HP | INSULIN-M |
| 7.6.216 | CRP | EGF | GLUCOSE | HBA1C | HP | TRIG |
| 7.6.217 | CRP | EGF | GLUCOSE | HBA1C | HSPA1B | INSULIN-M |
| 7.6.218 | CRP | EGF | GLUCOSE | HBA1C | HSPA1B | LEP |
| 7.6.219 | CRP | EGF | GLUCOSE | HBA1C | HSPA1B | TRIG |
| 7.6.220 | CRP | EGF | GLUCOSE | HBA1C | IGFBP2 | INSULIN-M |
| 7.6.221 | CRP | EGF | GLUCOSE | HBA1C | IL2RB | TRIG |
| 7.6.222 | CRP | EGF | GLUCOSE | HBA1C | INSULIN-M | SHBG |
| 7.6.223 | CRP | EGF | GLUCOSE | HBA1C | INSULIN-M | TIMP2 |
| 7.6.224 | CRP | EGF | GLUCOSE | HBA1C | INSULIN-M | TRIG |
| 7.6.225 | CRP | EGF | GLUCOSE | HBA1C | LEP | TRIG |
| 7.6.226 | CRP | EGF | GLUCOSE | HBA1C | SHBG | TRIG |
| 7.6.227 | CRP | EGF | GLUCOSE | HBA1C | TIMP2 | TRIG |
| 7.6.228 | CRP | EGF | GLUCOSE | HSPA1B | TIMP2 | TRIG |
| 7.6.229 | CRP | ENG | FGA | GLUCOSE | GPT | INSULIN-M |
| 7.6.230 | CRP | ENG | FGA | GLUCOSE | HBA1C | INSULIN-M |
| 7.6.231 | CRP | ENG | FGA | GLUCOSE | HBA1C | TRIG |
| 7.6.232 | CRP | ENG | FTH1 | GLUCOSE | GPT | HBA1C |
| 7.6.233 | CRP | ENG | FTH1 | GLUCOSE | GPT | INSULIN-M |
| 7.6.234 | CRP | ENG | FTH1 | GLUCOSE | HBA1C | INSULIN-M |
| 7.6.235 | CRP | ENG | FTH1 | GLUCOSE | HBA1C | LEP |
| 7.6.236 | CRP | ENG | FTH1 | GLUCOSE | HBA1C | TRIG |
| 7.6.237 | CRP | ENG | FTH1 | GLUCOSE | HSPA1B | INSULIN-M |
| 7.6.238 | CRP | ENG | GLUCOSE | GPT | HBA1C | HP |
| 7.6.239 | CRP | ENG | GLUCOSE | GPT | HBA1C | IGF1R |
| 7.6.240 | CRP | ENG | GLUCOSE | GPT | HBA1C | IGFBP2 |

FIGURE 11D (continued)

| Panel No. | Marker 1 | Marker 2 | Marker 3 | Marker 4 | Marker 5 | Marker 6 |
|---|---|---|---|---|---|---|
| 7.6.241 | CRP | ENG | GLUCOSE | GPT | HBA1C | IL2RB |
| 7.6.242 | CRP | ENG | GLUCOSE | GPT | HBA1C | INSULIN-M |
| 7.6.243 | CRP | ENG | GLUCOSE | GPT | HBA1C | LEP |
| 7.6.244 | CRP | ENG | GLUCOSE | GPT | HBA1C | TIMP2 |
| 7.6.245 | CRP | ENG | GLUCOSE | GPT | HBA1C | TRIG |
| 7.6.246 | CRP | ENG | GLUCOSE | GPT | HP | INSULIN-M |
| 7.6.247 | CRP | ENG | GLUCOSE | GPT | HSPA1B | INSULIN-M |
| 7.6.248 | CRP | ENG | GLUCOSE | GPT | IGFBP1 | INSULIN-M |
| 7.6.249 | CRP | ENG | GLUCOSE | GPT | IGFBP2 | INSULIN-M |
| 7.6.250 | CRP | ENG | GLUCOSE | GPT | IL2RA | INSULIN-M |
| 7.6.251 | CRP | ENG | GLUCOSE | GPT | IL6R | INSULIN-M |
| 7.6.252 | CRP | ENG | GLUCOSE | GPT | INSULIN-M | LEP |
| 7.6.253 | CRP | ENG | GLUCOSE | GPT | INSULIN-M | SCp |
| 7.6.254 | CRP | ENG | GLUCOSE | GPT | INSULIN-M | SHBG |
| 7.6.255 | CRP | ENG | GLUCOSE | GPT | INSULIN-M | TIMP2 |
| 7.6.256 | CRP | ENG | GLUCOSE | GPT | INSULIN-M | TRIG |
| 7.6.257 | CRP | ENG | GLUCOSE | GPT | INSULIN-M | VWF |
| 7.6.258 | CRP | ENG | GLUCOSE | GPT | LEP | TRIG |
| 7.6.259 | CRP | ENG | GLUCOSE | HBA1C | HP | INSULIN-M |
| 7.6.260 | CRP | ENG | GLUCOSE | HBA1C | HP | TRIG |
| 7.6.261 | CRP | ENG | GLUCOSE | HBA1C | HSPA1B | INSULIN-M |
| 7.6.262 | CRP | ENG | GLUCOSE | HBA1C | HSPA1B | TRIG |
| 7.6.263 | CRP | ENG | GLUCOSE | HBA1C | IGF1R | INSULIN-M |
| 7.6.264 | CRP | ENG | GLUCOSE | HBA1C | IGF1R | TRIG |
| 7.6.265 | CRP | ENG | GLUCOSE | HBA1C | IGFBP1 | INSULIN-M |
| 7.6.266 | CRP | ENG | GLUCOSE | HBA1C | IGFBP1 | TRIG |
| 7.6.267 | CRP | ENG | GLUCOSE | HBA1C | IGFBP2 | INSULIN-M |
| 7.6.268 | CRP | ENG | GLUCOSE | HBA1C | IGFBP2 | TRIG |
| 7.6.269 | CRP | ENG | GLUCOSE | HBA1C | IL2RA | INSULIN-M |
| 7.6.270 | CRP | ENG | GLUCOSE | HBA1C | IL2RA | TRIG |
| 7.6.271 | CRP | ENG | GLUCOSE | HBA1C | IL2RB | INSULIN-M |
| 7.6.272 | CRP | ENG | GLUCOSE | HBA1C | IL2RB | TRIG |
| 7.6.273 | CRP | ENG | GLUCOSE | HBA1C | IL6R | INSULIN-M |
| 7.6.274 | CRP | ENG | GLUCOSE | HBA1C | IL6R | TRIG |
| 7.6.275 | CRP | ENG | GLUCOSE | HBA1C | INSULIN-M | LEP |
| 7.6.276 | CRP | ENG | GLUCOSE | HBA1C | INSULIN-M | SCp |
| 7.6.277 | CRP | ENG | GLUCOSE | HBA1C | INSULIN-M | SHBG |
| 7.6.278 | CRP | ENG | GLUCOSE | HBA1C | INSULIN-M | TIMP2 |
| 7.6.279 | CRP | ENG | GLUCOSE | HBA1C | INSULIN-M | TRIG |
| 7.6.280 | CRP | ENG | GLUCOSE | HBA1C | INSULIN-M | VWF |

FIGURE 11D (continued)

| Panel No. | Marker 1 | Marker 2 | Marker 3 | Marker 4 | Marker 5 | Marker 6 |
|---|---|---|---|---|---|---|
| 7.6.281 | CRP | ENG | GLUCOSE | HBA1C | LEP | TRIG |
| 7.6.282 | CRP | ENG | GLUCOSE | HBA1C | SCp | TRIG |
| 7.6.283 | CRP | ENG | GLUCOSE | HBA1C | SHBG | TRIG |
| 7.6.284 | CRP | ENG | GLUCOSE | HBA1C | TIMP2 | TRIG |
| 7.6.285 | CRP | ENG | GLUCOSE | HBA1C | TRIG | VWF |
| 7.6.286 | CRP | ENG | GLUCOSE | HP | HSPA1B | INSULIN-M |
| 7.6.287 | CRP | ENG | GLUCOSE | HP | INSULIN-M | SHBG |
| 7.6.288 | CRP | ENG | GLUCOSE | HSPA1B | IGFBP2 | INSULIN-M |
| 7.6.289 | CRP | ENG | GLUCOSE | HSPA1B | IL2RA | INSULIN-M |
| 7.6.290 | CRP | ENG | GLUCOSE | HSPA1B | IL2RA | TRIG |
| 7.6.291 | CRP | ENG | GLUCOSE | HSPA1B | INSULIN-M | LEP |
| 7.6.292 | CRP | ENG | GLUCOSE | HSPA1B | INSULIN-M | SHBG |
| 7.6.293 | CRP | ENG | GLUCOSE | HSPA1B | LEP | TRIG |
| 7.6.294 | CRP | FGA | GLUCOSE | GPT | HBA1C | HP |
| 7.6.295 | CRP | FGA | GLUCOSE | GPT | HBA1C | INSULIN-M |
| 7.6.296 | CRP | FGA | GLUCOSE | GPT | HP | INSULIN-M |
| 7.6.297 | CRP | FGA | GLUCOSE | HBA1C | HP | INSULIN-M |
| 7.6.298 | CRP | FGA | GLUCOSE | HBA1C | HP | TRIG |
| 7.6.299 | CRP | FGA | GLUCOSE | HBA1C | HSPA1B | INSULIN-M |
| 7.6.300 | CRP | FGA | GLUCOSE | HBA1C | INSULIN-M | TRIG |
| 7.6.301 | CRP | FGA | GLUCOSE | HBA1C | TIMP2 | TRIG |
| 7.6.302 | CRP | FTH1 | GLUCOSE | GPT | HBA1C | HP |
| 7.6.303 | CRP | FTH1 | GLUCOSE | GPT | HBA1C | INSULIN-M |
| 7.6.304 | CRP | FTH1 | GLUCOSE | HBA1C | HP | INSULIN-M |
| 7.6.305 | CRP | FTH1 | GLUCOSE | HBA1C | HP | TRIG |
| 7.6.306 | CRP | FTH1 | GLUCOSE | HBA1C | INSULIN-M | TRIG |
| 7.6.307 | CRP | FTH1 | GLUCOSE | HBA1C | TIMP2 | TRIG |
| 7.6.308 | CRP | GLUCOSE | GPT | HBA1C | HP | HSPA1B |
| 7.6.309 | CRP | GLUCOSE | GPT | HBA1C | HP | IGF1R |
| 7.6.310 | CRP | GLUCOSE | GPT | HBA1C | HP | IGFBP1 |
| 7.6.311 | CRP | GLUCOSE | GPT | HBA1C | HP | IGFBP2 |
| 7.6.312 | CRP | GLUCOSE | GPT | HBA1C | HP | IL2RA |
| 7.6.313 | CRP | GLUCOSE | GPT | HBA1C | HP | IL2RB |
| 7.6.314 | CRP | GLUCOSE | GPT | HBA1C | HP | INSULIN-M |
| 7.6.315 | CRP | GLUCOSE | GPT | HBA1C | HP | LEP |
| 7.6.316 | CRP | GLUCOSE | GPT | HBA1C | HP | SCp |
| 7.6.317 | CRP | GLUCOSE | GPT | HBA1C | HP | SHBG |
| 7.6.318 | CRP | GLUCOSE | GPT | HBA1C | HP | TIMP2 |
| 7.6.319 | CRP | GLUCOSE | GPT | HBA1C | HP | TRIG |
| 7.6.320 | CRP | GLUCOSE | GPT | HBA1C | HP | VWF |

FIGURE 11D (continued)

| Panel No. | Marker 1 | Marker 2 | Marker 3 | Marker 4 | Marker 5 | Marker 6 |
|---|---|---|---|---|---|---|
| 7.6.321 | CRP | GLUCOSE | GPT | HBA1C | HSPA1B | INSULIN-M |
| 7.6.322 | CRP | GLUCOSE | GPT | HBA1C | IGF1R | INSULIN-M |
| 7.6.323 | CRP | GLUCOSE | GPT | HBA1C | IGFBP1 | INSULIN-M |
| 7.6.324 | CRP | GLUCOSE | GPT | HBA1C | IGFBP2 | INSULIN-M |
| 7.6.325 | CRP | GLUCOSE | GPT | HBA1C | IL2RA | INSULIN-M |
| 7.6.326 | CRP | GLUCOSE | GPT | HBA1C | IL2RB | INSULIN-M |
| 7.6.327 | CRP | GLUCOSE | GPT | HBA1C | IL2RB | LEP |
| 7.6.328 | CRP | GLUCOSE | GPT | HBA1C | IL2RB | TRIG |
| 7.6.329 | CRP | GLUCOSE | GPT | HBA1C | IL6R | INSULIN-M |
| 7.6.330 | CRP | GLUCOSE | GPT | HBA1C | INSULIN-M | LEP |
| 7.6.331 | CRP | GLUCOSE | GPT | HBA1C | INSULIN-M | SCp |
| 7.6.332 | CRP | GLUCOSE | GPT | HBA1C | INSULIN-M | SHBG |
| 7.6.333 | CRP | GLUCOSE | GPT | HBA1C | INSULIN-M | TIMP2 |
| 7.6.334 | CRP | GLUCOSE | GPT | HBA1C | INSULIN-M | TRIG |
| 7.6.335 | CRP | GLUCOSE | GPT | HBA1C | INSULIN-M | VWF |
| 7.6.336 | CRP | GLUCOSE | GPT | HBA1C | LEP | TRIG |
| 7.6.337 | CRP | GLUCOSE | GPT | HBA1C | TIMP2 | TRIG |
| 7.6.338 | CRP | GLUCOSE | GPT | HP | HSPA1B | INSULIN-M |
| 7.6.339 | CRP | GLUCOSE | GPT | HP | IGFBP2 | INSULIN-M |
| 7.6.340 | CRP | GLUCOSE | GPT | HP | INSULIN-M | LEP |
| 7.6.341 | CRP | GLUCOSE | GPT | HP | INSULIN-M | SCp |
| 7.6.342 | CRP | GLUCOSE | GPT | HP | INSULIN-M | SHBG |
| 7.6.343 | CRP | GLUCOSE | GPT | HP | INSULIN-M | TRIG |
| 7.6.344 | CRP | GLUCOSE | GPT | HP | LEP | TRIG |
| 7.6.345 | CRP | GLUCOSE | HBA1C | HP | HSPA1B | INSULIN-M |
| 7.6.346 | CRP | GLUCOSE | HBA1C | HP | HSPA1B | TRIG |
| 7.6.347 | CRP | GLUCOSE | HBA1C | HP | IGF1R | INSULIN-M |
| 7.6.348 | CRP | GLUCOSE | HBA1C | HP | IGF1R | TRIG |
| 7.6.349 | CRP | GLUCOSE | HBA1C | HP | IGFBP1 | INSULIN-M |
| 7.6.350 | CRP | GLUCOSE | HBA1C | HP | IGFBP1 | TRIG |
| 7.6.351 | CRP | GLUCOSE | HBA1C | HP | IGFBP2 | INSULIN-M |
| 7.6.352 | CRP | GLUCOSE | HBA1C | HP | IGFBP2 | TRIG |
| 7.6.353 | CRP | GLUCOSE | HBA1C | HP | IL2RA | INSULIN-M |
| 7.6.354 | CRP | GLUCOSE | HBA1C | HP | IL2RA | TRIG |
| 7.6.355 | CRP | GLUCOSE | HBA1C | HP | IL2RB | INSULIN-M |
| 7.6.356 | CRP | GLUCOSE | HBA1C | HP | IL2RB | TRIG |
| 7.6.357 | CRP | GLUCOSE | HBA1C | HP | IL6R | INSULIN-M |
| 7.6.358 | CRP | GLUCOSE | HBA1C | HP | IL6R | TRIG |
| 7.6.359 | CRP | GLUCOSE | HBA1C | HP | INSULIN-M | LEP |
| 7.6.360 | CRP | GLUCOSE | HBA1C | HP | INSULIN-M | SCp |

FIGURE 11D (continued)

| Panel No. | Marker 1 | Marker 2 | Marker 3 | Marker 4 | Marker 5 | Marker 6 |
|---|---|---|---|---|---|---|
| 7.6.361 | CRP | GLUCOSE | HBA1C | HP | INSULIN-M | SHBG |
| 7.6.362 | CRP | GLUCOSE | HBA1C | HP | INSULIN-M | TIMP2 |
| 7.6.363 | CRP | GLUCOSE | HBA1C | HP | INSULIN-M | TRIG |
| 7.6.364 | CRP | GLUCOSE | HBA1C | HP | INSULIN-M | VWF |
| 7.6.365 | CRP | GLUCOSE | HBA1C | HP | LEP | TRIG |
| 7.6.366 | CRP | GLUCOSE | HBA1C | HP | SCp | TRIG |
| 7.6.367 | CRP | GLUCOSE | HBA1C | HP | SHBG | TRIG |
| 7.6.368 | CRP | GLUCOSE | HBA1C | HP | TIMP2 | TRIG |
| 7.6.369 | CRP | GLUCOSE | HBA1C | HP | TRIG | VWF |
| 7.6.370 | CRP | GLUCOSE | HBA1C | HSPA1B | IGFBP2 | INSULIN-M |
| 7.6.371 | CRP | GLUCOSE | HBA1C | HSPA1B | IL2RA | INSULIN-M |
| 7.6.372 | CRP | GLUCOSE | HBA1C | HSPA1B | IL2RA | TRIG |
| 7.6.373 | CRP | GLUCOSE | HBA1C | HSPA1B | IL2RB | INSULIN-M |
| 7.6.374 | CRP | GLUCOSE | HBA1C | HSPA1B | IL2RB | TRIG |
| 7.6.375 | CRP | GLUCOSE | HBA1C | HSPA1B | IL6R | INSULIN-M |
| 7.6.376 | CRP | GLUCOSE | HBA1C | HSPA1B | INSULIN-M | LEP |
| 7.6.377 | CRP | GLUCOSE | HBA1C | HSPA1B | INSULIN-M | TIMP2 |
| 7.6.378 | CRP | GLUCOSE | HBA1C | HSPA1B | INSULIN-M | TRIG |
| 7.6.379 | CRP | GLUCOSE | HBA1C | HSPA1B | LEP | TRIG |
| 7.6.380 | CRP | GLUCOSE | HBA1C | HSPA1B | TIMP2 | TRIG |
| 7.6.381 | CRP | GLUCOSE | HBA1C | IGFBP1 | INSULIN-M | TRIG |
| 7.6.382 | CRP | GLUCOSE | HBA1C | IGFBP2 | INSULIN-M | TRIG |
| 7.6.383 | CRP | GLUCOSE | HBA1C | IGFBP2 | TIMP2 | TRIG |
| 7.6.384 | CRP | GLUCOSE | HBA1C | IL2RA | TIMP2 | TRIG |
| 7.6.385 | CRP | GLUCOSE | HBA1C | IL2RB | INSULIN-M | TRIG |
| 7.6.386 | CRP | GLUCOSE | HBA1C | IL2RB | TIMP2 | TRIG |
| 7.6.387 | CRP | GLUCOSE | HBA1C | IL6R | INSULIN-M | TIMP2 |
| 7.6.388 | CRP | GLUCOSE | HBA1C | IL6R | INSULIN-M | TRIG |
| 7.6.389 | CRP | GLUCOSE | HBA1C | IL6R | TIMP2 | TRIG |
| 7.6.390 | CRP | GLUCOSE | HBA1C | INSULIN-M | LEP | TRIG |
| 7.6.391 | CRP | GLUCOSE | HBA1C | INSULIN-M | SCp | TRIG |
| 7.6.392 | CRP | GLUCOSE | HBA1C | INSULIN-M | SHBG | TRIG |
| 7.6.393 | CRP | GLUCOSE | HBA1C | INSULIN-M | TIMP2 | TRIG |
| 7.6.394 | CRP | GLUCOSE | HBA1C | LEP | TIMP2 | TRIG |
| 7.6.395 | CRP | GLUCOSE | HBA1C | SCp | TIMP2 | TRIG |
| 7.6.396 | CRP | GLUCOSE | HBA1C | TIMP2 | TRIG | VWF |
| 7.6.397 | CRP | GLUCOSE | HP | HSPA1B | IGFBP2 | INSULIN-M |
| 7.6.398 | CRP | GLUCOSE | HP | INSULIN-M | SHBG | TRIG |
| 7.6.399 | CRP | GLUCOSE | HSPA1B | IL2RA | TIMP2 | TRIG |
| 7.6.400 | ENG | GLUCOSE | HBA1C | HSPA1B | LEP | TRIG |

FIGURE 11E

| Panel No. | Marker 1 | Marker 2 | Marker 3 | Marker 4 | Marker 5 | Marker 6 | Marker 7 |
|---|---|---|---|---|---|---|---|
| 7.7.1 | ADIPOQ | CCL2 | CRP | EGF | GLUCOSE | HSPA1B | LEP |
| 7.7.2 | ADIPOQ | CCL2 | CRP | ENG | GLUCOSE | GPT | HBA1C |
| 7.7.3 | ADIPOQ | CCL2 | CRP | ENG | GLUCOSE | GPT | LEP |
| 7.7.4 | ADIPOQ | CCL2 | CRP | ENG | GLUCOSE | HBA1C | INSULIN-M |
| 7.7.5 | ADIPOQ | CCL2 | CRP | GLUCOSE | GPT | HBA1C | HP |
| 7.7.6 | ADIPOQ | CCL2 | CRP | GLUCOSE | GPT | HBA1C | IGFBP2 |
| 7.7.7 | ADIPOQ | CCL2 | CRP | GLUCOSE | GPT | HBA1C | INSULIN-M |
| 7.7.8 | ADIPOQ | CCL2 | CRP | GLUCOSE | GPT | HBA1C | LEP |
| 7.7.9 | ADIPOQ | CCL2 | CRP | GLUCOSE | GPT | HBA1C | TIMP2 |
| 7.7.10 | ADIPOQ | CCL2 | CRP | GLUCOSE | GPT | HP | LEP |
| 7.7.11 | ADIPOQ | CCL2 | CRP | GLUCOSE | GPT | HSPA1B | LEP |
| 7.7.12 | ADIPOQ | CCL2 | CRP | GLUCOSE | HBA1C | HP | HSPA1B |
| 7.7.13 | ADIPOQ | CCL2 | CRP | GLUCOSE | HBA1C | HP | INSULIN-M |
| 7.7.14 | ADIPOQ | CCL2 | CRP | GLUCOSE | HBA1C | HP | LEP |
| 7.7.15 | ADIPOQ | CCL2 | CRP | GLUCOSE | HBA1C | HP | SHBG |
| 7.7.16 | ADIPOQ | CCL2 | CRP | GLUCOSE | HBA1C | HP | TIMP2 |
| 7.7.17 | ADIPOQ | CCL2 | CRP | GLUCOSE | HBA1C | HP | TRIG |
| 7.7.18 | ADIPOQ | CCL2 | CRP | GLUCOSE | HBA1C | HSPA1B | INSULIN-M |
| 7.7.19 | ADIPOQ | CCL2 | CRP | GLUCOSE | HBA1C | HSPA1B | LEP |
| 7.7.20 | ADIPOQ | CCL2 | CRP | GLUCOSE | HBA1C | LEP | TRIG |
| 7.7.21 | ADIPOQ | CCL2 | CRP | GLUCOSE | HBA1C | TIMP2 | TRIG |
| 7.7.22 | ADIPOQ | CCL2 | CRP | GLUCOSE | HP | HSPA1B | LEP |
| 7.7.23 | ADIPOQ | CCL2 | CRP | GLUCOSE | HSPA1B | IGFBP2 | LEP |
| 7.7.24 | ADIPOQ | CCL2 | CRP | GLUCOSE | HSPA1B | INSULIN-M | LEP |
| 7.7.25 | ADIPOQ | CCL2 | CRP | GLUCOSE | HSPA1B | LEP | TRIG |
| 7.7.26 | ADIPOQ | CD40 | CRP | GLUCOSE | GPT | HBA1C | LEP |
| 7.7.27 | ADIPOQ | CRP | EGF | GLUCOSE | GPT | HBA1C | LEP |
| 7.7.28 | ADIPOQ | CRP | EGF | GLUCOSE | GPT | HSPA1B | LEP |
| 7.7.29 | ADIPOQ | CRP | EGF | GLUCOSE | HBA1C | LEP | TRIG |
| 7.7.30 | ADIPOQ | CRP | EGF | GLUCOSE | HSPA1B | IGFBP2 | LEP |
| 7.7.31 | ADIPOQ | CRP | EGF | GLUCOSE | HSPA1B | LEP | TRIG |
| 7.7.32 | ADIPOQ | CRP | ENG | FTH1 | GLUCOSE | GPT | LEP |
| 7.7.33 | ADIPOQ | CRP | ENG | FTH1 | GLUCOSE | HSPA1B | LEP |
| 7.7.34 | ADIPOQ | CRP | ENG | GLUCOSE | GPT | HBA1C | INSULIN-M |
| 7.7.35 | ADIPOQ | CRP | ENG | GLUCOSE | GPT | HBA1C | LEP |
| 7.7.36 | ADIPOQ | CRP | ENG | GLUCOSE | GPT | HP | LEP |
| 7.7.37 | ADIPOQ | CRP | ENG | GLUCOSE | GPT | HSPA1B | LEP |
| 7.7.38 | ADIPOQ | CRP | ENG | GLUCOSE | GPT | IGFBP2 | LEP |
| 7.7.39 | ADIPOQ | CRP | ENG | GLUCOSE | GPT | LEP | TRIG |
| 7.7.40 | ADIPOQ | CRP | ENG | GLUCOSE | HBA1C | HP | INSULIN-M |

FIGURE 11E (continued)

| Panel No. | Marker 1 | Marker 2 | Marker 3 | Marker 4 | Marker 5 | Marker 6 | Marker 7 |
|---|---|---|---|---|---|---|---|
| 7.7.41 | ADIPOQ | CRP | ENG | GLUCOSE | HBA1C | HP | LEP |
| 7.7.42 | ADIPOQ | CRP | ENG | GLUCOSE | HBA1C | HSPA1B | INSULIN-M |
| 7.7.43 | ADIPOQ | CRP | ENG | GLUCOSE | HBA1C | HSPA1B | LEP |
| 7.7.44 | ADIPOQ | CRP | ENG | GLUCOSE | HBA1C | HSPA1B | TRIG |
| 7.7.45 | ADIPOQ | CRP | ENG | GLUCOSE | HBA1C | INSULIN-M | SHBG |
| 7.7.46 | ADIPOQ | CRP | ENG | GLUCOSE | HBA1C | LEP | TRIG |
| 7.7.47 | ADIPOQ | CRP | ENG | GLUCOSE | HBA1C | TIMP2 | TRIG |
| 7.7.48 | ADIPOQ | CRP | ENG | GLUCOSE | HP | HSPA1B | LEP |
| 7.7.49 | ADIPOQ | CRP | ENG | GLUCOSE | HSPA1B | IGFBP2 | LEP |
| 7.7.50 | ADIPOQ | CRP | ENG | GLUCOSE | HSPA1B | IL2RA | LEP |
| 7.7.51 | ADIPOQ | CRP | ENG | GLUCOSE | HSPA1B | INSULIN-M | LEP |
| 7.7.52 | ADIPOQ | CRP | ENG | GLUCOSE | HSPA1B | LEP | TRIG |
| 7.7.53 | ADIPOQ | CRP | FGA | GLUCOSE | GPT | HBA1C | INSULIN-M |
| 7.7.54 | ADIPOQ | CRP | FGA | GLUCOSE | GPT | HBA1C | LEP |
| 7.7.55 | ADIPOQ | CRP | FTH1 | GLUCOSE | GPT | HBA1C | LEP |
| 7.7.56 | ADIPOQ | CRP | FTH1 | GLUCOSE | GPT | HP | LEP |
| 7.7.57 | ADIPOQ | CRP | FTH1 | GLUCOSE | GPT | HSPA1B | LEP |
| 7.7.58 | ADIPOQ | CRP | FTH1 | GLUCOSE | HP | HSPA1B | LEP |
| 7.7.59 | ADIPOQ | CRP | GLUCOSE | GPT | HBA1C | HP | IGF1R |
| 7.7.60 | ADIPOQ | CRP | GLUCOSE | GPT | HBA1C | HP | IGFBP2 |
| 7.7.61 | ADIPOQ | CRP | GLUCOSE | GPT | HBA1C | HP | IL2RB |
| 7.7.62 | ADIPOQ | CRP | GLUCOSE | GPT | HBA1C | HP | INSULIN-M |
| 7.7.63 | ADIPOQ | CRP | GLUCOSE | GPT | HBA1C | HP | LEP |
| 7.7.64 | ADIPOQ | CRP | GLUCOSE | GPT | HBA1C | HP | SHBG |
| 7.7.65 | ADIPOQ | CRP | GLUCOSE | GPT | HBA1C | HP | TIMP2 |
| 7.7.66 | ADIPOQ | CRP | GLUCOSE | GPT | HBA1C | HP | TRIG |
| 7.7.67 | ADIPOQ | CRP | GLUCOSE | GPT | HBA1C | HSPA1B | INSULIN-M |
| 7.7.68 | ADIPOQ | CRP | GLUCOSE | GPT | HBA1C | HSPA1B | LEP |
| 7.7.69 | ADIPOQ | CRP | GLUCOSE | GPT | HBA1C | IGF1R | LEP |
| 7.7.70 | ADIPOQ | CRP | GLUCOSE | GPT | HBA1C | IGFBP1 | LEP |
| 7.7.71 | ADIPOQ | CRP | GLUCOSE | GPT | HBA1C | IGFBP2 | INSULIN-M |
| 7.7.72 | ADIPOQ | CRP | GLUCOSE | GPT | HBA1C | IGFBP2 | LEP |
| 7.7.73 | ADIPOQ | CRP | GLUCOSE | GPT | HBA1C | IGFBP2 | TIMP2 |
| 7.7.74 | ADIPOQ | CRP | GLUCOSE | GPT | HBA1C | IL2RA | LEP |
| 7.7.75 | ADIPOQ | CRP | GLUCOSE | GPT | HBA1C | IL2RB | LEP |
| 7.7.76 | ADIPOQ | CRP | GLUCOSE | GPT | HBA1C | IL6R | LEP |
| 7.7.77 | ADIPOQ | CRP | GLUCOSE | GPT | HBA1C | INSULIN-M | LEP |
| 7.7.78 | ADIPOQ | CRP | GLUCOSE | GPT | HBA1C | INSULIN-M | SHBG |
| 7.7.79 | ADIPOQ | CRP | GLUCOSE | GPT | HBA1C | INSULIN-M | TIMP2 |
| 7.7.80 | ADIPOQ | CRP | GLUCOSE | GPT | HBA1C | LEP | SHBG |

FIGURE 11E (continued)

| Panel No. | Marker 1 | Marker 2 | Marker 3 | Marker 4 | Marker 5 | Marker 6 | Marker 7 |
|---|---|---|---|---|---|---|---|
| 7.7.81 | ADIPOQ | CRP | GLUCOSE | GPT | HBA1C | LEP | TIMP2 |
| 7.7.82 | ADIPOQ | CRP | GLUCOSE | GPT | HBA1C | LEP | TRIG |
| 7.7.83 | ADIPOQ | CRP | GLUCOSE | GPT | HBA1C | LEP | VWF |
| 7.7.84 | ADIPOQ | CRP | GLUCOSE | GPT | HBA1C | TIMP2 | TRIG |
| 7.7.85 | ADIPOQ | CRP | GLUCOSE | GPT | HP | HSPA1B | LEP |
| 7.7.86 | ADIPOQ | CRP | GLUCOSE | GPT | HP | IGFBP2 | INSULIN-M |
| 7.7.87 | ADIPOQ | CRP | GLUCOSE | GPT | HP | IGFBP2 | LEP |
| 7.7.88 | ADIPOQ | CRP | GLUCOSE | GPT | HP | INSULIN-M | LEP |
| 7.7.89 | ADIPOQ | CRP | GLUCOSE | GPT | HP | INSULIN-M | SHBG |
| 7.7.90 | ADIPOQ | CRP | GLUCOSE | GPT | HP | LEP | SHBG |
| 7.7.91 | ADIPOQ | CRP | GLUCOSE | GPT | HP | LEP | TRIG |
| 7.7.92 | ADIPOQ | CRP | GLUCOSE | GPT | HP | LEP | VWF |
| 7.7.93 | ADIPOQ | CRP | GLUCOSE | GPT | HSPA1B | IGF1R | LEP |
| 7.7.94 | ADIPOQ | CRP | GLUCOSE | GPT | HSPA1B | IGFBP2 | LEP |
| 7.7.95 | ADIPOQ | CRP | GLUCOSE | GPT | HSPA1B | IL2RA | LEP |
| 7.7.96 | ADIPOQ | CRP | GLUCOSE | GPT | HSPA1B | IL2RB | LEP |
| 7.7.97 | ADIPOQ | CRP | GLUCOSE | GPT | HSPA1B | INSULIN-M | LEP |
| 7.7.98 | ADIPOQ | CRP | GLUCOSE | GPT | HSPA1B | LEP | TIMP2 |
| 7.7.99 | ADIPOQ | CRP | GLUCOSE | GPT | HSPA1B | LEP | TRIG |
| 7.7.100 | ADIPOQ | CRP | GLUCOSE | GPT | IGFBP2 | LEP | TIMP2 |
| 7.7.101 | ADIPOQ | CRP | GLUCOSE | HBA1C | HP | HSPA1B | IGFBP2 |
| 7.7.102 | ADIPOQ | CRP | GLUCOSE | HBA1C | HP | HSPA1B | INSULIN-M |
| 7.7.103 | ADIPOQ | CRP | GLUCOSE | HBA1C | HP | HSPA1B | LEP |
| 7.7.104 | ADIPOQ | CRP | GLUCOSE | HBA1C | HP | HSPA1B | TRIG |
| 7.7.105 | ADIPOQ | CRP | GLUCOSE | HBA1C | HP | IGFBP2 | INSULIN-M |
| 7.7.106 | ADIPOQ | CRP | GLUCOSE | HBA1C | HP | IGFBP2 | LEP |
| 7.7.107 | ADIPOQ | CRP | GLUCOSE | HBA1C | HP | INSULIN-M | LEP |
| 7.7.108 | ADIPOQ | CRP | GLUCOSE | HBA1C | HP | INSULIN-M | SHBG |
| 7.7.109 | ADIPOQ | CRP | GLUCOSE | HBA1C | HP | INSULIN-M | TIMP2 |
| 7.7.110 | ADIPOQ | CRP | GLUCOSE | HBA1C | HP | INSULIN-M | TRIG |
| 7.7.111 | ADIPOQ | CRP | GLUCOSE | HBA1C | HP | LEP | TIMP2 |
| 7.7.112 | ADIPOQ | CRP | GLUCOSE | HBA1C | HP | LEP | TRIG |
| 7.7.113 | ADIPOQ | CRP | GLUCOSE | HBA1C | HP | SHBG | TRIG |
| 7.7.114 | ADIPOQ | CRP | GLUCOSE | HBA1C | HP | TIMP2 | TRIG |
| 7.7.115 | ADIPOQ | CRP | GLUCOSE | HBA1C | HSPA1B | IGF1R | LEP |
| 7.7.116 | ADIPOQ | CRP | GLUCOSE | HBA1C | HSPA1B | IGFBP2 | INSULIN-M |
| 7.7.117 | ADIPOQ | CRP | GLUCOSE | HBA1C | HSPA1B | IGFBP2 | LEP |
| 7.7.118 | ADIPOQ | CRP | GLUCOSE | HBA1C | HSPA1B | INSULIN-M | LEP |
| 7.7.119 | ADIPOQ | CRP | GLUCOSE | HBA1C | HSPA1B | LEP | TIMP2 |
| 7.7.120 | ADIPOQ | CRP | GLUCOSE | HBA1C | HSPA1B | LEP | TRIG |

FIGURE 11E (continued)

| Panel No. | Marker 1 | Marker 2 | Marker 3 | Marker 4 | Marker 5 | Marker 6 | Marker 7 |
|---|---|---|---|---|---|---|---|
| 7.7.121 | ADIPOQ | CRP | GLUCOSE | HBA1C | HSPA1B | TIMP2 | TRIG |
| 7.7.122 | ADIPOQ | CRP | GLUCOSE | HBA1C | LEP | TIMP2 | TRIG |
| 7.7.123 | ADIPOQ | CRP | GLUCOSE | HP | HSPA1B | IGFBP2 | LEP |
| 7.7.124 | ADIPOQ | CRP | GLUCOSE | HP | HSPA1B | IL2RA | LEP |
| 7.7.125 | ADIPOQ | CRP | GLUCOSE | HP | HSPA1B | LEP | TIMP2 |
| 7.7.126 | ADIPOQ | CRP | GLUCOSE | HP | HSPA1B | LEP | TRIG |
| 7.7.127 | ADIPOQ | CRP | GLUCOSE | HSPA1B | IGFBP2 | IL2RB | LEP |
| 7.7.128 | ADIPOQ | CRP | GLUCOSE | HSPA1B | IGFBP2 | INSULIN-M | LEP |
| 7.7.129 | ADIPOQ | CRP | GLUCOSE | HSPA1B | IGFBP2 | LEP | TRIG |
| 7.7.130 | ADIPOQ | CRP | GLUCOSE | HSPA1B | IL6R | LEP | TRIG |
| 7.7.131 | ADIPOQ | CRP | GLUCOSE | HSPA1B | LEP | TIMP2 | TRIG |
| 7.7.132 | CCL2 | CD40 | CRP | GLUCOSE | GPT | HBA1C | HP |
| 7.7.133 | CCL2 | CD40 | CRP | GLUCOSE | GPT | HBA1C | INSULIN-M |
| 7.7.134 | CCL2 | CD40 | CRP | GLUCOSE | HBA1C | HP | INSULIN-M |
| 7.7.135 | CCL2 | CRP | EGF | ENG | GLUCOSE | HBA1C | INSULIN-M |
| 7.7.136 | CCL2 | CRP | EGF | GLUCOSE | GPT | HBA1C | HP |
| 7.7.137 | CCL2 | CRP | EGF | GLUCOSE | GPT | HBA1C | INSULIN-M |
| 7.7.138 | CCL2 | CRP | EGF | GLUCOSE | GPT | HBA1C | TRIG |
| 7.7.139 | CCL2 | CRP | EGF | GLUCOSE | HBA1C | HP | INSULIN-M |
| 7.7.140 | CCL2 | CRP | EGF | GLUCOSE | HBA1C | HSPA1B | INSULIN-M |
| 7.7.141 | CCL2 | CRP | EGF | GLUCOSE | HBA1C | HSPA1B | TRIG |
| 7.7.142 | CCL2 | CRP | EGF | GLUCOSE | HBA1C | INSULIN-M | SHBG |
| 7.7.143 | CCL2 | CRP | EGF | GLUCOSE | HBA1C | TIMP2 | TRIG |
| 7.7.144 | CCL2 | CRP | ENG | FGA | GLUCOSE | HBA1C | INSULIN-M |
| 7.7.145 | CCL2 | CRP | ENG | FTH1 | GLUCOSE | GPT | HBA1C |
| 7.7.146 | CCL2 | CRP | ENG | FTH1 | GLUCOSE | HBA1C | INSULIN-M |
| 7.7.147 | CCL2 | CRP | ENG | FTH1 | GLUCOSE | HBA1C | LEP |
| 7.7.148 | CCL2 | CRP | ENG | GLUCOSE | GPT | HBA1C | HP |
| 7.7.149 | CCL2 | CRP | ENG | GLUCOSE | GPT | HBA1C | INSULIN-M |
| 7.7.150 | CCL2 | CRP | ENG | GLUCOSE | GPT | HBA1C | LEP |
| 7.7.151 | CCL2 | CRP | ENG | GLUCOSE | GPT | HBA1C | TIMP2 |
| 7.7.152 | CCL2 | CRP | ENG | GLUCOSE | GPT | HBA1C | TRIG |
| 7.7.153 | CCL2 | CRP | ENG | GLUCOSE | GPT | HP | INSULIN-M |
| 7.7.154 | CCL2 | CRP | ENG | GLUCOSE | GPT | HSPA1B | INSULIN-M |
| 7.7.155 | CCL2 | CRP | ENG | GLUCOSE | GPT | INSULIN-M | SHBG |
| 7.7.156 | CCL2 | CRP | ENG | GLUCOSE | HBA1C | HP | HSPA1B |
| 7.7.157 | CCL2 | CRP | ENG | GLUCOSE | HBA1C | HP | INSULIN-M |
| 7.7.158 | CCL2 | CRP | ENG | GLUCOSE | HBA1C | HP | TRIG |
| 7.7.159 | CCL2 | CRP | ENG | GLUCOSE | HBA1C | HSPA1B | INSULIN-M |
| 7.7.160 | CCL2 | CRP | ENG | GLUCOSE | HBA1C | HSPA1B | TRIG |

FIGURE 11E (continued)

| Panel No. | Marker 1 | Marker 2 | Marker 3 | Marker 4 | Marker 5 | Marker 6 | Marker 7 |
|---|---|---|---|---|---|---|---|
| 7.7.161 | CCL2 | CRP | ENG | GLUCOSE | HBA1C | IGFBP2 | INSULIN-M |
| 7.7.162 | CCL2 | CRP | ENG | GLUCOSE | HBA1C | IL6R | INSULIN-M |
| 7.7.163 | CCL2 | CRP | ENG | GLUCOSE | HBA1C | INSULIN-M | LEP |
| 7.7.164 | CCL2 | CRP | ENG | GLUCOSE | HBA1C | INSULIN-M | SCp |
| 7.7.165 | CCL2 | CRP | ENG | GLUCOSE | HBA1C | INSULIN-M | SHBG |
| 7.7.166 | CCL2 | CRP | ENG | GLUCOSE | HBA1C | INSULIN-M | TIMP2 |
| 7.7.167 | CCL2 | CRP | ENG | GLUCOSE | HBA1C | INSULIN-M | TRIG |
| 7.7.168 | CCL2 | CRP | ENG | GLUCOSE | HBA1C | LEP | TRIG |
| 7.7.169 | CCL2 | CRP | ENG | GLUCOSE | HBA1C | SHBG | TRIG |
| 7.7.170 | CCL2 | CRP | ENG | GLUCOSE | HBA1C | TIMP2 | TRIG |
| 7.7.171 | CCL2 | CRP | ENG | GLUCOSE | HP | HSPA1B | INSULIN-M |
| 7.7.172 | CCL2 | CRP | FGA | GLUCOSE | GPT | HBA1C | HP |
| 7.7.173 | CCL2 | CRP | FGA | GLUCOSE | GPT | HBA1C | INSULIN-M |
| 7.7.174 | CCL2 | CRP | FGA | GLUCOSE | HBA1C | HP | INSULIN-M |
| 7.7.175 | CCL2 | CRP | FGA | GLUCOSE | HBA1C | HSPA1B | INSULIN-M |
| 7.7.176 | CCL2 | CRP | FTH1 | GLUCOSE | GPT | HBA1C | HP |
| 7.7.177 | CCL2 | CRP | FTH1 | GLUCOSE | GPT | HBA1C | INSULIN-M |
| 7.7.178 | CCL2 | CRP | FTH1 | GLUCOSE | HBA1C | HP | INSULIN-M |
| 7.7.179 | CCL2 | CRP | GLUCOSE | GPT | HBA1C | HP | HSPA1B |
| 7.7.180 | CCL2 | CRP | GLUCOSE | GPT | HBA1C | HP | IGF1R |
| 7.7.181 | CCL2 | CRP | GLUCOSE | GPT | HBA1C | HP | IGFBP1 |
| 7.7.182 | CCL2 | CRP | GLUCOSE | GPT | HBA1C | HP | IGFBP2 |
| 7.7.183 | CCL2 | CRP | GLUCOSE | GPT | HBA1C | HP | IL2RA |
| 7.7.184 | CCL2 | CRP | GLUCOSE | GPT | HBA1C | HP | IL2RB |
| 7.7.185 | CCL2 | CRP | GLUCOSE | GPT | HBA1C | HP | IL6R |
| 7.7.186 | CCL2 | CRP | GLUCOSE | GPT | HBA1C | HP | INSULIN-M |
| 7.7.187 | CCL2 | CRP | GLUCOSE | GPT | HBA1C | HP | LEP |
| 7.7.188 | CCL2 | CRP | GLUCOSE | GPT | HBA1C | HP | SCp |
| 7.7.189 | CCL2 | CRP | GLUCOSE | GPT | HBA1C | HP | SHBG |
| 7.7.190 | CCL2 | CRP | GLUCOSE | GPT | HBA1C | HP | TIMP2 |
| 7.7.191 | CCL2 | CRP | GLUCOSE | GPT | HBA1C | HP | TRIG |
| 7.7.192 | CCL2 | CRP | GLUCOSE | GPT | HBA1C | HP | VWF |
| 7.7.193 | CCL2 | CRP | GLUCOSE | GPT | HBA1C | HSPA1B | INSULIN-M |
| 7.7.194 | CCL2 | CRP | GLUCOSE | GPT | HBA1C | IGF1R | INSULIN-M |
| 7.7.195 | CCL2 | CRP | GLUCOSE | GPT | HBA1C | IGFBP1 | INSULIN-M |
| 7.7.196 | CCL2 | CRP | GLUCOSE | GPT | HBA1C | IGFBP2 | INSULIN-M |
| 7.7.197 | CCL2 | CRP | GLUCOSE | GPT | HBA1C | IL2RB | INSULIN-M |
| 7.7.198 | CCL2 | CRP | GLUCOSE | GPT | HBA1C | IL6R | INSULIN-M |
| 7.7.199 | CCL2 | CRP | GLUCOSE | GPT | HBA1C | INSULIN-M | LEP |
| 7.7.200 | CCL2 | CRP | GLUCOSE | GPT | HBA1C | INSULIN-M | SCp |

FIGURE 11E (continued)

| Panel No. | Marker 1 | Marker 2 | Marker 3 | Marker 4 | Marker 5 | Marker 6 | Marker 7 |
|---|---|---|---|---|---|---|---|
| 7.7.201 | CCL2 | CRP | GLUCOSE | GPT | HBA1C | INSULIN-M | SHBG |
| 7.7.202 | CCL2 | CRP | GLUCOSE | GPT | HBA1C | INSULIN-M | TIMP2 |
| 7.7.203 | CCL2 | CRP | GLUCOSE | GPT | HBA1C | INSULIN-M | TRIG |
| 7.7.204 | CCL2 | CRP | GLUCOSE | GPT | HBA1C | INSULIN-M | VWF |
| 7.7.205 | CCL2 | CRP | GLUCOSE | GPT | HBA1C | TIMP2 | TRIG |
| 7.7.206 | CCL2 | CRP | GLUCOSE | GPT | HP | HSPA1B | INSULIN-M |
| 7.7.207 | CCL2 | CRP | GLUCOSE | GPT | HP | IGFBP2 | INSULIN-M |
| 7.7.208 | CCL2 | CRP | GLUCOSE | GPT | HP | IL2RA | INSULIN-M |
| 7.7.209 | CCL2 | CRP | GLUCOSE | GPT | HP | INSULIN-M | LEP |
| 7.7.210 | CCL2 | CRP | GLUCOSE | GPT | HP | INSULIN-M | SHBG |
| 7.7.211 | CCL2 | CRP | GLUCOSE | HBA1C | HP | HSPA1B | IGFBP2 |
| 7.7.212 | CCL2 | CRP | GLUCOSE | HBA1C | HP | HSPA1B | INSULIN-M |
| 7.7.213 | CCL2 | CRP | GLUCOSE | HBA1C | HP | HSPA1B | LEP |
| 7.7.214 | CCL2 | CRP | GLUCOSE | HBA1C | HP | HSPA1B | TRIG |
| 7.7.215 | CCL2 | CRP | GLUCOSE | HBA1C | HP | IGF1R | INSULIN-M |
| 7.7.216 | CCL2 | CRP | GLUCOSE | HBA1C | HP | IGFBP1 | INSULIN-M |
| 7.7.217 | CCL2 | CRP | GLUCOSE | HBA1C | HP | IGFBP1 | TRIG |
| 7.7.218 | CCL2 | CRP | GLUCOSE | HBA1C | HP | IGFBP2 | INSULIN-M |
| 7.7.219 | CCL2 | CRP | GLUCOSE | HBA1C | HP | IGFBP2 | TRIG |
| 7.7.220 | CCL2 | CRP | GLUCOSE | HBA1C | HP | IL2RA | INSULIN-M |
| 7.7.221 | CCL2 | CRP | GLUCOSE | HBA1C | HP | IL2RB | INSULIN-M |
| 7.7.222 | CCL2 | CRP | GLUCOSE | HBA1C | HP | IL6R | INSULIN-M |
| 7.7.223 | CCL2 | CRP | GLUCOSE | HBA1C | HP | IL6R | TRIG |
| 7.7.224 | CCL2 | CRP | GLUCOSE | HBA1C | HP | INSULIN-M | LEP |
| 7.7.225 | CCL2 | CRP | GLUCOSE | HBA1C | HP | INSULIN-M | SCp |
| 7.7.226 | CCL2 | CRP | GLUCOSE | HBA1C | HP | INSULIN-M | SHBG |
| 7.7.227 | CCL2 | CRP | GLUCOSE | HBA1C | HP | INSULIN-M | TIMP2 |
| 7.7.228 | CCL2 | CRP | GLUCOSE | HBA1C | HP | INSULIN-M | TRIG |
| 7.7.229 | CCL2 | CRP | GLUCOSE | HBA1C | HP | INSULIN-M | VWF |
| 7.7.230 | CCL2 | CRP | GLUCOSE | HBA1C | HP | LEP | TRIG |
| 7.7.231 | CCL2 | CRP | GLUCOSE | HBA1C | HP | SHBG | TRIG |
| 7.7.232 | CCL2 | CRP | GLUCOSE | HBA1C | HP | TIMP2 | TRIG |
| 7.7.233 | CCL2 | CRP | GLUCOSE | HBA1C | HSPA1B | IGFBP2 | INSULIN-M |
| 7.7.234 | CCL2 | CRP | GLUCOSE | HBA1C | HSPA1B | IL6R | INSULIN-M |
| 7.7.235 | CCL2 | CRP | GLUCOSE | HBA1C | HSPA1B | INSULIN-M | SCp |
| 7.7.236 | CCL2 | CRP | GLUCOSE | HBA1C | HSPA1B | INSULIN-M | TIMP2 |
| 7.7.237 | CCL2 | CRP | GLUCOSE | HBA1C | HSPA1B | INSULIN-M | TRIG |
| 7.7.238 | CCL2 | CRP | GLUCOSE | HBA1C | HSPA1B | INSULIN-M | VWF |
| 7.7.239 | CCL2 | CRP | GLUCOSE | HBA1C | HSPA1B | LEP | TRIG |
| 7.7.240 | CCL2 | CRP | GLUCOSE | HBA1C | HSPA1B | TIMP2 | TRIG |

FIGURE 11E (continued)

| Panel No. | Marker 1 | Marker 2 | Marker 3 | Marker 4 | Marker 5 | Marker 6 | Marker 7 |
|---|---|---|---|---|---|---|---|
| 7.7.241 | CCL2 | CRP | GLUCOSE | HBA1C | IL6R | INSULIN-M | TIMP2 |
| 7.7.242 | CCL2 | CRP | GLUCOSE | HBA1C | IL6R | TIMP2 | TRIG |
| 7.7.243 | CCL2 | CRP | GLUCOSE | HBA1C | INSULIN-M | SCp | TRIG |
| 7.7.244 | CCL2 | CRP | GLUCOSE | HBA1C | INSULIN-M | TIMP2 | TRIG |
| 7.7.245 | CCL2 | CRP | GLUCOSE | HP | HSPA1B | INSULIN-M | SHBG |
| 7.7.246 | CCL2 | CRP | GLUCOSE | HP | HSPA1B | INSULIN-M | TIMP2 |
| 7.7.247 | CD40 | CRP | ENG | GLUCOSE | GPT | HBA1C | INSULIN-M |
| 7.7.248 | CD40 | CRP | GLUCOSE | GPT | HBA1C | HP | INSULIN-M |
| 7.7.249 | CRP | EGF | ENG | GLUCOSE | GPT | HBA1C | INSULIN-M |
| 7.7.250 | CRP | EGF | ENG | GLUCOSE | HBA1C | INSULIN-M | SHBG |
| 7.7.251 | CRP | EGF | GLUCOSE | GPT | HBA1C | HP | INSULIN-M |
| 7.7.252 | CRP | EGF | GLUCOSE | GPT | HBA1C | IGFBP2 | INSULIN-M |
| 7.7.253 | CRP | EGF | GLUCOSE | GPT | HBA1C | INSULIN-M | SHBG |
| 7.7.254 | CRP | EGF | GLUCOSE | HBA1C | HP | INSULIN-M | SHBG |
| 7.7.255 | CRP | EGF | GLUCOSE | HBA1C | HP | SHBG | TRIG |
| 7.7.256 | CRP | EGF | GLUCOSE | HBA1C | HSPA1B | IGFBP2 | INSULIN-M |
| 7.7.257 | CRP | EGF | GLUCOSE | HBA1C | HSPA1B | IL2RA | TRIG |
| 7.7.258 | CRP | EGF | GLUCOSE | HBA1C | HSPA1B | LEP | TRIG |
| 7.7.259 | CRP | EGF | GLUCOSE | HBA1C | HSPA1B | TIMP2 | TRIG |
| 7.7.260 | CRP | EGF | GLUCOSE | HSPA1B | IL2RA | TIMP2 | TRIG |
| 7.7.261 | CRP | ENG | FGA | GLUCOSE | GPT | HBA1C | INSULIN-M |
| 7.7.262 | CRP | ENG | FTH1 | GLUCOSE | GPT | HBA1C | INSULIN-M |
| 7.7.263 | CRP | ENG | FTH1 | GLUCOSE | GPT | HBA1C | LEP |
| 7.7.264 | CRP | ENG | FTH1 | GLUCOSE | GPT | HBA1C | TRIG |
| 7.7.265 | CRP | ENG | FTH1 | GLUCOSE | HBA1C | HP | INSULIN-M |
| 7.7.266 | CRP | ENG | FTH1 | GLUCOSE | HBA1C | HSPA1B | INSULIN-M |
| 7.7.267 | CRP | ENG | FTH1 | GLUCOSE | HBA1C | INSULIN-M | LEP |
| 7.7.268 | CRP | ENG | FTH1 | GLUCOSE | HBA1C | INSULIN-M | SHBG |
| 7.7.269 | CRP | ENG | FTH1 | GLUCOSE | HBA1C | LEP | TRIG |
| 7.7.270 | CRP | ENG | GLUCOSE | GPT | HBA1C | HP | IGFBP2 |
| 7.7.271 | CRP | ENG | GLUCOSE | GPT | HBA1C | HP | IL2RB |
| 7.7.272 | CRP | ENG | GLUCOSE | GPT | HBA1C | HP | INSULIN-M |
| 7.7.273 | CRP | ENG | GLUCOSE | GPT | HBA1C | HP | LEP |
| 7.7.274 | CRP | ENG | GLUCOSE | GPT | HBA1C | HP | SHBG |
| 7.7.275 | CRP | ENG | GLUCOSE | GPT | HBA1C | HP | TRIG |
| 7.7.276 | CRP | ENG | GLUCOSE | GPT | HBA1C | HSPA1B | INSULIN-M |
| 7.7.277 | CRP | ENG | GLUCOSE | GPT | HBA1C | IGF1R | INSULIN-M |
| 7.7.278 | CRP | ENG | GLUCOSE | GPT | HBA1C | IGFBP1 | INSULIN-M |
| 7.7.279 | CRP | ENG | GLUCOSE | GPT | HBA1C | IGFBP2 | IL2RA |
| 7.7.280 | CRP | ENG | GLUCOSE | GPT | HBA1C | IGFBP2 | INSULIN-M |

FIGURE 11E (continued)

| Panel No. | Marker 1 | Marker 2 | Marker 3 | Marker 4 | Marker 5 | Marker 6 | Marker 7 |
|---|---|---|---|---|---|---|---|
| 7.7.281 | CRP | ENG | GLUCOSE | GPT | HBA1C | IL2RA | INSULIN-M |
| 7.7.282 | CRP | ENG | GLUCOSE | GPT | HBA1C | IL2RA | TRIG |
| 7.7.283 | CRP | ENG | GLUCOSE | GPT | HBA1C | IL2RB | INSULIN-M |
| 7.7.284 | CRP | ENG | GLUCOSE | GPT | HBA1C | IL2RB | LEP |
| 7.7.285 | CRP | ENG | GLUCOSE | GPT | HBA1C | IL2RB | TRIG |
| 7.7.286 | CRP | ENG | GLUCOSE | GPT | HBA1C | IL6R | INSULIN-M |
| 7.7.287 | CRP | ENG | GLUCOSE | GPT | HBA1C | INSULIN-M | LEP |
| 7.7.288 | CRP | ENG | GLUCOSE | GPT | HBA1C | INSULIN-M | SCp |
| 7.7.289 | CRP | ENG | GLUCOSE | GPT | HBA1C | INSULIN-M | SHBG |
| 7.7.290 | CRP | ENG | GLUCOSE | GPT | HBA1C | INSULIN-M | TIMP2 |
| 7.7.291 | CRP | ENG | GLUCOSE | GPT | HBA1C | INSULIN-M | TRIG |
| 7.7.292 | CRP | ENG | GLUCOSE | GPT | HBA1C | INSULIN-M | VWF |
| 7.7.293 | CRP | ENG | GLUCOSE | GPT | HBA1C | LEP | TRIG |
| 7.7.294 | CRP | ENG | GLUCOSE | GPT | HBA1C | TIMP2 | TRIG |
| 7.7.295 | CRP | ENG | GLUCOSE | GPT | HP | IGFBP2 | INSULIN-M |
| 7.7.296 | CRP | ENG | GLUCOSE | GPT | HP | INSULIN-M | SHBG |
| 7.7.297 | CRP | ENG | GLUCOSE | GPT | HSPA1B | IGFBP2 | IL2RA |
| 7.7.298 | CRP | ENG | GLUCOSE | GPT | HSPA1B | IGFBP2 | INSULIN-M |
| 7.7.299 | CRP | ENG | GLUCOSE | GPT | HSPA1B | IL2RA | INSULIN-M |
| 7.7.300 | CRP | ENG | GLUCOSE | GPT | HSPA1B | IL2RA | TRIG |
| 7.7.301 | CRP | ENG | GLUCOSE | GPT | HSPA1B | INSULIN-M | LEP |
| 7.7.302 | CRP | ENG | GLUCOSE | GPT | HSPA1B | INSULIN-M | SHBG |
| 7.7.303 | CRP | ENG | GLUCOSE | GPT | IGFBP2 | INSULIN-M | SCp |
| 7.7.304 | CRP | ENG | GLUCOSE | HBA1C | HP | HSPA1B | INSULIN-M |
| 7.7.305 | CRP | ENG | GLUCOSE | HBA1C | HP | HSPA1B | TRIG |
| 7.7.306 | CRP | ENG | GLUCOSE | HBA1C | HP | IGFBP2 | INSULIN-M |
| 7.7.307 | CRP | ENG | GLUCOSE | HBA1C | HP | INSULIN-M | SHBG |
| 7.7.308 | CRP | ENG | GLUCOSE | HBA1C | HP | INSULIN-M | TRIG |
| 7.7.309 | CRP | ENG | GLUCOSE | HBA1C | HP | LEP | TRIG |
| 7.7.310 | CRP | ENG | GLUCOSE | HBA1C | HP | SHBG | TRIG |
| 7.7.311 | CRP | ENG | GLUCOSE | HBA1C | HSPA1B | IGFBP2 | INSULIN-M |
| 7.7.312 | CRP | ENG | GLUCOSE | HBA1C | HSPA1B | IL2RA | INSULIN-M |
| 7.7.313 | CRP | ENG | GLUCOSE | HBA1C | HSPA1B | IL2RA | TRIG |
| 7.7.314 | CRP | ENG | GLUCOSE | HBA1C | HSPA1B | IL2RB | TRIG |
| 7.7.315 | CRP | ENG | GLUCOSE | HBA1C | HSPA1B | INSULIN-M | SHBG |
| 7.7.316 | CRP | ENG | GLUCOSE | HBA1C | HSPA1B | INSULIN-M | TIMP2 |
| 7.7.317 | CRP | ENG | GLUCOSE | HBA1C | HSPA1B | INSULIN-M | TRIG |
| 7.7.318 | CRP | ENG | GLUCOSE | HBA1C | HSPA1B | LEP | TRIG |
| 7.7.319 | CRP | ENG | GLUCOSE | HBA1C | HSPA1B | TIMP2 | TRIG |
| 7.7.320 | CRP | ENG | GLUCOSE | HBA1C | IL2RB | LEP | TRIG |

FIGURE 11E (continued)

| Panel No. | Marker 1 | Marker 2 | Marker 3 | Marker 4 | Marker 5 | Marker 6 | Marker 7 |
|---|---|---|---|---|---|---|---|
| 7.7.321 | CRP | ENG | GLUCOSE | HBA1C | INSULIN-M | LEP | TRIG |
| 7.7.322 | CRP | ENG | GLUCOSE | HBA1C | INSULIN-M | SCp | TRIG |
| 7.7.323 | CRP | ENG | GLUCOSE | HBA1C | INSULIN-M | SHBG | TRIG |
| 7.7.324 | CRP | ENG | GLUCOSE | HBA1C | INSULIN-M | TIMP2 | TRIG |
| 7.7.325 | CRP | ENG | GLUCOSE | HSPA1B | IL2RA | LEP | TRIG |
| 7.7.326 | CRP | ENG | GLUCOSE | HSPA1B | IL2RA | TIMP2 | TRIG |
| 7.7.327 | CRP | FGA | GLUCOSE | GPT | HBA1C | HP | INSULIN-M |
| 7.7.328 | CRP | FGA | GLUCOSE | GPT | HBA1C | INSULIN-M | TIMP2 |
| 7.7.329 | CRP | FGA | GLUCOSE | HBA1C | HP | HSPA1B | INSULIN-M |
| 7.7.330 | CRP | FGA | GLUCOSE | HBA1C | HP | INSULIN-M | SHBG |
| 7.7.331 | CRP | FTH1 | GLUCOSE | GPT | HBA1C | HP | INSULIN-M |
| 7.7.332 | CRP | FTH1 | GLUCOSE | GPT | HBA1C | HP | LEP |
| 7.7.333 | CRP | FTH1 | GLUCOSE | HBA1C | HP | IGFBP2 | INSULIN-M |
| 7.7.334 | CRP | FTH1 | GLUCOSE | HBA1C | HP | INSULIN-M | SHBG |
| 7.7.335 | CRP | FTH1 | GLUCOSE | HBA1C | HP | INSULIN-M | TRIG |
| 7.7.336 | CRP | GLUCOSE | GPT | HBA1C | HP | HSPA1B | IL2RB |
| 7.7.337 | CRP | GLUCOSE | GPT | HBA1C | HP | HSPA1B | INSULIN-M |
| 7.7.338 | CRP | GLUCOSE | GPT | HBA1C | HP | IGF1R | IGFBP2 |
| 7.7.339 | CRP | GLUCOSE | GPT | HBA1C | HP | IGF1R | INSULIN-M |
| 7.7.340 | CRP | GLUCOSE | GPT | HBA1C | HP | IGF1R | TRIG |
| 7.7.341 | CRP | GLUCOSE | GPT | HBA1C | HP | IGFBP1 | INSULIN-M |
| 7.7.342 | CRP | GLUCOSE | GPT | HBA1C | HP | IGFBP2 | IL2RB |
| 7.7.343 | CRP | GLUCOSE | GPT | HBA1C | HP | IGFBP2 | INSULIN-M |
| 7.7.344 | CRP | GLUCOSE | GPT | HBA1C | HP | IGFBP2 | LEP |
| 7.7.345 | CRP | GLUCOSE | GPT | HBA1C | HP | IGFBP2 | SHBG |
| 7.7.346 | CRP | GLUCOSE | GPT | HBA1C | HP | IGFBP2 | TIMP2 |
| 7.7.347 | CRP | GLUCOSE | GPT | HBA1C | HP | IGFBP2 | TRIG |
| 7.7.348 | CRP | GLUCOSE | GPT | HBA1C | HP | IL2RA | INSULIN-M |
| 7.7.349 | CRP | GLUCOSE | GPT | HBA1C | HP | IL2RB | INSULIN-M |
| 7.7.350 | CRP | GLUCOSE | GPT | HBA1C | HP | IL2RB | LEP |
| 7.7.351 | CRP | GLUCOSE | GPT | HBA1C | HP | IL2RB | SHBG |
| 7.7.352 | CRP | GLUCOSE | GPT | HBA1C | HP | IL2RB | TRIG |
| 7.7.353 | CRP | GLUCOSE | GPT | HBA1C | HP | IL6R | INSULIN-M |
| 7.7.354 | CRP | GLUCOSE | GPT | HBA1C | HP | INSULIN-M | LEP |
| 7.7.355 | CRP | GLUCOSE | GPT | HBA1C | HP | INSULIN-M | SCp |
| 7.7.356 | CRP | GLUCOSE | GPT | HBA1C | HP | INSULIN-M | SHBG |
| 7.7.357 | CRP | GLUCOSE | GPT | HBA1C | HP | INSULIN-M | TIMP2 |
| 7.7.358 | CRP | GLUCOSE | GPT | HBA1C | HP | INSULIN-M | TRIG |
| 7.7.359 | CRP | GLUCOSE | GPT | HBA1C | HP | INSULIN-M | VWF |
| 7.7.360 | CRP | GLUCOSE | GPT | HBA1C | HP | LEP | SHBG |

FIGURE 11E (continued)

| Panel No. | Marker 1 | Marker 2 | Marker 3 | Marker 4 | Marker 5 | Marker 6 | Marker 7 |
|---|---|---|---|---|---|---|---|
| 7.7.361 | CRP | GLUCOSE | GPT | HBA1C | HP | LEP | TIMP2 |
| 7.7.362 | CRP | GLUCOSE | GPT | HBA1C | HP | LEP | TRIG |
| 7.7.363 | CRP | GLUCOSE | GPT | HBA1C | HP | SHBG | TRIG |
| 7.7.364 | CRP | GLUCOSE | GPT | HBA1C | HP | TIMP2 | TRIG |
| 7.7.365 | CRP | GLUCOSE | GPT | HBA1C | HSPA1B | IGFBP2 | INSULIN-M |
| 7.7.366 | CRP | GLUCOSE | GPT | HBA1C | IGFBP2 | IL2RB | INSULIN-M |
| 7.7.367 | CRP | GLUCOSE | GPT | HBA1C | IGFBP2 | INSULIN-M | SCp |
| 7.7.368 | CRP | GLUCOSE | GPT | HBA1C | IGFBP2 | INSULIN-M | TIMP2 |
| 7.7.369 | CRP | GLUCOSE | GPT | HBA1C | IL6R | INSULIN-M | TIMP2 |
| 7.7.370 | CRP | GLUCOSE | GPT | HP | IGFBP2 | INSULIN-M | SCp |
| 7.7.371 | CRP | GLUCOSE | GPT | HP | IGFBP2 | INSULIN-M | SHBG |
| 7.7.372 | CRP | GLUCOSE | GPT | HP | IGFBP2 | INSULIN-M | TIMP2 |
| 7.7.373 | CRP | GLUCOSE | HBA1C | HP | HSPA1B | IGFBP2 | INSULIN-M |
| 7.7.374 | CRP | GLUCOSE | HBA1C | HP | HSPA1B | IGFBP2 | TRIG |
| 7.7.375 | CRP | GLUCOSE | HBA1C | HP | HSPA1B | IL2RA | INSULIN-M |
| 7.7.376 | CRP | GLUCOSE | HBA1C | HP | HSPA1B | INSULIN-M | LEP |
| 7.7.377 | CRP | GLUCOSE | HBA1C | HP | HSPA1B | INSULIN-M | SHBG |
| 7.7.378 | CRP | GLUCOSE | HBA1C | HP | HSPA1B | INSULIN-M | TIMP2 |
| 7.7.379 | CRP | GLUCOSE | HBA1C | HP | HSPA1B | INSULIN-M | TRIG |
| 7.7.380 | CRP | GLUCOSE | HBA1C | HP | HSPA1B | LEP | TRIG |
| 7.7.381 | CRP | GLUCOSE | HBA1C | HP | HSPA1B | TIMP2 | TRIG |
| 7.7.382 | CRP | GLUCOSE | HBA1C | HP | IGFBP2 | INSULIN-M | SHBG |
| 7.7.383 | CRP | GLUCOSE | HBA1C | HP | IGFBP2 | INSULIN-M | TIMP2 |
| 7.7.384 | CRP | GLUCOSE | HBA1C | HP | IGFBP2 | INSULIN-M | TRIG |
| 7.7.385 | CRP | GLUCOSE | HBA1C | HP | IGFBP2 | TIMP2 | TRIG |
| 7.7.386 | CRP | GLUCOSE | HBA1C | HP | IL6R | INSULIN-M | SHBG |
| 7.7.387 | CRP | GLUCOSE | HBA1C | HP | INSULIN-M | LEP | TRIG |
| 7.7.388 | CRP | GLUCOSE | HBA1C | HP | INSULIN-M | SCp | SHBG |
| 7.7.389 | CRP | GLUCOSE | HBA1C | HP | INSULIN-M | SCp | TRIG |
| 7.7.390 | CRP | GLUCOSE | HBA1C | HP | INSULIN-M | SHBG | TIMP2 |
| 7.7.391 | CRP | GLUCOSE | HBA1C | HP | INSULIN-M | SHBG | TRIG |
| 7.7.392 | CRP | GLUCOSE | HBA1C | HP | INSULIN-M | SHBG | VWF |
| 7.7.393 | CRP | GLUCOSE | HBA1C | HP | INSULIN-M | TIMP2 | TRIG |
| 7.7.394 | CRP | GLUCOSE | HBA1C | HP | SHBG | TIMP2 | TRIG |
| 7.7.395 | CRP | GLUCOSE | HBA1C | HSPA1B | IL2RA | TIMP2 | TRIG |
| 7.7.396 | CRP | GLUCOSE | HBA1C | HSPA1B | IL2RB | TIMP2 | TRIG |
| 7.7.397 | CRP | GLUCOSE | HBA1C | HSPA1B | IL6R | TIMP2 | TRIG |
| 7.7.398 | CRP | GLUCOSE | HBA1C | HSPA1B | INSULIN-M | TIMP2 | TRIG |
| 7.7.399 | CRP | GLUCOSE | HBA1C | HSPA1B | LEP | TIMP2 | TRIG |
| 7.7.400 | ENG | GLUCOSE | HBA1C | HSPA1B | IL2RA | LEP | TRIG |

FIGURE 12

| | | |
|---|---|---|
| ACE | CRP | GLUCOSE |
| ADIPOQ | CRP | GLUCOSE |
| AGER | CRP | GLUCOSE |
| AHSG | CRP | GLUCOSE |
| ANG | CRP | GLUCOSE |
| APOA1 | CRP | GLUCOSE |
| APOB | CRP | GLUCOSE |
| APOE | CRP | GLUCOSE |
| BAX | CRP | GLUCOSE |
| BCL2 | CRP | GLUCOSE |
| C3 | CRP | GLUCOSE |
| CCL2 | CRP | GLUCOSE |
| CD14 | CRP | GLUCOSE |
| CD40 | CRP | GLUCOSE |
| CDK5 | CRP | GLUCOSE |
| CHOL | CRP | GLUCOSE |
| CRP | CTSB | GLUCOSE |
| CRP | DPP4 | GLUCOSE |
| CRP | EGF | GLUCOSE |
| CRP | ENG | GLUCOSE |
| CRP | FAS | GLUCOSE |
| CRP | FGA | GLUCOSE |
| CRP | FTH1 | GLUCOSE |
| CRP | GH1 | GLUCOSE |
| CRP | GLUCOSE | GPT |
| CRP | GLUCOSE | HBA1C |
| CRP | GLUCOSE | HDL |
| CRP | GLUCOSE | HGF |
| CRP | GLUCOSE | HP |
| CRP | GLUCOSE | HSPA1B |
| CRP | GLUCOSE | ICAM1 |
| CRP | GLUCOSE | IGF1 |
| CRP | GLUCOSE | IGF1R |
| CRP | GLUCOSE | IGFBP1 |
| CRP | GLUCOSE | IGFBP2 |
| CRP | GLUCOSE | IGFBP3 |
| CCL2 | GLUCOSE | IL18 |
| CRP | GLUCOSE | IL18 |
| GLUCOSE | HBA1C | IL18 |
| GLUCOSE | HSPA1B | IL18 |

FIGURE 12 (continued)

| | | |
|---|---|---|
| CRP | GLUCOSE | IL2RA |
| CRP | GLUCOSE | IL2RB |
| CRP | GLUCOSE | IL6 |
| CRP | GLUCOSE | IL6R |
| CRP | GLUCOSE | IL6ST |
| CRP | GLUCOSE | IL8 |
| CRP | GLUCOSE | INHBA |
| ADIPOQ | GLUCOSE | INSULIN |
| BCL2 | GLUCOSE | INSULIN |
| C3 | GLUCOSE | INSULIN |
| CCL2 | GLUCOSE | INSULIN |
| CD14 | GLUCOSE | INSULIN |
| CDK5 | GLUCOSE | INSULIN |
| CRP | GLUCOSE | INSULIN |
| DPP4 | GLUCOSE | INSULIN |
| FTH1 | GLUCOSE | INSULIN |
| GH1 | GLUCOSE | INSULIN |
| GLUCOSE | GPT | INSULIN |
| GLUCOSE | HBA1C | INSULIN |
| GLUCOSE | HGF | INSULIN |
| GLUCOSE | HSPA1B | INSULIN |
| GLUCOSE | IGF1 | INSULIN |
| GLUCOSE | IL18 | INSULIN |
| GLUCOSE | IL2RA | INSULIN |
| GLUCOSE | IL6ST | INSULIN |
| GLUCOSE | IL8 | INSULIN |
| CRP | GLUCOSE | LDL |
| GLUCOSE | INSULIN | LDL |
| CRP | GLUCOSE | LEP |
| FTH1 | GLUCOSE | LEP |
| GLUCOSE | IL18 | LEP |
| GLUCOSE | INSULIN | LEP |
| CRP | GLUCOSE | PLAT |
| GLUCOSE | IL18 | PLAT |
| GLUCOSE | INSULIN | PLAT |
| CRP | GLUCOSE | POMC |
| CRP | GLUCOSE | Proinsulin |
| CRP | GLUCOSE | RETN |
| CRP | GLUCOSE | SELE |
| CRP | GLUCOSE | SELP |

FIGURE 12 (continued)

| | | |
|---|---|---|
| GLUCOSE | INSULIN | SELP |
| CRP | GLUCOSE | SERPINE1 |
| CRP | GLUCOSE | SGK |
| GLUCOSE | IL18 | SGK |
| GLUCOSE | INSULIN | SGK |
| CRP | GLUCOSE | SHBG |
| CRP | GLUCOSE | TGFB1 |
| CRP | GLUCOSE | TIMP2 |
| CRP | GLUCOSE | TNFRSF1B |
| GLUCOSE | INSULIN | TNFRSF1B |
| CRP | GLUCOSE | TRIG |
| GLUCOSE | HBA1C | TRIG |
| GLUCOSE | IL18 | TRIG |
| GLUCOSE | INSULIN | TRIG |
| GLUCOSE | LEP | TRIG |
| CRP | GLUCOSE | VCAM1 |
| GLUCOSE | INSULIN | VCAM1 |
| CRP | GLUCOSE | VEGF |
| GLUCOSE | INSULIN | VEGF |
| CRP | GLUCOSE | VWF |
| GLUCOSE | INSULIN | VWF |

FIGURE 13

| | | | |
|---|---|---|---|
| ADIPOQ | ANG | CRP | GLUCOSE |
| ADIPOQ | C3 | CRP | GLUCOSE |
| ADIPOQ | C3 | GLUCOSE | INSULIN |
| ADIPOQ | CCL2 | CRP | GLUCOSE |
| ADIPOQ | CCL2 | GLUCOSE | IL18 |
| ADIPOQ | CCL2 | GLUCOSE | INSULIN |
| ADIPOQ | CCL2 | GLUCOSE | LEP |
| ADIPOQ | CDK5 | CRP | GLUCOSE |
| ADIPOQ | CDK5 | GLUCOSE | INSULIN |
| ADIPOQ | CRP | ENG | GLUCOSE |
| ADIPOQ | CRP | FTH1 | GLUCOSE |
| ADIPOQ | CRP | GLUCOSE | GPT |
| ADIPOQ | CRP | GLUCOSE | HBA1C |
| ADIPOQ | CRP | GLUCOSE | HDL |
| ADIPOQ | CRP | GLUCOSE | HGF |
| ADIPOQ | CRP | GLUCOSE | HSPA1B |
| ADIPOQ | CRP | GLUCOSE | IGFBP1 |
| ADIPOQ | CRP | GLUCOSE | IGFBP2 |
| ADIPOQ | CRP | GLUCOSE | IL18 |
| ADIPOQ | CRP | GLUCOSE | IL2RA |
| ADIPOQ | CRP | GLUCOSE | INHBA |
| ADIPOQ | CRP | GLUCOSE | INSULIN |
| ADIPOQ | CRP | GLUCOSE | LEP |
| ADIPOQ | CRP | GLUCOSE | PLAT |
| ADIPOQ | CRP | GLUCOSE | SERPINE1 |
| ADIPOQ | CRP | GLUCOSE | TRIG |
| ADIPOQ | CRP | GLUCOSE | VEGF |
| ADIPOQ | CRP | GLUCOSE | VWF |
| ADIPOQ | ENG | GLUCOSE | INSULIN |
| ADIPOQ | FTH1 | GLUCOSE | IL18 |
| ADIPOQ | FTH1 | GLUCOSE | INSULIN |
| ADIPOQ | FTH1 | GLUCOSE | LEP |
| ADIPOQ | GLUCOSE | GPT | INSULIN |
| ADIPOQ | GLUCOSE | GPT | LEP |
| ADIPOQ | GLUCOSE | HBA1C | IL18 |
| ADIPOQ | GLUCOSE | HBA1C | INSULIN |
| ADIPOQ | GLUCOSE | HBA1C | LEP |
| ADIPOQ | GLUCOSE | HBA1C | TRIG |
| ADIPOQ | GLUCOSE | HDL | INSULIN |
| ADIPOQ | GLUCOSE | HDL | LEP |

FIGURE 13 (continued)

| | | | |
|---|---|---|---|
| ADIPOQ | GLUCOSE | HGF | INSULIN |
| ADIPOQ | GLUCOSE | HSPA1B | IL18 |
| ADIPOQ | GLUCOSE | HSPA1B | INSULIN |
| ADIPOQ | GLUCOSE | HSPA1B | LEP |
| ADIPOQ | GLUCOSE | IGFBP1 | INSULIN |
| ADIPOQ | GLUCOSE | IGFBP2 | IL18 |
| ADIPOQ | GLUCOSE | IGFBP2 | INSULIN |
| ADIPOQ | GLUCOSE | IL18 | INSULIN |
| ADIPOQ | GLUCOSE | IL18 | LEP |
| ADIPOQ | GLUCOSE | IL18 | PLAT |
| ADIPOQ | GLUCOSE | IL18 | TRIG |
| ADIPOQ | GLUCOSE | IL18 | VEGF |
| ADIPOQ | GLUCOSE | IL18 | VWF |
| ADIPOQ | GLUCOSE | IL2RA | INSULIN |
| ADIPOQ | GLUCOSE | IL2RA | LEP |
| ADIPOQ | GLUCOSE | INSULIN | LEP |
| ADIPOQ | GLUCOSE | INSULIN | PLAT |
| ADIPOQ | GLUCOSE | INSULIN | TRIG |
| ADIPOQ | GLUCOSE | INSULIN | VEGF |
| ADIPOQ | GLUCOSE | INSULIN | VWF |
| ADIPOQ | GLUCOSE | LEP | PLAT |
| ADIPOQ | GLUCOSE | LEP | TRIG |
| ADIPOQ | GLUCOSE | LEP | VEGF |
| ADIPOQ | GLUCOSE | LEP | VWF |
| ANG | C3 | CRP | GLUCOSE |
| ANG | C3 | GLUCOSE | INSULIN |
| ANG | CCL2 | CRP | GLUCOSE |
| ANG | CCL2 | GLUCOSE | IL18 |
| ANG | CCL2 | GLUCOSE | INSULIN |
| ANG | CDK5 | CRP | GLUCOSE |
| ANG | CDK5 | GLUCOSE | INSULIN |
| ANG | CRP | ENG | GLUCOSE |
| ANG | CRP | FTH1 | GLUCOSE |
| ANG | CRP | GLUCOSE | GPT |
| ANG | CRP | GLUCOSE | HBA1C |
| ANG | CRP | GLUCOSE | HDL |
| ANG | CRP | GLUCOSE | HGF |
| ANG | CRP | GLUCOSE | HSPA1B |
| ANG | CRP | GLUCOSE | IGFBP1 |
| ANG | CRP | GLUCOSE | IGFBP2 |

FIGURE 13 (continued)

| | | | |
|---|---|---|---|
| ANG | CRP | GLUCOSE | IL18 |
| ANG | CRP | GLUCOSE | IL2RA |
| ANG | CRP | GLUCOSE | INHBA |
| ANG | CRP | GLUCOSE | INSULIN |
| ANG | CRP | GLUCOSE | LEP |
| ANG | CRP | GLUCOSE | PLAT |
| ANG | CRP | GLUCOSE | SERPINE1 |
| ANG | CRP | GLUCOSE | TRIG |
| ANG | CRP | GLUCOSE | VEGF |
| ANG | CRP | GLUCOSE | VWF |
| ANG | ENG | GLUCOSE | INSULIN |
| ANG | FTH1 | GLUCOSE | IL18 |
| ANG | FTH1 | GLUCOSE | INSULIN |
| ANG | FTH1 | GLUCOSE | LEP |
| ANG | GLUCOSE | GPT | INSULIN |
| ANG | GLUCOSE | HBA1C | IL18 |
| ANG | GLUCOSE | HBA1C | INSULIN |
| ANG | GLUCOSE | HBA1C | LEP |
| ANG | GLUCOSE | HBA1C | TRIG |
| ANG | GLUCOSE | HDL | INSULIN |
| ANG | GLUCOSE | HGF | INSULIN |
| ANG | GLUCOSE | HSPA1B | IL18 |
| ANG | GLUCOSE | HSPA1B | INSULIN |
| ANG | GLUCOSE | IGFBP2 | INSULIN |
| ANG | GLUCOSE | IL18 | INSULIN |
| ANG | GLUCOSE | IL18 | LEP |
| ANG | GLUCOSE | IL18 | PLAT |
| ANG | GLUCOSE | IL18 | TRIG |
| ANG | GLUCOSE | IL18 | VWF |
| ANG | GLUCOSE | IL2RA | INSULIN |
| ANG | GLUCOSE | INSULIN | LEP |
| ANG | GLUCOSE | INSULIN | PLAT |
| ANG | GLUCOSE | INSULIN | TRIG |
| ANG | GLUCOSE | INSULIN | VEGF |
| ANG | GLUCOSE | INSULIN | VWF |
| ANG | GLUCOSE | LEP | TRIG |
| C3 | CCL2 | CRP | GLUCOSE |
| C3 | CCL2 | GLUCOSE | IL18 |
| C3 | CCL2 | GLUCOSE | INSULIN |
| C3 | CDK5 | CRP | GLUCOSE |

FIGURE 13 (continued)

| C3 | CDK5 | GLUCOSE | INSULIN |
|----|------|---------|---------|
| C3 | CRP | ENG | GLUCOSE |
| C3 | CRP | FTH1 | GLUCOSE |
| C3 | CRP | GLUCOSE | GPT |
| C3 | CRP | GLUCOSE | HBA1C |
| C3 | CRP | GLUCOSE | HDL |
| C3 | CRP | GLUCOSE | HGF |
| C3 | CRP | GLUCOSE | HSPA1B |
| C3 | CRP | GLUCOSE | IGFBP1 |
| C3 | CRP | GLUCOSE | IGFBP2 |
| C3 | CRP | GLUCOSE | IL18 |
| C3 | CRP | GLUCOSE | IL2RA |
| C3 | CRP | GLUCOSE | INHBA |
| C3 | CRP | GLUCOSE | INSULIN |
| C3 | CRP | GLUCOSE | LEP |
| C3 | CRP | GLUCOSE | PLAT |
| C3 | CRP | GLUCOSE | SERPINE1 |
| C3 | CRP | GLUCOSE | TRIG |
| C3 | CRP | GLUCOSE | VEGF |
| C3 | CRP | GLUCOSE | VWF |
| C3 | ENG | GLUCOSE | INSULIN |
| C3 | FTH1 | GLUCOSE | IL18 |
| C3 | FTH1 | GLUCOSE | INSULIN |
| C3 | FTH1 | GLUCOSE | LEP |
| C3 | GLUCOSE | GPT | INSULIN |
| C3 | GLUCOSE | HBA1C | IL18 |
| C3 | GLUCOSE | HBA1C | INSULIN |
| C3 | GLUCOSE | HBA1C | LEP |
| C3 | GLUCOSE | HBA1C | TRIG |
| C3 | GLUCOSE | HDL | INSULIN |
| C3 | GLUCOSE | HGF | INSULIN |
| C3 | GLUCOSE | HSPA1B | INSULIN |
| C3 | GLUCOSE | IGFBP1 | INSULIN |
| C3 | GLUCOSE | IGFBP2 | INSULIN |
| C3 | GLUCOSE | IL18 | INSULIN |
| C3 | GLUCOSE | IL18 | LEP |
| C3 | GLUCOSE | IL18 | TRIG |
| C3 | GLUCOSE | IL2RA | INSULIN |
| C3 | GLUCOSE | INHBA | INSULIN |
| C3 | GLUCOSE | INSULIN | LEP |

FIGURE 13 (continued)

| C3 | GLUCOSE | INSULIN | PLAT |
|---|---|---|---|
| C3 | GLUCOSE | INSULIN | SERPINE1 |
| C3 | GLUCOSE | INSULIN | TRIG |
| C3 | GLUCOSE | INSULIN | VEGF |
| C3 | GLUCOSE | INSULIN | VWF |
| C3 | GLUCOSE | LEP | TRIG |
| CCL2 | CDK5 | CRP | GLUCOSE |
| CCL2 | CDK5 | GLUCOSE | IL18 |
| CCL2 | CDK5 | GLUCOSE | INSULIN |
| CCL2 | CRP | ENG | GLUCOSE |
| CCL2 | CRP | FTH1 | GLUCOSE |
| CCL2 | CRP | GLUCOSE | GPT |
| CCL2 | CRP | GLUCOSE | HBA1C |
| CCL2 | CRP | GLUCOSE | HDL |
| CCL2 | CRP | GLUCOSE | HGF |
| CCL2 | CRP | GLUCOSE | HSPA1B |
| CCL2 | CRP | GLUCOSE | IGFBP1 |
| CCL2 | CRP | GLUCOSE | IGFBP2 |
| CCL2 | CRP | GLUCOSE | IL18 |
| CCL2 | CRP | GLUCOSE | IL2RA |
| CCL2 | CRP | GLUCOSE | INHBA |
| CCL2 | CRP | GLUCOSE | INSULIN |
| CCL2 | CRP | GLUCOSE | LEP |
| CCL2 | CRP | GLUCOSE | PLAT |
| CCL2 | CRP | GLUCOSE | SERPINE1 |
| CCL2 | CRP | GLUCOSE | TRIG |
| CCL2 | CRP | GLUCOSE | VEGF |
| CCL2 | CRP | GLUCOSE | VWF |
| CCL2 | ENG | GLUCOSE | IL18 |
| CCL2 | ENG | GLUCOSE | INSULIN |
| CCL2 | FTH1 | GLUCOSE | HBA1C |
| CCL2 | FTH1 | GLUCOSE | HGF |
| CCL2 | FTH1 | GLUCOSE | IL18 |
| CCL2 | FTH1 | GLUCOSE | IL2RA |
| CCL2 | FTH1 | GLUCOSE | INSULIN |
| CCL2 | FTH1 | GLUCOSE | LEP |
| CCL2 | FTH1 | GLUCOSE | PLAT |
| CCL2 | FTH1 | GLUCOSE | TRIG |
| CCL2 | GLUCOSE | GPT | IL18 |
| CCL2 | GLUCOSE | GPT | INSULIN |

FIGURE 13 (continued)

| | | | |
|---|---|---|---|
| CCL2 | GLUCOSE | GPT | LEP |
| CCL2 | GLUCOSE | HBA1C | HDL |
| CCL2 | GLUCOSE | HBA1C | HGF |
| CCL2 | GLUCOSE | HBA1C | HSPA1B |
| CCL2 | GLUCOSE | HBA1C | IL18 |
| CCL2 | GLUCOSE | HBA1C | INSULIN |
| CCL2 | GLUCOSE | HBA1C | LEP |
| CCL2 | GLUCOSE | HBA1C | PLAT |
| CCL2 | GLUCOSE | HBA1C | TRIG |
| CCL2 | GLUCOSE | HBA1C | VWF |
| CCL2 | GLUCOSE | HDL | IL18 |
| CCL2 | GLUCOSE | HDL | INSULIN |
| CCL2 | GLUCOSE | HDL | LEP |
| CCL2 | GLUCOSE | HGF | IL18 |
| CCL2 | GLUCOSE | HGF | INSULIN |
| CCL2 | GLUCOSE | HGF | PLAT |
| CCL2 | GLUCOSE | HGF | TRIG |
| CCL2 | GLUCOSE | HSPA1B | IL18 |
| CCL2 | GLUCOSE | HSPA1B | INSULIN |
| CCL2 | GLUCOSE | HSPA1B | LEP |
| CCL2 | GLUCOSE | IGFBP1 | IL18 |
| CCL2 | GLUCOSE | IGFBP1 | INSULIN |
| CCL2 | GLUCOSE | IGFBP2 | IL18 |
| CCL2 | GLUCOSE | IGFBP2 | INSULIN |
| CCL2 | GLUCOSE | IL18 | IL2RA |
| CCL2 | GLUCOSE | IL18 | INSULIN |
| CCL2 | GLUCOSE | IL18 | LEP |
| CCL2 | GLUCOSE | IL18 | PLAT |
| CCL2 | GLUCOSE | IL18 | SERPINE1 |
| CCL2 | GLUCOSE | IL18 | TRIG |
| CCL2 | GLUCOSE | IL18 | VEGF |
| CCL2 | GLUCOSE | IL18 | VWF |
| CCL2 | GLUCOSE | IL2RA | INSULIN |
| CCL2 | GLUCOSE | IL2RA | LEP |
| CCL2 | GLUCOSE | IL2RA | TRIG |
| CCL2 | GLUCOSE | INHBA | INSULIN |
| CCL2 | GLUCOSE | INSULIN | LEP |
| CCL2 | GLUCOSE | INSULIN | PLAT |
| CCL2 | GLUCOSE | INSULIN | SERPINE1 |
| CCL2 | GLUCOSE | INSULIN | TRIG |

FIGURE 13 (continued)

| | | | |
|---|---|---|---|
| CCL2 | GLUCOSE | INSULIN | VEGF |
| CCL2 | GLUCOSE | INSULIN | VWF |
| CCL2 | GLUCOSE | LEP | PLAT |
| CCL2 | GLUCOSE | LEP | TRIG |
| CCL2 | GLUCOSE | LEP | VEGF |
| CCL2 | GLUCOSE | LEP | VWF |
| CCL2 | GLUCOSE | PLAT | TRIG |
| CCL2 | GLUCOSE | TRIG | VEGF |
| CCL2 | GLUCOSE | TRIG | VWF |
| CDK5 | CRP | ENG | GLUCOSE |
| CDK5 | CRP | FTH1 | GLUCOSE |
| CDK5 | CRP | GLUCOSE | GPT |
| CDK5 | CRP | GLUCOSE | HBA1C |
| CDK5 | CRP | GLUCOSE | HDL |
| CDK5 | CRP | GLUCOSE | HGF |
| CDK5 | CRP | GLUCOSE | HSPA1B |
| CDK5 | CRP | GLUCOSE | IGFBP1 |
| CDK5 | CRP | GLUCOSE | IGFBP2 |
| CDK5 | CRP | GLUCOSE | IL18 |
| CDK5 | CRP | GLUCOSE | IL2RA |
| CDK5 | CRP | GLUCOSE | INHBA |
| CDK5 | CRP | GLUCOSE | INSULIN |
| CDK5 | CRP | GLUCOSE | LEP |
| CDK5 | CRP | GLUCOSE | PLAT |
| CDK5 | CRP | GLUCOSE | SERPINE1 |
| CDK5 | CRP | GLUCOSE | TRIG |
| CDK5 | CRP | GLUCOSE | VEGF |
| CDK5 | CRP | GLUCOSE | VWF |
| CDK5 | ENG | GLUCOSE | INSULIN |
| CDK5 | FTH1 | GLUCOSE | IL18 |
| CDK5 | FTH1 | GLUCOSE | INSULIN |
| CDK5 | FTH1 | GLUCOSE | LEP |
| CDK5 | GLUCOSE | GPT | INSULIN |
| CDK5 | GLUCOSE | HBA1C | IL18 |
| CDK5 | GLUCOSE | HBA1C | INSULIN |
| CDK5 | GLUCOSE | HBA1C | LEP |
| CDK5 | GLUCOSE | HBA1C | TRIG |
| CDK5 | GLUCOSE | HDL | INSULIN |
| CDK5 | GLUCOSE | HGF | INSULIN |
| CDK5 | GLUCOSE | HSPA1B | IL18 |

FIGURE 13 (continued)

| | | | |
|---|---|---|---|
| CDK5 | GLUCOSE | HSPA1B | INSULIN |
| CDK5 | GLUCOSE | IGFBP1 | INSULIN |
| CDK5 | GLUCOSE | IGFBP2 | INSULIN |
| CDK5 | GLUCOSE | IL18 | IL2RA |
| CDK5 | GLUCOSE | IL18 | INSULIN |
| CDK5 | GLUCOSE | IL18 | LEP |
| CDK5 | GLUCOSE | IL18 | PLAT |
| CDK5 | GLUCOSE | IL18 | TRIG |
| CDK5 | GLUCOSE | IL18 | VEGF |
| CDK5 | GLUCOSE | IL2RA | INSULIN |
| CDK5 | GLUCOSE | INHBA | INSULIN |
| CDK5 | GLUCOSE | INSULIN | LEP |
| CDK5 | GLUCOSE | INSULIN | PLAT |
| CDK5 | GLUCOSE | INSULIN | SERPINE1 |
| CDK5 | GLUCOSE | INSULIN | TRIG |
| CDK5 | GLUCOSE | INSULIN | VEGF |
| CDK5 | GLUCOSE | INSULIN | VWF |
| CDK5 | GLUCOSE | LEP | TRIG |
| CRP | ENG | FTH1 | GLUCOSE |
| CRP | ENG | GLUCOSE | GPT |
| CRP | ENG | GLUCOSE | HBA1C |
| CRP | ENG | GLUCOSE | HDL |
| CRP | ENG | GLUCOSE | HGF |
| CRP | ENG | GLUCOSE | HSPA1B |
| CRP | ENG | GLUCOSE | IGFBP1 |
| CRP | ENG | GLUCOSE | IGFBP2 |
| CRP | ENG | GLUCOSE | IL18 |
| CRP | ENG | GLUCOSE | IL2RA |
| CRP | ENG | GLUCOSE | INHBA |
| CRP | ENG | GLUCOSE | INSULIN |
| CRP | ENG | GLUCOSE | LEP |
| CRP | ENG | GLUCOSE | PLAT |
| CRP | ENG | GLUCOSE | SERPINE1 |
| CRP | ENG | GLUCOSE | TRIG |
| CRP | ENG | GLUCOSE | VEGF |
| CRP | ENG | GLUCOSE | VWF |
| CRP | FTH1 | GLUCOSE | GPT |
| CRP | FTH1 | GLUCOSE | HBA1C |
| CRP | FTH1 | GLUCOSE | HDL |
| CRP | FTH1 | GLUCOSE | HGF |

FIGURE 13 (continued)

| CRP | FTH1 | GLUCOSE | HSPA1B |
|---|---|---|---|
| CRP | FTH1 | GLUCOSE | IGFBP1 |
| CRP | FTH1 | GLUCOSE | IGFBP2 |
| CRP | FTH1 | GLUCOSE | IL18 |
| CRP | FTH1 | GLUCOSE | IL2RA |
| CRP | FTH1 | GLUCOSE | INHBA |
| CRP | FTH1 | GLUCOSE | INSULIN |
| CRP | FTH1 | GLUCOSE | LEP |
| CRP | FTH1 | GLUCOSE | PLAT |
| CRP | FTH1 | GLUCOSE | SERPINE1 |
| CRP | FTH1 | GLUCOSE | TRIG |
| CRP | FTH1 | GLUCOSE | VEGF |
| CRP | FTH1 | GLUCOSE | VWF |
| CRP | GLUCOSE | GPT | HBA1C |
| CRP | GLUCOSE | GPT | HDL |
| CRP | GLUCOSE | GPT | HGF |
| CRP | GLUCOSE | GPT | HSPA1B |
| CRP | GLUCOSE | GPT | IGFBP1 |
| CRP | GLUCOSE | GPT | IGFBP2 |
| CRP | GLUCOSE | GPT | IL18 |
| CRP | GLUCOSE | GPT | IL2RA |
| CRP | GLUCOSE | GPT | INHBA |
| CRP | GLUCOSE | GPT | INSULIN |
| CRP | GLUCOSE | GPT | LEP |
| CRP | GLUCOSE | GPT | PLAT |
| CRP | GLUCOSE | GPT | SERPINE1 |
| CRP | GLUCOSE | GPT | TRIG |
| CRP | GLUCOSE | GPT | VEGF |
| CRP | GLUCOSE | GPT | VWF |
| CRP | GLUCOSE | HBA1C | HDL |
| CRP | GLUCOSE | HBA1C | HGF |
| CRP | GLUCOSE | HBA1C | HSPA1B |
| CRP | GLUCOSE | HBA1C | IGFBP1 |
| CRP | GLUCOSE | HBA1C | IGFBP2 |
| CRP | GLUCOSE | HBA1C | IL18 |
| CRP | GLUCOSE | HBA1C | IL2RA |
| CRP | GLUCOSE | HBA1C | INHBA |
| CRP | GLUCOSE | HBA1C | INSULIN |
| CRP | GLUCOSE | HBA1C | LEP |
| CRP | GLUCOSE | HBA1C | PLAT |

FIGURE 13 (continued)

| CRP | GLUCOSE | HBA1C | SERPINE1 |
|---|---|---|---|
| CRP | GLUCOSE | HBA1C | TRIG |
| CRP | GLUCOSE | HBA1C | VEGF |
| CRP | GLUCOSE | HBA1C | VWF |
| CRP | GLUCOSE | HDL | HGF |
| CRP | GLUCOSE | HDL | HSPA1B |
| CRP | GLUCOSE | HDL | IGFBP1 |
| CRP | GLUCOSE | HDL | IGFBP2 |
| CRP | GLUCOSE | HDL | IL18 |
| CRP | GLUCOSE | HDL | IL2RA |
| CRP | GLUCOSE | HDL | INHBA |
| CRP | GLUCOSE | HDL | INSULIN |
| CRP | GLUCOSE | HDL | LEP |
| CRP | GLUCOSE | HDL | PLAT |
| CRP | GLUCOSE | HDL | SERPINE1 |
| CRP | GLUCOSE | HDL | TRIG |
| CRP | GLUCOSE | HDL | VEGF |
| CRP | GLUCOSE | HDL | VWF |
| CRP | GLUCOSE | HGF | HSPA1B |
| CRP | GLUCOSE | HGF | IGFBP1 |
| CRP | GLUCOSE | HGF | IGFBP2 |
| CRP | GLUCOSE | HGF | IL18 |
| CRP | GLUCOSE | HGF | IL2RA |
| CRP | GLUCOSE | HGF | INHBA |
| CRP | GLUCOSE | HGF | INSULIN |
| CRP | GLUCOSE | HGF | LEP |
| CRP | GLUCOSE | HGF | PLAT |
| CRP | GLUCOSE | HGF | SERPINE1 |
| CRP | GLUCOSE | HGF | TRIG |
| CRP | GLUCOSE | HGF | VEGF |
| CRP | GLUCOSE | HGF | VWF |
| CRP | GLUCOSE | HSPA1B | IGFBP1 |
| CRP | GLUCOSE | HSPA1B | IGFBP2 |
| CRP | GLUCOSE | HSPA1B | IL18 |
| CRP | GLUCOSE | HSPA1B | IL2RA |
| CRP | GLUCOSE | HSPA1B | INHBA |
| CRP | GLUCOSE | HSPA1B | INSULIN |
| CRP | GLUCOSE | HSPA1B | LEP |
| CRP | GLUCOSE | HSPA1B | PLAT |
| CRP | GLUCOSE | HSPA1B | SERPINE1 |

FIGURE 13 (continued)

| CRP | GLUCOSE | HSPA1B | TRIG |
|---|---|---|---|
| CRP | GLUCOSE | HSPA1B | VEGF |
| CRP | GLUCOSE | HSPA1B | VWF |
| CRP | GLUCOSE | IGFBP1 | IGFBP2 |
| CRP | GLUCOSE | IGFBP1 | IL18 |
| CRP | GLUCOSE | IGFBP1 | IL2RA |
| CRP | GLUCOSE | IGFBP1 | INHBA |
| CRP | GLUCOSE | IGFBP1 | INSULIN |
| CRP | GLUCOSE | IGFBP1 | LEP |
| CRP | GLUCOSE | IGFBP1 | PLAT |
| CRP | GLUCOSE | IGFBP1 | SERPINE1 |
| CRP | GLUCOSE | IGFBP1 | TRIG |
| CRP | GLUCOSE | IGFBP1 | VEGF |
| CRP | GLUCOSE | IGFBP1 | VWF |
| CRP | GLUCOSE | IGFBP2 | IL18 |
| CRP | GLUCOSE | IGFBP2 | IL2RA |
| CRP | GLUCOSE | IGFBP2 | INHBA |
| CRP | GLUCOSE | IGFBP2 | INSULIN |
| CRP | GLUCOSE | IGFBP2 | LEP |
| CRP | GLUCOSE | IGFBP2 | PLAT |
| CRP | GLUCOSE | IGFBP2 | SERPINE1 |
| CRP | GLUCOSE | IGFBP2 | TRIG |
| CRP | GLUCOSE | IGFBP2 | VEGF |
| CRP | GLUCOSE | IGFBP2 | VWF |
| CRP | GLUCOSE | IL18 | IL2RA |
| CRP | GLUCOSE | IL18 | INHBA |
| CRP | GLUCOSE | IL18 | INSULIN |
| CRP | GLUCOSE | IL18 | LEP |
| CRP | GLUCOSE | IL18 | PLAT |
| CRP | GLUCOSE | IL18 | SERPINE1 |
| CRP | GLUCOSE | IL18 | TRIG |
| CRP | GLUCOSE | IL18 | VEGF |
| CRP | GLUCOSE | IL18 | VWF |
| CRP | GLUCOSE | IL2RA | INHBA |
| CRP | GLUCOSE | IL2RA | INSULIN |
| CRP | GLUCOSE | IL2RA | LEP |
| CRP | GLUCOSE | IL2RA | PLAT |
| CRP | GLUCOSE | IL2RA | SERPINE1 |
| CRP | GLUCOSE | IL2RA | TRIG |
| CRP | GLUCOSE | IL2RA | VEGF |

FIGURE 13 (continued)

| CRP | GLUCOSE | IL2RA | VWF |
|---|---|---|---|
| CRP | GLUCOSE | INHBA | INSULIN |
| CRP | GLUCOSE | INHBA | LEP |
| CRP | GLUCOSE | INHBA | PLAT |
| CRP | GLUCOSE | INHBA | SERPINE1 |
| CRP | GLUCOSE | INHBA | TRIG |
| CRP | GLUCOSE | INHBA | VEGF |
| CRP | GLUCOSE | INHBA | VWF |
| CRP | GLUCOSE | INSULIN | LEP |
| CRP | GLUCOSE | INSULIN | PLAT |
| CRP | GLUCOSE | INSULIN | SERPINE1 |
| CRP | GLUCOSE | INSULIN | TRIG |
| CRP | GLUCOSE | INSULIN | VEGF |
| CRP | GLUCOSE | INSULIN | VWF |
| CRP | GLUCOSE | LEP | PLAT |
| CRP | GLUCOSE | LEP | SERPINE1 |
| CRP | GLUCOSE | LEP | TRIG |
| CRP | GLUCOSE | LEP | VEGF |
| CRP | GLUCOSE | LEP | VWF |
| CRP | GLUCOSE | PLAT | SERPINE1 |
| CRP | GLUCOSE | PLAT | TRIG |
| CRP | GLUCOSE | PLAT | VEGF |
| CRP | GLUCOSE | PLAT | VWF |
| CRP | GLUCOSE | SERPINE1 | TRIG |
| CRP | GLUCOSE | SERPINE1 | VEGF |
| CRP | GLUCOSE | SERPINE1 | VWF |
| CRP | GLUCOSE | TRIG | VEGF |
| CRP | GLUCOSE | TRIG | VWF |
| CRP | GLUCOSE | VEGF | VWF |
| ENG | FTH1 | GLUCOSE | HBA1C |
| ENG | FTH1 | GLUCOSE | IL18 |
| ENG | FTH1 | GLUCOSE | INSULIN |
| ENG | FTH1 | GLUCOSE | LEP |
| ENG | GLUCOSE | GPT | IL18 |
| ENG | GLUCOSE | GPT | INSULIN |
| ENG | GLUCOSE | HBA1C | IL18 |
| ENG | GLUCOSE | HBA1C | INSULIN |
| ENG | GLUCOSE | HBA1C | LEP |
| ENG | GLUCOSE | HBA1C | TRIG |
| ENG | GLUCOSE | HDL | INSULIN |

FIGURE 13 (continued)

| | | | |
|---|---|---|---|
| ENG | GLUCOSE | HGF | IL18 |
| ENG | GLUCOSE | HGF | INSULIN |
| ENG | GLUCOSE | HSPA1B | IL18 |
| ENG | GLUCOSE | HSPA1B | INSULIN |
| ENG | GLUCOSE | IGFBP1 | INSULIN |
| ENG | GLUCOSE | IGFBP2 | IL18 |
| ENG | GLUCOSE | IGFBP2 | INSULIN |
| ENG | GLUCOSE | IL18 | IL2RA |
| ENG | GLUCOSE | IL18 | INSULIN |
| ENG | GLUCOSE | IL18 | LEP |
| ENG | GLUCOSE | IL18 | PLAT |
| ENG | GLUCOSE | IL18 | TRIG |
| ENG | GLUCOSE | IL18 | VEGF |
| ENG | GLUCOSE | IL18 | VWF |
| ENG | GLUCOSE | IL2RA | INSULIN |
| ENG | GLUCOSE | INSULIN | LEP |
| ENG | GLUCOSE | INSULIN | PLAT |
| ENG | GLUCOSE | INSULIN | SERPINE1 |
| ENG | GLUCOSE | INSULIN | TRIG |
| ENG | GLUCOSE | INSULIN | VEGF |
| ENG | GLUCOSE | INSULIN | VWF |
| ENG | GLUCOSE | LEP | TRIG |
| FTH1 | GLUCOSE | GPT | HBA1C |
| FTH1 | GLUCOSE | GPT | HGF |
| FTH1 | GLUCOSE | GPT | IL18 |
| FTH1 | GLUCOSE | GPT | INSULIN |
| FTH1 | GLUCOSE | GPT | LEP |
| FTH1 | GLUCOSE | HBA1C | HDL |
| FTH1 | GLUCOSE | HBA1C | HGF |
| FTH1 | GLUCOSE | HBA1C | HSPA1B |
| FTH1 | GLUCOSE | HBA1C | IGFBP2 |
| FTH1 | GLUCOSE | HBA1C | IL18 |
| FTH1 | GLUCOSE | HBA1C | IL2RA |
| FTH1 | GLUCOSE | HBA1C | INSULIN |
| FTH1 | GLUCOSE | HBA1C | LEP |
| FTH1 | GLUCOSE | HBA1C | PLAT |
| FTH1 | GLUCOSE | HBA1C | SERPINE1 |
| FTH1 | GLUCOSE | HBA1C | TRIG |
| FTH1 | GLUCOSE | HBA1C | VEGF |
| FTH1 | GLUCOSE | HBA1C | VWF |

FIGURE 13 (continued)

| | | | |
|---|---|---|---|
| FTH1 | GLUCOSE | HDL | IL18 |
| FTH1 | GLUCOSE | HDL | INSULIN |
| FTH1 | GLUCOSE | HDL | LEP |
| FTH1 | GLUCOSE | HGF | IL18 |
| FTH1 | GLUCOSE | HGF | IL2RA |
| FTH1 | GLUCOSE | HGF | INSULIN |
| FTH1 | GLUCOSE | HGF | LEP |
| FTH1 | GLUCOSE | HGF | PLAT |
| FTH1 | GLUCOSE | HGF | TRIG |
| FTH1 | GLUCOSE | HSPA1B | IL18 |
| FTH1 | GLUCOSE | HSPA1B | INSULIN |
| FTH1 | GLUCOSE | HSPA1B | LEP |
| FTH1 | GLUCOSE | IGFBP1 | IL18 |
| FTH1 | GLUCOSE | IGFBP1 | INSULIN |
| FTH1 | GLUCOSE | IGFBP1 | LEP |
| FTH1 | GLUCOSE | IGFBP2 | IL18 |
| FTH1 | GLUCOSE | IGFBP2 | INSULIN |
| FTH1 | GLUCOSE | IGFBP2 | LEP |
| FTH1 | GLUCOSE | IL18 | IL2RA |
| FTH1 | GLUCOSE | IL18 | INHBA |
| FTH1 | GLUCOSE | IL18 | INSULIN |
| FTH1 | GLUCOSE | IL18 | LEP |
| FTH1 | GLUCOSE | IL18 | PLAT |
| FTH1 | GLUCOSE | IL18 | SERPINE1 |
| FTH1 | GLUCOSE | IL18 | TRIG |
| FTH1 | GLUCOSE | IL18 | VEGF |
| FTH1 | GLUCOSE | IL18 | VWF |
| FTH1 | GLUCOSE | IL2RA | INSULIN |
| FTH1 | GLUCOSE | IL2RA | LEP |
| FTH1 | GLUCOSE | IL2RA | TRIG |
| FTH1 | GLUCOSE | IL2RA | VEGF |
| FTH1 | GLUCOSE | INHBA | INSULIN |
| FTH1 | GLUCOSE | INHBA | LEP |
| FTH1 | GLUCOSE | INSULIN | LEP |
| FTH1 | GLUCOSE | INSULIN | PLAT |
| FTH1 | GLUCOSE | INSULIN | SERPINE1 |
| FTH1 | GLUCOSE | INSULIN | TRIG |
| FTH1 | GLUCOSE | INSULIN | VEGF |
| FTH1 | GLUCOSE | INSULIN | VWF |
| FTH1 | GLUCOSE | LEP | PLAT |

FIGURE 13(continued)

| | | | |
|---|---|---|---|
| FTH1 | GLUCOSE | LEP | SERPINE1 |
| FTH1 | GLUCOSE | LEP | TRIG |
| FTH1 | GLUCOSE | LEP | VEGF |
| FTH1 | GLUCOSE | LEP | VWF |
| FTH1 | GLUCOSE | TRIG | VEGF |
| GLUCOSE | GPT | HBA1C | HDL |
| GLUCOSE | GPT | HBA1C | HGF |
| GLUCOSE | GPT | HBA1C | IL18 |
| GLUCOSE | GPT | HBA1C | INSULIN |
| GLUCOSE | GPT | HBA1C | LEP |
| GLUCOSE | GPT | HBA1C | TRIG |
| GLUCOSE | GPT | HDL | IL18 |
| GLUCOSE | GPT | HDL | INSULIN |
| GLUCOSE | GPT | HDL | LEP |
| GLUCOSE | GPT | HGF | IL18 |
| GLUCOSE | GPT | HGF | INSULIN |
| GLUCOSE | GPT | HSPA1B | IL18 |
| GLUCOSE | GPT | HSPA1B | INSULIN |
| GLUCOSE | GPT | IGFBP1 | INSULIN |
| GLUCOSE | GPT | IGFBP2 | IL18 |
| GLUCOSE | GPT | IGFBP2 | INSULIN |
| GLUCOSE | GPT | IL18 | IL2RA |
| GLUCOSE | GPT | IL18 | INSULIN |
| GLUCOSE | GPT | IL18 | LEP |
| GLUCOSE | GPT | IL18 | PLAT |
| GLUCOSE | GPT | IL18 | TRIG |
| GLUCOSE | GPT | IL18 | VEGF |
| GLUCOSE | GPT | IL18 | VWF |
| GLUCOSE | GPT | IL2RA | INSULIN |
| GLUCOSE | GPT | INHBA | INSULIN |
| GLUCOSE | GPT | INSULIN | LEP |
| GLUCOSE | GPT | INSULIN | PLAT |
| GLUCOSE | GPT | INSULIN | SERPINE1 |
| GLUCOSE | GPT | INSULIN | TRIG |
| GLUCOSE | GPT | INSULIN | VEGF |
| GLUCOSE | GPT | INSULIN | VWF |
| GLUCOSE | GPT | LEP | TRIG |
| GLUCOSE | GPT | LEP | VEGF |
| GLUCOSE | HBA1C | HDL | HGF |
| GLUCOSE | HBA1C | HDL | HSPA1B |

FIGURE 13 (continued)

| GLUCOSE | HBA1C | HDL | IL18 |
|---|---|---|---|
| GLUCOSE | HBA1C | HDL | IL2RA |
| GLUCOSE | HBA1C | HDL | INSULIN |
| GLUCOSE | HBA1C | HDL | LEP |
| GLUCOSE | HBA1C | HDL | PLAT |
| GLUCOSE | HBA1C | HDL | TRIG |
| GLUCOSE | HBA1C | HDL | VEGF |
| GLUCOSE | HBA1C | HDL | VWF |
| GLUCOSE | HBA1C | HGF | HSPA1B |
| GLUCOSE | HBA1C | HGF | IL18 |
| GLUCOSE | HBA1C | HGF | INSULIN |
| GLUCOSE | HBA1C | HGF | LEP |
| GLUCOSE | HBA1C | HGF | PLAT |
| GLUCOSE | HBA1C | HGF | TRIG |
| GLUCOSE | HBA1C | HSPA1B | IL18 |
| GLUCOSE | HBA1C | HSPA1B | INSULIN |
| GLUCOSE | HBA1C | HSPA1B | LEP |
| GLUCOSE | HBA1C | HSPA1B | TRIG |
| GLUCOSE | HBA1C | IGFBP1 | IL18 |
| GLUCOSE | HBA1C | IGFBP1 | INSULIN |
| GLUCOSE | HBA1C | IGFBP1 | LEP |
| GLUCOSE | HBA1C | IGFBP1 | TRIG |
| GLUCOSE | HBA1C | IGFBP2 | IL18 |
| GLUCOSE | HBA1C | IGFBP2 | INSULIN |
| GLUCOSE | HBA1C | IGFBP2 | LEP |
| GLUCOSE | HBA1C | IGFBP2 | TRIG |
| GLUCOSE | HBA1C | IL18 | IL2RA |
| GLUCOSE | HBA1C | IL18 | INHBA |
| GLUCOSE | HBA1C | IL18 | INSULIN |
| GLUCOSE | HBA1C | IL18 | LEP |
| GLUCOSE | HBA1C | IL18 | PLAT |
| GLUCOSE | HBA1C | IL18 | SERPINE1 |
| GLUCOSE | HBA1C | IL18 | TRIG |
| GLUCOSE | HBA1C | IL18 | VEGF |
| GLUCOSE | HBA1C | IL18 | VWF |
| GLUCOSE | HBA1C | IL2RA | INSULIN |
| GLUCOSE | HBA1C | IL2RA | LEP |
| GLUCOSE | HBA1C | IL2RA | PLAT |
| GLUCOSE | HBA1C | IL2RA | TRIG |
| GLUCOSE | HBA1C | INHBA | INSULIN |

FIGURE 13 (continued)

| GLUCOSE | HBA1C | INSULIN | LEP |
|---|---|---|---|
| GLUCOSE | HBA1C | INSULIN | PLAT |
| GLUCOSE | HBA1C | INSULIN | SERPINE1 |
| GLUCOSE | HBA1C | INSULIN | TRIG |
| GLUCOSE | HBA1C | INSULIN | VEGF |
| GLUCOSE | HBA1C | INSULIN | VWF |
| GLUCOSE | HBA1C | LEP | PLAT |
| GLUCOSE | HBA1C | LEP | SERPINE1 |
| GLUCOSE | HBA1C | LEP | TRIG |
| GLUCOSE | HBA1C | LEP | VEGF |
| GLUCOSE | HBA1C | LEP | VWF |
| GLUCOSE | HBA1C | PLAT | TRIG |
| GLUCOSE | HBA1C | SERPINE1 | TRIG |
| GLUCOSE | HBA1C | TRIG | VEGF |
| GLUCOSE | HBA1C | TRIG | VWF |
| GLUCOSE | HDL | HGF | IL18 |
| GLUCOSE | HDL | HGF | INSULIN |
| GLUCOSE | HDL | HSPA1B | IL18 |
| GLUCOSE | HDL | HSPA1B | INSULIN |
| GLUCOSE | HDL | HSPA1B | LEP |
| GLUCOSE | HDL | IGFBP2 | INSULIN |
| GLUCOSE | HDL | IL18 | IL2RA |
| GLUCOSE | HDL | IL18 | INSULIN |
| GLUCOSE | HDL | IL18 | LEP |
| GLUCOSE | HDL | IL18 | PLAT |
| GLUCOSE | HDL | IL18 | TRIG |
| GLUCOSE | HDL | IL18 | VEGF |
| GLUCOSE | HDL | IL18 | VWF |
| GLUCOSE | HDL | IL2RA | INSULIN |
| GLUCOSE | HDL | IL2RA | LEP |
| GLUCOSE | HDL | INSULIN | LEP |
| GLUCOSE | HDL | INSULIN | PLAT |
| GLUCOSE | HDL | INSULIN | SERPINE1 |
| GLUCOSE | HDL | INSULIN | TRIG |
| GLUCOSE | HDL | INSULIN | VEGF |
| GLUCOSE | HDL | INSULIN | VWF |
| GLUCOSE | HDL | LEP | PLAT |
| GLUCOSE | HDL | LEP | TRIG |
| GLUCOSE | HDL | LEP | VEGF |
| GLUCOSE | HDL | LEP | VWF |

FIGURE 13 (continued)

| | | | |
|---|---|---|---|
| GLUCOSE | HGF | HSPA1B | IL18 |
| GLUCOSE | HGF | HSPA1B | INSULIN |
| GLUCOSE | HGF | IGFBP1 | INSULIN |
| GLUCOSE | HGF | IGFBP2 | IL18 |
| GLUCOSE | HGF | IGFBP2 | INSULIN |
| GLUCOSE | HGF | IL18 | IL2RA |
| GLUCOSE | HGF | IL18 | INSULIN |
| GLUCOSE | HGF | IL18 | LEP |
| GLUCOSE | HGF | IL18 | PLAT |
| GLUCOSE | HGF | IL18 | TRIG |
| GLUCOSE | HGF | IL18 | VEGF |
| GLUCOSE | HGF | IL18 | VWF |
| GLUCOSE | HGF | IL2RA | INSULIN |
| GLUCOSE | HGF | IL2RA | TRIG |
| GLUCOSE | HGF | INHBA | INSULIN |
| GLUCOSE | HGF | INSULIN | LEP |
| GLUCOSE | HGF | INSULIN | PLAT |
| GLUCOSE | HGF | INSULIN | SERPINE1 |
| GLUCOSE | HGF | INSULIN | TRIG |
| GLUCOSE | HGF | INSULIN | VEGF |
| GLUCOSE | HGF | INSULIN | VWF |
| GLUCOSE | HGF | LEP | TRIG |
| GLUCOSE | HGF | PLAT | TRIG |
| GLUCOSE | HSPA1B | IGFBP1 | IL18 |
| GLUCOSE | HSPA1B | IGFBP1 | INSULIN |
| GLUCOSE | HSPA1B | IGFBP2 | IL18 |
| GLUCOSE | HSPA1B | IGFBP2 | INSULIN |
| GLUCOSE | HSPA1B | IL18 | IL2RA |
| GLUCOSE | HSPA1B | IL18 | INHBA |
| GLUCOSE | HSPA1B | IL18 | INSULIN |
| GLUCOSE | HSPA1B | IL18 | LEP |
| GLUCOSE | HSPA1B | IL18 | PLAT |
| GLUCOSE | HSPA1B | IL18 | TRIG |
| GLUCOSE | HSPA1B | IL18 | VEGF |
| GLUCOSE | HSPA1B | IL18 | VWF |
| GLUCOSE | HSPA1B | IL2RA | INSULIN |
| GLUCOSE | HSPA1B | IL2RA | TRIG |
| GLUCOSE | HSPA1B | INHBA | INSULIN |
| GLUCOSE | HSPA1B | INSULIN | LEP |
| GLUCOSE | HSPA1B | INSULIN | PLAT |

FIGURE 13 (continued)

| | | | |
|---|---|---|---|
| GLUCOSE | HSPA1B | INSULIN | SERPINE1 |
| GLUCOSE | HSPA1B | INSULIN | TRIG |
| GLUCOSE | HSPA1B | INSULIN | VEGF |
| GLUCOSE | HSPA1B | INSULIN | VWF |
| GLUCOSE | HSPA1B | LEP | TRIG |
| GLUCOSE | HSPA1B | LEP | VEGF |
| GLUCOSE | IGFBP1 | IL18 | INSULIN |
| GLUCOSE | IGFBP1 | IL18 | LEP |
| GLUCOSE | IGFBP1 | IL18 | PLAT |
| GLUCOSE | IGFBP1 | IL18 | TRIG |
| GLUCOSE | IGFBP1 | IL18 | VEGF |
| GLUCOSE | IGFBP1 | IL18 | VWF |
| GLUCOSE | IGFBP1 | IL2RA | INSULIN |
| GLUCOSE | IGFBP1 | INSULIN | LEP |
| GLUCOSE | IGFBP1 | INSULIN | PLAT |
| GLUCOSE | IGFBP1 | INSULIN | TRIG |
| GLUCOSE | IGFBP1 | INSULIN | VEGF |
| GLUCOSE | IGFBP1 | INSULIN | VWF |
| GLUCOSE | IGFBP1 | LEP | TRIG |
| GLUCOSE | IGFBP2 | IL18 | IL2RA |
| GLUCOSE | IGFBP2 | IL18 | INSULIN |
| GLUCOSE | IGFBP2 | IL18 | LEP |
| GLUCOSE | IGFBP2 | IL18 | PLAT |
| GLUCOSE | IGFBP2 | IL18 | TRIG |
| GLUCOSE | IGFBP2 | IL18 | VEGF |
| GLUCOSE | IGFBP2 | IL18 | VWF |
| GLUCOSE | IGFBP2 | IL2RA | INSULIN |
| GLUCOSE | IGFBP2 | INSULIN | LEP |
| GLUCOSE | IGFBP2 | INSULIN | PLAT |
| GLUCOSE | IGFBP2 | INSULIN | SERPINE1 |
| GLUCOSE | IGFBP2 | INSULIN | TRIG |
| GLUCOSE | IGFBP2 | INSULIN | VEGF |
| GLUCOSE | IGFBP2 | INSULIN | VWF |
| GLUCOSE | IGFBP2 | LEP | TRIG |
| GLUCOSE | IL18 | IL2RA | INSULIN |
| GLUCOSE | IL18 | IL2RA | LEP |
| GLUCOSE | IL18 | IL2RA | PLAT |
| GLUCOSE | IL18 | IL2RA | TRIG |
| GLUCOSE | IL18 | IL2RA | VEGF |
| GLUCOSE | IL18 | IL2RA | VWF |

FIGURE 13 (continued)

| | | | |
|---|---|---|---|
| GLUCOSE | IL18 | INHBA | INSULIN |
| GLUCOSE | IL18 | INHBA | LEP |
| GLUCOSE | IL18 | INHBA | PLAT |
| GLUCOSE | IL18 | INHBA | TRIG |
| GLUCOSE | IL18 | INSULIN | LEP |
| GLUCOSE | IL18 | INSULIN | PLAT |
| GLUCOSE | IL18 | INSULIN | SERPINE1 |
| GLUCOSE | IL18 | INSULIN | TRIG |
| GLUCOSE | IL18 | INSULIN | VEGF |
| GLUCOSE | IL18 | INSULIN | VWF |
| GLUCOSE | IL18 | LEP | PLAT |
| GLUCOSE | IL18 | LEP | SERPINE1 |
| GLUCOSE | IL18 | LEP | TRIG |
| GLUCOSE | IL18 | LEP | VEGF |
| GLUCOSE | IL18 | LEP | VWF |
| GLUCOSE | IL18 | PLAT | SERPINE1 |
| GLUCOSE | IL18 | PLAT | TRIG |
| GLUCOSE | IL18 | PLAT | VEGF |
| GLUCOSE | IL18 | PLAT | VWF |
| GLUCOSE | IL18 | SERPINE1 | TRIG |
| GLUCOSE | IL18 | SERPINE1 | VWF |
| GLUCOSE | IL18 | TRIG | VEGF |
| GLUCOSE | IL18 | TRIG | VWF |
| GLUCOSE | IL18 | VEGF | VWF |
| GLUCOSE | IL2RA | INHBA | INSULIN |
| GLUCOSE | IL2RA | INSULIN | LEP |
| GLUCOSE | IL2RA | INSULIN | PLAT |
| GLUCOSE | IL2RA | INSULIN | SERPINE1 |
| GLUCOSE | IL2RA | INSULIN | TRIG |
| GLUCOSE | IL2RA | INSULIN | VEGF |
| GLUCOSE | IL2RA | INSULIN | VWF |
| GLUCOSE | IL2RA | LEP | PLAT |
| GLUCOSE | IL2RA | LEP | TRIG |
| GLUCOSE | IL2RA | LEP | VEGF |
| GLUCOSE | IL2RA | PLAT | TRIG |
| GLUCOSE | IL2RA | TRIG | VEGF |
| GLUCOSE | IL2RA | TRIG | VWF |
| GLUCOSE | INHBA | INSULIN | LEP |
| GLUCOSE | INHBA | INSULIN | PLAT |
| GLUCOSE | INHBA | INSULIN | TRIG |

FIGURE 13 (continued)

| | | | |
|---|---|---|---|
| GLUCOSE | INHBA | INSULIN | VEGF |
| GLUCOSE | INHBA | INSULIN | VWF |
| GLUCOSE | INHBA | LEP | TRIG |
| GLUCOSE | INSULIN | LEP | PLAT |
| GLUCOSE | INSULIN | LEP | SERPINE1 |
| GLUCOSE | INSULIN | LEP | TRIG |
| GLUCOSE | INSULIN | LEP | VEGF |
| GLUCOSE | INSULIN | LEP | VWF |
| GLUCOSE | INSULIN | PLAT | SERPINE1 |
| GLUCOSE | INSULIN | PLAT | TRIG |
| GLUCOSE | INSULIN | PLAT | VEGF |
| GLUCOSE | INSULIN | PLAT | VWF |
| GLUCOSE | INSULIN | SERPINE1 | TRIG |
| GLUCOSE | INSULIN | SERPINE1 | VEGF |
| GLUCOSE | INSULIN | SERPINE1 | VWF |
| GLUCOSE | INSULIN | TRIG | VEGF |
| GLUCOSE | INSULIN | TRIG | VWF |
| GLUCOSE | INSULIN | VEGF | VWF |
| GLUCOSE | LEP | PLAT | TRIG |
| GLUCOSE | LEP | PLAT | VEGF |
| GLUCOSE | LEP | TRIG | VEGF |
| GLUCOSE | LEP | TRIG | VWF |
| GLUCOSE | LEP | VEGF | VWF |
| GLUCOSE | PLAT | TRIG | VEGF |
| GLUCOSE | PLAT | TRIG | VWF |
| GLUCOSE | TRIG | VEGF | VWF |

FIGURE 14

| | | | | |
|---|---|---|---|---|
| ADIPOQ | ANG | CRP | GLUCOSE | INSULIN |
| ADIPOQ | C3 | CRP | GLUCOSE | HBA1C |
| ADIPOQ | CCL2 | CRP | FTH1 | GLUCOSE |
| ADIPOQ | CCL2 | CRP | GLUCOSE | HBA1C |
| ADIPOQ | CCL2 | CRP | GLUCOSE | INSULIN |
| ADIPOQ | CCL2 | CRP | GLUCOSE | PLAT |
| ADIPOQ | CDK5 | CRP | GLUCOSE | HBA1C |
| ADIPOQ | CDK5 | CRP | GLUCOSE | INSULIN |
| ADIPOQ | CRP | ENG | FTH1 | GLUCOSE |
| ADIPOQ | CRP | ENG | GLUCOSE | HBA1C |
| ADIPOQ | CRP | ENG | GLUCOSE | INSULIN |
| ADIPOQ | CRP | FTH1 | GLUCOSE | HBA1C |
| ADIPOQ | CRP | FTH1 | GLUCOSE | IL18 |
| ADIPOQ | CRP | FTH1 | GLUCOSE | INSULIN |
| ADIPOQ | CRP | FTH1 | GLUCOSE | LEP |
| ADIPOQ | CRP | GLUCOSE | GPT | HBA1C |
| ADIPOQ | CRP | GLUCOSE | HBA1C | IL18 |
| ADIPOQ | CRP | GLUCOSE | HBA1C | INSULIN |
| ADIPOQ | CRP | GLUCOSE | HBA1C | LEP |
| ADIPOQ | CRP | GLUCOSE | HBA1C | PLAT |
| ADIPOQ | CRP | GLUCOSE | HBA1C | TRIG |
| ADIPOQ | CRP | GLUCOSE | IL18 | INSULIN |
| ADIPOQ | CRP | GLUCOSE | IL18 | LEP |
| ADIPOQ | CRP | GLUCOSE | IL18 | PLAT |
| ADIPOQ | CRP | GLUCOSE | INSULIN | PLAT |
| ADIPOQ | CRP | GLUCOSE | LEP | PLAT |
| ANG | CCL2 | CRP | FTH1 | GLUCOSE |
| ANG | CCL2 | CRP | GLUCOSE | HBA1C |
| ANG | CCL2 | CRP | GLUCOSE | INSULIN |
| ANG | CRP | FTH1 | GLUCOSE | HBA1C |
| ANG | CRP | FTH1 | GLUCOSE | INSULIN |
| ANG | CRP | GLUCOSE | HBA1C | IL18 |
| ANG | CRP | GLUCOSE | HBA1C | INSULIN |
| ANG | CRP | GLUCOSE | HBA1C | TRIG |
| ANG | CRP | GLUCOSE | IL18 | INSULIN |
| ANG | CRP | GLUCOSE | INSULIN | PLAT |
| C3 | CCL2 | CRP | GLUCOSE | INSULIN |
| C3 | CRP | GLUCOSE | HBA1C | IL18 |
| C3 | CRP | GLUCOSE | HBA1C | INSULIN |
| CCL2 | CDK5 | CRP | GLUCOSE | HBA1C |

FIGURE 14 (continued)

| | | | | |
|---|---|---|---|---|
| CCL2 | CDK5 | CRP | GLUCOSE | INSULIN |
| CCL2 | CRP | ENG | FTH1 | GLUCOSE |
| CCL2 | CRP | FTH1 | GLUCOSE | HBA1C |
| CCL2 | CRP | FTH1 | GLUCOSE | INSULIN |
| CCL2 | CRP | FTH1 | GLUCOSE | LEP |
| CCL2 | CRP | GLUCOSE | HBA1C | HDL |
| CCL2 | CRP | GLUCOSE | HBA1C | IGFBP1 |
| CCL2 | CRP | GLUCOSE | HBA1C | IL18 |
| CCL2 | CRP | GLUCOSE | HBA1C | INSULIN |
| CCL2 | CRP | GLUCOSE | HBA1C | PLAT |
| CCL2 | CRP | GLUCOSE | HBA1C | TRIG |
| CCL2 | CRP | GLUCOSE | HSPA1B | INSULIN |
| CCL2 | CRP | GLUCOSE | IL18 | INSULIN |
| CCL2 | CRP | GLUCOSE | INSULIN | PLAT |
| CDK5 | CRP | GLUCOSE | HBA1C | IL18 |
| CDK5 | CRP | GLUCOSE | HBA1C | INSULIN |
| CRP | ENG | FTH1 | GLUCOSE | HBA1C |
| CRP | ENG | FTH1 | GLUCOSE | IL18 |
| CRP | ENG | FTH1 | GLUCOSE | INSULIN |
| CRP | ENG | GLUCOSE | HBA1C | IL18 |
| CRP | ENG | GLUCOSE | HBA1C | INSULIN |
| CRP | ENG | GLUCOSE | HBA1C | TRIG |
| CRP | ENG | GLUCOSE | IL18 | INSULIN |
| CRP | FTH1 | GLUCOSE | GPT | INSULIN |
| CRP | FTH1 | GLUCOSE | HBA1C | HDL |
| CRP | FTH1 | GLUCOSE | HBA1C | IL18 |
| CRP | FTH1 | GLUCOSE | HBA1C | IL2RA |
| CRP | FTH1 | GLUCOSE | HBA1C | INSULIN |
| CRP | FTH1 | GLUCOSE | HBA1C | LEP |
| CRP | FTH1 | GLUCOSE | HBA1C | PLAT |
| CRP | FTH1 | GLUCOSE | HBA1C | TRIG |
| CRP | FTH1 | GLUCOSE | IL18 | INSULIN |
| CRP | FTH1 | GLUCOSE | INSULIN | PLAT |
| CRP | GLUCOSE | GPT | HBA1C | IL18 |
| CRP | GLUCOSE | GPT | HBA1C | INSULIN |
| CRP | GLUCOSE | HBA1C | HDL | IL18 |
| CRP | GLUCOSE | HBA1C | HDL | INSULIN |
| CRP | GLUCOSE | HBA1C | HDL | PLAT |
| CRP | GLUCOSE | HBA1C | HSPA1B | IL18 |
| CRP | GLUCOSE | HBA1C | HSPA1B | INSULIN |

FIGURE 14 (continued)

| CRP | GLUCOSE | HBA1C | IGFBP1 | IL18 |
|---|---|---|---|---|
| CRP | GLUCOSE | HBA1C | IGFBP2 | IL18 |
| CRP | GLUCOSE | HBA1C | IGFBP2 | INSULIN |
| CRP | GLUCOSE | HBA1C | IL18 | INSULIN |
| CRP | GLUCOSE | HBA1C | IL18 | LEP |
| CRP | GLUCOSE | HBA1C | IL18 | PLAT |
| CRP | GLUCOSE | HBA1C | IL18 | TRIG |
| CRP | GLUCOSE | HBA1C | IL18 | VEGF |
| CRP | GLUCOSE | HBA1C | IL2RA | INSULIN |
| CRP | GLUCOSE | HBA1C | INSULIN | PLAT |
| CRP | GLUCOSE | HBA1C | INSULIN | TRIG |
| CRP | GLUCOSE | HBA1C | INSULIN | VEGF |
| CRP | GLUCOSE | HBA1C | PLAT | TRIG |
| CRP | GLUCOSE | HSPA1B | IL18 | INSULIN |
| CRP | GLUCOSE | IL18 | INSULIN | PLAT |
| FTH1 | GLUCOSE | HBA1C | IL18 | INSULIN |
| FTH1 | GLUCOSE | HBA1C | IL18 | LEP |
| FTH1 | GLUCOSE | HBA1C | INSULIN | PLAT |
| GLUCOSE | HBA1C | IL18 | INSULIN | PLAT |

FIGURE 15

| ADIPOQ | ANG | CRP | FTH1 | GLUCOSE | HBA1C |
|---|---|---|---|---|---|
| ADIPOQ | ANG | CRP | FTH1 | GLUCOSE | INSULIN |
| ADIPOQ | ANG | CRP | GLUCOSE | HBA1C | IL18 |
| ADIPOQ | CCL2 | CRP | FTH1 | GLUCOSE | HBA1C |
| ADIPOQ | CCL2 | CRP | FTH1 | GLUCOSE | INSULIN |
| ADIPOQ | CCL2 | CRP | FTH1 | GLUCOSE | LEP |
| ADIPOQ | CCL2 | CRP | GLUCOSE | HBA1C | IL18 |
| ADIPOQ | CCL2 | CRP | GLUCOSE | HBA1C | INSULIN |
| ADIPOQ | CCL2 | CRP | GLUCOSE | HBA1C | PLAT |
| ADIPOQ | CCL2 | CRP | GLUCOSE | INSULIN | PLAT |
| ADIPOQ | CDK5 | CRP | FTH1 | GLUCOSE | HBA1C |
| ADIPOQ | CRP | ENG | FTH1 | GLUCOSE | HBA1C |
| ADIPOQ | CRP | ENG | FTH1 | GLUCOSE | INSULIN |
| ADIPOQ | CRP | ENG | FTH1 | GLUCOSE | LEP |
| ADIPOQ | CRP | FTH1 | GLUCOSE | HBA1C | IL18 |
| ADIPOQ | CRP | FTH1 | GLUCOSE | HBA1C | INSULIN |
| ADIPOQ | CRP | FTH1 | GLUCOSE | HBA1C | LEP |
| ADIPOQ | CRP | FTH1 | GLUCOSE | HBA1C | PLAT |
| ADIPOQ | CRP | FTH1 | GLUCOSE | IL18 | LEP |
| ADIPOQ | CRP | FTH1 | GLUCOSE | INSULIN | PLAT |
| ADIPOQ | CRP | FTH1 | GLUCOSE | LEP | PLAT |
| ADIPOQ | CRP | GLUCOSE | HBA1C | IL18 | INSULIN |
| ADIPOQ | CRP | GLUCOSE | HBA1C | IL18 | LEP |
| ADIPOQ | CRP | GLUCOSE | HBA1C | IL18 | PLAT |
| ADIPOQ | CRP | GLUCOSE | HBA1C | INSULIN | PLAT |
| ADIPOQ | CRP | GLUCOSE | HBA1C | LEP | PLAT |
| ADIPOQ | CRP | GLUCOSE | HBA1C | PLAT | TRIG |
| ADIPOQ | CRP | GLUCOSE | IL18 | LEP | PLAT |
| ANG | CCL2 | CRP | FTH1 | GLUCOSE | HBA1C |
| ANG | CCL2 | CRP | FTH1 | GLUCOSE | INSULIN |
| ANG | CCL2 | CRP | GLUCOSE | HBA1C | INSULIN |
| ANG | CRP | ENG | FTH1 | GLUCOSE | HBA1C |
| ANG | CRP | ENG | FTH1 | GLUCOSE | INSULIN |
| ANG | CRP | FTH1 | GLUCOSE | HBA1C | IL18 |
| ANG | CRP | FTH1 | GLUCOSE | HBA1C | IL2RA |
| ANG | CRP | FTH1 | GLUCOSE | HBA1C | INSULIN |
| ANG | CRP | FTH1 | GLUCOSE | HBA1C | LEP |
| ANG | CRP | FTH1 | GLUCOSE | HBA1C | TRIG |
| ANG | CRP | FTH1 | GLUCOSE | INSULIN | PLAT |
| ANG | CRP | GLUCOSE | HBA1C | IL18 | INSULIN |

FIGURE 15 (continued)

| | | | | | |
|---|---|---|---|---|---|
| ANG | CRP | GLUCOSE | HBA1C | IL18 | PLAT |
| ANG | CRP | GLUCOSE | HBA1C | INSULIN | PLAT |
| C3 | CCL2 | CRP | FTH1 | GLUCOSE | HBA1C |
| C3 | CCL2 | CRP | GLUCOSE | HBA1C | INSULIN |
| C3 | CRP | FTH1 | GLUCOSE | HBA1C | INSULIN |
| C3 | CRP | GLUCOSE | HBA1C | IL18 | INSULIN |
| CCL2 | CDK5 | CRP | FTH1 | GLUCOSE | HBA1C |
| CCL2 | CDK5 | CRP | FTH1 | GLUCOSE | INSULIN |
| CCL2 | CDK5 | CRP | GLUCOSE | HBA1C | INSULIN |
| CCL2 | CRP | ENG | FTH1 | GLUCOSE | HBA1C |
| CCL2 | CRP | ENG | FTH1 | GLUCOSE | INSULIN |
| CCL2 | CRP | ENG | GLUCOSE | HBA1C | INSULIN |
| CCL2 | CRP | FTH1 | GLUCOSE | GPT | HBA1C |
| CCL2 | CRP | FTH1 | GLUCOSE | GPT | INSULIN |
| CCL2 | CRP | FTH1 | GLUCOSE | HBA1C | IGFBP1 |
| CCL2 | CRP | FTH1 | GLUCOSE | HBA1C | IL18 |
| CCL2 | CRP | FTH1 | GLUCOSE | HBA1C | INSULIN |
| CCL2 | CRP | FTH1 | GLUCOSE | HBA1C | LEP |
| CCL2 | CRP | FTH1 | GLUCOSE | HBA1C | PLAT |
| CCL2 | CRP | FTH1 | GLUCOSE | HBA1C | TRIG |
| CCL2 | CRP | FTH1 | GLUCOSE | INSULIN | PLAT |
| CCL2 | CRP | GLUCOSE | GPT | HBA1C | INSULIN |
| CCL2 | CRP | GLUCOSE | HBA1C | HSPA1B | INSULIN |
| CCL2 | CRP | GLUCOSE | HBA1C | IL18 | INSULIN |
| CCL2 | CRP | GLUCOSE | HBA1C | IL18 | PLAT |
| CCL2 | CRP | GLUCOSE | HBA1C | INSULIN | PLAT |
| CCL2 | CRP | GLUCOSE | HBA1C | PLAT | TRIG |
| CCL2 | CRP | GLUCOSE | IL18 | INSULIN | PLAT |
| CCL2 | FTH1 | GLUCOSE | HBA1C | INSULIN | PLAT |
| CDK5 | CRP | FTH1 | GLUCOSE | HBA1C | INSULIN |
| CRP | ENG | FTH1 | GLUCOSE | GPT | INSULIN |
| CRP | ENG | FTH1 | GLUCOSE | HBA1C | IL18 |
| CRP | ENG | FTH1 | GLUCOSE | HBA1C | INSULIN |
| CRP | ENG | FTH1 | GLUCOSE | HBA1C | LEP |
| CRP | ENG | FTH1 | GLUCOSE | HBA1C | TRIG |
| CRP | ENG | FTH1 | GLUCOSE | IL18 | INSULIN |
| CRP | ENG | FTH1 | GLUCOSE | IL2RA | INSULIN |
| CRP | ENG | FTH1 | GLUCOSE | INSULIN | PLAT |
| CRP | ENG | FTH1 | GLUCOSE | INSULIN | TRIG |
| CRP | ENG | FTH1 | GLUCOSE | INSULIN | VEGF |

FIGURE 15 (continued)

| CRP | ENG | GLUCOSE | HBA1C | IL18 | INSULIN |
|---|---|---|---|---|---|
| CRP | ENG | GLUCOSE | HBA1C | IL18 | PLAT |
| CRP | ENG | GLUCOSE | HBA1C | IL18 | TRIG |
| CRP | ENG | GLUCOSE | HBA1C | INSULIN | PLAT |
| CRP | FTH1 | GLUCOSE | GPT | HBA1C | INSULIN |
| CRP | FTH1 | GLUCOSE | HBA1C | HGF | INSULIN |
| CRP | FTH1 | GLUCOSE | HBA1C | HSPA1B | INSULIN |
| CRP | FTH1 | GLUCOSE | HBA1C | IL18 | INSULIN |
| CRP | FTH1 | GLUCOSE | HBA1C | IL18 | LEP |
| CRP | FTH1 | GLUCOSE | HBA1C | IL18 | PLAT |
| CRP | FTH1 | GLUCOSE | HBA1C | IL2RA | INSULIN |
| CRP | FTH1 | GLUCOSE | HBA1C | INSULIN | LEP |
| CRP | FTH1 | GLUCOSE | HBA1C | INSULIN | PLAT |
| CRP | FTH1 | GLUCOSE | HBA1C | INSULIN | TRIG |
| CRP | FTH1 | GLUCOSE | HBA1C | INSULIN | VEGF |
| CRP | GLUCOSE | GPT | HBA1C | IL18 | INSULIN |
| CRP | GLUCOSE | HBA1C | HSPA1B | IL18 | INSULIN |
| CRP | GLUCOSE | HBA1C | IL18 | INSULIN | PLAT |
| CRP | GLUCOSE | HBA1C | IL18 | PLAT | TRIG |
| FTH1 | GLUCOSE | HBA1C | IL18 | INSULIN | PLAT |

FIGURE 16

| ADIPOQ | ANG | CRP | FTH1 | GLUCOSE | HBA1C | IL18 |
|---|---|---|---|---|---|---|
| ADIPOQ | ANG | CRP | FTH1 | GLUCOSE | HBA1C | INSULIN |
| ADIPOQ | ANG | CRP | FTH1 | GLUCOSE | HBA1C | LEP |
| ADIPOQ | ANG | CRP | FTH1 | GLUCOSE | HBA1C | PLAT |
| ADIPOQ | ANG | CRP | GLUCOSE | HBA1C | IL18 | PLAT |
| ADIPOQ | ANG | CRP | GLUCOSE | HBA1C | INSULIN | PLAT |
| ADIPOQ | C3 | CRP | FTH1 | GLUCOSE | HBA1C | INSULIN |
| ADIPOQ | C3 | CRP | FTH1 | GLUCOSE | HBA1C | LEP |
| ADIPOQ | CCL2 | CRP | ENG | FTH1 | GLUCOSE | HBA1C |
| ADIPOQ | CCL2 | CRP | ENG | FTH1 | GLUCOSE | LEP |
| ADIPOQ | CCL2 | CRP | FTH1 | GLUCOSE | HBA1C | INSULIN |
| ADIPOQ | CCL2 | CRP | FTH1 | GLUCOSE | HBA1C | LEP |
| ADIPOQ | CCL2 | CRP | FTH1 | GLUCOSE | HBA1C | PLAT |
| ADIPOQ | CCL2 | CRP | FTH1 | GLUCOSE | LEP | PLAT |
| ADIPOQ | CCL2 | CRP | GLUCOSE | HBA1C | IL18 | PLAT |
| ADIPOQ | CCL2 | CRP | GLUCOSE | HBA1C | INSULIN | PLAT |
| ADIPOQ | CDK5 | CRP | FTH1 | GLUCOSE | HBA1C | LEP |
| ADIPOQ | CRP | ENG | FTH1 | GLUCOSE | HBA1C | IL18 |
| ADIPOQ | CRP | ENG | FTH1 | GLUCOSE | HBA1C | INSULIN |
| ADIPOQ | CRP | ENG | FTH1 | GLUCOSE | HBA1C | LEP |
| ADIPOQ | CRP | ENG | FTH1 | GLUCOSE | HBA1C | PLAT |
| ADIPOQ | CRP | ENG | FTH1 | GLUCOSE | IL18 | LEP |
| ADIPOQ | CRP | ENG | FTH1 | GLUCOSE | INSULIN | PLAT |
| ADIPOQ | CRP | ENG | FTH1 | GLUCOSE | LEP | PLAT |
| ADIPOQ | CRP | FTH1 | GLUCOSE | GPT | HBA1C | LEP |
| ADIPOQ | CRP | FTH1 | GLUCOSE | HBA1C | HSPA1B | LEP |
| ADIPOQ | CRP | FTH1 | GLUCOSE | HBA1C | IL18 | INSULIN |
| ADIPOQ | CRP | FTH1 | GLUCOSE | HBA1C | IL18 | LEP |
| ADIPOQ | CRP | FTH1 | GLUCOSE | HBA1C | IL18 | PLAT |
| ADIPOQ | CRP | FTH1 | GLUCOSE | HBA1C | INSULIN | LEP |
| ADIPOQ | CRP | FTH1 | GLUCOSE | HBA1C | INSULIN | PLAT |
| ADIPOQ | CRP | FTH1 | GLUCOSE | HBA1C | LEP | PLAT |
| ADIPOQ | CRP | GLUCOSE | HBA1C | IL18 | INSULIN | PLAT |
| ADIPOQ | CRP | GLUCOSE | HBA1C | IL18 | LEP | PLAT |
| ANG | CCL2 | CRP | FTH1 | GLUCOSE | HBA1C | IL18 |
| ANG | CCL2 | CRP | FTH1 | GLUCOSE | HBA1C | INSULIN |
| ANG | CCL2 | CRP | FTH1 | GLUCOSE | HBA1C | LEP |
| ANG | CCL2 | CRP | FTH1 | GLUCOSE | HBA1C | PLAT |
| ANG | CCL2 | CRP | FTH1 | GLUCOSE | INSULIN | PLAT |
| ANG | CCL2 | CRP | GLUCOSE | HBA1C | INSULIN | PLAT |

FIGURE 16 (continued)

| ANG | CDK5 | CRP | FTH1 | GLUCOSE | HBA1C | INSULIN |
|---|---|---|---|---|---|---|
| ANG | CRP | ENG | FTH1 | GLUCOSE | HBA1C | IL18 |
| ANG | CRP | ENG | FTH1 | GLUCOSE | HBA1C | INSULIN |
| ANG | CRP | FTH1 | GLUCOSE | GPT | HBA1C | INSULIN |
| ANG | CRP | FTH1 | GLUCOSE | HBA1C | HSPA1B | INSULIN |
| ANG | CRP | FTH1 | GLUCOSE | HBA1C | IL18 | INSULIN |
| ANG | CRP | FTH1 | GLUCOSE | HBA1C | IL18 | LEP |
| ANG | CRP | FTH1 | GLUCOSE | HBA1C | IL18 | PLAT |
| ANG | CRP | FTH1 | GLUCOSE | HBA1C | IL2RA | INSULIN |
| ANG | CRP | FTH1 | GLUCOSE | HBA1C | INSULIN | LEP |
| ANG | CRP | FTH1 | GLUCOSE | HBA1C | INSULIN | PLAT |
| ANG | CRP | FTH1 | GLUCOSE | HBA1C | INSULIN | TRIG |
| ANG | CRP | FTH1 | GLUCOSE | HBA1C | PLAT | TRIG |
| ANG | CRP | GLUCOSE | HBA1C | IL18 | INSULIN | PLAT |
| C3 | CCL2 | CRP | FTH1 | GLUCOSE | HBA1C | INSULIN |
| C3 | CRP | ENG | FTH1 | GLUCOSE | HBA1C | INSULIN |
| C3 | CRP | FTH1 | GLUCOSE | HBA1C | IL18 | INSULIN |
| CCL2 | CDK5 | CRP | FTH1 | GLUCOSE | HBA1C | INSULIN |
| CCL2 | CRP | ENG | FTH1 | GLUCOSE | GPT | HBA1C |
| CCL2 | CRP | ENG | FTH1 | GLUCOSE | GPT | INSULIN |
| CCL2 | CRP | ENG | FTH1 | GLUCOSE | HBA1C | IL18 |
| CCL2 | CRP | ENG | FTH1 | GLUCOSE | HBA1C | INSULIN |
| CCL2 | CRP | ENG | FTH1 | GLUCOSE | HBA1C | LEP |
| CCL2 | CRP | ENG | FTH1 | GLUCOSE | HBA1C | PLAT |
| CCL2 | CRP | ENG | FTH1 | GLUCOSE | HBA1C | TRIG |
| CCL2 | CRP | ENG | FTH1 | GLUCOSE | INSULIN | PLAT |
| CCL2 | CRP | FTH1 | GLUCOSE | GPT | HBA1C | INSULIN |
| CCL2 | CRP | FTH1 | GLUCOSE | HBA1C | HSPA1B | INSULIN |
| CCL2 | CRP | FTH1 | GLUCOSE | HBA1C | IL18 | INSULIN |
| CCL2 | CRP | FTH1 | GLUCOSE | HBA1C | IL18 | LEP |
| CCL2 | CRP | FTH1 | GLUCOSE | HBA1C | IL18 | PLAT |
| CCL2 | CRP | FTH1 | GLUCOSE | HBA1C | INSULIN | LEP |
| CCL2 | CRP | FTH1 | GLUCOSE | HBA1C | INSULIN | PLAT |
| CCL2 | CRP | FTH1 | GLUCOSE | HBA1C | INSULIN | VEGF |
| CCL2 | CRP | FTH1 | GLUCOSE | HBA1C | LEP | PLAT |
| CCL2 | CRP | GLUCOSE | HBA1C | IL18 | INSULIN | PLAT |
| CDK5 | CRP | ENG | FTH1 | GLUCOSE | HBA1C | INSULIN |
| CRP | ENG | FTH1 | GLUCOSE | GPT | HBA1C | IL18 |
| CRP | ENG | FTH1 | GLUCOSE | GPT | HBA1C | INSULIN |
| CRP | ENG | FTH1 | GLUCOSE | GPT | HBA1C | LEP |

FIGURE 16 (continued)

| CRP | ENG | FTH1 | GLUCOSE | HBA1C | HDL | INSULIN |
|---|---|---|---|---|---|---|
| CRP | ENG | FTH1 | GLUCOSE | HBA1C | HGF | INSULIN |
| CRP | ENG | FTH1 | GLUCOSE | HBA1C | HSPA1B | INSULIN |
| CRP | ENG | FTH1 | GLUCOSE | HBA1C | IGFBP2 | INSULIN |
| CRP | ENG | FTH1 | GLUCOSE | HBA1C | IL18 | INSULIN |
| CRP | ENG | FTH1 | GLUCOSE | HBA1C | IL18 | LEP |
| CRP | ENG | FTH1 | GLUCOSE | HBA1C | IL18 | PLAT |
| CRP | ENG | FTH1 | GLUCOSE | HBA1C | IL18 | TRIG |
| CRP | ENG | FTH1 | GLUCOSE | HBA1C | IL2RA | INSULIN |
| CRP | ENG | FTH1 | GLUCOSE | HBA1C | INSULIN | LEP |
| CRP | ENG | FTH1 | GLUCOSE | HBA1C | INSULIN | PLAT |
| CRP | ENG | FTH1 | GLUCOSE | HBA1C | INSULIN | SERPINE1 |
| CRP | ENG | FTH1 | GLUCOSE | HBA1C | INSULIN | TRIG |
| CRP | ENG | FTH1 | GLUCOSE | HBA1C | INSULIN | VEGF |
| CRP | ENG | FTH1 | GLUCOSE | HBA1C | LEP | TRIG |
| CRP | ENG | GLUCOSE | HBA1C | IL18 | INSULIN | PLAT |
| CRP | FTH1 | GLUCOSE | HBA1C | HSPA1B | IL18 | INSULIN |
| CRP | FTH1 | GLUCOSE | HBA1C | IL18 | INSULIN | PLAT |
| CRP | FTH1 | GLUCOSE | HBA1C | IL2RA | INSULIN | PLAT |
| CRP | FTH1 | GLUCOSE | HBA1C | INSULIN | PLAT | TRIG |

FIGURE 17

| ADIPOQ | CCL2 | CRP | ENG | FTH1 | GLUCOSE | HBA1C | INSULIN |
|---|---|---|---|---|---|---|---|
| ADIPOQ | CCL2 | CRP | ENG | FTH1 | GLUCOSE | HBA1C | LEP |
| ADIPOQ | CCL2 | CRP | ENG | FTH1 | GLUCOSE | HBA1C | PLAT |
| ADIPOQ | CCL2 | CRP | ENG | FTH1 | GLUCOSE | INSULIN | PLAT |
| ADIPOQ | CCL2 | CRP | ENG | FTH1 | GLUCOSE | LEP | PLAT |
| ADIPOQ | CCL2 | CRP | FTH1 | GLUCOSE | HBA1C | HSPA1B | LEP |
| ADIPOQ | CCL2 | CRP | FTH1 | GLUCOSE | HBA1C | IL18 | INSULIN |
| ADIPOQ | CCL2 | CRP | FTH1 | GLUCOSE | HBA1C | IL18 | LEP |
| ADIPOQ | CCL2 | CRP | FTH1 | GLUCOSE | HBA1C | IL18 | PLAT |
| ADIPOQ | CCL2 | CRP | FTH1 | GLUCOSE | HBA1C | INSULIN | LEP |
| ADIPOQ | CCL2 | CRP | FTH1 | GLUCOSE | HBA1C | INSULIN | PLAT |
| ADIPOQ | CCL2 | CRP | FTH1 | GLUCOSE | HBA1C | LEP | PLAT |
| ADIPOQ | CCL2 | CRP | GLUCOSE | HBA1C | IL18 | INSULIN | PLAT |
| ADIPOQ | CRP | ENG | FTH1 | GLUCOSE | GPT | HBA1C | INSULIN |
| ADIPOQ | CRP | ENG | FTH1 | GLUCOSE | GPT | HBA1C | LEP |
| ADIPOQ | CRP | ENG | FTH1 | GLUCOSE | HBA1C | HSPA1B | INSULIN |
| ADIPOQ | CRP | ENG | FTH1 | GLUCOSE | HBA1C | HSPA1B | LEP |
| ADIPOQ | CRP | ENG | FTH1 | GLUCOSE | HBA1C | IL18 | INSULIN |
| ADIPOQ | CRP | ENG | FTH1 | GLUCOSE | HBA1C | IL18 | LEP |
| ADIPOQ | CRP | ENG | FTH1 | GLUCOSE | HBA1C | IL18 | PLAT |
| ADIPOQ | CRP | ENG | FTH1 | GLUCOSE | HBA1C | INSULIN | LEP |
| ADIPOQ | CRP | ENG | FTH1 | GLUCOSE | HBA1C | INSULIN | PLAT |
| ADIPOQ | CRP | ENG | FTH1 | GLUCOSE | HBA1C | INSULIN | VEGF |
| ADIPOQ | CRP | ENG | FTH1 | GLUCOSE | HBA1C | LEP | PLAT |
| ADIPOQ | CRP | ENG | FTH1 | GLUCOSE | HBA1C | LEP | TRIG |
| ADIPOQ | CRP | ENG | FTH1 | GLUCOSE | HBA1C | LEP | VEGF |
| ADIPOQ | CRP | ENG | FTH1 | GLUCOSE | HBA1C | PLAT | TRIG |
| ADIPOQ | CRP | ENG | FTH1 | GLUCOSE | IL18 | LEP | PLAT |
| ADIPOQ | CRP | FTH1 | GLUCOSE | GPT | HBA1C | INSULIN | PLAT |
| ADIPOQ | CRP | FTH1 | GLUCOSE | GPT | HBA1C | LEP | PLAT |
| ADIPOQ | CRP | FTH1 | GLUCOSE | HBA1C | HSPA1B | IL18 | LEP |
| ADIPOQ | CRP | FTH1 | GLUCOSE | HBA1C | HSPA1B | INSULIN | PLAT |
| ADIPOQ | CRP | FTH1 | GLUCOSE | HBA1C | HSPA1B | LEP | PLAT |
| ADIPOQ | CRP | FTH1 | GLUCOSE | HBA1C | IL18 | INSULIN | LEP |
| ADIPOQ | CRP | FTH1 | GLUCOSE | HBA1C | IL18 | INSULIN | PLAT |
| ADIPOQ | CRP | FTH1 | GLUCOSE | HBA1C | IL18 | LEP | PLAT |
| ADIPOQ | CRP | FTH1 | GLUCOSE | HBA1C | IL2RA | INSULIN | PLAT |
| ADIPOQ | CRP | FTH1 | GLUCOSE | HBA1C | INSULIN | LEP | PLAT |
| ADIPOQ | CRP | FTH1 | GLUCOSE | HBA1C | INSULIN | PLAT | TRIG |
| ADIPOQ | CRP | FTH1 | GLUCOSE | HBA1C | LEP | PLAT | TRIG |

FIGURE 17 (continued)

| | | | | | | | |
|---|---|---|---|---|---|---|---|
| ADIPOQ | CRP | FTH1 | GLUCOSE | HBA1C | LEP | PLAT | VEGF |
| ADIPOQ | CRP | GLUCOSE | HBA1C | IL18 | INSULIN | LEP | PLAT |
| CCL2 | CRP | ENG | FTH1 | GLUCOSE | GPT | HBA1C | INSULIN |
| CCL2 | CRP | ENG | FTH1 | GLUCOSE | GPT | HBA1C | LEP |
| CCL2 | CRP | ENG | FTH1 | GLUCOSE | GPT | HBA1C | PLAT |
| CCL2 | CRP | ENG | FTH1 | GLUCOSE | GPT | INSULIN | PLAT |
| CCL2 | CRP | ENG | FTH1 | GLUCOSE | HBA1C | HGF | INSULIN |
| CCL2 | CRP | ENG | FTH1 | GLUCOSE | HBA1C | HSPA1B | INSULIN |
| CCL2 | CRP | ENG | FTH1 | GLUCOSE | HBA1C | IGFBP1 | INSULIN |
| CCL2 | CRP | ENG | FTH1 | GLUCOSE | HBA1C | IGFBP1 | PLAT |
| CCL2 | CRP | ENG | FTH1 | GLUCOSE | HBA1C | IL18 | INSULIN |
| CCL2 | CRP | ENG | FTH1 | GLUCOSE | HBA1C | IL18 | LEP |
| CCL2 | CRP | ENG | FTH1 | GLUCOSE | HBA1C | IL18 | PLAT |
| CCL2 | CRP | ENG | FTH1 | GLUCOSE | HBA1C | IL2RA | INSULIN |
| CCL2 | CRP | ENG | FTH1 | GLUCOSE | HBA1C | INSULIN | LEP |
| CCL2 | CRP | ENG | FTH1 | GLUCOSE | HBA1C | INSULIN | PLAT |
| CCL2 | CRP | ENG | FTH1 | GLUCOSE | HBA1C | INSULIN | TRIG |
| CCL2 | CRP | ENG | FTH1 | GLUCOSE | HBA1C | INSULIN | VEGF |
| CCL2 | CRP | ENG | FTH1 | GLUCOSE | HBA1C | LEP | PLAT |
| CCL2 | CRP | ENG | FTH1 | GLUCOSE | HBA1C | LEP | TRIG |
| CCL2 | CRP | ENG | FTH1 | GLUCOSE | HBA1C | PLAT | TRIG |
| CCL2 | CRP | FTH1 | GLUCOSE | GPT | HBA1C | INSULIN | PLAT |
| CCL2 | CRP | FTH1 | GLUCOSE | HBA1C | HGF | INSULIN | PLAT |
| CCL2 | CRP | FTH1 | GLUCOSE | HBA1C | HSPA1B | IL18 | INSULIN |
| CCL2 | CRP | FTH1 | GLUCOSE | HBA1C | HSPA1B | INSULIN | PLAT |
| CCL2 | CRP | FTH1 | GLUCOSE | HBA1C | IGFBP1 | INSULIN | PLAT |
| CCL2 | CRP | FTH1 | GLUCOSE | HBA1C | IL18 | INSULIN | PLAT |
| CCL2 | CRP | FTH1 | GLUCOSE | HBA1C | IL2RA | INSULIN | PLAT |
| CCL2 | CRP | FTH1 | GLUCOSE | HBA1C | INSULIN | LEP | PLAT |
| CCL2 | CRP | FTH1 | GLUCOSE | HBA1C | INSULIN | PLAT | TRIG |
| CCL2 | CRP | FTH1 | GLUCOSE | HBA1C | INSULIN | PLAT | VEGF |
| CCL2 | CRP | GLUCOSE | HBA1C | HSPA1B | IL18 | INSULIN | PLAT |
| CRP | ENG | FTH1 | GLUCOSE | GPT | HBA1C | IL18 | INSULIN |
| CRP | ENG | FTH1 | GLUCOSE | GPT | HBA1C | IL18 | LEP |
| CRP | ENG | FTH1 | GLUCOSE | GPT | HBA1C | IL2RA | INSULIN |
| CRP | ENG | FTH1 | GLUCOSE | GPT | HBA1C | INSULIN | LEP |
| CRP | ENG | FTH1 | GLUCOSE | GPT | HBA1C | INSULIN | PLAT |
| CRP | ENG | FTH1 | GLUCOSE | HBA1C | HGF | IL18 | INSULIN |
| CRP | ENG | FTH1 | GLUCOSE | HBA1C | HGF | INSULIN | PLAT |
| CRP | ENG | FTH1 | GLUCOSE | HBA1C | HSPA1B | IL18 | INSULIN |

FIGURE 17 (continued)

| CRP | ENG | FTH1 | GLUCOSE | HBA1C | HSPA1B | IL18 | LEP |
|---|---|---|---|---|---|---|---|
| CRP | ENG | FTH1 | GLUCOSE | HBA1C | HSPA1B | INSULIN | PLAT |
| CRP | ENG | FTH1 | GLUCOSE | HBA1C | IGFBP1 | IL18 | INSULIN |
| CRP | ENG | FTH1 | GLUCOSE | HBA1C | IL18 | IL2RA | INSULIN |
| CRP | ENG | FTH1 | GLUCOSE | HBA1C | IL18 | INSULIN | LEP |
| CRP | ENG | FTH1 | GLUCOSE | HBA1C | IL18 | INSULIN | PLAT |
| CRP | ENG | FTH1 | GLUCOSE | HBA1C | IL18 | INSULIN | TRIG |
| CRP | ENG | FTH1 | GLUCOSE | HBA1C | IL18 | INSULIN | VEGF |
| CRP | ENG | FTH1 | GLUCOSE | HBA1C | IL18 | LEP | PLAT |
| CRP | ENG | FTH1 | GLUCOSE | HBA1C | IL18 | LEP | TRIG |
| CRP | ENG | FTH1 | GLUCOSE | HBA1C | IL18 | PLAT | TRIG |
| CRP | ENG | FTH1 | GLUCOSE | HBA1C | IL2RA | INSULIN | PLAT |
| CRP | ENG | FTH1 | GLUCOSE | HBA1C | INSULIN | LEP | PLAT |
| CRP | ENG | FTH1 | GLUCOSE | HBA1C | INSULIN | PLAT | TRIG |
| CRP | ENG | FTH1 | GLUCOSE | HBA1C | INSULIN | PLAT | VEGF |
| CRP | ENG | FTH1 | GLUCOSE | HBA1C | LEP | PLAT | TRIG |
| CRP | FTH1 | GLUCOSE | HBA1C | HSPA1B | IL18 | INSULIN | PLAT |
| CRP | FTH1 | GLUCOSE | HBA1C | IL18 | INSULIN | LEP | PLAT |
| CRP | FTH1 | GLUCOSE | HBA1C | IL18 | INSULIN | PLAT | TRIG |
| CRP | FTH1 | GLUCOSE | HBA1C | IL18 | INSULIN | PLAT | VEGF |

FIGURE 18

| ADIPOQ | CCL2 | CRP | ENG | FTH1 | GLUCOSE | GPT | HBA1C | INSULIN |
|---|---|---|---|---|---|---|---|---|
| ADIPOQ | CCL2 | CRP | ENG | FTH1 | GLUCOSE | GPT | HBA1C | LEP |
| ADIPOQ | CCL2 | CRP | ENG | FTH1 | GLUCOSE | GPT | HBA1C | PLAT |
| ADIPOQ | CCL2 | CRP | ENG | FTH1 | GLUCOSE | HBA1C | HSPA1B | INSULIN |
| ADIPOQ | CCL2 | CRP | ENG | FTH1 | GLUCOSE | HBA1C | HSPA1B | LEP |
| ADIPOQ | CCL2 | CRP | ENG | FTH1 | GLUCOSE | HBA1C | HSPA1B | PLAT |
| ADIPOQ | CCL2 | CRP | ENG | FTH1 | GLUCOSE | HBA1C | IL18 | INSULIN |
| ADIPOQ | CCL2 | CRP | ENG | FTH1 | GLUCOSE | HBA1C | IL18 | LEP |
| ADIPOQ | CCL2 | CRP | ENG | FTH1 | GLUCOSE | HBA1C | IL18 | PLAT |
| ADIPOQ | CCL2 | CRP | ENG | FTH1 | GLUCOSE | HBA1C | INSULIN | LEP |
| ADIPOQ | CCL2 | CRP | ENG | FTH1 | GLUCOSE | HBA1C | INSULIN | PLAT |
| ADIPOQ | CCL2 | CRP | ENG | FTH1 | GLUCOSE | HBA1C | LEP | PLAT |
| ADIPOQ | CCL2 | CRP | ENG | FTH1 | GLUCOSE | HBA1C | PLAT | TRIG |
| ADIPOQ | CCL2 | CRP | ENG | FTH1 | GLUCOSE | HSPA1B | LEP | PLAT |
| ADIPOQ | CCL2 | CRP | ENG | FTH1 | GLUCOSE | IL18 | LEP | PLAT |
| ADIPOQ | CCL2 | CRP | ENG | FTH1 | GLUCOSE | INSULIN | LEP | PLAT |
| ADIPOQ | CCL2 | CRP | FTH1 | GLUCOSE | GPT | HBA1C | INSULIN | PLAT |
| ADIPOQ | CCL2 | CRP | FTH1 | GLUCOSE | GPT | HBA1C | LEP | PLAT |
| ADIPOQ | CCL2 | CRP | FTH1 | GLUCOSE | HBA1C | HSPA1B | INSULIN | PLAT |
| ADIPOQ | CCL2 | CRP | FTH1 | GLUCOSE | HBA1C | HSPA1B | LEP | PLAT |
| ADIPOQ | CCL2 | CRP | FTH1 | GLUCOSE | HBA1C | IL18 | INSULIN | PLAT |
| ADIPOQ | CCL2 | CRP | FTH1 | GLUCOSE | HBA1C | IL18 | LEP | PLAT |
| ADIPOQ | CCL2 | CRP | FTH1 | GLUCOSE | HBA1C | INSULIN | LEP | PLAT |
| ADIPOQ | CCL2 | CRP | FTH1 | GLUCOSE | HBA1C | INSULIN | PLAT | VEGF |
| ADIPOQ | CCL2 | CRP | FTH1 | GLUCOSE | HBA1C | LEP | PLAT | TRIG |
| ADIPOQ | CCL2 | CRP | FTH1 | GLUCOSE | HBA1C | LEP | PLAT | VEGF |
| ADIPOQ | CRP | ENG | FTH1 | GLUCOSE | GPT | HBA1C | IL18 | INSULIN |
| ADIPOQ | CRP | ENG | FTH1 | GLUCOSE | GPT | HBA1C | IL18 | LEP |
| ADIPOQ | CRP | ENG | FTH1 | GLUCOSE | GPT | HBA1C | IL18 | PLAT |
| ADIPOQ | CRP | ENG | FTH1 | GLUCOSE | GPT | HBA1C | INSULIN | LEP |
| ADIPOQ | CRP | ENG | FTH1 | GLUCOSE | GPT | HBA1C | INSULIN | PLAT |
| ADIPOQ | CRP | ENG | FTH1 | GLUCOSE | GPT | HBA1C | LEP | PLAT |
| ADIPOQ | CRP | ENG | FTH1 | GLUCOSE | HBA1C | HGF | INSULIN | PLAT |
| ADIPOQ | CRP | ENG | FTH1 | GLUCOSE | HBA1C | HGF | LEP | PLAT |
| ADIPOQ | CRP | ENG | FTH1 | GLUCOSE | HBA1C | HSPA1B | IL18 | LEP |
| ADIPOQ | CRP | ENG | FTH1 | GLUCOSE | HBA1C | HSPA1B | INSULIN | LEP |
| ADIPOQ | CRP | ENG | FTH1 | GLUCOSE | HBA1C | HSPA1B | INSULIN | PLAT |
| ADIPOQ | CRP | ENG | FTH1 | GLUCOSE | HBA1C | HSPA1B | LEP | PLAT |
| ADIPOQ | CRP | ENG | FTH1 | GLUCOSE | HBA1C | IGFBP1 | INSULIN | PLAT |
| ADIPOQ | CRP | ENG | FTH1 | GLUCOSE | HBA1C | IGFBP1 | LEP | PLAT |

FIGURE 18 (continued)

| ADIPOQ | CRP | ENG  | FTH1    | GLUCOSE | HBA1C  | IL18   | INSULIN | LEP     |
|--------|-----|------|---------|---------|--------|--------|---------|---------|
| ADIPOQ | CRP | ENG  | FTH1    | GLUCOSE | HBA1C  | IL18   | INSULIN | PLAT    |
| ADIPOQ | CRP | ENG  | FTH1    | GLUCOSE | HBA1C  | IL18   | LEP     | PLAT    |
| ADIPOQ | CRP | ENG  | FTH1    | GLUCOSE | HBA1C  | IL18   | LEP     | TRIG    |
| ADIPOQ | CRP | ENG  | FTH1    | GLUCOSE | HBA1C  | IL18   | LEP     | VEGF    |
| ADIPOQ | CRP | ENG  | FTH1    | GLUCOSE | HBA1C  | IL18   | PLAT    | TRIG    |
| ADIPOQ | CRP | ENG  | FTH1    | GLUCOSE | HBA1C  | IL2RA  | INSULIN | PLAT    |
| ADIPOQ | CRP | ENG  | FTH1    | GLUCOSE | HBA1C  | IL2RA  | LEP     | PLAT    |
| ADIPOQ | CRP | ENG  | FTH1    | GLUCOSE | HBA1C  | INSULIN| LEP     | PLAT    |
| ADIPOQ | CRP | ENG  | FTH1    | GLUCOSE | HBA1C  | INSULIN| PLAT    | TRIG    |
| ADIPOQ | CRP | ENG  | FTH1    | GLUCOSE | HBA1C  | INSULIN| PLAT    | VEGF    |
| ADIPOQ | CRP | ENG  | FTH1    | GLUCOSE | HBA1C  | LEP    | PLAT    | TRIG    |
| ADIPOQ | CRP | ENG  | FTH1    | GLUCOSE | HBA1C  | LEP    | PLAT    | VEGF    |
| ADIPOQ | CRP | ENG  | FTH1    | GLUCOSE | HSPA1B | IL18   | LEP     | PLAT    |
| ADIPOQ | CRP | FTH1 | GLUCOSE | GPT     | HBA1C  | IL18   | INSULIN | PLAT    |
| ADIPOQ | CRP | FTH1 | GLUCOSE | HBA1C   | HSPA1B | IL18   | INSULIN | PLAT    |
| ADIPOQ | CRP | FTH1 | GLUCOSE | HBA1C   | HSPA1B | IL18   | LEP     | PLAT    |
| ADIPOQ | CRP | FTH1 | GLUCOSE | HBA1C   | IGFBP1 | IL18   | INSULIN | PLAT    |
| ADIPOQ | CRP | FTH1 | GLUCOSE | HBA1C   | IL18   | INSULIN| LEP     | PLAT    |
| ADIPOQ | CRP | FTH1 | GLUCOSE | HBA1C   | IL18   | LEP    | PLAT    | TRIG    |
| ADIPOQ | ENG | FTH1 | GLUCOSE | HBA1C   | HSPA1B | IL18   | LEP     | PLAT    |
| CCL2   | CRP | ENG  | FTH1    | GLUCOSE | GPT    | HBA1C  | HSPA1B  | INSULIN |
| CCL2   | CRP | ENG  | FTH1    | GLUCOSE | GPT    | HBA1C  | IL18    | INSULIN |
| CCL2   | CRP | ENG  | FTH1    | GLUCOSE | GPT    | HBA1C  | IL18    | LEP     |
| CCL2   | CRP | ENG  | FTH1    | GLUCOSE | GPT    | HBA1C  | IL2RA   | INSULIN |
| CCL2   | CRP | ENG  | FTH1    | GLUCOSE | GPT    | HBA1C  | INSULIN | LEP     |
| CCL2   | CRP | ENG  | FTH1    | GLUCOSE | GPT    | HBA1C  | INSULIN | PLAT    |
| CCL2   | CRP | ENG  | FTH1    | GLUCOSE | GPT    | HBA1C  | INSULIN | VEGF    |
| CCL2   | CRP | ENG  | FTH1    | GLUCOSE | GPT    | HBA1C  | LEP     | PLAT    |
| CCL2   | CRP | ENG  | FTH1    | GLUCOSE | HBA1C  | HGF    | INSULIN | PLAT    |
| CCL2   | CRP | ENG  | FTH1    | GLUCOSE | HBA1C  | HSPA1B | IL18    | INSULIN |
| CCL2   | CRP | ENG  | FTH1    | GLUCOSE | HBA1C  | HSPA1B | IL18    | LEP     |
| CCL2   | CRP | ENG  | FTH1    | GLUCOSE | HBA1C  | HSPA1B | INSULIN | LEP     |
| CCL2   | CRP | ENG  | FTH1    | GLUCOSE | HBA1C  | HSPA1B | INSULIN | PLAT    |
| CCL2   | CRP | ENG  | FTH1    | GLUCOSE | HBA1C  | HSPA1B | LEP     | PLAT    |
| CCL2   | CRP | ENG  | FTH1    | GLUCOSE | HBA1C  | IGFBP1 | INSULIN | PLAT    |
| CCL2   | CRP | ENG  | FTH1    | GLUCOSE | HBA1C  | IL18   | INSULIN | LEP     |
| CCL2   | CRP | ENG  | FTH1    | GLUCOSE | HBA1C  | IL18   | INSULIN | PLAT    |
| CCL2   | CRP | ENG  | FTH1    | GLUCOSE | HBA1C  | IL18   | LEP     | PLAT    |
| CCL2   | CRP | ENG  | FTH1    | GLUCOSE | HBA1C  | IL2RA  | INSULIN | PLAT    |

FIGURE 18 (continued)

| CCL2 | CRP | ENG | FTH1 | GLUCOSE | HBA1C | INSULIN | LEP | PLAT |
|---|---|---|---|---|---|---|---|---|
| CCL2 | CRP | ENG | FTH1 | GLUCOSE | HBA1C | INSULIN | PLAT | TRIG |
| CCL2 | CRP | ENG | FTH1 | GLUCOSE | HBA1C | INSULIN | PLAT | VEGF |
| CCL2 | CRP | ENG | FTH1 | GLUCOSE | HBA1C | LEP | PLAT | TRIG |
| CCL2 | CRP | FTH1 | GLUCOSE | HBA1C | HSPA1B | IL18 | INSULIN | PLAT |
| CCL2 | CRP | FTH1 | GLUCOSE | HBA1C | IL18 | INSULIN | LEP | PLAT |
| CRP | ENG | FTH1 | GLUCOSE | GPT | HBA1C | HSPA1B | IL18 | INSULIN |
| CRP | ENG | FTH1 | GLUCOSE | GPT | HBA1C | IL18 | INSULIN | LEP |
| CRP | ENG | FTH1 | GLUCOSE | GPT | HBA1C | IL18 | INSULIN | PLAT |
| CRP | ENG | FTH1 | GLUCOSE | GPT | HBA1C | IL2RA | INSULIN | PLAT |
| CRP | ENG | FTH1 | GLUCOSE | GPT | HBA1C | INSULIN | LEP | PLAT |
| CRP | ENG | FTH1 | GLUCOSE | HBA1C | HGF | IL18 | INSULIN | PLAT |
| CRP | ENG | FTH1 | GLUCOSE | HBA1C | HSPA1B | IL18 | INSULIN | LEP |
| CRP | ENG | FTH1 | GLUCOSE | HBA1C | HSPA1B | IL18 | INSULIN | PLAT |
| CRP | ENG | FTH1 | GLUCOSE | HBA1C | IGFBP1 | IL18 | INSULIN | PLAT |
| CRP | ENG | FTH1 | GLUCOSE | HBA1C | IL18 | IL2RA | INSULIN | PLAT |
| CRP | ENG | FTH1 | GLUCOSE | HBA1C | IL18 | INSULIN | LEP | PLAT |
| CRP | ENG | FTH1 | GLUCOSE | HBA1C | IL18 | INSULIN | PLAT | TRIG |
| CRP | ENG | FTH1 | GLUCOSE | HBA1C | IL18 | INSULIN | PLAT | VEGF |
| CRP | ENG | FTH1 | GLUCOSE | HBA1C | IL18 | LEP | PLAT | TRIG |

FIGURE 19

| |
|---|
| ADIPOQ; CCL2; CRP; ENG; FTH1; GLUCOSE; GPT; HBA1C; HSPA1B; LEP |
| ADIPOQ; CCL2; CRP; ENG; FTH1; GLUCOSE; GPT; HBA1C; IL18; LEP |
| ADIPOQ; CCL2; CRP; ENG; FTH1; GLUCOSE; GPT; HBA1C; IL18; PLAT |
| ADIPOQ; CCL2; CRP; ENG; FTH1; GLUCOSE; GPT; HBA1C; INSULIN; LEP |
| ADIPOQ; CCL2; CRP; ENG; FTH1; GLUCOSE; GPT; HBA1C; INSULIN; PLAT |
| ADIPOQ; CCL2; CRP; ENG; FTH1; GLUCOSE; GPT; HBA1C; LEP; PLAT |
| ADIPOQ; CCL2; CRP; ENG; FTH1; GLUCOSE; HBA1C; HGF; INSULIN; PLAT |
| ADIPOQ; CCL2; CRP; ENG; FTH1; GLUCOSE; HBA1C; HGF; LEP; PLAT |
| ADIPOQ; CCL2; CRP; ENG; FTH1; GLUCOSE; HBA1C; HSPA1B; IL18; LEP |
| ADIPOQ; CCL2; CRP; ENG; FTH1; GLUCOSE; HBA1C; HSPA1B; INSULIN; LEP |
| ADIPOQ; CCL2; CRP; ENG; FTH1; GLUCOSE; HBA1C; HSPA1B; INSULIN; PLAT |
| ADIPOQ; CCL2; CRP; ENG; FTH1; GLUCOSE; HBA1C; HSPA1B; LEP; PLAT |
| ADIPOQ; CCL2; CRP; ENG; FTH1; GLUCOSE; HBA1C; IGFBP1; INSULIN; PLAT |
| ADIPOQ; CCL2; CRP; ENG; FTH1; GLUCOSE; HBA1C; IGFBP1; LEP; PLAT |
| ADIPOQ; CCL2; CRP; ENG; FTH1; GLUCOSE; HBA1C; IL18; INSULIN; PLAT |
| ADIPOQ; CCL2; CRP; ENG; FTH1; GLUCOSE; HBA1C; IL18; LEP; PLAT |
| ADIPOQ; CCL2; CRP; ENG; FTH1; GLUCOSE; HBA1C; IL2RA; INSULIN; PLAT |
| ADIPOQ; CCL2; CRP; ENG; FTH1; GLUCOSE; HBA1C; IL2RA; LEP; PLAT |
| ADIPOQ; CCL2; CRP; ENG; FTH1; GLUCOSE; HBA1C; INSULIN; LEP; PLAT |
| ADIPOQ; CCL2; CRP; ENG; FTH1; GLUCOSE; HBA1C; INSULIN; PLAT; TRIG |
| ADIPOQ; CCL2; CRP; ENG; FTH1; GLUCOSE; HBA1C; INSULIN; PLAT; VEGF |
| ADIPOQ; CCL2; CRP; ENG; FTH1; GLUCOSE; HBA1C; LEP; PLAT; TRIG |
| ADIPOQ; CCL2; CRP; ENG; FTH1; GLUCOSE; HBA1C; LEP; PLAT; VEGF |
| ADIPOQ; CCL2; CRP; ENG; FTH1; GLUCOSE; HSPA1B; INSULIN; LEP; PLAT |
| ADIPOQ; CCL2; CRP; FTH1; GLUCOSE; GPT; HBA1C; INSULIN; LEP; PLAT |
| ADIPOQ; CCL2; CRP; FTH1; GLUCOSE; HBA1C; HSPA1B; IL18; INSULIN; PLAT |
| ADIPOQ; CCL2; CRP; FTH1; GLUCOSE; HBA1C; HSPA1B; IL18; LEP; PLAT |
| ADIPOQ; CCL2; CRP; FTH1; GLUCOSE; HBA1C; HSPA1B; INSULIN; LEP; PLAT |
| ADIPOQ; CCL2; CRP; FTH1; GLUCOSE; HBA1C; IL18; INSULIN; LEP; PLAT |
| ADIPOQ; CRP; ENG; FTH1; GLUCOSE; GPT; HBA1C; HGF; LEP; PLAT |
| ADIPOQ; CRP; ENG; FTH1; GLUCOSE; GPT; HBA1C; HSPA1B; IL18; LEP |
| ADIPOQ; CRP; ENG; FTH1; GLUCOSE; GPT; HBA1C; HSPA1B; LEP; PLAT |
| ADIPOQ; CRP; ENG; FTH1; GLUCOSE; GPT; HBA1C; IGFBP1; LEP; PLAT |
| ADIPOQ; CRP; ENG; FTH1; GLUCOSE; GPT; HBA1C; IL18; INSULIN; LEP |
| ADIPOQ; CRP; ENG; FTH1; GLUCOSE; GPT; HBA1C; IL18; INSULIN; PLAT |
| ADIPOQ; CRP; ENG; FTH1; GLUCOSE; GPT; HBA1C; IL18; LEP; PLAT |
| ADIPOQ; CRP; ENG; FTH1; GLUCOSE; GPT; HBA1C; IL2RA; INSULIN; PLAT |
| ADIPOQ; CRP; ENG; FTH1; GLUCOSE; GPT; HBA1C; IL2RA; LEP; PLAT |
| ADIPOQ; CRP; ENG; FTH1; GLUCOSE; GPT; HBA1C; INSULIN; LEP; PLAT |
| ADIPOQ; CRP; ENG; FTH1; GLUCOSE; GPT; HBA1C; LEP; PLAT; TRIG |

FIGURE 19 (continued)

| |
|---|
| ADIPOQ; CRP; ENG; FTH1; GLUCOSE; GPT; HBA1C; LEP; PLAT; VEGF |
| ADIPOQ; CRP; ENG; FTH1; GLUCOSE; HBA1C; HGF; IL18; INSULIN; PLAT |
| ADIPOQ; CRP; ENG; FTH1; GLUCOSE; HBA1C; HGF; IL18; LEP; PLAT |
| ADIPOQ; CRP; ENG; FTH1; GLUCOSE; HBA1C; HGF; INSULIN; LEP; PLAT |
| ADIPOQ; CRP; ENG; FTH1; GLUCOSE; HBA1C; HSPA1B; IL18; INSULIN; PLAT |
| ADIPOQ; CRP; ENG; FTH1; GLUCOSE; HBA1C; HSPA1B; IL18; LEP; PLAT |
| ADIPOQ; CRP; ENG; FTH1; GLUCOSE; HBA1C; HSPA1B; INSULIN; LEP; PLAT |
| ADIPOQ; CRP; ENG; FTH1; GLUCOSE; HBA1C; HSPA1B; LEP; PLAT; TRIG |
| ADIPOQ; CRP; ENG; FTH1; GLUCOSE; HBA1C; HSPA1B; LEP; PLAT; VEGF |
| ADIPOQ; CRP; ENG; FTH1; GLUCOSE; HBA1C; IGFBP1; IL18; INSULIN; PLAT |
| ADIPOQ; CRP; ENG; FTH1; GLUCOSE; HBA1C; IGFBP1; IL18; LEP; PLAT |
| ADIPOQ; CRP; ENG; FTH1; GLUCOSE; HBA1C; IGFBP1; INSULIN; LEP; PLAT |
| ADIPOQ; CRP; ENG; FTH1; GLUCOSE; HBA1C; IL18; IL2RA; INSULIN; PLAT |
| ADIPOQ; CRP; ENG; FTH1; GLUCOSE; HBA1C; IL18; IL2RA; LEP; PLAT |
| ADIPOQ; CRP; ENG; FTH1; GLUCOSE; HBA1C; IL18; INSULIN; LEP; PLAT |
| ADIPOQ; CRP; ENG; FTH1; GLUCOSE; HBA1C; IL18; INSULIN; PLAT; TRIG |
| ADIPOQ; CRP; ENG; FTH1; GLUCOSE; HBA1C; IL18; INSULIN; PLAT; VEGF |
| ADIPOQ; CRP; ENG; FTH1; GLUCOSE; HBA1C; IL18; LEP; PLAT; TRIG |
| ADIPOQ; CRP; ENG; FTH1; GLUCOSE; HBA1C; IL18; LEP; PLAT; VEGF |
| ADIPOQ; CRP; ENG; FTH1; GLUCOSE; HBA1C; IL2RA; INSULIN; LEP; PLAT |
| ADIPOQ; CRP; ENG; FTH1; GLUCOSE; HBA1C; IL2RA; LEP; PLAT; TRIG |
| ADIPOQ; CRP; ENG; FTH1; GLUCOSE; HBA1C; INSULIN; LEP; PLAT; TRIG |
| ADIPOQ; CRP; ENG; FTH1; GLUCOSE; HBA1C; INSULIN; LEP; PLAT; VEGF |
| ADIPOQ; CRP; ENG; FTH1; GLUCOSE; HBA1C; LEP; PLAT; TRIG; VEGF |
| ADIPOQ; CRP; FTH1; GLUCOSE; HBA1C; HSPA1B; IL18; INSULIN; LEP; PLAT |
| CCL2; CRP; ENG; FTH1; GLUCOSE; GPT; HBA1C; HGF; INSULIN; PLAT |
| CCL2; CRP; ENG; FTH1; GLUCOSE; GPT; HBA1C; HSPA1B; IL18; INSULIN |
| CCL2; CRP; ENG; FTH1; GLUCOSE; GPT; HBA1C; HSPA1B; INSULIN; LEP |
| CCL2; CRP; ENG; FTH1; GLUCOSE; GPT; HBA1C; HSPA1B; INSULIN; PLAT |
| CCL2; CRP; ENG; FTH1; GLUCOSE; GPT; HBA1C; IGFBP1; INSULIN; PLAT |
| CCL2; CRP; ENG; FTH1; GLUCOSE; GPT; HBA1C; IL18; INSULIN; PLAT |
| CCL2; CRP; ENG; FTH1; GLUCOSE; GPT; HBA1C; IL18; LEP; PLAT |
| CCL2; CRP; ENG; FTH1; GLUCOSE; GPT; HBA1C; IL2RA; INSULIN; PLAT |
| CCL2; CRP; ENG; FTH1; GLUCOSE; GPT; HBA1C; INSULIN; LEP; PLAT |
| CCL2; CRP; ENG; FTH1; GLUCOSE; GPT; HBA1C; INSULIN; PLAT; TRIG |
| CCL2; CRP; ENG; FTH1; GLUCOSE; GPT; HBA1C; INSULIN; PLAT; VEGF |
| CCL2; CRP; ENG; FTH1; GLUCOSE; HBA1C; HGF; HSPA1B; INSULIN; PLAT |
| CCL2; CRP; ENG; FTH1; GLUCOSE; HBA1C; HGF; IL18; INSULIN; PLAT |
| CCL2; CRP; ENG; FTH1; GLUCOSE; HBA1C; HGF; INSULIN; LEP; PLAT |
| CCL2; CRP; ENG; FTH1; GLUCOSE; HBA1C; HSPA1B; IGFBP1; INSULIN; PLAT |

FIGURE 19 (continued)

| |
|---|
| CCL2; CRP; ENG; FTH1; GLUCOSE; HBA1C; HSPA1B; IL18; INSULIN; LEP |
| CCL2; CRP; ENG; FTH1; GLUCOSE; HBA1C; HSPA1B; IL18; INSULIN; PLAT |
| CCL2; CRP; ENG; FTH1; GLUCOSE; HBA1C; HSPA1B; IL18; LEP; PLAT |
| CCL2; CRP; ENG; FTH1; GLUCOSE; HBA1C; HSPA1B; IL2RA; INSULIN; PLAT |
| CCL2; CRP; ENG; FTH1; GLUCOSE; HBA1C; HSPA1B; INSULIN; LEP; PLAT |
| CCL2; CRP; ENG; FTH1; GLUCOSE; HBA1C; HSPA1B; INSULIN; PLAT; TRIG |
| CCL2; CRP; ENG; FTH1; GLUCOSE; HBA1C; HSPA1B; INSULIN; PLAT; VEGF |
| CCL2; CRP; ENG; FTH1; GLUCOSE; HBA1C; HSPA1B; LEP; PLAT; TRIG |
| CCL2; CRP; ENG; FTH1; GLUCOSE; HBA1C; IL18; INSULIN; LEP; PLAT |
| CCL2; CRP; ENG; FTH1; GLUCOSE; HBA1C; IL18; INSULIN; PLAT; TRIG |
| CCL2; CRP; ENG; FTH1; GLUCOSE; HBA1C; IL18; INSULIN; PLAT; VEGF |
| CCL2; CRP; ENG; FTH1; GLUCOSE; HBA1C; IL18; LEP; PLAT; TRIG |
| CCL2; CRP; ENG; FTH1; GLUCOSE; HBA1C; INSULIN; LEP; PLAT; TRIG |
| CCL2; CRP; ENG; FTH1; GLUCOSE; HBA1C; INSULIN; LEP; PLAT; VEGF |
| CCL2; CRP; ENG; FTH1; GLUCOSE; HBA1C; INSULIN; PLAT; TRIG; VEGF |
| CCL2; ENG; FTH1; GLUCOSE; HBA1C; HSPA1B; IL18; INSULIN; LEP; PLAT |
| CRP; ENG; FTH1; GLUCOSE; GPT; HBA1C; IL18; IL2RA; INSULIN; PLAT |
| CRP; ENG; FTH1; GLUCOSE; GPT; HBA1C; IL18; INSULIN; LEP; PLAT |
| CRP; ENG; FTH1; GLUCOSE; HBA1C; HSPA1B; IL18; INSULIN; LEP; PLAT |
| CRP; ENG; FTH1; GLUCOSE; HBA1C; IL18; INSULIN; LEP; PLAT; TRIG |

FIGURE 20

| ADIPOQ | CCL2 | CRP | ENG | FTH1 | GLUCOSE | GPT | HBA1C | HGF | INSULIN | PLAT |
|---|---|---|---|---|---|---|---|---|---|---|
| ADIPOQ | CCL2 | CRP | ENG | FTH1 | GLUCOSE | GPT | HBA1C | HGF | LEP | PLAT |
| ADIPOQ | CCL2 | CRP | ENG | FTH1 | GLUCOSE | GPT | HBA1C | HSPA1B | IL18 | LEP |
| ADIPOQ | CCL2 | CRP | ENG | FTH1 | GLUCOSE | GPT | HBA1C | HSPA1B | INSULIN | PLAT |
| ADIPOQ | CCL2 | CRP | ENG | FTH1 | GLUCOSE | GPT | HBA1C | HSPA1B | LEP | PLAT |
| ADIPOQ | CCL2 | CRP | ENG | FTH1 | GLUCOSE | GPT | HBA1C | IGFBP1 | INSULIN | PLAT |
| ADIPOQ | CCL2 | CRP | ENG | FTH1 | GLUCOSE | GPT | HBA1C | IGFBP1 | LEP | PLAT |
| ADIPOQ | CCL2 | CRP | ENG | FTH1 | GLUCOSE | GPT | HBA1C | IL18 | INSULIN | PLAT |
| ADIPOQ | CCL2 | CRP | ENG | FTH1 | GLUCOSE | GPT | HBA1C | IL18 | LEP | PLAT |
| ADIPOQ | CCL2 | CRP | ENG | FTH1 | GLUCOSE | GPT | HBA1C | IL2RA | INSULIN | PLAT |
| ADIPOQ | CCL2 | CRP | ENG | FTH1 | GLUCOSE | GPT | HBA1C | IL2RA | LEP | PLAT |
| ADIPOQ | CCL2 | CRP | ENG | FTH1 | GLUCOSE | GPT | HBA1C | INSULIN | LEP | PLAT |
| ADIPOQ | CCL2 | CRP | ENG | FTH1 | GLUCOSE | GPT | HBA1C | INSULIN | PLAT | TRIG |
| ADIPOQ | CCL2 | CRP | ENG | FTH1 | GLUCOSE | GPT | HBA1C | INSULIN | PLAT | VEGF |
| ADIPOQ | CCL2 | CRP | ENG | FTH1 | GLUCOSE | GPT | HBA1C | LEP | PLAT | TRIG |
| ADIPOQ | CCL2 | CRP | ENG | FTH1 | GLUCOSE | GPT | HBA1C | LEP | PLAT | VEGF |
| ADIPOQ | CCL2 | CRP | ENG | FTH1 | GLUCOSE | HBA1C | HGF | HSPA1B | LEP | PLAT |
| ADIPOQ | CCL2 | CRP | ENG | FTH1 | GLUCOSE | HBA1C | HGF | IL18 | INSULIN | PLAT |
| ADIPOQ | CCL2 | CRP | ENG | FTH1 | GLUCOSE | HBA1C | HGF | IL18 | LEP | PLAT |
| ADIPOQ | CCL2 | CRP | ENG | FTH1 | GLUCOSE | HBA1C | HGF | INSULIN | LEP | PLAT |
| ADIPOQ | CCL2 | CRP | ENG | FTH1 | GLUCOSE | HBA1C | HSPA1B | IGFBP1 | LEP | PLAT |
| ADIPOQ | CCL2 | CRP | ENG | FTH1 | GLUCOSE | HBA1C | HSPA1B | IL18 | INSULIN | LEP |
| ADIPOQ | CCL2 | CRP | ENG | FTH1 | GLUCOSE | HBA1C | HSPA1B | IL18 | INSULIN | PLAT |
| ADIPOQ | CCL2 | CRP | ENG | FTH1 | GLUCOSE | HBA1C | HSPA1B | IL18 | LEP | PLAT |
| ADIPOQ | CCL2 | CRP | ENG | FTH1 | GLUCOSE | HBA1C | HSPA1B | IL2RA | INSULIN | PLAT |
| ADIPOQ | CCL2 | CRP | ENG | FTH1 | GLUCOSE | HBA1C | HSPA1B | IL2RA | LEP | PLAT |
| ADIPOQ | CCL2 | CRP | ENG | FTH1 | GLUCOSE | HBA1C | HSPA1B | INSULIN | LEP | PLAT |

FIGURE 20 (continued)

| ADIPOQ | CCL2 | CRP | ENG | FTH1 | GLUCOSE | HBA1C | HSPA1B | INSULIN | PLAT | TRIG |
| ADIPOQ | CCL2 | CRP | ENG | FTH1 | GLUCOSE | HBA1C | HSPA1B | LEP | PLAT | TRIG |
| ADIPOQ | CCL2 | CRP | ENG | FTH1 | GLUCOSE | HBA1C | HSPA1B | LEP | PLAT | VEGF |
| ADIPOQ | CCL2 | CRP | ENG | FTH1 | GLUCOSE | HBA1C | IGFBP1 | IL18 | INSULIN | PLAT |
| ADIPOQ | CCL2 | CRP | ENG | FTH1 | GLUCOSE | HBA1C | IGFBP1 | IL18 | LEP | PLAT |
| ADIPOQ | CCL2 | CRP | ENG | FTH1 | GLUCOSE | HBA1C | IGFBP1 | INSULIN | LEP | PLAT |
| ADIPOQ | CCL2 | CRP | ENG | FTH1 | GLUCOSE | HBA1C | IL18 | IL2RA | LEP | PLAT |
| ADIPOQ | CCL2 | CRP | ENG | FTH1 | GLUCOSE | HBA1C | IL18 | INSULIN | LEP | PLAT |
| ADIPOQ | CCL2 | CRP | ENG | FTH1 | GLUCOSE | HBA1C | IL18 | INSULIN | PLAT | TRIG |
| ADIPOQ | CCL2 | CRP | ENG | FTH1 | GLUCOSE | HBA1C | IL18 | INSULIN | PLAT | VEGF |
| ADIPOQ | CCL2 | CRP | ENG | FTH1 | GLUCOSE | HBA1C | IL18 | LEP | PLAT | TRIG |
| ADIPOQ | CCL2 | CRP | ENG | FTH1 | GLUCOSE | HBA1C | IL18 | LEP | PLAT | VEGF |
| ADIPOQ | CCL2 | CRP | ENG | FTH1 | GLUCOSE | HBA1C | IL2RA | INSULIN | LEP | PLAT |
| ADIPOQ | CCL2 | CRP | ENG | FTH1 | GLUCOSE | HBA1C | INSULIN | LEP | PLAT | TRIG |
| ADIPOQ | CCL2 | CRP | ENG | FTH1 | GLUCOSE | HBA1C | INSULIN | LEP | PLAT | VEGF |
| ADIPOQ | CCL2 | CRP | ENG | FTH1 | GLUCOSE | HBA1C | LEP | PLAT | TRIG | VEGF |
| ADIPOQ | CCL2 | CRP | FTH1 | GLUCOSE | HBA1C | HSPA1B | IL18 | INSULIN | LEP | PLAT |
| ADIPOQ | CRP | ENG | FTH1 | GLUCOSE | GPT | HBA1C | HGF | IL18 | LEP | PLAT |
| ADIPOQ | CRP | ENG | FTH1 | GLUCOSE | GPT | HBA1C | HGF | INSULIN | LEP | PLAT |
| ADIPOQ | CRP | ENG | FTH1 | GLUCOSE | GPT | HBA1C | HSPA1B | IL18 | INSULIN | PLAT |
| ADIPOQ | CRP | ENG | FTH1 | GLUCOSE | GPT | HBA1C | HSPA1B | IL18 | LEP | PLAT |
| ADIPOQ | CRP | ENG | FTH1 | GLUCOSE | GPT | HBA1C | HSPA1B | IL2RA | LEP | PLAT |
| ADIPOQ | CRP | ENG | FTH1 | GLUCOSE | GPT | HBA1C | HSPA1B | INSULIN | LEP | PLAT |
| ADIPOQ | CRP | ENG | FTH1 | GLUCOSE | GPT | HBA1C | HSPA1B | LEP | PLAT | VEGF |
| ADIPOQ | CRP | ENG | FTH1 | GLUCOSE | GPT | HBA1C | IGFBP1 | IL18 | LEP | PLAT |
| ADIPOQ | CRP | ENG | FTH1 | GLUCOSE | GPT | HBA1C | IGFBP1 | INSULIN | LEP | PLAT |

FIGURE 20(continued)

| ADIPOQ | CRP | ENG | FTH1 | GLUCOSE | GPT | HBA1C | IL18 | IL2RA | INSULIN | PLAT |
|---|---|---|---|---|---|---|---|---|---|---|
| ADIPOQ | CRP | ENG | FTH1 | GLUCOSE | GPT | HBA1C | IL18 | IL2RA | LEP | PLAT |
| ADIPOQ | CRP | ENG | FTH1 | GLUCOSE | GPT | HBA1C | IL18 | INSULIN | LEP | PLAT |
| ADIPOQ | CRP | ENG | FTH1 | GLUCOSE | GPT | HBA1C | IL18 | LEP | PLAT | TRIG |
| ADIPOQ | CRP | ENG | FTH1 | GLUCOSE | GPT | HBA1C | IL18 | LEP | PLAT | VEGF |
| ADIPOQ | CRP | ENG | FTH1 | GLUCOSE | GPT | HBA1C | IL2RA | INSULIN | LEP | PLAT |
| ADIPOQ | CRP | ENG | FTH1 | GLUCOSE | GPT | HBA1C | INSULIN | LEP | PLAT | TRIG |
| ADIPOQ | CRP | ENG | FTH1 | GLUCOSE | GPT | HBA1C | INSULIN | LEP | PLAT | VEGF |
| ADIPOQ | CRP | ENG | FTH1 | GLUCOSE | GPT | HBA1C | LEP | PLAT | TRIG | VEGF |
| ADIPOQ | CRP | ENG | FTH1 | GLUCOSE | HBA1C | HGF | HSPA1B | IL18 | LEP | PLAT |
| ADIPOQ | CRP | ENG | FTH1 | GLUCOSE | HBA1C | HGF | IL18 | INSULIN | LEP | PLAT |
| ADIPOQ | CRP | ENG | FTH1 | GLUCOSE | HBA1C | HSPA1B | IGFBP1 | IL18 | LEP | PLAT |
| ADIPOQ | CRP | ENG | FTH1 | GLUCOSE | HBA1C | HSPA1B | IL18 | IL2RA | INSULIN | PLAT |
| ADIPOQ | CRP | ENG | FTH1 | GLUCOSE | HBA1C | HSPA1B | IL18 | IL2RA | LEP | PLAT |
| ADIPOQ | CRP | ENG | FTH1 | GLUCOSE | HBA1C | HSPA1B | IL18 | INSULIN | LEP | PLAT |
| ADIPOQ | CRP | ENG | FTH1 | GLUCOSE | HBA1C | HSPA1B | IL18 | INSULIN | PLAT | TRIG |
| ADIPOQ | CRP | ENG | FTH1 | GLUCOSE | HBA1C | HSPA1B | IL18 | LEP | PLAT | TRIG |
| ADIPOQ | CRP | ENG | FTH1 | GLUCOSE | HBA1C | HSPA1B | IL18 | LEP | PLAT | VEGF |
| ADIPOQ | CRP | ENG | FTH1 | GLUCOSE | HBA1C | HSPA1B | IL2RA | INSULIN | LEP | PLAT |
| ADIPOQ | CRP | ENG | FTH1 | GLUCOSE | HBA1C | HSPA1B | INSULIN | LEP | PLAT | TRIG |
| ADIPOQ | CRP | ENG | FTH1 | GLUCOSE | HBA1C | HSPA1B | LEP | PLAT | TRIG | VEGF |
| ADIPOQ | CRP | ENG | FTH1 | GLUCOSE | HBA1C | IGFBP1 | IL18 | INSULIN | LEP | PLAT |
| ADIPOQ | CRP | ENG | FTH1 | GLUCOSE | HBA1C | IL18 | IL2RA | INSULIN | LEP | PLAT |
| ADIPOQ | CRP | ENG | FTH1 | GLUCOSE | HBA1C | IL18 | INSULIN | LEP | PLAT | TRIG |
| ADIPOQ | CRP | ENG | FTH1 | GLUCOSE | HBA1C | IL18 | INSULIN | LEP | PLAT | VEGF |
| ADIPOQ | CRP | ENG | FTH1 | GLUCOSE | HBA1C | IL18 | LEP | PLAT | TRIG | VEGF |
| CCL2 | CRP | ENG | FTH1 | GLUCOSE | GPT | HBA1C | HSPA1B | IL18 | INSULIN | PLAT |

FIGURE 20 (continued)

| | | | | | | | | | |
|---|---|---|---|---|---|---|---|---|---|
| CCL2 | CRP | ENG | FTH1 | GLUCOSE | GPT | HBA1C | HSPA1B | IL2RA | INSULIN | PLAT |
| CCL2 | CRP | ENG | FTH1 | GLUCOSE | GPT | HBA1C | HSPA1B | INSULIN | LEP | PLAT |
| CCL2 | CRP | ENG | FTH1 | GLUCOSE | GPT | HBA1C | IL18 | IL2RA | INSULIN | PLAT |
| CCL2 | CRP | ENG | FTH1 | GLUCOSE | GPT | HBA1C | IL18 | INSULIN | LEP | PLAT |
| CCL2 | CRP | ENG | FTH1 | GLUCOSE | GPT | HBA1C | IL18 | INSULIN | PLAT | VEGF |
| CCL2 | CRP | ENG | FTH1 | GLUCOSE | GPT | HBA1C | IL2RA | INSULIN | LEP | PLAT |
| CCL2 | CRP | ENG | FTH1 | GLUCOSE | GPT | HBA1C | INSULIN | LEP | PLAT | TRIG |
| CCL2 | CRP | ENG | FTH1 | GLUCOSE | GPT | HBA1C | INSULIN | LEP | PLAT | VEGF |
| CCL2 | CRP | ENG | FTH1 | GLUCOSE | HBA1C | HGF | HSPA1B | IL18 | INSULIN | PLAT |
| CCL2 | CRP | ENG | FTH1 | GLUCOSE | HBA1C | HSPA1B | IGFBP1 | IL18 | INSULIN | PLAT |
| CCL2 | CRP | ENG | FTH1 | GLUCOSE | HBA1C | HSPA1B | IL18 | IL2RA | INSULIN | PLAT |
| CCL2 | CRP | ENG | FTH1 | GLUCOSE | HBA1C | HSPA1B | IL18 | INSULIN | LEP | PLAT |
| CCL2 | CRP | ENG | FTH1 | GLUCOSE | HBA1C | HSPA1B | IL18 | INSULIN | PLAT | TRIG |
| CCL2 | CRP | ENG | FTH1 | GLUCOSE | HBA1C | HSPA1B | IL18 | INSULIN | PLAT | VEGF |
| CCL2 | CRP | ENG | FTH1 | GLUCOSE | HBA1C | HSPA1B | IL18 | LEP | PLAT | TRIG |
| CCL2 | CRP | ENG | FTH1 | GLUCOSE | HBA1C | HSPA1B | IL2RA | INSULIN | LEP | PLAT |
| CCL2 | CRP | ENG | FTH1 | GLUCOSE | HBA1C | HSPA1B | IL2RA | INSULIN | PLAT | TRIG |
| CCL2 | CRP | ENG | FTH1 | GLUCOSE | HBA1C | HSPA1B | INSULIN | LEP | PLAT | TRIG |
| CCL2 | CRP | ENG | FTH1 | GLUCOSE | HBA1C | HSPA1B | INSULIN | LEP | PLAT | VEGF |
| CCL2 | CRP | ENG | FTH1 | GLUCOSE | HBA1C | IL18 | INSULIN | LEP | PLAT | TRIG |

FIGURE 21

| ADIPOQ | CCL2 | CRP | ENG | FTH1 | GLUCOSE | GPT | HBA1C | HGF | HSPA1B | INSULIN | PLAT |
|---|---|---|---|---|---|---|---|---|---|---|---|
| ADIPOQ | CCL2 | CRP | ENG | FTH1 | GLUCOSE | GPT | HBA1C | HGF | HSPA1B | LEP | PLAT |
| ADIPOQ | CCL2 | CRP | ENG | FTH1 | GLUCOSE | GPT | HBA1C | HGF | IL18 | INSULIN | PLAT |
| ADIPOQ | CCL2 | CRP | ENG | FTH1 | GLUCOSE | GPT | HBA1C | HGF | IL18 | LEP | PLAT |
| ADIPOQ | CCL2 | CRP | ENG | FTH1 | GLUCOSE | GPT | HBA1C | HGF | IL2RA | INSULIN | PLAT |
| ADIPOQ | CCL2 | CRP | ENG | FTH1 | GLUCOSE | GPT | HBA1C | HGF | INSULIN | LEP | PLAT |
| ADIPOQ | CCL2 | CRP | ENG | FTH1 | GLUCOSE | GPT | HBA1C | HGF | LEP | PLAT | VEGF |
| ADIPOQ | CCL2 | CRP | ENG | FTH1 | GLUCOSE | GPT | HBA1C | HSPA1B | IGFBP1 | LEP | PLAT |
| ADIPOQ | CCL2 | CRP | ENG | FTH1 | GLUCOSE | GPT | HBA1C | HSPA1B | IL18 | INSULIN | PLAT |
| ADIPOQ | CCL2 | CRP | ENG | FTH1 | GLUCOSE | GPT | HBA1C | HSPA1B | IL18 | LEP | PLAT |
| ADIPOQ | CCL2 | CRP | ENG | FTH1 | GLUCOSE | GPT | HBA1C | HSPA1B | IL2RA | INSULIN | PLAT |
| ADIPOQ | CCL2 | CRP | ENG | FTH1 | GLUCOSE | GPT | HBA1C | HSPA1B | IL2RA | LEP | PLAT |
| ADIPOQ | CCL2 | CRP | ENG | FTH1 | GLUCOSE | GPT | HBA1C | HSPA1B | INSULIN | LEP | PLAT |
| ADIPOQ | CCL2 | CRP | ENG | FTH1 | GLUCOSE | GPT | HBA1C | HSPA1B | INSULIN | PLAT | TRIG |
| ADIPOQ | CCL2 | CRP | ENG | FTH1 | GLUCOSE | GPT | HBA1C | HSPA1B | LEP | PLAT | TRIG |
| ADIPOQ | CCL2 | CRP | ENG | FTH1 | GLUCOSE | GPT | HBA1C | HSPA1B | LEP | PLAT | VEGF |
| ADIPOQ | CCL2 | CRP | ENG | FTH1 | GLUCOSE | GPT | HBA1C | IGFBP1 | IL18 | INSULIN | PLAT |
| ADIPOQ | CCL2 | CRP | ENG | FTH1 | GLUCOSE | GPT | HBA1C | IGFBP1 | IL18 | LEP | PLAT |
| ADIPOQ | CCL2 | CRP | ENG | FTH1 | GLUCOSE | GPT | HBA1C | IGFBP1 | INSULIN | LEP | PLAT |
| ADIPOQ | CCL2 | CRP | ENG | FTH1 | GLUCOSE | GPT | HBA1C | IGFBP1 | LEP | PLAT | TRIG |
| ADIPOQ | CCL2 | CRP | ENG | FTH1 | GLUCOSE | GPT | HBA1C | IGFBP1 | LEP | PLAT | VEGF |
| ADIPOQ | CCL2 | CRP | ENG | FTH1 | GLUCOSE | GPT | HBA1C | IL18 | IL2RA | INSULIN | PLAT |
| ADIPOQ | CCL2 | CRP | ENG | FTH1 | GLUCOSE | GPT | HBA1C | IL18 | IL2RA | LEP | PLAT |
| ADIPOQ | CCL2 | CRP | ENG | FTH1 | GLUCOSE | GPT | HBA1C | IL18 | INSULIN | LEP | PLAT |
| ADIPOQ | CCL2 | CRP | ENG | FTH1 | GLUCOSE | GPT | HBA1C | IL18 | INSULIN | PLAT | VEGF |
| ADIPOQ | CCL2 | CRP | ENG | FTH1 | GLUCOSE | GPT | HBA1C | IL18 | LEP | PLAT | TRIG |
| ADIPOQ | CCL2 | CRP | ENG | FTH1 | GLUCOSE | GPT | HBA1C | IL18 | LEP | PLAT | VEGF |

FIGURE 21 (continued)

| ADIPOQ | CCL2 | CRP | ENG | FTH1 | GLUCOSE | GPT | HBA1C | IL2RA | INSULIN | LEP | PLAT |
| --- | --- | --- | --- | --- | --- | --- | --- | --- | --- | --- | --- |
| ADIPOQ | CCL2 | CRP | ENG | FTH1 | GLUCOSE | GPT | HBA1C | INSULIN | LEP | PLAT | TRIG |
| ADIPOQ | CCL2 | CRP | ENG | FTH1 | GLUCOSE | GPT | HBA1C | INSULIN | LEP | PLAT | VEGF |
| ADIPOQ | CCL2 | CRP | ENG | FTH1 | GLUCOSE | GPT | HBA1C | LEP | PLAT | TRIG | VEGF |
| ADIPOQ | CCL2 | CRP | ENG | FTH1 | GLUCOSE | HBA1C | HGF | HSPA1B | IL18 | INSULIN | PLAT |
| ADIPOQ | CCL2 | CRP | ENG | FTH1 | GLUCOSE | HBA1C | HGF | HSPA1B | IL18 | LEP | PLAT |
| ADIPOQ | CCL2 | CRP | ENG | FTH1 | GLUCOSE | HBA1C | HGF | HSPA1B | INSULIN | LEP | PLAT |
| ADIPOQ | CCL2 | CRP | ENG | FTH1 | GLUCOSE | HBA1C | HGF | HSPA1B | LEP | PLAT | VEGF |
| ADIPOQ | CCL2 | CRP | ENG | FTH1 | GLUCOSE | HBA1C | HGF | IL18 | INSULIN | LEP | PLAT |
| ADIPOQ | CCL2 | CRP | ENG | FTH1 | GLUCOSE | HBA1C | HGF | IL18 | LEP | PLAT | TRIG |
| ADIPOQ | CCL2 | CRP | ENG | FTH1 | GLUCOSE | HBA1C | HGF | INSULIN | LEP | PLAT | TRIG |
| ADIPOQ | CCL2 | CRP | ENG | FTH1 | GLUCOSE | HBA1C | HGF | INSULIN | LEP | PLAT | VEGF |
| ADIPOQ | CCL2 | CRP | ENG | FTH1 | GLUCOSE | HBA1C | HSPA1B | IGFBP1 | IL18 | INSULIN | PLAT |
| ADIPOQ | CCL2 | CRP | ENG | FTH1 | GLUCOSE | HBA1C | HSPA1B | IGFBP1 | IL18 | LEP | PLAT |
| ADIPOQ | CCL2 | CRP | ENG | FTH1 | GLUCOSE | HBA1C | HSPA1B | IGFBP1 | IL2RA | LEP | PLAT |
| ADIPOQ | CCL2 | CRP | ENG | FTH1 | GLUCOSE | HBA1C | HSPA1B | IGFBP1 | INSULIN | LEP | PLAT |
| ADIPOQ | CCL2 | CRP | ENG | FTH1 | GLUCOSE | HBA1C | HSPA1B | IGFBP1 | LEP | PLAT | TRIG |
| ADIPOQ | CCL2 | CRP | ENG | FTH1 | GLUCOSE | HBA1C | HSPA1B | IGFBP1 | LEP | PLAT | VEGF |
| ADIPOQ | CCL2 | CRP | ENG | FTH1 | GLUCOSE | HBA1C | HSPA1B | IL18 | IL2RA | INSULIN | PLAT |
| ADIPOQ | CCL2 | CRP | ENG | FTH1 | GLUCOSE | HBA1C | HSPA1B | IL18 | IL2RA | LEP | PLAT |
| ADIPOQ | CCL2 | CRP | ENG | FTH1 | GLUCOSE | HBA1C | HSPA1B | IL18 | INSULIN | LEP | PLAT |
| ADIPOQ | CCL2 | CRP | ENG | FTH1 | GLUCOSE | HBA1C | HSPA1B | IL18 | INSULIN | PLAT | TRIG |
| ADIPOQ | CCL2 | CRP | ENG | FTH1 | GLUCOSE | HBA1C | HSPA1B | IL18 | INSULIN | PLAT | VEGF |
| ADIPOQ | CCL2 | CRP | ENG | FTH1 | GLUCOSE | HBA1C | HSPA1B | IL18 | LEP | PLAT | TRIG |
| ADIPOQ | CCL2 | CRP | ENG | FTH1 | GLUCOSE | HBA1C | HSPA1B | IL18 | LEP | PLAT | VEGF |
| ADIPOQ | CCL2 | CRP | ENG | FTH1 | GLUCOSE | HBA1C | HSPA1B | IL2RA | INSULIN | LEP | PLAT |

FIGURE 21 (continued)

| ADIPOQ | CCL2 | CRP | ENG | FTH1 | GLUCOSE | HBA1C | HSPA1B | IL2RA | LEP | PLAT | TRIG |
|---|---|---|---|---|---|---|---|---|---|---|---|
| ADIPOQ | CCL2 | CRP | ENG | FTH1 | GLUCOSE | HBA1C | HSPA1B | IL2RA | LEP | PLAT | VEGF |
| ADIPOQ | CCL2 | CRP | ENG | FTH1 | GLUCOSE | HBA1C | HSPA1B | INSULIN | LEP | PLAT | TRIG |
| ADIPOQ | CCL2 | CRP | ENG | FTH1 | GLUCOSE | HBA1C | HSPA1B | INSULIN | LEP | PLAT | VEGF |
| ADIPOQ | CCL2 | CRP | ENG | FTH1 | GLUCOSE | HBA1C | HSPA1B | LEP | PLAT | TRIG | VEGF |
| ADIPOQ | CCL2 | CRP | ENG | FTH1 | GLUCOSE | HBA1C | IGFBP1 | IL18 | INSULIN | LEP | PLAT |
| ADIPOQ | CCL2 | CRP | ENG | FTH1 | GLUCOSE | HBA1C | IGFBP1 | IL18 | LEP | PLAT | TRIG |
| ADIPOQ | CCL2 | CRP | ENG | FTH1 | GLUCOSE | HBA1C | IGFBP1 | IL18 | LEP | PLAT | VEGF |
| ADIPOQ | CCL2 | CRP | ENG | FTH1 | GLUCOSE | HBA1C | IGFBP1 | INSULIN | LEP | PLAT | TRIG |
| ADIPOQ | CCL2 | CRP | ENG | FTH1 | GLUCOSE | HBA1C | IGFBP1 | INSULIN | LEP | PLAT | VEGF |
| ADIPOQ | CCL2 | CRP | ENG | FTH1 | GLUCOSE | HBA1C | IL18 | IL2RA | INSULIN | LEP | PLAT |
| ADIPOQ | CCL2 | CRP | ENG | FTH1 | GLUCOSE | HBA1C | IL18 | INSULIN | LEP | PLAT | TRIG |
| ADIPOQ | CCL2 | CRP | ENG | FTH1 | GLUCOSE | HBA1C | IL18 | INSULIN | LEP | PLAT | VEGF |
| ADIPOQ | CCL2 | CRP | ENG | FTH1 | GLUCOSE | HBA1C | IL18 | LEP | PLAT | TRIG | VEGF |
| ADIPOQ | CCL2 | CRP | ENG | FTH1 | GLUCOSE | HBA1C | INSULIN | LEP | PLAT | TRIG | VEGF |
| ADIPOQ | CRP | ENG | FTH1 | GLUCOSE | GPT | HBA1C | HGF | HSPA1B | IL18 | LEP | PLAT |
| ADIPOQ | CRP | ENG | FTH1 | GLUCOSE | GPT | HBA1C | HGF | IL18 | INSULIN | LEP | PLAT |
| ADIPOQ | CRP | ENG | FTH1 | GLUCOSE | GPT | HBA1C | HSPA1B | IGFBP1 | IL18 | LEP | PLAT |
| ADIPOQ | CRP | ENG | FTH1 | GLUCOSE | GPT | HBA1C | HSPA1B | IL18 | IL2RA | LEP | PLAT |
| ADIPOQ | CRP | ENG | FTH1 | GLUCOSE | GPT | HBA1C | HSPA1B | IL18 | INSULIN | LEP | PLAT |
| ADIPOQ | CRP | ENG | FTH1 | GLUCOSE | GPT | HBA1C | HSPA1B | IL18 | LEP | PLAT | TRIG |
| ADIPOQ | CRP | ENG | FTH1 | GLUCOSE | GPT | HBA1C | HSPA1B | IL18 | LEP | PLAT | VEGF |
| ADIPOQ | CRP | ENG | FTH1 | GLUCOSE | GPT | HBA1C | HSPA1B | IL2RA | INSULIN | LEP | PLAT |
| ADIPOQ | CRP | ENG | FTH1 | GLUCOSE | GPT | HBA1C | HSPA1B | INSULIN | LEP | PLAT | TRIG |
| ADIPOQ | CRP | ENG | FTH1 | GLUCOSE | GPT | HBA1C | HSPA1B | INSULIN | LEP | PLAT | VEGF |
| ADIPOQ | CRP | ENG | FTH1 | GLUCOSE | GPT | HBA1C | IGFBP1 | IL18 | INSULIN | LEP | PLAT |
| ADIPOQ | CRP | ENG | FTH1 | GLUCOSE | GPT | HBA1C | IL18 | IL2RA | INSULIN | LEP | PLAT |

FIGURE 21 (continued)

| ADIPOQ | CRP | ENG | FTH1 | GLUCOSE | GPT | HBA1C | IL18 | INSULIN | LEP | PLAT | TRIG |
|---|---|---|---|---|---|---|---|---|---|---|---|
| ADIPOQ | CRP | ENG | FTH1 | GLUCOSE | GPT | HBA1C | IL18 | INSULIN | LEP | PLAT | VEGF |
| ADIPOQ | CRP | ENG | FTH1 | GLUCOSE | GPT | HBA1C | INSULIN | LEP | PLAT | TRIG | VEGF |
| ADIPOQ | CRP | ENG | FTH1 | GLUCOSE | HBA1C | HGF | HSPA1B | IL18 | INSULIN | LEP | PLAT |
| ADIPOQ | CRP | ENG | FTH1 | GLUCOSE | HBA1C | HGF | HSPA1B | IL18 | LEP | PLAT | TRIG |
| ADIPOQ | CRP | ENG | FTH1 | GLUCOSE | HBA1C | HSPA1B | IGFBP1 | IL18 | INSULIN | LEP | PLAT |
| ADIPOQ | CRP | ENG | FTH1 | GLUCOSE | HBA1C | HSPA1B | IGFBP1 | IL18 | LEP | PLAT | TRIG |
| ADIPOQ | CRP | ENG | FTH1 | GLUCOSE | HBA1C | HSPA1B | IL18 | IL2RA | INSULIN | LEP | PLAT |
| ADIPOQ | CRP | ENG | FTH1 | GLUCOSE | HBA1C | HSPA1B | IL18 | INSULIN | LEP | PLAT | TRIG |
| ADIPOQ | CRP | ENG | FTH1 | GLUCOSE | HBA1C | HSPA1B | IL18 | INSULIN | LEP | PLAT | VEGF |
| ADIPOQ | CRP | ENG | FTH1 | GLUCOSE | HBA1C | HSPA1B | IL18 | LEP | PLAT | TRIG | VEGF |
| ADIPOQ | CRP | ENG | FTH1 | GLUCOSE | HBA1C | IL18 | IL2RA | INSULIN | LEP | PLAT | TRIG |
| ADIPOQ | CRP | ENG | FTH1 | GLUCOSE | HBA1C | IL18 | INSULIN | LEP | PLAT | TRIG | VEGF |
| CCL2 | CRP | ENG | FTH1 | GLUCOSE | GPT | HBA1C | HSPA1B | IL18 | IL2RA | INSULIN | PLAT |
| CCL2 | CRP | ENG | FTH1 | GLUCOSE | GPT | HBA1C | HSPA1B | IL18 | INSULIN | LEP | PLAT |
| CCL2 | CRP | ENG | FTH1 | GLUCOSE | GPT | HBA1C | HSPA1B | IL2RA | INSULIN | LEP | PLAT |
| CCL2 | CRP | ENG | FTH1 | GLUCOSE | HBA1C | HGF | HSPA1B | IL18 | INSULIN | LEP | PLAT |
| CCL2 | CRP | ENG | FTH1 | GLUCOSE | HBA1C | HSPA1B | IGFBP1 | IL18 | INSULIN | LEP | PLAT |
| CCL2 | CRP | ENG | FTH1 | GLUCOSE | HBA1C | HSPA1B | IL18 | INSULIN | LEP | PLAT | TRIG |
| CCL2 | CRP | ENG | FTH1 | GLUCOSE | HBA1C | HSPA1B | IL18 | INSULIN | LEP | PLAT | VEGF |

FIGURE 22

| ADIPOQ | CCL2 | CRP | ENG | FTH1 | GLUCOSE | GPT | HBA1C | HGF | HSPA1B | IL18 | INSULIN | PLAT |
| --- | --- | --- | --- | --- | --- | --- | --- | --- | --- | --- | --- | --- |
| ADIPOQ | CCL2 | CRP | ENG | FTH1 | GLUCOSE | GPT | HBA1C | HGF | HSPA1B | IL18 | LEP | PLAT |
| ADIPOQ | CCL2 | CRP | ENG | FTH1 | GLUCOSE | GPT | HBA1C | HGF | HSPA1B | INSULIN | LEP | PLAT |
| ADIPOQ | CCL2 | CRP | ENG | FTH1 | GLUCOSE | GPT | HBA1C | HGF | HSPA1B | LEP | PLAT | TRIG |
| ADIPOQ | CCL2 | CRP | ENG | FTH1 | GLUCOSE | GPT | HBA1C | HGF | HSPA1B | LEP | PLAT | VEGF |
| ADIPOQ | CCL2 | CRP | ENG | FTH1 | GLUCOSE | GPT | HBA1C | HGF | IGFBP1 | IL18 | LEP | PLAT |
| ADIPOQ | CCL2 | CRP | ENG | FTH1 | GLUCOSE | GPT | HBA1C | HGF | IGFBP1 | INSULIN | LEP | PLAT |
| ADIPOQ | CCL2 | CRP | ENG | FTH1 | GLUCOSE | GPT | HBA1C | HGF | IL18 | INSULIN | LEP | PLAT |
| ADIPOQ | CCL2 | CRP | ENG | FTH1 | GLUCOSE | GPT | HBA1C | HGF | IL18 | LEP | PLAT | TRIG |
| ADIPOQ | CCL2 | CRP | ENG | FTH1 | GLUCOSE | GPT | HBA1C | HGF | IL18 | LEP | PLAT | VEGF |
| ADIPOQ | CCL2 | CRP | ENG | FTH1 | GLUCOSE | GPT | HBA1C | HGF | IL2RA | INSULIN | LEP | PLAT |
| ADIPOQ | CCL2 | CRP | ENG | FTH1 | GLUCOSE | GPT | HBA1C | HGF | INSULIN | LEP | PLAT | TRIG |
| ADIPOQ | CCL2 | CRP | ENG | FTH1 | GLUCOSE | GPT | HBA1C | HGF | INSULIN | LEP | PLAT | VEGF |
| ADIPOQ | CCL2 | CRP | ENG | FTH1 | GLUCOSE | GPT | HBA1C | HSPA1B | IGFBP1 | IL18 | INSULIN | PLAT |
| ADIPOQ | CCL2 | CRP | ENG | FTH1 | GLUCOSE | GPT | HBA1C | HSPA1B | IGFBP1 | IL18 | LEP | PLAT |
| ADIPOQ | CCL2 | CRP | ENG | FTH1 | GLUCOSE | GPT | HBA1C | HSPA1B | IGFBP1 | INSULIN | LEP | PLAT |
| ADIPOQ | CCL2 | CRP | ENG | FTH1 | GLUCOSE | GPT | HBA1C | HSPA1B | IGFBP1 | LEP | PLAT | TRIG |
| ADIPOQ | CCL2 | CRP | ENG | FTH1 | GLUCOSE | GPT | HBA1C | HSPA1B | IGFBP1 | LEP | PLAT | VEGF |
| ADIPOQ | CCL2 | CRP | ENG | FTH1 | GLUCOSE | GPT | HBA1C | HSPA1B | IL18 | IL2RA | INSULIN | PLAT |
| ADIPOQ | CCL2 | CRP | ENG | FTH1 | GLUCOSE | GPT | HBA1C | HSPA1B | IL18 | IL2RA | LEP | PLAT |
| ADIPOQ | CCL2 | CRP | ENG | FTH1 | GLUCOSE | GPT | HBA1C | HSPA1B | IL18 | INSULIN | LEP | PLAT |
| ADIPOQ | CCL2 | CRP | ENG | FTH1 | GLUCOSE | GPT | HBA1C | HSPA1B | IL18 | INSULIN | PLAT | TRIG |
| ADIPOQ | CCL2 | CRP | ENG | FTH1 | GLUCOSE | GPT | HBA1C | HSPA1B | IL18 | INSULIN | PLAT | VEGF |
| ADIPOQ | CCL2 | CRP | ENG | FTH1 | GLUCOSE | GPT | HBA1C | HSPA1B | IL18 | LEP | PLAT | TRIG |
| ADIPOQ | CCL2 | CRP | ENG | FTH1 | GLUCOSE | GPT | HBA1C | HSPA1B | IL18 | LEP | PLAT | VEGF |
| ADIPOQ | CCL2 | CRP | ENG | FTH1 | GLUCOSE | GPT | HBA1C | HSPA1B | IL2RA | INSULIN | LEP | PLAT |
| ADIPOQ | CCL2 | CRP | ENG | FTH1 | GLUCOSE | GPT | HBA1C | HSPA1B | IL2RA | LEP | PLAT | VEGF |

FIGURE 22 (continued)

| ADIPOQ | CCL2 | CRP | ENG | FTH1 | GLUCOSE | GPT | HBA1C | HSPA1B | INSULIN | LEP | PLAT | TRIG |
|--------|------|-----|-----|------|---------|-----|-------|--------|---------|-----|------|------|
| ADIPOQ | CCL2 | CRP | ENG | FTH1 | GLUCOSE | GPT | HBA1C | HSPA1B | INSULIN | LEP | PLAT | VEGF |
| ADIPOQ | CCL2 | CRP | ENG | FTH1 | GLUCOSE | GPT | HBA1C | HSPA1B | LEP | PLAT | TRIG | VEGF |
| ADIPOQ | CCL2 | CRP | ENG | FTH1 | GLUCOSE | GPT | HBA1C | IGFBP1 | IL18 | INSULIN | LEP | PLAT |
| ADIPOQ | CCL2 | CRP | ENG | FTH1 | GLUCOSE | GPT | HBA1C | IGFBP1 | IL18 | LEP | PLAT | TRIG |
| ADIPOQ | CCL2 | CRP | ENG | FTH1 | GLUCOSE | GPT | HBA1C | IGFBP1 | IL18 | LEP | PLAT | VEGF |
| ADIPOQ | CCL2 | CRP | ENG | FTH1 | GLUCOSE | GPT | HBA1C | IGFBP1 | IL2RA | INSULIN | LEP | PLAT |
| ADIPOQ | CCL2 | CRP | ENG | FTH1 | GLUCOSE | GPT | HBA1C | IGFBP1 | INSULIN | LEP | PLAT | TRIG |
| ADIPOQ | CCL2 | CRP | ENG | FTH1 | GLUCOSE | GPT | HBA1C | IGFBP1 | INSULIN | LEP | PLAT | VEGF |
| ADIPOQ | CCL2 | CRP | ENG | FTH1 | GLUCOSE | GPT | HBA1C | IL18 | IL2RA | INSULIN | LEP | PLAT |
| ADIPOQ | CCL2 | CRP | ENG | FTH1 | GLUCOSE | GPT | HBA1C | IL18 | INSULIN | LEP | PLAT | TRIG |
| ADIPOQ | CCL2 | CRP | ENG | FTH1 | GLUCOSE | GPT | HBA1C | IL18 | INSULIN | LEP | PLAT | VEGF |
| ADIPOQ | CCL2 | CRP | ENG | FTH1 | GLUCOSE | GPT | HBA1C | IL18 | LEP | PLAT | TRIG | VEGF |
| ADIPOQ | CCL2 | CRP | ENG | FTH1 | GLUCOSE | GPT | HBA1C | IL2RA | INSULIN | LEP | PLAT | TRIG |
| ADIPOQ | CCL2 | CRP | ENG | FTH1 | GLUCOSE | GPT | HBA1C | IL2RA | INSULIN | LEP | PLAT | VEGF |
| ADIPOQ | CCL2 | CRP | ENG | FTH1 | GLUCOSE | GPT | HBA1C | INSULIN | LEP | PLAT | TRIG | VEGF |
| ADIPOQ | CCL2 | CRP | ENG | FTH1 | GLUCOSE | HBA1C | HGF | HSPA1B | IGFBP1 | IL18 | LEP | PLAT |
| ADIPOQ | CCL2 | CRP | ENG | FTH1 | GLUCOSE | HBA1C | HGF | HSPA1B | IGFBP1 | INSULIN | LEP | PLAT |
| ADIPOQ | CCL2 | CRP | ENG | FTH1 | GLUCOSE | HBA1C | HGF | HSPA1B | IL18 | IL2RA | LEP | PLAT |
| ADIPOQ | CCL2 | CRP | ENG | FTH1 | GLUCOSE | HBA1C | HGF | HSPA1B | IL18 | INSULIN | LEP | PLAT |
| ADIPOQ | CCL2 | CRP | ENG | FTH1 | GLUCOSE | HBA1C | HGF | HSPA1B | IL18 | LEP | PLAT | TRIG |
| ADIPOQ | CCL2 | CRP | ENG | FTH1 | GLUCOSE | HBA1C | HGF | HSPA1B | IL18 | LEP | PLAT | VEGF |
| ADIPOQ | CCL2 | CRP | ENG | FTH1 | GLUCOSE | HBA1C | HGF | HSPA1B | IL2RA | INSULIN | LEP | PLAT |
| ADIPOQ | CCL2 | CRP | ENG | FTH1 | GLUCOSE | HBA1C | HGF | HSPA1B | INSULIN | LEP | PLAT | TRIG |
| ADIPOQ | CCL2 | CRP | ENG | FTH1 | GLUCOSE | HBA1C | HGF | HSPA1B | INSULIN | LEP | PLAT | VEGF |
| ADIPOQ | CCL2 | CRP | ENG | FTH1 | GLUCOSE | HBA1C | HGF | IGFBP1 | IL18 | INSULIN | LEP | PLAT |

FIGURE 22 (continued)

| ADIPOQ | CCL2 | CRP | ENG | FTH1 | GLUCOSE | HBA1C | HGF | IL18 | INSULIN | LEP | PLAT | TRIG |
|---|---|---|---|---|---|---|---|---|---|---|---|---|
| ADIPOQ | CCL2 | CRP | ENG | FTH1 | GLUCOSE | HBA1C | HGF | IL18 | INSULIN | LEP | PLAT | VEGF |
| ADIPOQ | CCL2 | CRP | ENG | FTH1 | GLUCOSE | HBA1C | HSPA1B | IGFBP1 | IL18 | IL2RA | INSULIN | PLAT |
| ADIPOQ | CCL2 | CRP | ENG | FTH1 | GLUCOSE | HBA1C | HSPA1B | IGFBP1 | IL18 | IL2RA | LEP | PLAT |
| ADIPOQ | CCL2 | CRP | ENG | FTH1 | GLUCOSE | HBA1C | HSPA1B | IGFBP1 | IL18 | INSULIN | LEP | PLAT |
| ADIPOQ | CCL2 | CRP | ENG | FTH1 | GLUCOSE | HBA1C | HSPA1B | IGFBP1 | IL18 | LEP | PLAT | TRIG |
| ADIPOQ | CCL2 | CRP | ENG | FTH1 | GLUCOSE | HBA1C | HSPA1B | IGFBP1 | IL18 | LEP | PLAT | VEGF |
| ADIPOQ | CCL2 | CRP | ENG | FTH1 | GLUCOSE | HBA1C | HSPA1B | IGFBP1 | IL2RA | INSULIN | LEP | PLAT |
| ADIPOQ | CCL2 | CRP | ENG | FTH1 | GLUCOSE | HBA1C | HSPA1B | IGFBP1 | IL2RA | LEP | PLAT | VEGF |
| ADIPOQ | CCL2 | CRP | ENG | FTH1 | GLUCOSE | HBA1C | HSPA1B | IGFBP1 | INSULIN | LEP | PLAT | TRIG |
| ADIPOQ | CCL2 | CRP | ENG | FTH1 | GLUCOSE | HBA1C | HSPA1B | IGFBP1 | INSULIN | LEP | PLAT | VEGF |
| ADIPOQ | CCL2 | CRP | ENG | FTH1 | GLUCOSE | HBA1C | HSPA1B | IL18 | IL2RA | INSULIN | LEP | PLAT |
| ADIPOQ | CCL2 | CRP | ENG | FTH1 | GLUCOSE | HBA1C | HSPA1B | IL18 | IL2RA | INSULIN | PLAT | TRIG |
| ADIPOQ | CCL2 | CRP | ENG | FTH1 | GLUCOSE | HBA1C | HSPA1B | IL18 | IL2RA | LEP | PLAT | TRIG |
| ADIPOQ | CCL2 | CRP | ENG | FTH1 | GLUCOSE | HBA1C | HSPA1B | IL18 | IL2RA | LEP | PLAT | VEGF |
| ADIPOQ | CCL2 | CRP | ENG | FTH1 | GLUCOSE | HBA1C | HSPA1B | IL18 | INSULIN | LEP | PLAT | TRIG |
| ADIPOQ | CCL2 | CRP | ENG | FTH1 | GLUCOSE | HBA1C | HSPA1B | IL18 | INSULIN | LEP | PLAT | VEGF |
| ADIPOQ | CCL2 | CRP | ENG | FTH1 | GLUCOSE | HBA1C | HSPA1B | IL18 | LEP | PLAT | TRIG | VEGF |
| ADIPOQ | CCL2 | CRP | ENG | FTH1 | GLUCOSE | HBA1C | HSPA1B | IL2RA | INSULIN | LEP | PLAT | TRIG |
| ADIPOQ | CCL2 | CRP | ENG | FTH1 | GLUCOSE | HBA1C | HSPA1B | IL2RA | INSULIN | LEP | PLAT | VEGF |
| ADIPOQ | CCL2 | CRP | ENG | FTH1 | GLUCOSE | HBA1C | HSPA1B | INSULIN | LEP | PLAT | TRIG | VEGF |
| ADIPOQ | CCL2 | CRP | ENG | FTH1 | GLUCOSE | HBA1C | IGFBP1 | IL18 | INSULIN | LEP | PLAT | TRIG |
| ADIPOQ | CCL2 | CRP | ENG | FTH1 | GLUCOSE | HBA1C | IGFBP1 | IL18 | INSULIN | LEP | PLAT | VEGF |
| ADIPOQ | CCL2 | CRP | ENG | FTH1 | GLUCOSE | HBA1C | IL18 | INSULIN | LEP | PLAT | TRIG | VEGF |
| ADIPOQ | CRP | ENG | FTH1 | GLUCOSE | GPT | HBA1C | HGF | HSPA1B | IL18 | INSULIN | LEP | PLAT |
| ADIPOQ | CRP | ENG | FTH1 | GLUCOSE | GPT | HBA1C | HGF | HSPA1B | IL18 | LEP | PLAT | VEGF |
| ADIPOQ | CRP | ENG | FTH1 | GLUCOSE | GPT | HBA1C | HSPA1B | IGFBP1 | IL18 | IL2RA | LEP | PLAT |

FIGURE 22 (continued)

| ADIPOQ | CRP | ENG | FTH1 | GLUCOSE | GPT | HBA1C | HSPA1B | IGFBP1 | IL18 | INSULIN | LEP | PLAT |
|---|---|---|---|---|---|---|---|---|---|---|---|---|
| ADIPOQ | CRP | ENG | FTH1 | GLUCOSE | GPT | HBA1C | HSPA1B | IGFBP1 | IL18 | LEP | PLAT | VEGF |
| ADIPOQ | CRP | ENG | FTH1 | GLUCOSE | GPT | HBA1C | HSPA1B | IL18 | IL2RA | INSULIN | LEP | PLAT |
| ADIPOQ | CRP | ENG | FTH1 | GLUCOSE | GPT | HBA1C | HSPA1B | IL18 | IL2RA | LEP | PLAT | VEGF |
| ADIPOQ | CRP | ENG | FTH1 | GLUCOSE | GPT | HBA1C | HSPA1B | IL18 | INSULIN | LEP | PLAT | TRIG |
| ADIPOQ | CRP | ENG | FTH1 | GLUCOSE | GPT | HBA1C | HSPA1B | IL18 | INSULIN | LEP | PLAT | VEGF |
| ADIPOQ | CRP | ENG | FTH1 | GLUCOSE | GPT | HBA1C | HSPA1B | IL18 | LEP | PLAT | TRIG | VEGF |
| ADIPOQ | CRP | ENG | FTH1 | GLUCOSE | GPT | HBA1C | HSPA1B | IL2RA | INSULIN | LEP | PLAT | VEGF |
| ADIPOQ | CRP | ENG | FTH1 | GLUCOSE | GPT | HBA1C | IL18 | INSULIN | LEP | PLAT | TRIG | VEGF |
| ADIPOQ | CRP | ENG | FTH1 | GLUCOSE | HBA1C | HGF | HSPA1B | IL18 | IL2RA | INSULIN | LEP | PLAT |
| ADIPOQ | CRP | ENG | FTH1 | GLUCOSE | HBA1C | HGF | HSPA1B | IL18 | INSULIN | LEP | PLAT | TRIG |
| ADIPOQ | CRP | ENG | FTH1 | GLUCOSE | HBA1C | HGF | HSPA1B | IL18 | INSULIN | LEP | PLAT | VEGF |
| ADIPOQ | CRP | ENG | FTH1 | GLUCOSE | HBA1C | HSPA1B | IGFBP1 | IL18 | INSULIN | LEP | PLAT | TRIG |
| ADIPOQ | CRP | ENG | FTH1 | GLUCOSE | HBA1C | HSPA1B | IL18 | IL2RA | INSULIN | LEP | PLAT | TRIG |
| ADIPOQ | CRP | ENG | FTH1 | GLUCOSE | HBA1C | HSPA1B | IL18 | IL2RA | INSULIN | LEP | PLAT | VEGF |
| ADIPOQ | CRP | ENG | FTH1 | GLUCOSE | HBA1C | HSPA1B | IL18 | INSULIN | LEP | PLAT | TRIG | VEGF |
| CCL2 | CRP | ENG | FTH1 | GLUCOSE | GPT | HBA1C | HSPA1B | IGFBP1 | IL18 | INSULIN | LEP | PLAT |
| CCL2 | CRP | ENG | FTH1 | GLUCOSE | GPT | HBA1C | HSPA1B | IL18 | IL2RA | INSULIN | LEP | PLAT |
| CCL2 | CRP | ENG | FTH1 | GLUCOSE | GPT | HBA1C | HSPA1B | IL18 | INSULIN | LEP | PLAT | TRIG |
| CCL2 | CRP | ENG | FTH1 | GLUCOSE | GPT | HBA1C | HSPA1B | IL18 | INSULIN | LEP | PLAT | VEGF |

FIGURE 23

| |
|---|
| ADIPOQ; CCL2; CRP; ENG; FTH1; GLUCOSE; GPT; HBA1C; HGF; HSPA1B; IGFBP1; IL18; LEP; PLAT |
| ADIPOQ; CCL2; CRP; ENG; FTH1; GLUCOSE; GPT; HBA1C; HGF; HSPA1B; IGFBP1; INSULIN; LEP; PLAT |
| ADIPOQ; CCL2; CRP; ENG; FTH1; GLUCOSE; GPT; HBA1C; HGF; HSPA1B; IGFBP1; LEP; PLAT; VEGF |
| ADIPOQ; CCL2; CRP; ENG; FTH1; GLUCOSE; GPT; HBA1C; HGF; HSPA1B; IL18; IL2RA; INSULIN; PLAT |
| ADIPOQ; CCL2; CRP; ENG; FTH1; GLUCOSE; GPT; HBA1C; HGF; HSPA1B; IL18; IL2RA; LEP; PLAT |
| ADIPOQ; CCL2; CRP; ENG; FTH1; GLUCOSE; GPT; HBA1C; HGF; HSPA1B; IL18; INSULIN; LEP; PLAT |
| ADIPOQ; CCL2; CRP; ENG; FTH1; GLUCOSE; GPT; HBA1C; HGF; HSPA1B; IL18; LEP; PLAT; TRIG |
| ADIPOQ; CCL2; CRP; ENG; FTH1; GLUCOSE; GPT; HBA1C; HGF; HSPA1B; IL18; LEP; PLAT; VEGF |
| ADIPOQ; CCL2; CRP; ENG; FTH1; GLUCOSE; GPT; HBA1C; HGF; HSPA1B; IL2RA; INSULIN; LEP; PLAT |
| ADIPOQ; CCL2; CRP; ENG; FTH1; GLUCOSE; GPT; HBA1C; HGF; HSPA1B; INSULIN; LEP; PLAT; TRIG |
| ADIPOQ; CCL2; CRP; ENG; FTH1; GLUCOSE; GPT; HBA1C; HGF; HSPA1B; INSULIN; LEP; PLAT; VEGF |
| ADIPOQ; CCL2; CRP; ENG; FTH1; GLUCOSE; GPT; HBA1C; HGF; HSPA1B; LEP; PLAT; TRIG; VEGF |
| ADIPOQ; CCL2; CRP; ENG; FTH1; GLUCOSE; GPT; HBA1C; HGF; IGFBP1; IL18; INSULIN; LEP; PLAT |
| ADIPOQ; CCL2; CRP; ENG; FTH1; GLUCOSE; GPT; HBA1C; HGF; IGFBP1; IL2RA; INSULIN; LEP; PLAT |
| ADIPOQ; CCL2; CRP; ENG; FTH1; GLUCOSE; GPT; HBA1C; HGF; IGFBP1; INSULIN; LEP; PLAT; VEGF |
| ADIPOQ; CCL2; CRP; ENG; FTH1; GLUCOSE; GPT; HBA1C; HGF; IL18; IL2RA; INSULIN; LEP; PLAT |
| ADIPOQ; CCL2; CRP; ENG; FTH1; GLUCOSE; GPT; HBA1C; HGF; IL18; INSULIN; LEP; PLAT; TRIG |
| ADIPOQ; CCL2; CRP; ENG; FTH1; GLUCOSE; GPT; HBA1C; HGF; IL18; INSULIN; LEP; PLAT; VEGF |
| ADIPOQ; CCL2; CRP; ENG; FTH1; GLUCOSE; GPT; HBA1C; HGF; IL2RA; INSULIN; LEP; PLAT; TRIG |
| ADIPOQ; CCL2; CRP; ENG; FTH1; GLUCOSE; GPT; HBA1C; HGF; IL2RA; INSULIN; LEP; PLAT; VEGF |
| ADIPOQ; CCL2; CRP; ENG; FTH1; GLUCOSE; GPT; HBA1C; HGF; INSULIN; LEP; PLAT; TRIG; VEGF |
| ADIPOQ; CCL2; CRP; ENG; FTH1; GLUCOSE; GPT; HBA1C; HSPA1B; IGFBP1; IL18; IL2RA; INSULIN; PLAT |
| ADIPOQ; CCL2; CRP; ENG; FTH1; GLUCOSE; GPT; HBA1C; HSPA1B; IGFBP1; IL18; IL2RA; LEP; PLAT |
| ADIPOQ; CCL2; CRP; ENG; FTH1; GLUCOSE; GPT; HBA1C; HSPA1B; IGFBP1; IL18; INSULIN; LEP; PLAT |
| ADIPOQ; CCL2; CRP; ENG; FTH1; GLUCOSE; GPT; HBA1C; HSPA1B; IGFBP1; IL18; INSULIN; PLAT; VEGF |
| ADIPOQ; CCL2; CRP; ENG; FTH1; GLUCOSE; GPT; HBA1C; HSPA1B; IGFBP1; IL18; LEP; PLAT; TRIG |
| ADIPOQ; CCL2; CRP; ENG; FTH1; GLUCOSE; GPT; HBA1C; HSPA1B; IGFBP1; IL18; LEP; PLAT; VEGF |

FIGURE 23 (continued)

| |
|---|
| ADIPOQ; CCL2; CRP; ENG; FTH1; GLUCOSE; GPT; HBA1C; HSPA1B; IGFBP1; IL2RA; INSULIN; LEP; PLAT |
| ADIPOQ; CCL2; CRP; ENG; FTH1; GLUCOSE; GPT; HBA1C; HSPA1B; IGFBP1; IL2RA; LEP; PLAT; TRIG |
| ADIPOQ; CCL2; CRP; ENG; FTH1; GLUCOSE; GPT; HBA1C; HSPA1B; IGFBP1; IL2RA; LEP; PLAT; VEGF |
| ADIPOQ; CCL2; CRP; ENG; FTH1; GLUCOSE; GPT; HBA1C; HSPA1B; IGFBP1; INSULIN; LEP; PLAT; TRIG |
| ADIPOQ; CCL2; CRP; ENG; FTH1; GLUCOSE; GPT; HBA1C; HSPA1B; IGFBP1; INSULIN; LEP; PLAT; VEGF |
| ADIPOQ; CCL2; CRP; ENG; FTH1; GLUCOSE; GPT; HBA1C; HSPA1B; IGFBP1; LEP; PLAT; TRIG; VEGF |
| ADIPOQ; CCL2; CRP; ENG; FTH1; GLUCOSE; GPT; HBA1C; HSPA1B; IL18; IL2RA; INSULIN; LEP; PLAT |
| ADIPOQ; CCL2; CRP; ENG; FTH1; GLUCOSE; GPT; HBA1C; HSPA1B; IL18; IL2RA; INSULIN; PLAT; VEGF |
| ADIPOQ; CCL2; CRP; ENG; FTH1; GLUCOSE; GPT; HBA1C; HSPA1B; IL18; IL2RA; LEP; PLAT; TRIG |
| ADIPOQ; CCL2; CRP; ENG; FTH1; GLUCOSE; GPT; HBA1C; HSPA1B; IL18; IL2RA; LEP; PLAT; VEGF |
| ADIPOQ; CCL2; CRP; ENG; FTH1; GLUCOSE; GPT; HBA1C; HSPA1B; IL18; INSULIN; LEP; PLAT; TRIG |
| ADIPOQ; CCL2; CRP; ENG; FTH1; GLUCOSE; GPT; HBA1C; HSPA1B; IL18; INSULIN; LEP; PLAT; VEGF |
| ADIPOQ; CCL2; CRP; ENG; FTH1; GLUCOSE; GPT; HBA1C; HSPA1B; IL18; INSULIN; PLAT; TRIG; VEGF |
| ADIPOQ; CCL2; CRP; ENG; FTH1; GLUCOSE; GPT; HBA1C; HSPA1B; IL18; LEP; PLAT; TRIG; VEGF |
| ADIPOQ; CCL2; CRP; ENG; FTH1; GLUCOSE; GPT; HBA1C; HSPA1B; IL2RA; INSULIN; LEP; PLAT; TRIG |
| ADIPOQ; CCL2; CRP; ENG; FTH1; GLUCOSE; GPT; HBA1C; HSPA1B; IL2RA; INSULIN; LEP; PLAT; VEGF |
| ADIPOQ; CCL2; CRP; ENG; FTH1; GLUCOSE; GPT; HBA1C; HSPA1B; IL2RA; LEP; PLAT; TRIG; VEGF |
| ADIPOQ; CCL2; CRP; ENG; FTH1; GLUCOSE; GPT; HBA1C; HSPA1B; INSULIN; LEP; PLAT; TRIG; VEGF |
| ADIPOQ; CCL2; CRP; ENG; FTH1; GLUCOSE; GPT; HBA1C; IGFBP1; IL18; IL2RA; INSULIN; LEP; PLAT |
| ADIPOQ; CCL2; CRP; ENG; FTH1; GLUCOSE; GPT; HBA1C; IGFBP1; IL18; IL2RA; LEP; PLAT; VEGF |
| ADIPOQ; CCL2; CRP; ENG; FTH1; GLUCOSE; GPT; HBA1C; IGFBP1; IL18; INSULIN; LEP; PLAT; TRIG |
| ADIPOQ; CCL2; CRP; ENG; FTH1; GLUCOSE; GPT; HBA1C; IGFBP1; IL18; INSULIN; LEP; PLAT; VEGF |
| ADIPOQ; CCL2; CRP; ENG; FTH1; GLUCOSE; GPT; HBA1C; IGFBP1; IL18; LEP; PLAT; TRIG; VEGF |
| ADIPOQ; CCL2; CRP; ENG; FTH1; GLUCOSE; GPT; HBA1C; IGFBP1; IL2RA; INSULIN; LEP; PLAT; TRIG |
| ADIPOQ; CCL2; CRP; ENG; FTH1; GLUCOSE; GPT; HBA1C; IGFBP1; IL2RA; INSULIN; LEP; PLAT; VEGF |
| ADIPOQ; CCL2; CRP; ENG; FTH1; GLUCOSE; GPT; HBA1C; IGFBP1; INSULIN; LEP; PLAT; TRIG; VEGF |
| ADIPOQ; CCL2; CRP; ENG; FTH1; GLUCOSE; GPT; HBA1C; IL18; IL2RA; INSULIN; LEP; PLAT; TRIG |

FIGURE 23 (continued)

| |
|---|
| ADIPOQ; CCL2; CRP; ENG; FTH1; GLUCOSE; GPT; HBA1C; IL18; IL2RA; INSULIN; LEP; PLAT; VEGF |
| ADIPOQ; CCL2; CRP; ENG; FTH1; GLUCOSE; GPT; HBA1C; IL18; INSULIN; LEP; PLAT; TRIG; VEGF |
| ADIPOQ; CCL2; CRP; ENG; FTH1; GLUCOSE; GPT; HBA1C; IL2RA; INSULIN; LEP; PLAT; TRIG; VEGF |
| ADIPOQ; CCL2; CRP; ENG; FTH1; GLUCOSE; HBA1C; HGF; HSPA1B; IGFBP1; IL18; IL2RA; LEP; PLAT |
| ADIPOQ; CCL2; CRP; ENG; FTH1; GLUCOSE; HBA1C; HGF; HSPA1B; IGFBP1; IL18; INSULIN; LEP; PLAT |
| ADIPOQ; CCL2; CRP; ENG; FTH1; GLUCOSE; HBA1C; HGF; HSPA1B; IGFBP1; IL18; LEP; PLAT; TRIG |
| ADIPOQ; CCL2; CRP; ENG; FTH1; GLUCOSE; HBA1C; HGF; HSPA1B; IGFBP1; IL18; LEP; PLAT; VEGF |
| ADIPOQ; CCL2; CRP; ENG; FTH1; GLUCOSE; HBA1C; HGF; HSPA1B; IGFBP1; INSULIN; LEP; PLAT; TRIG |
| ADIPOQ; CCL2; CRP; ENG; FTH1; GLUCOSE; HBA1C; HGF; HSPA1B; IL18; IL2RA; INSULIN; LEP; PLAT |
| ADIPOQ; CCL2; CRP; ENG; FTH1; GLUCOSE; HBA1C; HGF; HSPA1B; IL18; IL2RA; LEP; PLAT; TRIG |
| ADIPOQ; CCL2; CRP; ENG; FTH1; GLUCOSE; HBA1C; HGF; HSPA1B; IL18; INSULIN; LEP; PLAT; TRIG |
| ADIPOQ; CCL2; CRP; ENG; FTH1; GLUCOSE; HBA1C; HGF; HSPA1B; IL18; INSULIN; LEP; PLAT; VEGF |
| ADIPOQ; CCL2; CRP; ENG; FTH1; GLUCOSE; HBA1C; HGF; HSPA1B; IL18; LEP; PLAT; TRIG; VEGF |
| ADIPOQ; CCL2; CRP; ENG; FTH1; GLUCOSE; HBA1C; HGF; HSPA1B; IL2RA; INSULIN; LEP; PLAT; TRIG |
| ADIPOQ; CCL2; CRP; ENG; FTH1; GLUCOSE; HBA1C; HGF; HSPA1B; IL2RA; INSULIN; LEP; PLAT; VEGF |
| ADIPOQ; CCL2; CRP; ENG; FTH1; GLUCOSE; HBA1C; HGF; HSPA1B; INSULIN; LEP; PLAT; TRIG; VEGF |
| ADIPOQ; CCL2; CRP; ENG; FTH1; GLUCOSE; HBA1C; HGF; IL18; INSULIN; LEP; PLAT; TRIG; VEGF |
| ADIPOQ; CCL2; CRP; ENG; FTH1; GLUCOSE; HBA1C; HSPA1B; IGFBP1; IL18; IL2RA; INSULIN; LEP; PLAT |
| ADIPOQ; CCL2; CRP; ENG; FTH1; GLUCOSE; HBA1C; HSPA1B; IGFBP1; IL18; IL2RA; LEP; PLAT; TRIG |
| ADIPOQ; CCL2; CRP; ENG; FTH1; GLUCOSE; HBA1C; HSPA1B; IGFBP1; IL18; IL2RA; LEP; PLAT; VEGF |
| ADIPOQ; CCL2; CRP; ENG; FTH1; GLUCOSE; HBA1C; HSPA1B; IGFBP1; IL18; INSULIN; LEP; PLAT; TRIG |
| ADIPOQ; CCL2; CRP; ENG; FTH1; GLUCOSE; HBA1C; HSPA1B; IGFBP1; IL18; INSULIN; LEP; PLAT; VEGF |
| ADIPOQ; CCL2; CRP; ENG; FTH1; GLUCOSE; HBA1C; HSPA1B; IGFBP1; IL18; LEP; PLAT; TRIG; VEGF |
| ADIPOQ; CCL2; CRP; ENG; FTH1; GLUCOSE; HBA1C; HSPA1B; IGFBP1; IL2RA; INSULIN; LEP; PLAT; TRIG |
| ADIPOQ; CCL2; CRP; ENG; FTH1; GLUCOSE; HBA1C; HSPA1B; IGFBP1; INSULIN; LEP; PLAT; TRIG; VEGF |
| ADIPOQ; CCL2; CRP; ENG; FTH1; GLUCOSE; HBA1C; HSPA1B; IL18; IL2RA; INSULIN; LEP; PLAT; TRIG |
| ADIPOQ; CCL2; CRP; ENG; FTH1; GLUCOSE; HBA1C; HSPA1B; IL18; IL2RA; INSULIN; LEP; PLAT; VEGF |
| ADIPOQ; CCL2; CRP; ENG; FTH1; GLUCOSE; HBA1C; HSPA1B; IL18; IL2RA; LEP; PLAT; TRIG; VEGF |

FIGURE 23 (continued)

| |
|---|
| ADIPOQ; CCL2; CRP; ENG; FTH1; GLUCOSE; HBA1C; HSPA1B; IL18; INSULIN; LEP; PLAT; TRIG; VEGF |
| ADIPOQ; CCL2; CRP; ENG; FTH1; GLUCOSE; HBA1C; HSPA1B; IL2RA; INSULIN; LEP; PLAT; TRIG; VEGF |
| ADIPOQ; CCL2; CRP; ENG; FTH1; GLUCOSE; HBA1C; IGFBP1; IL18; INSULIN; LEP; PLAT; TRIG; VEGF |
| ADIPOQ; CRP; ENG; FTH1; GLUCOSE; GPT; HBA1C; HGF; HSPA1B; IGFBP1; IL18; INSULIN; LEP; PLAT |
| ADIPOQ; CRP; ENG; FTH1; GLUCOSE; GPT; HBA1C; HGF; HSPA1B; IL18; IL2RA; INSULIN; LEP; PLAT |
| ADIPOQ; CRP; ENG; FTH1; GLUCOSE; GPT; HBA1C; HGF; HSPA1B; IL18; INSULIN; LEP; PLAT; TRIG |
| ADIPOQ; CRP; ENG; FTH1; GLUCOSE; GPT; HBA1C; HGF; HSPA1B; IL18; INSULIN; LEP; PLAT; VEGF |
| ADIPOQ; CRP; ENG; FTH1; GLUCOSE; GPT; HBA1C; HSPA1B; IGFBP1; IL18; IL2RA; INSULIN; LEP; PLAT |
| ADIPOQ; CRP; ENG; FTH1; GLUCOSE; GPT; HBA1C; HSPA1B; IGFBP1; IL18; INSULIN; LEP; PLAT; TRIG |
| ADIPOQ; CRP; ENG; FTH1; GLUCOSE; GPT; HBA1C; HSPA1B; IGFBP1; IL18; INSULIN; LEP; PLAT; VEGF |
| ADIPOQ; CRP; ENG; FTH1; GLUCOSE; GPT; HBA1C; HSPA1B; IGFBP1; IL18; LEP; PLAT; TRIG; VEGF |
| ADIPOQ; CRP; ENG; FTH1; GLUCOSE; GPT; HBA1C; HSPA1B; IL18; IL2RA; INSULIN; LEP; PLAT; TRIG |
| ADIPOQ; CRP; ENG; FTH1; GLUCOSE; GPT; HBA1C; HSPA1B; IL18; IL2RA; INSULIN; LEP; PLAT; VEGF |
| ADIPOQ; CRP; ENG; FTH1; GLUCOSE; GPT; HBA1C; HSPA1B; IL18; INSULIN; LEP; PLAT; TRIG; VEGF |
| ADIPOQ; CRP; ENG; FTH1; GLUCOSE; HBA1C; HGF; HSPA1B; IL18; IL2RA; INSULIN; LEP; PLAT; TRIG |
| ADIPOQ; CRP; ENG; FTH1; GLUCOSE; HBA1C; HGF; HSPA1B; IL18; INSULIN; LEP; PLAT; TRIG; VEGF |
| ADIPOQ; CRP; ENG; FTH1; GLUCOSE; HBA1C; HSPA1B; IGFBP1; IL18; IL2RA; INSULIN; LEP; PLAT; TRIG |
| ADIPOQ; CRP; ENG; FTH1; GLUCOSE; HBA1C; HSPA1B; IL18; IL2RA; INSULIN; LEP; PLAT; TRIG; VEGF |

FIGURE 24

| |
|---|
| ADIPOQ; CCL2; CRP; ENG; FTH1; GLUCOSE; GPT; HBA1C; HGF; HSPA1B; IGFBP1; IL18; IL2RA; INSULIN; PLAT |
| ADIPOQ; CCL2; CRP; ENG; FTH1; GLUCOSE; GPT; HBA1C; HGF; HSPA1B; IGFBP1; IL18; IL2RA; LEP; PLAT |
| ADIPOQ; CCL2; CRP; ENG; FTH1; GLUCOSE; GPT; HBA1C; HGF; HSPA1B; IGFBP1; IL18; INSULIN; LEP; PLAT |
| ADIPOQ; CCL2; CRP; ENG; FTH1; GLUCOSE; GPT; HBA1C; HGF; HSPA1B; IGFBP1; IL18; INSULIN; PLAT; VEGF |
| ADIPOQ; CCL2; CRP; ENG; FTH1; GLUCOSE; GPT; HBA1C; HGF; HSPA1B; IGFBP1; IL18; LEP; PLAT; TRIG |
| ADIPOQ; CCL2; CRP; ENG; FTH1; GLUCOSE; GPT; HBA1C; HGF; HSPA1B; IGFBP1; IL18; LEP; PLAT; VEGF |
| ADIPOQ; CCL2; CRP; ENG; FTH1; GLUCOSE; GPT; HBA1C; HGF; HSPA1B; IGFBP1; IL2RA; INSULIN; LEP; PLAT |
| ADIPOQ; CCL2; CRP; ENG; FTH1; GLUCOSE; GPT; HBA1C; HGF; HSPA1B; IGFBP1; IL2RA; LEP; PLAT; TRIG |
| ADIPOQ; CCL2; CRP; ENG; FTH1; GLUCOSE; GPT; HBA1C; HGF; HSPA1B; IGFBP1; IL2RA; LEP; PLAT; VEGF |
| ADIPOQ; CCL2; CRP; ENG; FTH1; GLUCOSE; GPT; HBA1C; HGF; HSPA1B; IGFBP1; INSULIN; LEP; PLAT; TRIG |
| ADIPOQ; CCL2; CRP; ENG; FTH1; GLUCOSE; GPT; HBA1C; HGF; HSPA1B; IGFBP1; INSULIN; LEP; PLAT; VEGF |
| ADIPOQ; CCL2; CRP; ENG; FTH1; GLUCOSE; GPT; HBA1C; HGF; HSPA1B; IGFBP1; LEP; PLAT; TRIG; VEGF |
| ADIPOQ; CCL2; CRP; ENG; FTH1; GLUCOSE; GPT; HBA1C; HGF; HSPA1B; IL18; IL2RA; INSULIN; LEP; PLAT |
| ADIPOQ; CCL2; CRP; ENG; FTH1; GLUCOSE; GPT; HBA1C; HGF; HSPA1B; IL18; IL2RA; INSULIN; PLAT; VEGF |
| ADIPOQ; CCL2; CRP; ENG; FTH1; GLUCOSE; GPT; HBA1C; HGF; HSPA1B; IL18; IL2RA; LEP; PLAT; TRIG |
| ADIPOQ; CCL2; CRP; ENG; FTH1; GLUCOSE; GPT; HBA1C; HGF; HSPA1B; IL18; IL2RA; LEP; PLAT; VEGF |
| ADIPOQ; CCL2; CRP; ENG; FTH1; GLUCOSE; GPT; HBA1C; HGF; HSPA1B; IL18; INSULIN; LEP; PLAT; TRIG |
| ADIPOQ; CCL2; CRP; ENG; FTH1; GLUCOSE; GPT; HBA1C; HGF; HSPA1B; IL18; INSULIN; LEP; PLAT; VEGF |
| ADIPOQ; CCL2; CRP; ENG; FTH1; GLUCOSE; GPT; HBA1C; HGF; HSPA1B; IL18; INSULIN; PLAT; TRIG; VEGF |
| ADIPOQ; CCL2; CRP; ENG; FTH1; GLUCOSE; GPT; HBA1C; HGF; HSPA1B; IL18; LEP; PLAT; TRIG; VEGF |
| ADIPOQ; CCL2; CRP; ENG; FTH1; GLUCOSE; GPT; HBA1C; HGF; HSPA1B; IL2RA; INSULIN; LEP; PLAT; TRIG |
| ADIPOQ; CCL2; CRP; ENG; FTH1; GLUCOSE; GPT; HBA1C; HGF; HSPA1B; IL2RA; INSULIN; LEP; PLAT; VEGF |
| ADIPOQ; CCL2; CRP; ENG; FTH1; GLUCOSE; GPT; HBA1C; HGF; HSPA1B; IL2RA; LEP; PLAT; TRIG; VEGF |
| ADIPOQ; CCL2; CRP; ENG; FTH1; GLUCOSE; GPT; HBA1C; HGF; HSPA1B; INSULIN; LEP; PLAT; TRIG; VEGF |
| ADIPOQ; CCL2; CRP; ENG; FTH1; GLUCOSE; GPT; HBA1C; HGF; IGFBP1; IL18; IL2RA; INSULIN; LEP; PLAT |
| ADIPOQ; CCL2; CRP; ENG; FTH1; GLUCOSE; GPT; HBA1C; HGF; IGFBP1; IL18; IL2RA; LEP; PLAT; VEGF |
| ADIPOQ; CCL2; CRP; ENG; FTH1; GLUCOSE; GPT; HBA1C; HGF; IGFBP1; IL18; INSULIN; LEP; PLAT; TRIG |

FIGURE 24 (continued)

| |
|---|
| ADIPOQ; CCL2; CRP; ENG; FTH1; GLUCOSE; GPT; HBA1C; HGF; IGFBP1; IL18; INSULIN; LEP; PLAT; VEGF |
| ADIPOQ; CCL2; CRP; ENG; FTH1; GLUCOSE; GPT; HBA1C; HGF; IGFBP1; IL18; LEP; PLAT; TRIG; VEGF |
| ADIPOQ; CCL2; CRP; ENG; FTH1; GLUCOSE; GPT; HBA1C; HGF; IGFBP1; IL2RA; INSULIN; LEP; PLAT; TRIG |
| ADIPOQ; CCL2; CRP; ENG; FTH1; GLUCOSE; GPT; HBA1C; HGF; IGFBP1; IL2RA; INSULIN; LEP; PLAT; VEGF |
| ADIPOQ; CCL2; CRP; ENG; FTH1; GLUCOSE; GPT; HBA1C; HGF; IGFBP1; INSULIN; LEP; PLAT; TRIG; VEGF |
| ADIPOQ; CCL2; CRP; ENG; FTH1; GLUCOSE; GPT; HBA1C; HGF; IL18; IL2RA; INSULIN; LEP; PLAT; TRIG |
| ADIPOQ; CCL2; CRP; ENG; FTH1; GLUCOSE; GPT; HBA1C; HGF; IL18; IL2RA; INSULIN; LEP; PLAT; VEGF |
| ADIPOQ; CCL2; CRP; ENG; FTH1; GLUCOSE; GPT; HBA1C; HGF; IL18; INSULIN; LEP; PLAT; TRIG; VEGF |
| ADIPOQ; CCL2; CRP; ENG; FTH1; GLUCOSE; GPT; HBA1C; HGF; IL2RA; INSULIN; LEP; PLAT; TRIG; VEGF |
| ADIPOQ; CCL2; CRP; ENG; FTH1; GLUCOSE; GPT; HBA1C; HSPA1B; IGFBP1; IL18; IL2RA; INSULIN; LEP; PLAT |
| ADIPOQ; CCL2; CRP; ENG; FTH1; GLUCOSE; GPT; HBA1C; HSPA1B; IGFBP1; IL18; IL2RA; INSULIN; PLAT; TRIG |
| ADIPOQ; CCL2; CRP; ENG; FTH1; GLUCOSE; GPT; HBA1C; HSPA1B; IGFBP1; IL18; IL2RA; INSULIN; PLAT; VEGF |
| ADIPOQ; CCL2; CRP; ENG; FTH1; GLUCOSE; GPT; HBA1C; HSPA1B; IGFBP1; IL18; IL2RA; LEP; PLAT; TRIG |
| ADIPOQ; CCL2; CRP; ENG; FTH1; GLUCOSE; GPT; HBA1C; HSPA1B; IGFBP1; IL18; IL2RA; LEP; PLAT; VEGF |
| ADIPOQ; CCL2; CRP; ENG; FTH1; GLUCOSE; GPT; HBA1C; HSPA1B; IGFBP1; IL18; INSULIN; LEP; PLAT; TRIG |
| ADIPOQ; CCL2; CRP; ENG; FTH1; GLUCOSE; GPT; HBA1C; HSPA1B; IGFBP1; IL18; INSULIN; LEP; PLAT; VEGF |
| ADIPOQ; CCL2; CRP; ENG; FTH1; GLUCOSE; GPT; HBA1C; HSPA1B; IGFBP1; IL18; INSULIN; PLAT; TRIG; VEGF |
| ADIPOQ; CCL2; CRP; ENG; FTH1; GLUCOSE; GPT; HBA1C; HSPA1B; IGFBP1; IL18; LEP; PLAT; TRIG; VEGF |
| ADIPOQ; CCL2; CRP; ENG; FTH1; GLUCOSE; GPT; HBA1C; HSPA1B; IGFBP1; IL2RA; INSULIN; LEP; PLAT; TRIG |
| ADIPOQ; CCL2; CRP; ENG; FTH1; GLUCOSE; GPT; HBA1C; HSPA1B; IGFBP1; IL2RA; INSULIN; LEP; PLAT; VEGF |
| ADIPOQ; CCL2; CRP; ENG; FTH1; GLUCOSE; GPT; HBA1C; HSPA1B; IGFBP1; IL2RA; LEP; PLAT; TRIG; VEGF |
| ADIPOQ; CCL2; CRP; ENG; FTH1; GLUCOSE; GPT; HBA1C; HSPA1B; IGFBP1; INSULIN; LEP; PLAT; TRIG; VEGF |
| ADIPOQ; CCL2; CRP; ENG; FTH1; GLUCOSE; GPT; HBA1C; HSPA1B; IL18; IL2RA; INSULIN; LEP; PLAT; TRIG |
| ADIPOQ; CCL2; CRP; ENG; FTH1; GLUCOSE; GPT; HBA1C; HSPA1B; IL18; IL2RA; INSULIN; LEP; PLAT; VEGF |
| ADIPOQ; CCL2; CRP; ENG; FTH1; GLUCOSE; GPT; HBA1C; HSPA1B; IL18; IL2RA; INSULIN; PLAT; TRIG; VEGF |
| ADIPOQ; CCL2; CRP; ENG; FTH1; GLUCOSE; GPT; HBA1C; HSPA1B; IL18; IL2RA; LEP; PLAT; TRIG; VEGF |

FIGURE 24 (continued)

| |
|---|
| ADIPOQ; CCL2; CRP; ENG; FTH1; GLUCOSE; GPT; HBA1C; HSPA1B; IL18; INSULIN; LEP; PLAT; TRIG; VEGF |
| ADIPOQ; CCL2; CRP; ENG; FTH1; GLUCOSE; GPT; HBA1C; HSPA1B; IL2RA; INSULIN; LEP; PLAT; TRIG; VEGF |
| ADIPOQ; CCL2; CRP; ENG; FTH1; GLUCOSE; GPT; HBA1C; IGFBP1; IL18; IL2RA; INSULIN; LEP; PLAT; TRIG |
| ADIPOQ; CCL2; CRP; ENG; FTH1; GLUCOSE; GPT; HBA1C; IGFBP1; IL18; IL2RA; INSULIN; LEP; PLAT; VEGF |
| ADIPOQ; CCL2; CRP; ENG; FTH1; GLUCOSE; GPT; HBA1C; IGFBP1; IL18; IL2RA; LEP; PLAT; TRIG; VEGF |
| ADIPOQ; CCL2; CRP; ENG; FTH1; GLUCOSE; GPT; HBA1C; IGFBP1; IL18; INSULIN; LEP; PLAT; TRIG; VEGF |
| ADIPOQ; CCL2; CRP; ENG; FTH1; GLUCOSE; GPT; HBA1C; IGFBP1; IL2RA; INSULIN; LEP; PLAT; TRIG; VEGF |
| ADIPOQ; CCL2; CRP; ENG; FTH1; GLUCOSE; GPT; HBA1C; IL18; IL2RA; INSULIN; LEP; PLAT; TRIG; VEGF |
| ADIPOQ; CCL2; CRP; ENG; FTH1; GLUCOSE; HBA1C; HGF; HSPA1B; IGFBP1; IL18; IL2RA; INSULIN; LEP; PLAT |
| ADIPOQ; CCL2; CRP; ENG; FTH1; GLUCOSE; HBA1C; HGF; HSPA1B; IGFBP1; IL18; IL2RA; LEP; PLAT; TRIG |
| ADIPOQ; CCL2; CRP; ENG; FTH1; GLUCOSE; HBA1C; HGF; HSPA1B; IGFBP1; IL18; IL2RA; LEP; PLAT; VEGF |
| ADIPOQ; CCL2; CRP; ENG; FTH1; GLUCOSE; HBA1C; HGF; HSPA1B; IGFBP1; IL18; INSULIN; LEP; PLAT; TRIG |
| ADIPOQ; CCL2; CRP; ENG; FTH1; GLUCOSE; HBA1C; HGF; HSPA1B; IGFBP1; IL18; INSULIN; LEP; PLAT; VEGF |
| ADIPOQ; CCL2; CRP; ENG; FTH1; GLUCOSE; HBA1C; HGF; HSPA1B; IGFBP1; IL18; LEP; PLAT; TRIG; VEGF |
| ADIPOQ; CCL2; CRP; ENG; FTH1; GLUCOSE; HBA1C; HGF; HSPA1B; IGFBP1; IL2RA; INSULIN; LEP; PLAT; TRIG |
| ADIPOQ; CCL2; CRP; ENG; FTH1; GLUCOSE; HBA1C; HGF; HSPA1B; IGFBP1; IL2RA; INSULIN; LEP; PLAT; VEGF |
| ADIPOQ; CCL2; CRP; ENG; FTH1; GLUCOSE; HBA1C; HGF; HSPA1B; IGFBP1; INSULIN; LEP; PLAT; TRIG; VEGF |
| ADIPOQ; CCL2; CRP; ENG; FTH1; GLUCOSE; HBA1C; HGF; HSPA1B; IL18; IL2RA; INSULIN; LEP; PLAT; TRIG |
| ADIPOQ; CCL2; CRP; ENG; FTH1; GLUCOSE; HBA1C; HGF; HSPA1B; IL18; IL2RA; INSULIN; LEP; PLAT; VEGF |
| ADIPOQ; CCL2; CRP; ENG; FTH1; GLUCOSE; HBA1C; HGF; HSPA1B; IL18; IL2RA; LEP; PLAT; TRIG; VEGF |
| ADIPOQ; CCL2; CRP; ENG; FTH1; GLUCOSE; HBA1C; HGF; HSPA1B; IL18; INSULIN; LEP; PLAT; TRIG; VEGF |
| ADIPOQ; CCL2; CRP; ENG; FTH1; GLUCOSE; HBA1C; HGF; HSPA1B; IL2RA; INSULIN; LEP; PLAT; TRIG; VEGF |
| ADIPOQ; CCL2; CRP; ENG; FTH1; GLUCOSE; HBA1C; HGF; IGFBP1; IL18; INSULIN; LEP; PLAT; TRIG; VEGF |
| ADIPOQ; CCL2; CRP; ENG; FTH1; GLUCOSE; HBA1C; HGF; IL18; IL2RA; INSULIN; LEP; PLAT; TRIG; VEGF |
| ADIPOQ; CCL2; CRP; ENG; FTH1; GLUCOSE; HBA1C; HSPA1B; IGFBP1; IL18; IL2RA; INSULIN; LEP; PLAT; TRIG |
| ADIPOQ; CCL2; CRP; ENG; FTH1; GLUCOSE; HBA1C; HSPA1B; IGFBP1; IL18; IL2RA; INSULIN; LEP; PLAT; VEGF |
| ADIPOQ; CCL2; CRP; ENG; FTH1; GLUCOSE; HBA1C; HSPA1B; IGFBP1; IL18; IL2RA; LEP; PLAT; TRIG; VEGF |

FIGURE 24 (continued)

| |
|---|
| ADIPOQ; CCL2; CRP; ENG; FTH1; GLUCOSE; HBA1C; HSPA1B; IGFBP1; IL18; INSULIN; LEP; PLAT; TRIG; VEGF |
| ADIPOQ; CCL2; CRP; ENG; FTH1; GLUCOSE; HBA1C; HSPA1B; IGFBP1; IL2RA; INSULIN; LEP; PLAT; TRIG; VEGF |
| ADIPOQ; CCL2; CRP; ENG; FTH1; GLUCOSE; HBA1C; HSPA1B; IL18; IL2RA; INSULIN; LEP; PLAT; TRIG; VEGF |
| ADIPOQ; CRP; ENG; FTH1; GLUCOSE; GPT; HBA1C; HGF; HSPA1B; IGFBP1; IL18; IL2RA; INSULIN; LEP; PLAT |
| ADIPOQ; CRP; ENG; FTH1; GLUCOSE; GPT; HBA1C; HGF; HSPA1B; IGFBP1; IL18; INSULIN; LEP; PLAT; TRIG |
| ADIPOQ; CRP; ENG; FTH1; GLUCOSE; GPT; HBA1C; HGF; HSPA1B; IGFBP1; IL18; INSULIN; LEP; PLAT; VEGF |
| ADIPOQ; CRP; ENG; FTH1; GLUCOSE; GPT; HBA1C; HGF; HSPA1B; IL18; IL2RA; INSULIN; LEP; PLAT; TRIG |
| ADIPOQ; CRP; ENG; FTH1; GLUCOSE; GPT; HBA1C; HGF; HSPA1B; IL18; IL2RA; INSULIN; LEP; PLAT; VEGF |
| ADIPOQ; CRP; ENG; FTH1; GLUCOSE; GPT; HBA1C; HGF; HSPA1B; IL18; INSULIN; LEP; PLAT; TRIG; VEGF |
| ADIPOQ; CRP; ENG; FTH1; GLUCOSE; GPT; HBA1C; HSPA1B; IGFBP1; IL18; IL2RA; INSULIN; LEP; PLAT; TRIG |
| ADIPOQ; CRP; ENG; FTH1; GLUCOSE; GPT; HBA1C; HSPA1B; IGFBP1; IL18; IL2RA; INSULIN; LEP; PLAT; VEGF |
| ADIPOQ; CRP; ENG; FTH1; GLUCOSE; GPT; HBA1C; HSPA1B; IGFBP1; IL18; IL2RA; LEP; PLAT; TRIG; VEGF |
| ADIPOQ; CRP; ENG; FTH1; GLUCOSE; GPT; HBA1C; HSPA1B; IGFBP1; IL18; INSULIN; LEP; PLAT; TRIG; VEGF |
| ADIPOQ; CRP; ENG; FTH1; GLUCOSE; GPT; HBA1C; HSPA1B; IL18; IL2RA; INSULIN; LEP; PLAT; TRIG; VEGF |
| ADIPOQ; CRP; ENG; FTH1; GLUCOSE; HBA1C; HGF; HSPA1B; IGFBP1; IL18; IL2RA; INSULIN; LEP; PLAT; TRIG |
| ADIPOQ; CRP; ENG; FTH1; GLUCOSE; HBA1C; HGF; HSPA1B; IGFBP1; IL18; INSULIN; LEP; PLAT; TRIG; VEGF |
| ADIPOQ; CRP; ENG; FTH1; GLUCOSE; HBA1C; HGF; HSPA1B; IL18; IL2RA; INSULIN; LEP; PLAT; TRIG; VEGF |
| ADIPOQ; CRP; ENG; FTH1; GLUCOSE; HBA1C; HSPA1B; IGFBP1; IL18; IL2RA; INSULIN; LEP; PLAT; TRIG; VEGF |
| CCL2; CRP; ENG; FTH1; GLUCOSE; GPT; HBA1C; HGF; HSPA1B; IL18; IL2RA; INSULIN; LEP; PLAT; VEGF |
| CCL2; CRP; ENG; FTH1; GLUCOSE; GPT; HBA1C; HSPA1B; IGFBP1; IL18; IL2RA; INSULIN; LEP; PLAT; VEGF |

FIGURE 25

| |
|---|
| ADIPOQ; CCL2; CRP; ENG; FTH1; GLUCOSE; GPT; HBA1C; HGF; HSPA1B; IGFBP1; IL18; IL2RA; INSULIN; LEP; PLAT |
| ADIPOQ; CCL2; CRP; ENG; FTH1; GLUCOSE; GPT; HBA1C; HGF; HSPA1B; IGFBP1; IL18; IL2RA; INSULIN; LEP; TRIG |
| ADIPOQ; CCL2; CRP; ENG; FTH1; GLUCOSE; GPT; HBA1C; HGF; HSPA1B; IGFBP1; IL18; IL2RA; INSULIN; LEP; VEGF |
| ADIPOQ; CCL2; CRP; ENG; FTH1; GLUCOSE; GPT; HBA1C; HGF; HSPA1B; IGFBP1; IL18; IL2RA; INSULIN; PLAT; TRIG |
| ADIPOQ; CCL2; CRP; ENG; FTH1; GLUCOSE; GPT; HBA1C; HGF; HSPA1B; IGFBP1; IL18; IL2RA; INSULIN; PLAT; VEGF |
| ADIPOQ; CCL2; CRP; ENG; FTH1; GLUCOSE; GPT; HBA1C; HGF; HSPA1B; IGFBP1; IL18; IL2RA; LEP; PLAT; TRIG |
| ADIPOQ; CCL2; CRP; ENG; FTH1; GLUCOSE; GPT; HBA1C; HGF; HSPA1B; IGFBP1; IL18; IL2RA; LEP; PLAT; VEGF |
| ADIPOQ; CCL2; CRP; ENG; FTH1; GLUCOSE; GPT; HBA1C; HGF; HSPA1B; IGFBP1; IL18; IL2RA; LEP; TRIG; VEGF |
| ADIPOQ; CCL2; CRP; ENG; FTH1; GLUCOSE; GPT; HBA1C; HGF; HSPA1B; IGFBP1; IL18; IL2RA; PLAT; TRIG; VEGF |
| ADIPOQ; CCL2; CRP; ENG; FTH1; GLUCOSE; GPT; HBA1C; HGF; HSPA1B; IGFBP1; IL18; INSULIN; LEP; PLAT; TRIG |
| ADIPOQ; CCL2; CRP; ENG; FTH1; GLUCOSE; GPT; HBA1C; HGF; HSPA1B; IGFBP1; IL18; INSULIN; LEP; PLAT; VEGF |
| ADIPOQ; CCL2; CRP; ENG; FTH1; GLUCOSE; GPT; HBA1C; HGF; HSPA1B; IGFBP1; IL18; INSULIN; LEP; TRIG; VEGF |
| ADIPOQ; CCL2; CRP; ENG; FTH1; GLUCOSE; GPT; HBA1C; HGF; HSPA1B; IGFBP1; IL18; INSULIN; PLAT; TRIG; VEGF |
| ADIPOQ; CCL2; CRP; ENG; FTH1; GLUCOSE; GPT; HBA1C; HGF; HSPA1B; IGFBP1; IL18; LEP; PLAT; TRIG; VEGF |
| ADIPOQ; CCL2; CRP; ENG; FTH1; GLUCOSE; GPT; HBA1C; HGF; HSPA1B; IGFBP1; IL2RA; INSULIN; LEP; PLAT; TRIG |
| ADIPOQ; CCL2; CRP; ENG; FTH1; GLUCOSE; GPT; HBA1C; HGF; HSPA1B; IGFBP1; IL2RA; INSULIN; LEP; PLAT; VEGF |
| ADIPOQ; CCL2; CRP; ENG; FTH1; GLUCOSE; GPT; HBA1C; HGF; HSPA1B; IGFBP1; IL2RA; INSULIN; LEP; TRIG; VEGF |
| ADIPOQ; CCL2; CRP; ENG; FTH1; GLUCOSE; GPT; HBA1C; HGF; HSPA1B; IGFBP1; IL2RA; INSULIN; PLAT; TRIG; VEGF |
| ADIPOQ; CCL2; CRP; ENG; FTH1; GLUCOSE; GPT; HBA1C; HGF; HSPA1B; IGFBP1; IL2RA; LEP; PLAT; TRIG; VEGF |
| ADIPOQ; CCL2; CRP; ENG; FTH1; GLUCOSE; GPT; HBA1C; HGF; HSPA1B; IGFBP1; INSULIN; LEP; PLAT; TRIG; VEGF |
| ADIPOQ; CCL2; CRP; ENG; FTH1; GLUCOSE; GPT; HBA1C; HGF; HSPA1B; IL18; IL2RA; INSULIN; LEP; PLAT; TRIG |
| ADIPOQ; CCL2; CRP; ENG; FTH1; GLUCOSE; GPT; HBA1C; HGF; HSPA1B; IL18; IL2RA; INSULIN; LEP; PLAT; VEGF |
| ADIPOQ; CCL2; CRP; ENG; FTH1; GLUCOSE; GPT; HBA1C; HGF; HSPA1B; IL18; IL2RA; INSULIN; LEP; TRIG; VEGF |
| ADIPOQ; CCL2; CRP; ENG; FTH1; GLUCOSE; GPT; HBA1C; HGF; HSPA1B; IL18; IL2RA; INSULIN; PLAT; TRIG; VEGF |
| ADIPOQ; CCL2; CRP; ENG; FTH1; GLUCOSE; GPT; HBA1C; HGF; HSPA1B; IL18; IL2RA; LEP; PLAT; TRIG; VEGF |
| ADIPOQ; CCL2; CRP; ENG; FTH1; GLUCOSE; GPT; HBA1C; HGF; HSPA1B; IL18; INSULIN; LEP; PLAT; TRIG; VEGF |
| ADIPOQ; CCL2; CRP; ENG; FTH1; GLUCOSE; GPT; HBA1C; HGF; HSPA1B; IL2RA; INSULIN; LEP; PLAT; TRIG; VEGF |

FIGURE 25 (continued)

| |
|---|
| ADIPOQ; CCL2; CRP; ENG; FTH1; GLUCOSE; GPT; HBA1C; HGF; IGFBP1; IL18; IL2RA; INSULIN; LEP; PLAT; TRIG |
| ADIPOQ; CCL2; CRP; ENG; FTH1; GLUCOSE; GPT; HBA1C; HGF; IGFBP1; IL18; IL2RA; INSULIN; LEP; PLAT; VEGF |
| ADIPOQ; CCL2; CRP; ENG; FTH1; GLUCOSE; GPT; HBA1C; HGF; IGFBP1; IL18; IL2RA; INSULIN; PLAT; TRIG; VEGF |
| ADIPOQ; CCL2; CRP; ENG; FTH1; GLUCOSE; GPT; HBA1C; HGF; IGFBP1; IL18; IL2RA; LEP; PLAT; TRIG; VEGF |
| ADIPOQ; CCL2; CRP; ENG; FTH1; GLUCOSE; GPT; HBA1C; HGF; IGFBP1; IL18; INSULIN; LEP; PLAT; TRIG; VEGF |
| ADIPOQ; CCL2; CRP; ENG; FTH1; GLUCOSE; GPT; HBA1C; HGF; IGFBP1; IL2RA; INSULIN; LEP; PLAT; TRIG; VEGF |
| ADIPOQ; CCL2; CRP; ENG; FTH1; GLUCOSE; GPT; HBA1C; HGF; IL18; IL2RA; INSULIN; LEP; PLAT; TRIG; VEGF |
| ADIPOQ; CCL2; CRP; ENG; FTH1; GLUCOSE; GPT; HBA1C; HSPA1B; IGFBP1; IL18; IL2RA; INSULIN; LEP; PLAT; TRIG |
| ADIPOQ; CCL2; CRP; ENG; FTH1; GLUCOSE; GPT; HBA1C; HSPA1B; IGFBP1; IL18; IL2RA; INSULIN; LEP; PLAT; VEGF |
| ADIPOQ; CCL2; CRP; ENG; FTH1; GLUCOSE; GPT; HBA1C; HSPA1B; IGFBP1; IL18; IL2RA; INSULIN; LEP; TRIG; VEGF |
| ADIPOQ; CCL2; CRP; ENG; FTH1; GLUCOSE; GPT; HBA1C; HSPA1B; IGFBP1; IL18; IL2RA; INSULIN; PLAT; TRIG; VEGF |
| ADIPOQ; CCL2; CRP; ENG; FTH1; GLUCOSE; GPT; HBA1C; HSPA1B; IGFBP1; IL18; IL2RA; LEP; PLAT; TRIG; VEGF |
| ADIPOQ; CCL2; CRP; ENG; FTH1; GLUCOSE; GPT; HBA1C; HSPA1B; IGFBP1; IL18; INSULIN; LEP; PLAT; TRIG; VEGF |
| ADIPOQ; CCL2; CRP; ENG; FTH1; GLUCOSE; GPT; HBA1C; HSPA1B; IGFBP1; IL2RA; INSULIN; LEP; PLAT; TRIG; VEGF |
| ADIPOQ; CCL2; CRP; ENG; FTH1; GLUCOSE; GPT; HBA1C; HSPA1B; IL18; IL2RA; INSULIN; LEP; PLAT; TRIG; VEGF |
| ADIPOQ; CCL2; CRP; ENG; FTH1; GLUCOSE; GPT; HBA1C; IGFBP1; IL18; IL2RA; INSULIN; LEP; PLAT; TRIG; VEGF |
| ADIPOQ; CCL2; CRP; ENG; FTH1; GLUCOSE; GPT; HGF; HSPA1B; IGFBP1; IL18; IL2RA; INSULIN; LEP; PLAT; TRIG |
| ADIPOQ; CCL2; CRP; ENG; FTH1; GLUCOSE; GPT; HGF; HSPA1B; IGFBP1; IL18; IL2RA; INSULIN; LEP; PLAT; VEGF |
| ADIPOQ; CCL2; CRP; ENG; FTH1; GLUCOSE; GPT; HGF; HSPA1B; IGFBP1; IL18; IL2RA; LEP; PLAT; TRIG; VEGF |
| ADIPOQ; CCL2; CRP; ENG; FTH1; GLUCOSE; GPT; HGF; HSPA1B; IGFBP1; IL18; INSULIN; LEP; PLAT; TRIG; VEGF |
| ADIPOQ; CCL2; CRP; ENG; FTH1; GLUCOSE; GPT; HGF; HSPA1B; IGFBP1; IL2RA; INSULIN; LEP; PLAT; TRIG; VEGF |
| ADIPOQ; CCL2; CRP; ENG; FTH1; GLUCOSE; GPT; HGF; HSPA1B; IL18; IL2RA; INSULIN; LEP; PLAT; TRIG; VEGF |
| ADIPOQ; CCL2; CRP; ENG; FTH1; GLUCOSE; GPT; HSPA1B; IGFBP1; IL18; IL2RA; INSULIN; LEP; PLAT; TRIG; VEGF |
| ADIPOQ; CCL2; CRP; ENG; FTH1; GLUCOSE; HBA1C; HGF; HSPA1B; IGFBP1; IL18; IL2RA; INSULIN; LEP; PLAT; TRIG |
| ADIPOQ; CCL2; CRP; ENG; FTH1; GLUCOSE; HBA1C; HGF; HSPA1B; IGFBP1; IL18; IL2RA; INSULIN; LEP; PLAT; VEGF |
| ADIPOQ; CCL2; CRP; ENG; FTH1; GLUCOSE; HBA1C; HGF; HSPA1B; IGFBP1; IL18; IL2RA; INSULIN; LEP; TRIG; VEGF |

FIGURE 25 (continued)

| |
|---|
| ADIPOQ; CCL2; CRP; ENG; FTH1; GLUCOSE; HBA1C; HGF; HSPA1B; IGFBP1; IL18; IL2RA; INSULIN; PLAT; TRIG; VEGF |
| ADIPOQ; CCL2; CRP; ENG; FTH1; GLUCOSE; HBA1C; HGF; HSPA1B; IGFBP1; IL18; IL2RA; LEP; PLAT; TRIG; VEGF |
| ADIPOQ; CCL2; CRP; ENG; FTH1; GLUCOSE; HBA1C; HGF; HSPA1B; IGFBP1; IL18; INSULIN; LEP; PLAT; TRIG; VEGF |
| ADIPOQ; CCL2; CRP; ENG; FTH1; GLUCOSE; HBA1C; HGF; HSPA1B; IGFBP1; IL2RA; INSULIN; LEP; PLAT; TRIG; VEGF |
| ADIPOQ; CCL2; CRP; ENG; FTH1; GLUCOSE; HBA1C; HGF; HSPA1B; IL18; IL2RA; INSULIN; LEP; PLAT; TRIG; VEGF |
| ADIPOQ; CCL2; CRP; ENG; FTH1; GLUCOSE; HBA1C; HGF; IGFBP1; IL18; IL2RA; INSULIN; LEP; PLAT; TRIG; VEGF |
| ADIPOQ; CCL2; CRP; ENG; FTH1; GLUCOSE; HBA1C; HSPA1B; IGFBP1; IL18; IL2RA; INSULIN; LEP; PLAT; TRIG; VEGF |
| ADIPOQ; CCL2; CRP; ENG; FTH1; GLUCOSE; HGF; HSPA1B; IGFBP1; IL18; IL2RA; INSULIN; LEP; PLAT; TRIG; VEGF |
| ADIPOQ; CCL2; CRP; FTH1; GLUCOSE; GPT; HBA1C; HGF; HSPA1B; IGFBP1; IL18; IL2RA; INSULIN; LEP; PLAT; TRIG |
| ADIPOQ; CCL2; CRP; FTH1; GLUCOSE; GPT; HBA1C; HGF; HSPA1B; IGFBP1; IL18; IL2RA; INSULIN; LEP; PLAT; VEGF |
| ADIPOQ; CCL2; CRP; FTH1; GLUCOSE; GPT; HBA1C; HGF; HSPA1B; IGFBP1; IL18; IL2RA; LEP; PLAT; TRIG; VEGF |
| ADIPOQ; CCL2; CRP; FTH1; GLUCOSE; GPT; HBA1C; HGF; HSPA1B; IGFBP1; IL18; INSULIN; LEP; PLAT; TRIG; VEGF |
| ADIPOQ; CCL2; CRP; FTH1; GLUCOSE; GPT; HBA1C; HGF; HSPA1B; IGFBP1; IL2RA; INSULIN; LEP; PLAT; TRIG; VEGF |
| ADIPOQ; CCL2; CRP; FTH1; GLUCOSE; GPT; HBA1C; HGF; HSPA1B; IL18; IL2RA; INSULIN; LEP; PLAT; TRIG; VEGF |
| ADIPOQ; CCL2; CRP; FTH1; GLUCOSE; GPT; HBA1C; HSPA1B; IGFBP1; IL18; IL2RA; INSULIN; LEP; PLAT; TRIG; VEGF |
| ADIPOQ; CCL2; CRP; FTH1; GLUCOSE; HBA1C; HGF; HSPA1B; IGFBP1; IL18; IL2RA; INSULIN; LEP; PLAT; TRIG; VEGF |
| ADIPOQ; CCL2; ENG; FTH1; GLUCOSE; GPT; HBA1C; HGF; HSPA1B; IGFBP1; IL18; IL2RA; INSULIN; LEP; PLAT; TRIG |
| ADIPOQ; CCL2; ENG; FTH1; GLUCOSE; GPT; HBA1C; HGF; HSPA1B; IGFBP1; IL18; IL2RA; INSULIN; LEP; PLAT; VEGF |
| ADIPOQ; CCL2; ENG; FTH1; GLUCOSE; GPT; HBA1C; HGF; HSPA1B; IGFBP1; IL18; IL2RA; LEP; PLAT; TRIG; VEGF |
| ADIPOQ; CCL2; ENG; FTH1; GLUCOSE; GPT; HBA1C; HGF; HSPA1B; IGFBP1; IL18; INSULIN; LEP; PLAT; TRIG; VEGF |
| ADIPOQ; CCL2; ENG; FTH1; GLUCOSE; GPT; HBA1C; HGF; HSPA1B; IGFBP1; IL2RA; INSULIN; LEP; PLAT; TRIG; VEGF |
| ADIPOQ; CCL2; ENG; FTH1; GLUCOSE; GPT; HBA1C; HGF; HSPA1B; IL18; IL2RA; INSULIN; LEP; PLAT; TRIG; VEGF |
| ADIPOQ; CCL2; ENG; FTH1; GLUCOSE; GPT; HBA1C; HSPA1B; IGFBP1; IL18; IL2RA; INSULIN; LEP; PLAT; TRIG; VEGF |
| ADIPOQ; CCL2; ENG; FTH1; GLUCOSE; HBA1C; HGF; HSPA1B; IGFBP1; IL18; IL2RA; INSULIN; LEP; PLAT; TRIG; VEGF |
| ADIPOQ; CRP; ENG; FTH1; GLUCOSE; GPT; HBA1C; HGF; HSPA1B; IGFBP1; IL18; IL2RA; INSULIN; LEP; PLAT; TRIG |
| ADIPOQ; CRP; ENG; FTH1; GLUCOSE; GPT; HBA1C; HGF; HSPA1B; IGFBP1; IL18; IL2RA; INSULIN; LEP; PLAT; VEGF |
| ADIPOQ; CRP; ENG; FTH1; GLUCOSE; GPT; HBA1C; HGF; HSPA1B; IGFBP1; IL18; IL2RA; INSULIN; PLAT; TRIG; VEGF |

FIGURE 25 (continued)

| |
|---|
| ADIPOQ; CRP; ENG; FTH1; GLUCOSE; GPT; HBA1C; HGF; HSPA1B; IGFBP1; IL18; IL2RA; LEP; PLAT; TRIG; VEGF |
| ADIPOQ; CRP; ENG; FTH1; GLUCOSE; GPT; HBA1C; HGF; HSPA1B; IGFBP1; IL18; INSULIN; LEP; PLAT; TRIG; VEGF |
| ADIPOQ; CRP; ENG; FTH1; GLUCOSE; GPT; HBA1C; HGF; HSPA1B; IGFBP1; IL2RA; INSULIN; LEP; PLAT; TRIG; VEGF |
| ADIPOQ; CRP; ENG; FTH1; GLUCOSE; GPT; HBA1C; HGF; HSPA1B; IL18; IL2RA; INSULIN; LEP; PLAT; TRIG; VEGF |
| ADIPOQ; CRP; ENG; FTH1; GLUCOSE; GPT; HBA1C; HGF; IGFBP1; IL18; IL2RA; INSULIN; LEP; PLAT; TRIG; VEGF |
| ADIPOQ; CRP; ENG; FTH1; GLUCOSE; GPT; HBA1C; HSPA1B; IGFBP1; IL18; IL2RA; INSULIN; LEP; PLAT; TRIG; VEGF |
| ADIPOQ; CRP; ENG; FTH1; GLUCOSE; HBA1C; HGF; HSPA1B; IGFBP1; IL18; IL2RA; INSULIN; LEP; PLAT; TRIG; VEGF |
| ADIPOQ; ENG; FTH1; GLUCOSE; GPT; HBA1C; HGF; HSPA1B; IGFBP1; IL18; IL2RA; INSULIN; LEP; PLAT; TRIG; VEGF |
| CCL2; CRP; ENG; FTH1; GLUCOSE; GPT; HBA1C; HGF; HSPA1B; IGFBP1; IL18; IL2RA; INSULIN; LEP; PLAT; TRIG |
| CCL2; CRP; ENG; FTH1; GLUCOSE; GPT; HBA1C; HGF; HSPA1B; IGFBP1; IL18; IL2RA; INSULIN; LEP; PLAT; VEGF |
| CCL2; CRP; ENG; FTH1; GLUCOSE; GPT; HBA1C; HGF; HSPA1B; IGFBP1; IL18; IL2RA; INSULIN; PLAT; TRIG; VEGF |
| CCL2; CRP; ENG; FTH1; GLUCOSE; GPT; HBA1C; HGF; HSPA1B; IGFBP1; IL18; IL2RA; LEP; PLAT; TRIG; VEGF |
| CCL2; CRP; ENG; FTH1; GLUCOSE; GPT; HBA1C; HGF; HSPA1B; IGFBP1; IL18; INSULIN; LEP; PLAT; TRIG; VEGF |
| CCL2; CRP; ENG; FTH1; GLUCOSE; GPT; HBA1C; HGF; HSPA1B; IGFBP1; IL2RA; INSULIN; LEP; PLAT; TRIG; VEGF |
| CCL2; CRP; ENG; FTH1; GLUCOSE; GPT; HBA1C; HGF; HSPA1B; IL18; IL2RA; INSULIN; LEP; PLAT; TRIG; VEGF |
| CCL2; CRP; ENG; FTH1; GLUCOSE; GPT; HBA1C; HGF; IGFBP1; IL18; IL2RA; INSULIN; LEP; PLAT; TRIG; VEGF |
| CCL2; CRP; ENG; FTH1; GLUCOSE; GPT; HBA1C; HSPA1B; IGFBP1; IL18; IL2RA; INSULIN; LEP; PLAT; TRIG; VEGF |
| CCL2; CRP; ENG; FTH1; GLUCOSE; HBA1C; HGF; HSPA1B; IGFBP1; IL18; IL2RA; INSULIN; LEP; PLAT; TRIG; VEGF |
| CCL2; ENG; FTH1; GLUCOSE; GPT; HBA1C; HGF; HSPA1B; IGFBP1; IL18; IL2RA; INSULIN; LEP; PLAT; TRIG; VEGF |
| CRP; ENG; FTH1; GLUCOSE; GPT; HBA1C; HGF; HSPA1B; IGFBP1; IL18; IL2RA; INSULIN; LEP; PLAT; TRIG; VEGF |

FIGURE 26

| |
|---|
| ADIPOQ; CCL2; CRP; ENG; FTH1; GLUCOSE; GPT; HBA1C; HGF; HSPA1B; IGFBP1; IL18; IL2RA; INSULIN; LEP; PLAT; TRIG |
| ADIPOQ; CCL2; CRP; ENG; FTH1; GLUCOSE; GPT; HBA1C; HGF; HSPA1B; IGFBP1; IL18; IL2RA; INSULIN; LEP; PLAT; VEGF |
| ADIPOQ; CCL2; CRP; ENG; FTH1; GLUCOSE; GPT; HBA1C; HGF; HSPA1B; IGFBP1; IL18; IL2RA; INSULIN; LEP; TRIG; VEGF |
| ADIPOQ; CCL2; CRP; ENG; FTH1; GLUCOSE; GPT; HBA1C; HGF; HSPA1B; IGFBP1; IL18; IL2RA; INSULIN; PLAT; TRIG; VEGF |
| ADIPOQ; CCL2; CRP; ENG; FTH1; GLUCOSE; GPT; HBA1C; HGF; HSPA1B; IGFBP1; IL18; IL2RA; LEP; PLAT; TRIG; VEGF |
| ADIPOQ; CCL2; CRP; ENG; FTH1; GLUCOSE; GPT; HBA1C; HGF; HSPA1B; IGFBP1; IL18; INSULIN; LEP; PLAT; TRIG; VEGF |
| ADIPOQ; CCL2; CRP; ENG; FTH1; GLUCOSE; GPT; HBA1C; HGF; HSPA1B; IGFBP1; IL2RA; INSULIN; LEP; PLAT; TRIG; VEGF |
| ADIPOQ; CCL2; CRP; ENG; FTH1; GLUCOSE; GPT; HBA1C; HGF; HSPA1B; IL18; IL2RA; INSULIN; LEP; PLAT; TRIG; VEGF |
| ADIPOQ; CCL2; CRP; ENG; FTH1; GLUCOSE; GPT; HBA1C; HGF; IGFBP1; IL18; IL2RA; INSULIN; LEP; PLAT; TRIG; VEGF |
| ADIPOQ; CCL2; CRP; ENG; FTH1; GLUCOSE; GPT; HBA1C; HSPA1B; IGFBP1; IL18; IL2RA; INSULIN; LEP; PLAT; TRIG; VEGF |
| ADIPOQ; CCL2; CRP; ENG; FTH1; GLUCOSE; GPT; HGF; HSPA1B; IGFBP1; IL18; IL2RA; INSULIN; LEP; PLAT; TRIG; VEGF |
| ADIPOQ; CCL2; CRP; ENG; FTH1; GLUCOSE; HBA1C; HGF; HSPA1B; IGFBP1; IL18; IL2RA; INSULIN; LEP; PLAT; TRIG; VEGF |
| ADIPOQ; CCL2; CRP; ENG; FTH1; GPT; HBA1C; HGF; HSPA1B; IGFBP1; IL18; IL2RA; INSULIN; LEP; PLAT; TRIG; VEGF |
| ADIPOQ; CCL2; CRP; ENG; GLUCOSE; GPT; HBA1C; HGF; HSPA1B; IGFBP1; IL18; IL2RA; INSULIN; LEP; PLAT; TRIG; VEGF |
| ADIPOQ; CCL2; CRP; FTH1; GLUCOSE; GPT; HBA1C; HGF; HSPA1B; IGFBP1; IL18; IL2RA; INSULIN; LEP; PLAT; TRIG; VEGF |
| ADIPOQ; CCL2; ENG; FTH1; GLUCOSE; GPT; HBA1C; HGF; HSPA1B; IGFBP1; IL18; IL2RA; INSULIN; LEP; PLAT; TRIG; VEGF |
| ADIPOQ; CRP; ENG; FTH1; GLUCOSE; GPT; HBA1C; HGF; HSPA1B; IGFBP1; IL18; IL2RA; INSULIN; LEP; PLAT; TRIG; VEGF |
| CCL2; CRP; ENG; FTH1; GLUCOSE; GPT; HBA1C; HGF; HSPA1B; IGFBP1; IL18; IL2RA; INSULIN; LEP; PLAT; TRIG; VEGF |

| | | | | |
|---|---|---|---|---|
| GLUCOSE | ADIPOQ | CRP | HBA1C | CE18:2n6 |
| GLUCOSE | ADIPOQ | CRP | IL2RA | CE18:2n6 |
| GLUCOSE | ADIPOQ | INSULIN | IL2RA | CE18:2n6 |
| GLUCOSE | FTH | INSULIN | IL2RA | CE18:2n6 |
| GLUCOSE | HBA1C | FTH | INSULIN | CE18:2n6 |
| GLUCOSE | CRP | HBA1C | FTH | CE18:2n6 |
| GLUCOSE | CRP | INSULIN | IL2RA | CE18:2n6 |
| GLUCOSE | ADIPOQ | HBA1C | IL2RA | CE18:2n6 |
| GLUCOSE | CRP | FTH | INSULIN | CE18:2n6 |
| GLUCOSE | CRP | HBA1C | INSULIN | CE18:2n6 |
| GLUCOSE | HBA1C | FTH | IL2RA | CE18:2n6 |
| GLUCOSE | ADIPOQ | FTH | INSULIN | CE18:2n6 |
| GLUCOSE | HBA1C | INSULIN | IL2RA | CE18:2n6 |
| GLUCOSE | ADIPOQ | FTH | IL2RA | CE18:2n6 |
| GLUCOSE | ADIPOQ | CRP | INSULIN | CE18:2n6 |
| GLUCOSE | CRP | HBA1C | IL2RA | CE18:2n6 |
| GLUCOSE | ADIPOQ | HBA1C | FTH | CE18:2n6 |
| GLUCOSE | CRP | FTH | INSULIN | CE18:2n6 |
| GLUCOSE | CRP | FTH | IL2RA | CE18:2n6 |
| GLUCOSE | ADIPOQ | HBA1C | INSULIN | CE18:2n6 |

FIG 27

| | | | | |
|---|---|---|---|---|
| GLUCOSE | ADIPOQ | CRP | HBA1C | CE16:1n7 |
| GLUCOSE | ADIPOQ | CRP | IL2RA | CE16:1n7 |
| GLUCOSE | ADIPOQ | INSULIN | IL2RA | CE16:1n7 |
| GLUCOSE | FTH | INSULIN | IL2RA | CE16:1n7 |
| GLUCOSE | HBA1C | FTH | INSULIN | CE16:1n7 |
| GLUCOSE | CRP | HBA1C | FTH | CE16:1n7 |
| GLUCOSE | CRP | INSULIN | IL2RA | CE16:1n7 |
| GLUCOSE | ADIPOQ | HBA1C | IL2RA | CE16:1n7 |
| GLUCOSE | CRP | FTH | INSULIN | CE16:1n7 |
| GLUCOSE | CRP | HBA1C | INSULIN | CE16:1n7 |
| GLUCOSE | HBA1C | FTH | IL2RA | CE16:1n7 |
| GLUCOSE | ADIPOQ | FTH | INSULIN | CE16:1n7 |
| GLUCOSE | HBA1C | INSULIN | IL2RA | CE16:1n7 |
| GLUCOSE | ADIPOQ | FTH | IL2RA | CE16:1n7 |
| GLUCOSE | ADIPOQ | CRP | INSULIN | CE16:1n7 |
| GLUCOSE | CRP | HBA1C | IL2RA | CE16:1n7 |
| GLUCOSE | ADIPOQ | HBA1C | FTH | CE16:1n7 |
| GLUCOSE | CRP | FTH | INSULIN | CE16:1n7 |
| GLUCOSE | CRP | FTH | IL2RA | CE16:1n7 |
| GLUCOSE | ADIPOQ | HBA1C | INSULIN | CE16:1n7 |

FIG 28

| | | | | |
|---|---|---|---|---|
| GLUCOSE | ADIPOQ | CRP | HBA1C | CE18:2n6 |
| GLUCOSE | ADIPOQ | CRP | IL2RA | CE18:2n6 |
| GLUCOSE | ADIPOQ | INSULIN | IL2RA | CE18:2n6 |
| GLUCOSE | FTH | INSULIN | IL2RA | CE18:2n6 |
| GLUCOSE | HBA1C | FTH | INSULIN | CE18:2n6 |
| GLUCOSE | CRP | HBA1C | FTH | CE18:2n6 |
| GLUCOSE | CRP | INSULIN | IL2RA | CE18:2n6 |
| GLUCOSE | ADIPOQ | HBA1C | IL2RA | CE18:2n6 |
| GLUCOSE | CRP | FTH | INSULIN | CE18:2n6 |
| GLUCOSE | CRP | HBA1C | INSULIN | CE18:2n6 |
| GLUCOSE | HBA1C | FTH | IL2RA | CE18:2n6 |
| GLUCOSE | ADIPOQ | FTH | INSULIN | CE18:2n6 |
| GLUCOSE | HBA1C | INSULIN | IL2RA | CE18:2n6 |
| GLUCOSE | ADIPOQ | FTH | IL2RA | CE18:2n6 |
| GLUCOSE | ADIPOQ | CRP | INSULIN | CE18:2n6 |
| GLUCOSE | CRP | HBA1C | IL2RA | CE18:2n6 |
| GLUCOSE | ADIPOQ | HBA1C | FTH | CE18:2n6 |
| GLUCOSE | CRP | FTH | INSULIN | CE18:2n6 |
| GLUCOSE | CRP | FTH | IL2RA | CE18:2n6 |
| GLUCOSE | ADIPOQ | HBA1C | INSULIN | CE18:2n6 |

FIG 29

| | | | | |
|---|---|---|---|---|
| GLUCOSE | ADIPOQ | CRP | HBA1C | CE20:3n6 |
| GLUCOSE | ADIPOQ | CRP | IL2RA | CE20:3n6 |
| GLUCOSE | ADIPOQ | INSULIN | IL2RA | CE20:3n6 |
| GLUCOSE | FTH | INSULIN | IL2RA | CE20:3n6 |
| GLUCOSE | HBA1C | FTH | INSULIN | CE20:3n6 |
| GLUCOSE | CRP | HBA1C | FTH | CE20:3n6 |
| GLUCOSE | CRP | INSULIN | IL2RA | CE20:3n6 |
| GLUCOSE | ADIPOQ | HBA1C | IL2RA | CE20:3n6 |
| GLUCOSE | CRP | FTH | INSULIN | CE20:3n6 |
| GLUCOSE | CRP | HBA1C | INSULIN | CE20:3n6 |
| GLUCOSE | HBA1C | FTH | IL2RA | CE20:3n6 |
| GLUCOSE | ADIPOQ | FTH | INSULIN | CE20:3n6 |
| GLUCOSE | HBA1C | INSULIN | IL2RA | CE20:3n6 |
| GLUCOSE | ADIPOQ | FTH | IL2RA | CE20:3n6 |
| GLUCOSE | ADIPOQ | CRP | INSULIN | CE20:3n6 |
| GLUCOSE | CRP | HBA1C | IL2RA | CE20:3n6 |
| GLUCOSE | ADIPOQ | HBA1C | FTH | CE20:3n6 |
| GLUCOSE | CRP | FTH | INSULIN | CE20:3n6 |
| GLUCOSE | CRP | FTH | IL2RA | CE20:3n6 |
| GLUCOSE | ADIPOQ | HBA1C | INSULIN | CE20:3n6 |

FIG 30

| | | | | |
|---|---|---|---|---|
| GLUCOSE | ADIPOQ | CRP | HBA1C | CE16:0 |
| GLUCOSE | ADIPOQ | CRP | IL2RA | CE16:0 |
| GLUCOSE | ADIPOQ | INSULIN | IL2RA | CE16:0 |
| GLUCOSE | FTH | INSULIN | IL2RA | CE16:0 |
| GLUCOSE | HBA1C | FTH | INSULIN | CE16:0 |
| GLUCOSE | CRP | HBA1C | FTH | CE16:0 |
| GLUCOSE | CRP | INSULIN | IL2RA | CE16:0 |
| GLUCOSE | ADIPOQ | HBA1C | IL2RA | CE16:0 |
| GLUCOSE | CRP | FTH | INSULIN | CE16:0 |
| GLUCOSE | CRP | HBA1C | INSULIN | CE16:0 |
| GLUCOSE | HBA1C | FTH | IL2RA | CE16:0 |
| GLUCOSE | ADIPOQ | FTH | INSULIN | CE16:0 |
| GLUCOSE | HBA1C | INSULIN | IL2RA | CE16:0 |
| GLUCOSE | ADIPOQ | FTH | IL2RA | CE16:0 |
| GLUCOSE | ADIPOQ | CRP | INSULIN | CE16:0 |
| GLUCOSE | CRP | HBA1C | IL2RA | CE16:0 |
| GLUCOSE | ADIPOQ | HBA1C | FTH | CE16:0 |
| GLUCOSE | CRP | FTH | INSULIN | CE16:0 |
| GLUCOSE | CRP | FTH | IL2RA | CE16:0 |
| GLUCOSE | ADIPOQ | HBA1C | INSULIN | CE16:0 |

FIG 31

| | | | | |
|---|---|---|---|---|
| GLUCOSE | ADIPOQ | CRP | HBA1C | LY18:2n6 |
| GLUCOSE | ADIPOQ | CRP | IL2RA | LY18:2n6 |
| GLUCOSE | ADIPOQ | INSULIN | IL2RA | LY18:2n6 |
| GLUCOSE | FTH | INSULIN | IL2RA | LY18:2n6 |
| GLUCOSE | HBA1C | FTH | INSULIN | LY18:2n6 |
| GLUCOSE | CRP | HBA1C | FTH | LY18:2n6 |
| GLUCOSE | CRP | INSULIN | IL2RA | LY18:2n6 |
| GLUCOSE | ADIPOQ | HBA1C | IL2RA | LY18:2n6 |
| GLUCOSE | CRP | FTH | INSULIN | LY18:2n6 |
| GLUCOSE | CRP | HBA1C | INSULIN | LY18:2n6 |
| GLUCOSE | HBA1C | FTH | IL2RA | LY18:2n6 |
| GLUCOSE | ADIPOQ | FTH | INSULIN | LY18:2n6 |
| GLUCOSE | HBA1C | INSULIN | IL2RA | LY18:2n6 |
| GLUCOSE | ADIPOQ | FTH | IL2RA | LY18:2n6 |
| GLUCOSE | ADIPOQ | CRP | INSULIN | LY18:2n6 |
| GLUCOSE | CRP | HBA1C | IL2RA | LY18:2n6 |
| GLUCOSE | ADIPOQ | HBA1C | FTH | LY18:2n6 |
| GLUCOSE | CRP | FTH | INSULIN | LY18:2n6 |
| GLUCOSE | CRP | FTH | IL2RA | LY18:2n6 |
| GLUCOSE | ADIPOQ | HBA1C | INSULIN | LY18:2n6 |

FIG 32

| | | | | |
|---|---|---|---|---|
| GLUCOSE | ADIPOQ | CRP | HBA1C | LY18:1n7 |
| GLUCOSE | ADIPOQ | CRP | IL2RA | LY18:1n7 |
| GLUCOSE | ADIPOQ | INSULIN | IL2RA | LY18:1n7 |
| GLUCOSE | FTH | INSULIN | IL2RA | LY18:1n7 |
| GLUCOSE | HBA1C | FTH | INSULIN | LY18:1n7 |
| GLUCOSE | CRP | HBA1C | FTH | LY18:1n7 |
| GLUCOSE | CRP | INSULIN | IL2RA | LY18:1n7 |
| GLUCOSE | ADIPOQ | HBA1C | IL2RA | LY18:1n7 |
| GLUCOSE | CRP | FTH | INSULIN | LY18:1n7 |
| GLUCOSE | CRP | HBA1C | INSULIN | LY18:1n7 |
| GLUCOSE | HBA1C | FTH | IL2RA | LY18:1n7 |
| GLUCOSE | ADIPOQ | FTH | INSULIN | LY18:1n7 |
| GLUCOSE | HBA1C | INSULIN | IL2RA | LY18:1n7 |
| GLUCOSE | ADIPOQ | FTH | IL2RA | LY18:1n7 |
| GLUCOSE | ADIPOQ | CRP | INSULIN | LY18:1n7 |
| GLUCOSE | CRP | HBA1C | IL2RA | LY18:1n7 |
| GLUCOSE | ADIPOQ | HBA1C | FTH | LY18:1n7 |
| GLUCOSE | CRP | FTH | INSULIN | LY18:1n7 |
| GLUCOSE | CRP | FTH | IL2RA | LY18:1n7 |
| GLUCOSE | ADIPOQ | HBA1C | INSULIN | LY18:1n7 |

FIG 33

| | | | | |
|---|---|---|---|---|
| GLUCOSE | ADIPOQ | CRP | HBA1C | LY18:1n7 and LY18:1n9 |
| GLUCOSE | ADIPOQ | CRP | IL2RA | LY18:1n7 and LY18:1n9 |
| GLUCOSE | ADIPOQ | INSULIN | IL2RA | LY18:1n7 and LY18:1n9 |
| GLUCOSE | FTH | INSULIN | IL2RA | LY18:1n7 and LY18:1n9 |
| GLUCOSE | HBA1C | FTH | INSULIN | LY18:1n7 and LY18:1n9 |
| GLUCOSE | CRP | HBA1C | FTH | LY18:1n7 and LY18:1n9 |
| GLUCOSE | CRP | INSULIN | IL2RA | LY18:1n7 and LY18:1n9 |
| GLUCOSE | ADIPOQ | HBA1C | IL2RA | LY18:1n7 and LY18:1n9 |
| GLUCOSE | CRP | FTH | INSULIN | LY18:1n7 and LY18:1n9 |
| GLUCOSE | CRP | HBA1C | INSULIN | LY18:1n7 and LY18:1n9 |
| GLUCOSE | HBA1C | FTH | IL2RA | LY18:1n7 and LY18:1n9 |
| GLUCOSE | ADIPOQ | FTH | INSULIN | LY18:1n7 and LY18:1n9 |
| GLUCOSE | HBA1C | INSULIN | IL2RA | LY18:1n7 and LY18:1n9 |
| GLUCOSE | ADIPOQ | FTH | IL2RA | LY18:1n7 and LY18:1n9 |
| GLUCOSE | ADIPOQ | CRP | INSULIN | LY18:1n7 and LY18:1n9 |
| GLUCOSE | CRP | HBA1C | IL2RA | LY18:1n7 and LY18:1n9 |
| GLUCOSE | ADIPOQ | HBA1C | FTH | LY18:1n7 and LY18:1n9 |
| GLUCOSE | CRP | FTH | INSULIN | LY18:1n7 and LY18:1n9 |
| GLUCOSE | CRP | FTH | IL2RA | LY18:1n7 and LY18:1n9 |
| GLUCOSE | ADIPOQ | HBA1C | INSULIN | LY18:1n7 and LY18:1n9 |

FIG 34

| | | | | |
|---|---|---|---|---|
| GLUCOSE | ADIPOQ | CRP | HBA1C | LY18:1n9 |
| GLUCOSE | ADIPOQ | CRP | IL2RA | LY18:1n9 |
| GLUCOSE | ADIPOQ | INSULIN | IL2RA | LY18:1n9 |
| GLUCOSE | FTH | INSULIN | IL2RA | LY18:1n9 |
| GLUCOSE | HBA1C | FTH | INSULIN | LY18:1n9 |
| GLUCOSE | CRP | HBA1C | FTH | LY18:1n9 |
| GLUCOSE | CRP | INSULIN | IL2RA | LY18:1n9 |
| GLUCOSE | ADIPOQ | HBA1C | IL2RA | LY18:1n9 |
| GLUCOSE | CRP | FTH | INSULIN | LY18:1n9 |
| GLUCOSE | CRP | HBA1C | INSULIN | LY18:1n9 |
| GLUCOSE | HBA1C | FTH | IL2RA | LY18:1n9 |
| GLUCOSE | ADIPOQ | FTH | INSULIN | LY18:1n9 |
| GLUCOSE | HBA1C | INSULIN | IL2RA | LY18:1n9 |
| GLUCOSE | ADIPOQ | FTH | IL2RA | LY18:1n9 |
| GLUCOSE | ADIPOQ | CRP | INSULIN | LY18:1n9 |
| GLUCOSE | CRP | HBA1C | IL2RA | LY18:1n9 |
| GLUCOSE | ADIPOQ | HBA1C | FTH | LY18:1n9 |
| GLUCOSE | CRP | FTH | INSULIN | LY18:1n9 |
| GLUCOSE | CRP | FTH | IL2RA | LY18:1n9 |
| GLUCOSE | ADIPOQ | HBA1C | INSULIN | LY18:1n9 |

FIG 35

PROTEIN AND LIPID BIOMARKERS PROVIDING CONSISTENT IMPROVEMENT TO THE PREDICTION OF TYPE 2 DIABETES

This application is a 371 National Phase filing of PCT/US2010/054398, filed Oct. 28, 2010, which claims benefit of priority to U.S. Provisional Application No. 61/256,302 filed Oct. 29, 2009.

FIELD OF INVENTION

The invention relates to biomarkers associated with Diabetes, methods of using the biomarkers to determine the risk that an individual will develop Diabetes, and methods of screening a population to identify persons at risk for developing Diabetes and other diabetic conditions.

BACKGROUND

Fifteen million people in the United States have type 2 diabetes. In both human and economic terms, diabetes is one of the most costly diseases in the nation today. The cost of medical care and services to treat diabetes is estimated to have been $91.8 billion in 2002. Another $40.2 billion of lost productivity, disability and premature death is also attributable to the disease. One million new cases are diagnosed each year, and many people do not learn they have the disease until they develop one of its life-threatening complications, which include heart disease, stroke and kidney disease.

Diabetes has been attributed to both genetic and lifestyle factors, including obesity, age, sedentary lifestyle, hypertension, and use of drugs that block insulin action or antagonize insulin action. As a result, in the absence of a predictive diagnostic, single factors can not reliably be used to accurately assess an individual's propensity for developing the disease. Type 2 diabetes is typically diagnosed by measuring fasted plasma glucose, 2-hour plasma glucose or random plasma glucose (if symptoms are present). Persons with early-stage type 2 diabetes are usually asymptomatic and may not realize they are ill; they may live for many years with uncontrolled diabetes before symptoms ever occur. When they do occur, those symptoms are often related to a life-threatening complication. Treatment or lifestyle changes in the early stages of disease can delay and possibly even prevent development of diabetes and its related complications.

Treatment for prediabetes can slow or reverse the disease in some individuals, particularly in early stage disease. Lifestyle intervention or treatment with for instance, metformin in persons at high risk can reduce the incidence of diabetes by 58% and 31% respectively. Hence, a simple to administer method to monitor early stage disease progression, and determine efficacy of treatment, would greatly improve disease treatment and outcomes.

Type 2 Diabetes (non-insulin-dependent Diabetes or adult-onset Diabetes) results from insensitivity to insulin, and accounts for 90% of Diabetes worldwide. Gestational Diabetes is a loss of blood sugar control (hyperglycemia) that occurs during pregnancy. Type 2 Diabetes is characterized by disorders of insulin action and insulin secretion, either of which may be the predominant feature. Type 2 Diabetes patients are characterized with a relative, rather than absolute, insulin deficiency and are insulin resistant. At least initially, and often throughout their lifetime, these individuals do not need supplemental insulin treatment to survive. Type 2 Diabetes accounts for 90-95% of all cases of Diabetes and can go undiagnosed for many years because the hyperglycemia is often not severe enough to provoke noticeable symptoms of Diabetes or symptoms are simply not recognized. The majority of patients with Type 2 Diabetes are obese, and obesity itself may cause or aggravate insulin resistance. Many of those who are not obese by traditional weight criteria may have an increased percentage of body fat distributed predominantly in the abdominal region (visceral fat). Whereas patients with this form of Diabetes may have insulin levels that appear normal or elevated, the high blood glucose levels in these diabetic patients would be expected to result in even higher insulin values had their beta cell function been normal. Thus, insulin secretion is often defective and insufficient to compensate for the insulin resistance. On the other hand, some hyperglycemic individuals have essentially normal insulin action, but markedly impaired insulin secretion.

Pre-diabetics often have fasting glucose levels between normal and frank diabetic levels. Abnormal glucose tolerance, or "impaired glucose tolerance" can be an indication that an individual is on the path toward Diabetes; it requires the use of a 2-hour oral glucose tolerance test for its detection. However, it has been shown that impaired glucose tolerance is by itself entirely asymptomatic and unassociated with any functional disability. Indeed, insulin secretion is typically greater in response to a mixed meal than in response to a pure glucose load; as a result, most persons with impaired glucose tolerance are rarely, if ever, hyperglycemic in their daily lives, except when they undergo diagnostic glucose tolerance tests. Thus, the importance of impaired glucose tolerance resides exclusively in its ability to identify persons at increased risk of future disease (Stern et al, 2002)

Diabetes is generally diagnosed by determining blood glucose levels after fasting overnight (fasting plasma glucose level) or by determining blood glucose levels after fasting, followed by ingestion of glucose and a blood glucose measurement two hours after glucose administration (a glucose tolerance test). In studies conducted by Stern and colleagues (Stern et al., Diabetes Care 25:1851-1856, (2002)), the sensitivity and false-positive rates of impaired glucose tolerance as a predictor of future conversion to Type 2 Diabetes was 50.9% and 10.2%, respectively, representing an area under the Receiver-Operating Characteristic Curve of 77.5% (with a 95% confidence interval of 74.3-80.7%) and a P-value (calculated using Hosmer-Lemeshow goodness-of-fit) of 0.20. Because of the inconvenience associated with the two-hour glucose tolerance test, as well as the cost of the test, the test is seldom used in routine clinical practice. Moreover, patients whose Diabetes is diagnosed solely on the basis of an oral glucose tolerance test have a high rate of reversion to normal on follow-up and may in fact represent false-positive diagnoses (Burke et al., Diabetes Care 21:1266-1270 (1998)). Stern and others reported that such cases were almost 5 times more likely to revert to non-diabetic status after 7 to 8 years of follow-up compared with persons meeting conventional fasting or clinical diagnostic criteria.

Beyond glucose and HBA1c, several single time point biomarker measurements have been attempted for the use of risk assessment for future Diabetes. U.S. Patent Application No. 2003/0100486 proposes C-Reactive Protein (CRP) and Interleukin-6 (IL-6), both markers of systemic inflammation, used alone and as an adjunct to the measurement of HBA1c. However, for practical reasons relating to clinical performance, specifically poor specificity and high false positive rates, these tests have not been adopted.

Often a person with impaired glucose tolerance will be found to have at least one or more of the common arteriovascular disease risk factors (e.g., dyslipidemia and hypertension). This clustering has been termed "Syndrome X," or "Metabolic Syndrome" by some researchers and can be indicative of a diabetic or pre-diabetic condition. Alone, each component of the cluster conveys increased arteriovascular and diabetic disease risk, but together as a combination they become much more significant. This means that the management of persons with hyperglycemia and other features of Metabolic Syndrome should focus not only on blood glucose control but also include strategies for reduction of other arteriovascular disease risk factors. Furthermore, such risk factors are non-specific for Diabetes or pre-Diabetes and are not in themselves a basis for a diagnosis of Diabetes, or of diabetic status.

Risk prediction for Diabetes, pre-Diabetes, or a pre-diabetic condition can also encompass multi-variate risk prediction algorithms and computed indices that assess and estimate a subject's absolute risk for developing Diabetes, pre-Diabetes, or a pre-diabetic condition with reference to a historical cohort. Risk assessment using such predictive mathematical algorithms and computed indices has increasingly been incorporated into guidelines for diagnostic testing and treatment, and encompass indices obtained from and validated with, inter alia, multi-stage, stratified samples from a representative population. A plurality of conventional Diabetes risk factors is incorporated into predictive models. A notable example of such algorithms include the Framingham study (Kannel, W. B. et al, (1976) Am. J. Cardiol. 38: 46-51) and modifications of the Framingham Study, such as the National Cholesterol Education Program Expert Panel on Detection, Evaluation, and Treatment of High Blood Cholesterol in Adults (Adult Treatment Panel III).

Other Diabetes risk prediction algorithms include, without limitation, the San Antonio Heart Study (Stern, M. P. et al, (1984) Am. J. Epidemiol. 120: 834-851; Stern, M. P. et al, (1993) Diabetes 42: 706-714; Burke, J. P. et al, (1999) Arch. Intern. Med. 159: 1450-1456), Archimedes (Eddy, D. M. and Schlessinger, L. (2003) Diabetes Care 26(11): 3093-3101; Eddy, D. M. and Schlessinger, L. (2003) Diabetes Care 26(11): 3102-3110), the Finnish-based Diabetes Risk Score (Lindstrom, J. and Tuomilehto, J. (2003) Diabetes Care 26(3): 725-731), and the Ely Study (Griffin, S. J. et al, (2000) Diabetes Metab. Res. Rev. 16: 164-171), the contents of which are expressly incorporated herein by reference.

Despite the numerous studies and algorithms that have been used to assess the risk of Diabetes, pre-Diabetes, or a pre-diabetic condition, a need exists for accurate methods of assessing such risks or conditions. Furthermore, due to issues of practicality and the difficulty of the risk computations involved, there has been little adoption of such an approach by the primary care physician that is most likely to initially encounter the pre-diabetic or undiagnosed early diabetic. Clearly, there remains a need for more practical methods of assessing the risk of future Diabetes.

It is well documented that pre-Diabetes can be present for ten or more years before the detection of glycemic disorders like Diabetes. Treatment of pre-diabetics with drugs such as acarbose, metformin, troglitazone and rosiglitazone can postpone or prevent Diabetes; yet few pre-diabetics are treated. A major reason, as indicated above, is that no simple and unambiguous laboratory test exists to determine the actual risk of an individual to develop Diabetes. Furthermore, even in individuals known to be at risk of Diabetes, glycemic control remains the primary therapeutic monitoring endpoint, and is subject to the same limitations as its use in the prediction and diagnosis of frank Diabetes. Thus, there remains a need in the art for methods of identifying, diagnosing, and treatment of these individuals who are not yet diabetics, but who are at significant risk of developing Diabetes.

Tethys Bioscience continues to develop predicted test for Diabetes based on protein biomarkes, e.g. see WO 2007/044860.

Type 2 Diabetes and Lipid Metabolism

More than one mechanism for the development of type 2 diabetes exists. While all of the genetic causes and environmental factors involved in development of insulin resistance are unknown, impaired lipid metabolism has been shown to play an important role in the development of type 2 diabetes. Increased fasting plasma fatty acids are correlated with the development of obesity and insulin resistance in many populations and are an independent predictor of the development of type 2 diabetes.

One hypothesis for the development of increased plasma fatty acids and insulin resistance starts with the adipose tissue. Enlarged adipocytes release inflammatory cytokines into the plasma which feed back to alter the adipose' and other tissue's response to insulin. As the adipocytes become insulin resistant, they are unable to suppress lipolysis in response to insulin. These adipocytes are also unable to store additional fat, consequently reducing the uptake of fatty acids after a meal, resulting in excess fatty acids in the plasma. The overwhelming amount of fatty acids released by adipose tissue chronically increases plasma levels and diverts lipid into other tissues including liver, muscle, and pancreas.

In the liver, the increased fatty acids stimulate gluconeogenesis and glucose output from the liver. Chronic hyperinsulinemia and high plasma glucose concentrations stimulate liver de novo production of fatty acids. While the actual amount of fatty acids produced de novo is small, the conditions that increase fatty acid production also decrease liver fatty acid oxidation. This results in higher triglyceride esterification rates and increased availability of triglyceride for very low density lipoprotein synthesis and secretion. Along with the additional available substrate, decreased hepatocyte responsiveness to insulin may also increase release of very low density lipoprotein. The additional lipoprotein lipid released from the liver becomes substrate for lipase activity and release of free fatty acids into the plasma creating a positive feedback loop.

In the muscle, increased free fatty acids and intramuscular lipid is strongly correlated with impaired glucose metabolism. The muscle responds to chronically increased plasma fatty acids by decreasing glucose uptake thus increasing fasting and postprandial plasma glucose concentrations. Muscle tissue may also increase uptake and decrease oxidation of the fatty acids, resulting in increased intramuscular lipid. The decreased oxidative capacity of the muscle is due to dysfunctional mitochondria, though whether this is caused by the insulin resistant state, or a cause of it, is unknown.

Peripheral insulin resistance can exist without the development of overt diabetes. Development of type 2 diabetes occurs when the pancreatic β-cells fail to compensate for insulin resistance by increasing insulin output. The progression to diabetes is accompanied by loss of pancreatic β-cells as well as an increase in the basal rate of insulin secretion by the remaining cells, and the inability of these cells to respond to glucose. The loss of function and cell death is due to chronic exposure of β-cells to high levels of both fatty acids and glucose. Similar to the muscle, β-cells exposed to high concentrations of fatty acids have decreased lipid oxidation and increased intracellular triglycerides.

Type 2 diabetes is a disease of lipid metabolism as well as glucose metabolism. While there are multiple mechanisms for the development of insulin resistance and type 2 diabetes, alterations in lipid metabolism is a common theme. Even though there are differences between individuals and groups of individuals in exactly how lipid metabolism is altered, disordered lipid storage and metabolism occurs at very early stages of insulin resistance in all individuals with insulin resistance and could be considered a marker of the disease. By monitoring lipid metabolites and whole body lipid metabolism, it may be possible to define the alterations in lipids that occur with insulin resistance and type 2 diabetes, segregate groups of patients by their changed lipid metabolism, and predict who would respond to therapy. Some lipids have been identified which predict the development of insulin resistance or diagnosis of insulin sensitivity. However, the combination of specific lipids which improve the prediction of insulin resistance or diagnosis of a diabetic condition has not been previously shown.

What is needed are better testing methods that can be used to classify, diagnose, and monitor patients at risk of developing diabetes.

SUMMARY OF INVENTION

The instant invention relates to use of biomarkers, including protein biomarker and lipid metabolite biomarkers, for evaluating the risk that an individual will become diabetic, or for identifying members of a population at risk of developing Diabetes, and methods of calculating such risks, advising individuals of such risks, providing diagnostic test systems for calculating such risks, and various other embodiments as described herein.

The invention provides for a method of evaluating risk for developing a diabetic condition, the method comprising: (a) obtaining biomarker measurement data for an individual, wherein the biomarker measurement data is representative of measurements of biomarkers in at least one biological sample from the individual; wherein said biomarkers comprise: (i) glucose, (ii) at least three protein biomarkers selected from the protein biomarkers in Table 1 and (iii) at least one lipid metabolite selected from the lipid metabolites in Table 2; and (b) evaluating risk for the individual developing a diabetic condition based on an output from a model, wherein the model is executed based on an input of the biomarker measurement data.

In one embodiment, the obtaining step of this method comprises measuring the biomarkers in the at least one biological sample. Furthermore, these methods may further comprising a step, prior to the measuring the biomarkers, of obtaining at least one biological sample from the individual. In another embodiment, the step of obtaining biomarker measurement data comprises obtaining data representative of a measurement of the level of at least one biomarker from a preexisting record.

In addition, the invention provides for any of the preceding methods wherein the evaluating step includes comparing the biomarker measurement data from the individual with biomarker measurement data of the same biomarkers from a population, and evaluating risk for the individual developing a diabetic condition from the comparison.

In a related embodiment, any of the preceding methods further comprise the step of displaying the risk evaluation from step (b) on a visual display. In addition, any of the preceding methods further comprise printing or storing the risk evaluation on paper or an electronic storage medium. In a further embodiment, any of the preceding method further comprising advising said individual or a health care practitioner of said risk evaluation.

The invention also provides for any of the preceding methods that further comprise the step of obtaining clinical measurement data for the individual for at least one clinical parameter selected from the group consisting of age, body mass index (BMI), diastolic blood pressure (DBP), family history (FHX), past gestational diabetes mellitus (GDM), height (HT), hip circumference (Hip), race, sex, systolic blood pressure (SBP), waist circumference (Waist), and weight (WT), wherein the model is executed based on an input of the biomarker measurement data and the clinical measurement data.

The invention also provides for a method of evaluating risk for developing a diabetic condition, the method comprising: (a) obtaining measurements of biomarkers from at least one biological sample isolated from an individual, wherein said biomarkers comprise: (i) glucose, (ii) at least three protein biomarkers selected from the protein biomarkers in Table 1 and (iii) at least one lipid metabolite selected from the lipid metabolites in Table 2; and (b) calculating a risk for developing a diabetic condition from the output of a model, wherein the inputs to said model comprise said measurements of biomarkers, and wherein said model was developed by fitting data from a longitudinal study of a population of individuals and said fitted data comprises levels of said biomarkers and conversion to Diabetes in said selected population of individuals. In one embodiment, the obtaining step comprises measuring the biomarkers in the at least one biological sample.

In another embodiment, the preceding methods further comprise displaying the calculated risk from step (b) on a visual display. In a further embodiment, the preceding methods further comprising printing or storing the calculated risk on paper or an electronic storage medium. In addition, the preceding methods may further comprising advising said individual or a health care practitioner of said risk evaluation.

In a related embodiment, any of the preceding methods further comprise a step of obtaining at least one clinical measurement for the individual for at least one clinical parameter selected from the group consisting of age, body mass index (BMI), diastolic blood pressure (DBP), family history (FHX), past gestational diabetes mellitus (GDM), height (HT), hip circumference (Hip), race, sex, systolic blood pressure (SBP), waist circumference (Waist), and weight (WT), wherein the inputs to the model further comprise said at least one clinical measurement.

The biomarker measurement data or biomarker measurements of any of the methods of the invention may be obtained from an individual that has not been previously diagnosed as having Diabetes, pre-Diabetes, or a pre-diabetic condition. Alternatively, the biomarker measurement data or biomarker measurements of any of the methods of the invention may be obtained from an individual that has a pre-diabetic condition, and the method evaluates or calculates risk for the individual developing Diabetes. The individual from which the biomarker measurement data or biomarker measurements are obtained may be pregnant.

The invention provides for any of the methods of the invention, the diabetic condition is selected from the group consisting of Type 2 Diabetes, pre-Diabetes, Metabolic Syndrome, Impaired Glucose Tolerance, and Impaired Fasting Glycemia.

The invention also provides for any of the methods of the invention, wherein said at least one biological sample comprises whole blood, serum, or plasma. In addition, the invention provides for any of the methods of the invention wherein least one of said biomarker measurements is obtained by a method selected from the group consisting of immunoassay and enzymatic activity assay.

In another embodiment, the invention provides for any method of the invention, wherein the method using said biomarkers has an area under the ROC curve, reflecting the degree of diagnostic accuracy for predicting development of the diabetic condition, of at least 0.75, 0.76, 0.77, 0.78, 0.79, 0.80, 0.81, 0.82, 0.83, 0.84, or 0.85. In addition, the invention provides for any method of the invention wherein the method using said biomarkers has an area under the ROC curve, reflecting the degree of diagnostic accuracy for predicting development of the diabetic condition, of at least 0.02, 0.03, 0.04, 0.05, 0.06, 0.07, 0.08, 0.09, 0.10, 0.11, 0.12, 0.13, 0.14, or 0.15 greater than a corresponding method wherein the biomarkers consist of the glucose and the protein biomarkers but not the lipid metabolites.

In a further embodiment, the invention provides for a kit comprising reagents for measuring a group of biomarkers, wherein the biomarkers are: (i) glucose, (ii) at least three protein biomarkers selected from the protein biomarkers in Table 1 and (iii) at least one lipid metabolite selected from the lipid metabolites in Table 2. In addition, the invention provides for kits wherein one of the reagents comprises a detectable label. Furthermore, the invention provides for kits wherein the reagents for the protein biomarkers and lipid metabolites are attached to a solid support.

The invention also provides for a computer readable medium having computer executable instructions for evaluating risk for developing a diabetic condition, the computer readable medium comprising: a routine, stored on the computer readable medium and adapted to be executed by a processor, to store biomarker measurement data representing measurements of at least the following: (i) glucose, (ii) at least three protein biomarkers selected from the protein biomarkers in Table 1 and (iii) at least one lipid metabolite selected from the lipid metabolites in Table 2; and a routine stored on the computer readable medium and adapted to be executed by a processor to analyze the biomarker measurement data to evaluate a risk for developing a diabetic condition.

In another embodiment, the invention provides for a medical diagnostic test system for evaluating risk for developing a diabetic condition, the system comprising: a data collection tool adapted to collect biomarker measurement data representative of measurements of biomarkers in at least one biological sample from an individual, wherein said biomarkers comprise: (i) glucose, (ii) at least three protein biomarkers selected from the protein biomarkers in Table 1 and (iii) at least one lipid metabolite selected from the lipid metabolites in Table 2; and an analysis tool comprising a statistical analysis engine adapted to generate a representation of a correlation between a risk for developing a diabetic condition and measurements of the biomarkers, wherein the representation of the correlation is adapted to be executed to generate a result; and an index computation tool adapted to analyze the result to determine the individual's risk for developing a diabetic condition and represent the result as an index value.

The invention also provides for the medical diagnostic test system, wherein the analysis tool comprises a first analysis tool comprising a first statistical analysis engine, the system further comprising a second analysis tool comprising a second statistical analysis engine adapted to select the representation of the correlation between the risk for developing a diabetic condition and measurements of the biomarkers from among a plurality of representations capable of representing the correlation. In addition, the systems of the invention may further comprise a reporting tool adapted to generate a report comprising the index value.

In another embodiment, the invention provides for a method of developing a model for evaluation of risk for developing a diabetic condition, the method comprising: obtaining biomarker measurement data, wherein the biomarker measurement data is representative of measurements of biomarkers from a population and includes endpoints of the population; wherein said biomarkers for which measurement data is obtained comprise: (i) glucose, (ii) at least three protein biomarkers selected from the protein biomarkers in Table 1 and (iii) at least one lipid metabolite selected from the lipid metabolites in Table 2; inputting the biomarker measurement data of at least a subset of the population into a model; and training the model for endpoints using the inputted biomarker measurement data to derive a representation of a correlation between a risk of developing a diabetic condition and measurements of biomarkers in at least one biological sample from an individual.

The invention also provides for a method of evaluating the current status of a diabetic condition in an individual, the method comprising: obtaining biomarker measurement data, wherein the biomarker measurement data is representative of measurements of biomarkers in at least one biological sample from the individual, wherein said biomarkers comprise: (i) glucose, (ii) at least three protein biomarkers selected from the protein biomarkers in Table 1 and (iii) at least one lipid metabolite selected from the lipid metabolites in Table 2; and evaluating the current status of a diabetic condition in the individual based on an output from a model, wherein the model is executed based on an input of the biomarker measurement data.

In another embodiment, the invention provides for a method of evaluating a diabetic disease surrogate endpoint an individual, the method comprising: obtaining biomarker measurement data, wherein the biomarker measurement data is representative of measurements of biomarkers in at least one biological sample from the individual; wherein said biomarkers comprise: (i) glucose, (ii) at least three protein biomarkers selected from the protein biomarkers in Table 1 and (iii) at least one lipid metabolite selected from the lipid metabolites in Table 2; and evaluating a diabetic disease surrogate endpoint in the individual based on an output from a model, wherein the model is executed based on an input of the biomarker measurement data.

In one embodiment, the methods, kits, computer readable medium, or systems of the invention include those wherein said biomarkers comprise at least four, at least five, at least six, at least seven, at least eight, at least nine, or at least ten protein biomarkers from Table 1.

In other embodiments, the method, kit, computer readable medium, or systems of the invention include those wherein said at least three protein biomarkers are selected from the group consisting of adiponectin, C-reactive protein (CRP), HbA1c, IGFBP1, IGFBP2, Insulin, IL2RA, ferritin, and LEP.

In addition, the methods, kit,s computer readable medium, or systems of the invention include those wherein said at least three protein biomarkers are selected from the group consisting of: adiponectin, C-reactive protein (CRP), IL2RA, ferritin, insulin, and HbA1c.

In another embodiment, the methods, kits, computer readable medium, or systems of the invention include those wherein said at least three protein biomarkers include at least one glycemic index marker selected from insulin and HbA1c.

The invention also provides for methods, kits, computer readable medium, or systems, wherein said at least three protein biomarkers comprise adiponectin, insulin, and C-reactive protein.

The invention also provides for methods, kits, computer readable medium, or systems, wherein said at least three protein biomarkers comprise adiponectin, CRP and HbA1c.

In another embodiment, the invention provides for methods, kits, computer readable medium, or systems, wherein said at least three protein biomarkers are selected from the combinations of any one of FIGS. 8-26.

The invention also provides for methods, kits, computer readable medium, or systems, wherein said at least three protein markers and at least one lipid metabolite are selected from the combinations of any one of FIGS. 27-35.

In one embodiment of the invention, the methods, kits, computer readable medium or systems are those wherein said biomarkers comprise at least two, at least three, at least four, at least five, at least six, at least seven, at least eight, at least nine, or at least ten lipid metabolites from Table 2.

The invention also provides for methods, kits, computer readable medium, or systems wherein said at least one lipid metabolite comprises at least one cholesterol ester.

In another embodiment, the invention provides for methods, kits, computer readable medium, or systems, wherein said at least one lipid metabolite comprises at least one lipid metabolite selected from the group consisting of AC6:0, AC8:0, AC10:0, CE16:0, CE16:1n7, CE18:0, CE18:3n6, CE18:1n9, CE 18:2n6, CE20:3n6, CE20:4n3, TGTL, DG16:0, DG18:0, DG18:1n9, DG18:2n6, DG18:3n3, DGTL, FA16:0, FA16:1n7, FA18:1n9, FA18:2n6, FA24:0, LY16:1n7, LY18:1n7, LY18:1n9, LY18:2n6, PC16:1n7, PC18:2n6, PC18:3n6, PC18:1n7, PC20:3n9, PC22:4n6, PC22:5n3, PCdm18:0, PCdm18:1n9, PCdm16:0, PC20:3n6, PC20:4n3, PEdm18:1n9, PE16:1n7, PE18:2n6, PE20:2n6, PE22:0, PE24:1n9 PEdm18:0, TG16:0, TG16:1n7, TG18:0, TG18:1n7, TG18:1n9, TG18:2n6 and TG18:3n3.

In one embodiment, the invention provides for methods, kits, computer readable medium, or systems, wherein said at least one lipid metabolite selected from the group consisting of CE16:1n7, CE20:3n6, CE18:2n6, CE16:0, CE18:1n9, LY18:2n6, LY18:1n7 and LY18:1n9.

In another embodiment, the invention provides for methods, kits, computer readable medium, or systems, wherein said at least one lipid metabolite comprises CE 16:1n7.

The invention also provides for methods, kits, computer readable medium, or systems, wherein said at least one lipid metabolite comprises CE 20:3n6.

The invention also provides for methods, kits, computer readable medium, or systems, wherein said at least one lipid metabolite comprises CE18:2n6.

The invention also provides for methods, kits, computer readable medium, or systems, wherein said at least one lipid metabolite comprises CE16:0.

The invention also provides for methods, kits, computer readable medium, or systems, wherein said at least one lipid metabolite comprises CE18:1n9.

The invention also provides for methods, kits, computer readable medium, or systems, wherein said at least one lipid metabolite comprises LY18:2n6.

The invention also provides for methods, kits, computer readable medium, or systems, wherein said at least one lipid metabolite comprises LY18:1n7 or LY18:1n9.

In one embodiment, the invention provides for a method of prophylaxis for Diabetes comprising: obtaining risk score data representing a Diabetes risk score for an individual, wherein the Diabetes risk score is computed according to a method of the invention for calculating a risk of developing a diabetic condition; and generating prescription treatment data representing a prescription for a treatment regimen to delay or prevent the onset of Diabetes to an individual identified by the Diabetes risk score as being at elevated risk for Diabetes.

In a related embodiment, the invention provides for a method of prophylaxis for Diabetes comprising: evaluating or calculating risk, for at least one subject, of developing a diabetic condition according to any method of the invention; and treating a subject identified as being at elevated risk for a diabetic condition with a treatment regimen to delay or prevent the onset of Diabetes.

In the preceding methods of prophylaxis for Diabetes, the treatment regimen comprises at least one therapeutic selected from the group consisting of: INS, INS analogs, hypoglycemic agents, anti-inflammatory agents, lipid-reducing agents, calcium channel blockers, beta-adrenergic receptor blocking agents, cyclooxygenase-2 (COX-2) inhibitors, prodrugs of COX-2 inhibitors, angiotensin II antagonists, angiotensin converting enzyme (ACE) inhibitors, renin inhibitors, lipase inhibitors, amylin analogs, sodium-glucose cotransporter 2 inhibitors, dual adipose triglyceride lipase and PI3 kinase activators, antagonists of neuropeptide Y receptors, human hormone analogs, cannabinoid receptor antagonists, triple monoamine oxidase reuptake inhibitors, inhibitors of norepinephrine and dopamine reuptake, inhibitors of 11 Beta-hydroxysteroid dehydrogenase type 1 (11b-HSD1), inhibitors of cortisol synthesis, inhibitors of gluconeogenesis, glucokinase activators, antisense inhibitors of protein tyrosine phosphatase-1B, islet neogenesis therapy, and betahistine. In addition, in the method of phophylaxis for Diabetes the treatment region comprises at least one therapeutic at least one therapeutic selected from the group consisting of acarbose, metformin, troglitazone, and rosiglitazone.

In another embodiment, the invention provides a method of ranking or grouping a population of individuals, comprising: calculating for developing a diabetic condition according to the any method of the invention for individuals comprised within the population; and ranking individuals within the population relative to the remaining individuals in the population or dividing the population into at least two groups, based on factors comprising said risk for developing a diabetic condition.

In a further embodiment, the methods of ranking or grouping populations of individuals further comprising using ranking data representing the ranking or grouping of the population of individuals for one or more of the following purposes: to determine an individual's eligibility for health insurance; to determine an individual's premium for health insurance; to determine an individual's premium for membership in a health care plan, health maintenance organization, or preferred provider organization; and to assign health care practitioners to an individual in a health care plan, health maintenance organization, or preferred provider organization.

The invention also provides for methods of ranking or grouping individuals 5, further comprising using ranking data representing the ranking or grouping of the population of individuals for one or more purposes selected from the group consisting of: to recommend therapeutic intervention or lifestyle intervention to an individual or group of individuals; to manage the health care of an individual or group of individuals; to monitor the health of an individual or group of individuals; and to monitor the health care treatment, therapeutic intervention, or lifestyle intervention for an individual or group of individuals.

In an embodiment, the invention provides for a method of evaluating the current status of a diabetic condition in an individual, the method comprising: obtaining biomarker measurement data, wherein the biomarker measurement data is representative of measurements of biomarkers in at least one biological sample from the individual; and evaluating the current status of a diabetic condition in the individual based on an output from a model, wherein the model is executed based on an input of the biomarker measurement data; wherein said biomarkers comprise: (i) glucose, (ii) at least three protein biomarkers selected from the protein biomarkers in Table 1 and (iii) at least one lipid metabolite selected from the lipid metabolites in Table 2.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. With respect to aspects described as a range, all sub-ranges and individual values are specifically contemplated.

BRIEF DESCRIPTION OF DRAWINGS

FIG. 7 is a flow diagram of an example method for developing a model which may be used to evaluate a risk of a person, or group of people, for developing a diabetic condition.

FIG. 8 is a flow diagram of an example method for using a model to evaluate a risk of a subject (e.g., a person, or group of people) developing a diabetic condition.

FIG. 9 depicts particularly useful 3-panel combinations from an evaluation of the 75 parameters.

FIG. 10 (A-I) contains tables summarizing enumeration of fitted logistic regression models for various three-panel through eleven-panel ALLDBRISK combinations possible from a starting set of the 11 selected ALLDBRISK (Tier 1-2), as measured and calculated from the base population of Example 2.

FIG. 10A depicts 7 particularly useful combinations of panels of three biomarkers; each panel can be used alone, or with additional biomarkers in combination to the three markers listed.

FIG. 10B depicts 25 particularly useful combinations of panels of four biomarkers; each panel can be used alone, or with additional biomarkers in combination to the four markers listed.

FIG. 10C depicts 65 particularly useful combinations of panels of five biomarkers; each panel can be used alone, or with additional biomarkers in combination to the five markers listed.

FIG. 10D depicts 134 particularly useful combinations of panels of six biomarkers; each panel can be used alone, or with additional biomarkers in combination to the six markers listed.

FIG. 10E depicts 147 particularly useful combinations of panels of seven biomarkers; each panel can be used alone, or with additional biomarkers in combination to the seven markers listed.

FIG. 10F depicts 100 particularly useful combinations of panels of eight biomarkers; each panel can be used alone, or with additional biomarkers in combination to the eight markers listed.

FIG. 10G depicts 44 particularly useful combinations of panels of nine biomarkers; each panel can be used alone, or with additional biomarkers in combination to the nine markers listed.

FIG. 10H depicts 11 particularly useful combinations of panels of ten biomarkers; each panel can be used alone, or with additional biomarkers in combination to the ten markers listed.

FIG. 10I depicts a particularly useful combination of a panel of eleven biomarkers; the panel can be used alone, or with additional biomarkers in combination to the eleven markers listed.

FIG. 11 depicts is a table summarizing the complete enumeration of fitted logistic regression models for all three-panel, four-panel, five-panel, six-panel, and seven-panel ALLDBRISK combinations possible from a starting set of 26 selected ALLDBRISK (Tier 1-3).

FIG. 12 depicts selected particularly useful combinations of panels of three biomarkers; each panel can be used alone, or with additional biomarkers in combination to the three markers listed. These panels represent enumeration of fitted logistic regression models from a starting set of 65 selected ALLDBRISK, as measured and calculated from a larger base population and meet a predetermined cut off level (0.75 AUC or better).

FIG. 13 depicts selected particularly useful combinations of panels of four biomarkers; each panel can be used alone, or with additional biomarkers in combination to the four markers listed. These panels represent enumeration of fitted logistic regression models from a starting set of 26 selected ALLDBRISK, as measured and calculated from a larger base population and meet a predetermined cut off level (0.75 AUC or better).

FIG. 14 depicts selected particularly useful combinations of panels of five biomarkers; each panel can be used alone, or with additional biomarkers in combination to the five markers listed. These panels represent enumeration of fitted logistic regression models from a starting set of 26 selected ALLDBRISK, as measured and calculated from a larger base population and meet a predetermined cut off level (0.75 AUC or better).

FIG. 15 depicts selected particularly useful combinations of panels of six biomarkers; each panel can be used alone, or with additional biomarkers in combination to the six markers listed. These panels represent enumeration of fitted logistic regression models from a starting set of 26 selected ALLDBRISK, as measured and calculated from a larger base population and meet a predetermined cut off level (0.75 AUC or better).

FIG. 16 depicts selected particularly useful combinations of panels of seven biomarkers; each panel can be used alone, or with additional biomarkers in combination to the seven markers listed. These panels represent enumeration of fitted logistic regression models from a starting set of 26 selected ALLDBRISK, as measured and calculated from a larger base population and meet a predetermined cut off level (0.75 AUC or better).

FIG. 17 depicts selected particularly useful combinations of panels of eight biomarkers; each panel can be used alone, or with additional biomarkers in combination to the eight markers listed. These panels represent enumeration of fitted logistic regression models from a starting set of 18 selected ALLDBRISK, as measured and calculated from a larger base population and meet a predetermined cut off level (0.75 AUC or better).

FIG. 18 depicts selected particularly useful combinations of panels of nine biomarkers; each panel can be used alone, or with additional biomarkers in combination to the nine markers listed. These panels represent enumeration of fitted logistic regression models from a starting set of 18 selected ALLDBRISK, as measured and calculated from a larger base population and meet a predetermined cut off level (0.75 AUC or better).

FIG. 19 depicts selected particularly useful combinations of panels of ten biomarkers; each panel can be used alone, or with additional biomarkers in combination to the ten markers listed. These panels represent enumeration of fitted logistic regression models from a starting set of 185 selected ALLDBRISK, as measured and calculated from a larger base population and meet a predetermined cut off level (0.75 AUC or better).

FIG. 20 depicts selected particularly useful combinations of panels of eleven biomarkers; each panel can be used alone, or with additional biomarkers in combination to the eleven markers listed. These panels represent enumeration of fitted logistic regression models from a starting set of 18 selected ALLDBRISK, as measured and calculated from a larger base population and meet a predetermined cut off level (0.75 AUC or better).

FIG. 21 depicts selected particularly useful combinations of panels of twelve biomarkers; each panel can be used alone, or with additional biomarkers in combination to the twelve markers listed. These panels represent enumeration of fitted logistic regression models from a starting set of 18 selected ALLDBRISK, as measured and calculated from a larger base population and meet a predetermined cut off level (0.75 AUC or better).

FIG. 22 depicts selected particularly useful combinations of panels of thirteen biomarkers; each panel can be used alone, or with additional biomarkers in combination to the thirteen markers listed. These panels represent enumeration of fitted logistic regression models from a starting set of 18 selected ALLDBRISK, as measured and calculated from a larger base population and meet a predetermined cut off level (0.75 AUC or better).

FIG. 23 depicts selected particularly useful combinations of panels of fourteen biomarkers; each panel can be used alone, or with additional biomarkers in combination to the fourteen markers listed. These panels represent enumeration of fitted logistic regression models from a starting set of 18 selected ALLDBRISK, as measured and calculated from a larger base population and meet a predetermined cut off level (0.75 AUC or better).

FIG. 24 depicts selected particularly useful combinations of panels of fifteen biomarkers; each panel can be used alone, or with additional biomarkers in combination to the fifteen markers listed. These panels represent enumeration of fitted logistic regression models from a starting set of 18 selected ALLDBRISK, as measured and calculated from a larger base population and meet a predetermined cut off level (0.75 AUC or better).

FIG. 25 depicts selected particularly useful combinations of panels of sixteen biomarkers; each panel can be used alone, or with additional biomarkers in combination to the sixteen markers listed. These panels represent enumeration of fitted logistic regression models from a starting set of 18 selected ALLDBRISK, as measured and calculated from a larger base population and meet a predetermined cut off level (0.75 AUC or better).

FIG. 26 depicts selected particularly useful combinations of panels of seventeen biomarkers; each panel can be used alone, or with additional biomarkers in combination to the six markers listed. These panels represent enumeration of fitted logistic regression models from a starting set of 18 selected ALLDBRISK, as measured and calculated from a larger base population and meet a predetermined cut off level (0.75 AUC or better).

FIGS. 27-35 depict selected particularly useful combinations of panels of glucose, at least three protein biomarkers and at least one lipid metabolite.

DETAILED DESCRIPTION

Figure 1:
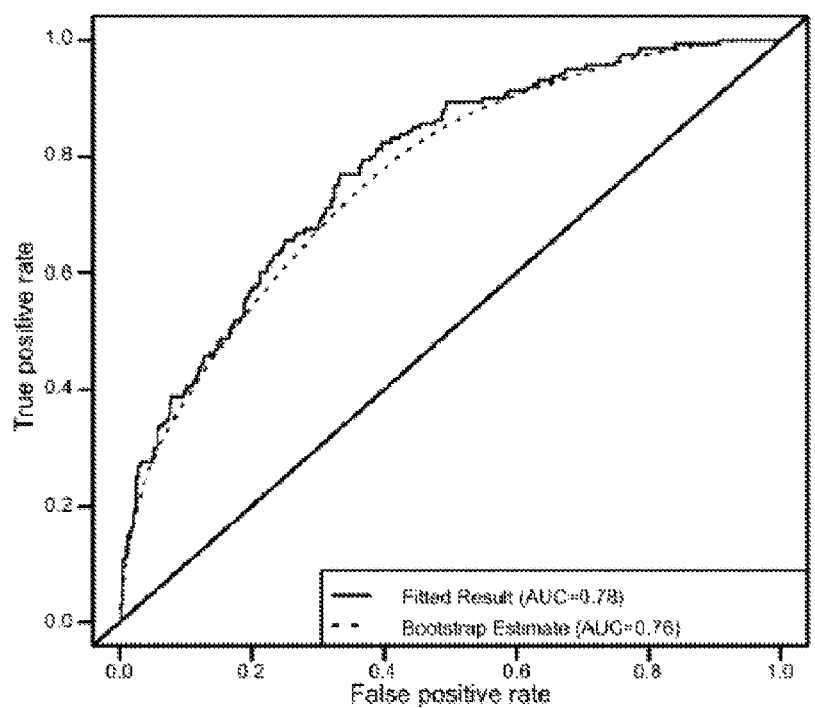
FIG. 1 provides the performance and validation of a model to assess risk of 5-year incidence of type 2 diabetes in the Inter99 cohort. ROC curves for a model that uses the levels of six biomarkers—fasting serum ADIPOQ, CRP, insulin, FTH1, and IL2RA, and fasting plasma glucose—that was developed using the entire data set (all 632 converters and non-converters, solid line), and validated using a bootstrap re-sampling approach (dotted line).

This invention includes a set of biological markers, including protein biomarkers and lipid metabolites, and an associated multivariate algorithm that provides significant discriminatory improvement when compared to current standards of care in assessing risk for Diabetes. This set of markers incorporates clinical measures, protein biomarkers, and lipid metabolites.

A key methodological component in this invention is the extraction of a relatively few number of the most informative markers out of a large set of potential marker candidates using a stepwise procedure of univariate and multivariate performance assessment and considerations of analytical stability/development. One noteworthy feature of this invention is the combination of proteins and lipid metabolites (and optionally other factors including blood glucose) in a single multivariate algorithm that provides better discriminatory performance over OGTT and any single class of markers alone.

The present invention relates to the identification of biomarkers associated with subjects having Diabetes, pre-Diabetes, or a pre-diabetic condition, or who are pre-disposed to developing Diabetes, pre-Diabetes, or a pre-diabetic condition. Accordingly, the present invention features methods for identifying subjects who are at risk of developing Diabetes, pre-Diabetes, or a pre-diabetic condition, including those subjects who are asymptomatic for Diabetes, pre-Diabetes, or a pre-diabetic condition by detection of the biomarkers disclosed herein. These biomarkers are also useful for monitoring subjects undergoing treatments and therapies for Diabetes, pre-Diabetes, or pre-diabetic conditions, and for selecting or modifying therapies and treatments that would be efficacious in subjects having Diabetes, pre-Diabetes, or a pre-diabetic condition, wherein selection and use of such treatments and therapies slow the progression of Diabetes, pre-Diabetes, or pre-diabetic conditions, or prevent their onset.

A list of 272 biomarkers (collectively referred to as ALL-DBRISK) are set out as Table 7 below, these biomarkers are analyte-based or individual history-based biomarkers for use in the present invention. A preferred subset of protein biomarkers for use in the present invention are set out in Table 1.

A prioritized list of markers was developed from 3 nested case control studies, Inter-99 (n=632), Botnia (n=387) and Joslin (n=94). The different studies had different objectives but all created models related to the development of diabetes. In Inter-99 markers were selected based on common marker selection techniques (e.g. stepwise selection, backward selection, univariate significance) individually or under 100 bootstrap replicates. Markers were ranked for each criteria and sorted by the average rank. The average ranking was categorized into four categories, always selected, often selected (>50% of the time), sometimes selected (<50%) and not selected. This prioritization scheme was repeated for the impaired fasting glucose subset and the normal fasting glucose subset. The Botnia data set was analyzed in a manner consistent with inter-99. The Joslin data set developed three models predicting 2 hour glucose after an oral glucose challenge (OGTT), Insulin sensitivity (CISI) and insulin resistance (Delta Insulin) and markers were selected using common selection techniques (univariate, forward, backward, or stepwise selection) under 100 bootstrap replicates. Significance of marker counts was judged by repeating the marker selection criteria on many permuted outcomes. Markers were divided into 4 categories as follows. always selected were those markers selected when all markers were allowed into the model, often selected were those models selected after removing glucose and insulin from consideration, sometimes selected are those models when all glycemic indices (Glucose, insulin, HbA1c, Fructosamine) are removed, and not selected.

TABLE 1

Preferred Protein Biomarkers

| Official Name | Entrez Gene Link |
| --- | --- |
| adiponectin, C1Q and collagen domain containing | ADIPOQ |
| advanced glycosylation end product-specific receptor | AGER |
| Angiogenin, ribonuclease, RNase A family, 5 | ANG |
| complement component 3 | C3 |
| chemokine (C-C motif) ligand 2 | CCL2 |
| cyclin-dependent kinase 5 | CDK5 |
| C-reactive protein, pentraxin-related | CRP |
| Fas ligand (TNF superfamily, member 6) | FASLG |

TABLE 1-continued

Preferred Protein Biomarkers

| Official Name | Entrez Gene Link |
| --- | --- |
| fibrinogen alpha chain | FGA |
| | FRUCTOSAMINE |
| Ferritin | FTH1 |
| glutamic-pyruvate transaminase (alanine aminotransferase) | GPT |
| Hemoglobin A1c | HBA1C |
| hepatocyte growth factor (hepapoietin A; scatter factor) | HGF |
| heat shock 70 kDa protein 1B | HSPA1B |
| insulin-like growth factor binding protein 1 | IGFBP1 |
| insulin-like growth factor binding protein 2 | IGFBP2 |
| insulin-like growth factor binding protein 3 | IGFBP3 |
| interleukin 18 (interferon-gamma-inducing factor) | IL18 |
| interleukin 2 receptor, alpha | IL2RA |
| inhibin, beta A (activin A, activin AB alpha polypeptide) | INHBA |
| insulin | INSULIN-M |
| leptin (obesity homolog, mouse) | LEP |
| matrix metallopeptidase 9 (gelatinase B, 92 kDa gelatinase, 92 kDa type IV collagenase) | MMP9 |
| plasminogen activator, tissue | PLAT |
| serpin peptidase inhibitor, clade E (nexin, plasminogen activator inhibitor type 1), member 1 | SERPINE1 |
| tumor necrosis factor receptor superfamily, member 1A | TNFRSF1A |
| vascular endothelial growth factor | VEGF |
| von Willebrand factor | VWF |

In one embodiment, the invention provides novel panels of biomarkers which can be measured and used to evaluate the risk that an individual will develop Diabetes in the future, for example, the risk that an individual will develop Diabetes in the next 1, 2, 2.5, 5, 7.5, or 10 years. Exemplary preferred panels are shown in FIGS. 8-26. Each panel depicted in a Figure is contemplated as an individual embodiment of the invention, when combined with one or more lipid metabolite biomarker as described herein in detail. Each panel defines a set of markers that can be employed with one or more lipid metabolites biomarkers for methods, improvements, kits, computer readable media, systems, and other aspects of the invention which employ such sets of markers.

In addition, FIGS. 27-31 provide exemplary preferred combinations of glucose, at least three protein biomarkers and at least one lipid metabolite. Each panel depicted in a Figure is contemplated as an individual embodiment of the invention, when combined with one or more lipid metabolite biomarker as described herein in detail. Each panel defines a set of markers that can be employed for methods, improvements, kits, computer readable media, systems, and other aspects of the invention which employ such sets of markers.

A list of lipid metabolite biomarkers is set out in Table 3 below. A preferred subset of the lipid metabolite biomarkers for use in the present invention are set out in Table 2:

TABLE 2

Lipid Metabolites

| | | | |
| --- | --- | --- | --- |
| AC6:0 | AC8:0 | AC10:0 | CE16:0 |
| CE16:1n7 | CE18:0 | CE18:3n6 | CE18:1n9 |
| CE 18:2n6 | CE20:3n6 | CE20:4n3 | TGTL |
| DG16:0 | DG18:0 | DG18:1n9 | DG18:2n6 |
| DG18:3n3 | DGTL | FA16:0 | FA16:1n7 |
| FA18:1n9 | FA18:2n6 | FA24:0 | LY16:1n7 |
| LY18:1n7 | LY18:1n9 | LY18:2n6 | PC16:1n7 |
| PC18:2n6 | PC18:3n6 | PC18:1n7 | PC20:3n9 |
| PC22:4n6 | PC22:5n3 | PCdm18:0 | PCdm18:1n9 |

TABLE 2-continued

Lipid Metabolites

| PCdm16:0 | PC20:3n6 | PC20:4n3 | PEdm18:1n9 |
| PE16:1n7 | PE18:2n6 | PE20:2n6 | PE22:0 |
| PE24:1n9 | PEdm18:0 | TG16:0 | TG16:1n7 |
| TG18:0 | TG18:1n7 | TG18:1n9 | TG18:2n6 |
| TG18:3n3 | | | |

The complete disclosures of International Patent Application Nos. PCT/US2008/002357 (Lipomics Technologies, Inc., published as WO 2008/106054 on 4 Sep. 2008) and PCT/US2008/060830 (Tethys Bioscience, published as WO 2008/131224 on 30 Oct. 2008); and related U.S. patent application Ser. Nos. 12/528,065 and 12/501,385 (Tethys, Publication No. 2009/0271124, 29 Oct. 2009) are incorporated herein in their entireties.

DEFINITIONS

"A", "an" and "the" include plural references unless the context clearly dictates otherwise.

As used herein "body fluid" includes, but is not limited to, fluids such as blood, plasma, serum, isolated lipoprotein fractions, saliva, urine, lymph, cerebrospinal fluid, and bile.

"Lipid class", as used herein, indicates classes of lipids such as, for example, neutral lipids, phospholipids, free fatty acids, total fatty acids, triglycerides, cholesterol esters, phosphatidylcholines, phosphatidylethanolamines, diglycerides, lysophatidylcholines, free cholesterol, monoacylglycerides, phosphatidylglycerol, phosphatidylinositol, phosphatidylserine, and sphingomyelin.

Chemical terms, unless otherwise defined, are used as known in the art.

It is understood that wherever embodiments are described herein with the language "comprising," otherwise analogous embodiments described in terms of "consisting of" and/or "consisting essentially of" are also provided.

As used herein, metabolites (or other biomarkers) that are "positively associated" or "positively correlated" with a condition or disorder include those metabolites whose levels or concentrations generally increase with the disorder relative to normal control subjects or a normal control reference. Metabolites (or other biomarkers) that are "negatively associated" or "negatively correlated" with a condition or disorder generally include those metabolites whose levels or concentrations decrease with the disorder relative to normal control subjects or a normal control reference.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"Biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors, non-analyte physiological markers of health status, or other factors or markers not measured from samples (e.g., biological samples such as bodily fluids), such as "clinical parameters" defined herein, as well as "traditional laboratory risk factors", also defined herein. Biomarkers also include any calculated indices created mathematically or combinations of any one or more of the foregoing measurements, including temporal trends and differences. The term "analyte" as used herein can mean any substance to be measured and can encompass electrolytes and elements, such as calcium.

Clinical parameters" or "CPs" encompasses all non-sample or non-analyte biomarkers of subject health status or other characteristics, such as, without limitation, age (AGE), race or ethnicity (RACE), gender (SEX), diastolic blood pressure (DBP) and systolic blood pressure (SBP), family history (FHX, including FHx1 for 1 parent and FHx2 for 2 parents), height (HT), weight (WT), waist (Waist) and hip (Hip) circumference, Waist-Hip ratio (WHr), body-mass index (BMI), past Gestational Diabetes Mellitus (GDM), and resting heart rate.

"Consideration" encompasses anything of value, including, but not limited to, monetary consideration, as well as non-monetary consideration including, but not limited to, related services or products, discounts on services or products, favored supplier relationships, more rapid reimbursements, etc.

"Diabetic condition" in the context of the present invention comprises type I and type II Diabetes mellitus, and pre-Diabetes (defined herein). It is also known in the art that Diabetic-related conditions include Diabetes and the pre-diabetic condition (defined herein).

"Diabetes mellitus" in the context of the present invention encompasses Type 1 Diabetes, both autoimmune and idiopathic and Type 2 Diabetes (referred to herein as "Diabetes" or "T2DM"). The World Health Organization defines the diagnostic value of fasting plasma glucose concentration to 7.0 mmol/l (126 mg/dl) and above for Diabetes mellitus (whole blood 6.1 mmol/l or 110 mg/dl), or 2-hour glucose level greater than or equal to 11.1 mmol/L (greater than or equal to 200 mg/dL). It may also be possible to diagnose Diabetes based on an HbA1c level of greater than 6%, for instance, ≥6.5%. Other values suggestive of or indicating high risk for Diabetes mellitus include elevated arterial pressure greater than or equal to 140/90 mm Hg; elevated plasma triglycerides (greater than or equal to 1.7 mmol/L; 150 mg/dL) and/or low HDL-cholesterol (<0.9 mmol/L, 35 mg/dl for men; <1.0 mmol/L, 39 mg/dL women); central obesity (males: waist to hip ratio>0.90; females: waist to hip ratio>0.85) and/or body mass index exceeding 30 kg/m2; microalbuminuria, where the urinary albumin excretion rate greater than or equal to 20 μg/min or albumin:creatinine ratio greater than or equal to 30 mg/g).

"Gestational Diabetes" refers to glucose intolerance during pregnancy. This condition results in high blood sugar that starts or is first diagnosed during pregnancy.

"FN" is false negative, which for a disease state test means classifying a disease subject incorrectly as non-disease or normal.

"FP" is false positive, which for a disease state test means classifying a normal subject incorrectly as having disease.

The terms "formula," "algorithm," and "model" are used interchangeably for any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use for the biomarkers are linear and non-linear equations and statistical classification analyses to determine the relationship between levels of biomarkers detected in a subject sample and the subject's risk of Diabetes. In panel and combination construction, of particular interest are structural and syntactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shruken Centroids (SC), StepAIC, Kth-Nearest Neighbor, Boosting, Decision Trees, Neural Networks, Bayesian Networks, Support Vector Machines, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, or kernel principal components analysis algorithms, among others. Many of these techniques are useful either combined with a ALLDBRISK selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as LeaveOne-Out (LOO) and 10-Fold cross-validation (10-Fold CV). A "DRS Formula" is a formula developed as described herein and used to calculate a Diabetes risk score from inputs comprising the results from biomarker testing as described herein. A DRS Formula is the preferred means for calculating a Diabetes risk score.

A "Health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (aka zero predicted subject outcome misclassifications or FP and FN), which all performance measures will favor over imperfection, but to differing degrees.

"Impaired glucose tolerance" (IGT) is a pre-diabetic condition defined as having a blood glucose level that is higher than normal, but not high enough to be classified as Diabetes Mellitus. A subject with IGT will have two-hour glucose levels of 140 to 199 mg/dL (7.8 to 11.0 mmol) on the 75-g oral glucose tolerance test. These glucose levels are above normal but below the level that is diagnostic for Diabetes. Subjects with impaired glucose tolerance or impaired fasting glucose have a significant risk of developing Diabetes and thus are an important target group for primary prevention.

"Insulin resistance" refers to a diabetic or pre-diabetic condition in which the cells of the body become resistant to the effects of insulin, that is, the normal response to a given amount of insulin is reduced. As a result, higher levels of insulin are needed in order for insulin to exert its effects.

The oral glucose tolerance test (OGTT) is principally used for diagnosis of Diabetes Mellitus or pre-diabetic conditions when blood glucose levels are equivocal, during pregnancy, or in epidemiological studies (Definition, Diagnosis and Classification of Diabetes Mellitus and its Complications, Part 1, World Health Organization, 1999). The OGTT should be administered in the morning after at least 3 days of unrestricted diet (greater than 150 g of carbohydrate daily) and usual physical activity. A reasonable (30-50 g) carbohydrate-containing meal should be consumed on the evening before the test. The test should be preceded by an overnight fast of 8-14 hours, during which water may be consumed. After collection of the fasting blood sample, the subject should drink 75 g of anhydrous glucose or 82.5 g of glucose monohydrate in 250-300 ml of water over the course of 5 minutes. For children, the test load should be 1.75 g of glucose per kg body weight up to a total of 75 g of glucose. Timing of the test is from the beginning of the drink. Blood samples must be collected 2 hours after the test load. As previously noted, a diagnosis of impaired glucose tolerance (IGT) has been noted as being only 50% sensitive, with a >10% false positive rate, for a 7.5 year conversion to Diabetes when used at the WHO cut-off points. This is a significant problem for the clinical utility of the test, as even relatively high risk ethnic groups have only a 10% rate of conversion to Diabetes over such a period unless otherwise enriched by other risk factors; in an unselected general population, the rate of conversion over such periods is typically estimated at 5-6%, or less than 1% per annum.

"Measuring" or "measurement" means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4th edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935. Hazard ratios and absolute and relative risk ratios within subject cohorts defined by a test are a further measurement of clinical accuracy and utility. In this last, multiple methods are frequently used to defining abnormal or disease values, including reference limits, discrimination limits, and risk thresholds as per Vasan, "Biomarkers of Cardiovascular Disease: Molecular Basis and Practical Considerations," Circulation 2006, 113: 2335-2362.

Analytical accuracy refers to the repeatability and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, Circulation 2006, 113: 2335-2362.

"Normal glucose levels" is used interchangeably with the term "normoglycemic" and "normal" and refers to a fasting venous plasma glucose concentration of less than 6.1 mmol/L (110 mg/dL). Although this amount is arbitrary, such values have been observed in subjects with proven normal glucose tolerance, although some may have IGT as measured by oral glucose tolerance test (OGTT). Glucose levels above normoglycemic are considered a pre-diabetic condition.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test.

"Positive predictive value" or "PPV" is calculated by TP/(TP+FP) or the true positive fraction of all positive test results. It is inherently impacted by the prevalence of the disease and pre-test probability of the population intended to be tested.

"Pre-Diabetes" or "pre-Diabetic," in the context of the present invention indicates the physiological state, in an individual or in a population, and absent any therapeutic intervention (diet, exercise, pharmaceutical, or otherwise) of having a higher than normal expected rate of disease conversion to frank Type 2 Diabetes Mellitus. Pre-Diabetes can also refer to those subjects or individuals, or a population of subjects or individuals who will, or are predicted to convert to frank Type 2 Diabetes Mellitus within a given time period or time horizon at a higher rate than that of the general, unselected population. Such absolute predicted rate of conversion to frank Type 2 Diabetes Mellitus in pre-Diabetes populations may be as low as 1 percent or more per annum, but preferably 2 percent per annum or more. It may also be stated in terms of a relative risk from normal between quartiles of risk or as a likelihood ratio between differing biomarker and index scores, including those coming from the invention. Unless otherwise noted, and without limitation, when a categorical positive diagnosis of pre-Diabetes is stated here, it is defined experimentally with reference to the group of subjects with a predicted conversion rate to Type 2 Diabetes mellitus of two percent (2%) or greater per annum over the coming 5.0 years, or ten percent (10%) or greater in the entire period, of those testing at a given threshold value (the selected pre-Diabetes clinical cutoff). When a continuous measure of Diabetes conversion risk is produced, pre-Diabetes encompasses any expected annual rate of conversion above that seen in a normal reference or general unselected normal prevalence population. When a complete study is retrospectively discussed in the Examples, pre-Diabetes encompasses the baseline condition of all of the "Converters" or "Cases" arms, each of whom converted to Type 2 Diabetes Mellitus during the study.

In an unselected individual population, pre-Diabetes overlaps with, but is not necessarily a complete superset of, or contained subset within, all those with "pre-diabetic conditions;" as many who will convert to Diabetes in a given time horizon are now apparently healthy, and with no obvious pre-diabetic condition, and many have pre-diabetic conditions but will not convert in a given time horizon; such is the diagnostic gap and need to be fulfilled by the invention. Taken as a population, individuals with pre-Diabetes have a predictable risk of conversion to Diabetes (absent therapeutic intervention) compared to individuals without pre-Diabetes and otherwise risk matched.

"Pre-diabetic condition" refers to a metabolic state that is intermediate between normal glucose homeostasis and metabolism and states seen in frank Diabetes Mellitus. Pre-diabetic conditions include, without limitation, Metabolic Syndrome ("Syndrome X"), Impaired Glucose Tolerance (IGT), and Impaired Fasting Glycemia (IFG). IGT refers to post-prandial abnormalities of glucose regulation, while IFG refers to abnormalities that are measured in a fasting state. The World Health Organization defines values for IFG as a fasting plasma glucose concentration of 6.1 mmol/L (100 mg/dL) or greater (whole blood 5.6 mmol/L; 100 mg/dL), but less than 7.0 mmol/L (126 mg/dL) (whole blood 6.1 mmol/L; 110 mg/dL). Metabolic syndrome according to the National Cholesterol Education Program (NCEP) criteria are defined as having at least three of the following: blood pressure greater than or equal to 130/85 mm Hg; fasting plasma glucose greater than or equal to 6.1 mmol/L; waist circumference>102 cm (men) or >88 cm (women); triglycerides greater than or equal to 1.7 mmol/L; and HDL cholesterol<1.0 mmol/L (men) or 1.3 mmol/L (women). Many individuals with pre-diabetic conditions will not convert to T2DM.

"Risk" in the context of the present invention, relates to the probability that an event will occur over a specific time period, as in the conversion to frank Diabetes, and can can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion. Alternative continuous measures which may be assessed in the context of the present invention include time to Diabetes conversion and therapeutic Diabetes conversion risk reduction ratios.

"Risk evaluation," or "evaluation of risk" in the context of the present invention encompasses making a prediction of the probability, odds, or likelihood that an event or disease state may occur, the rate of occurrence of the event or conversion from one disease state to another, i.e., from a normoglycemic condition to a pre-diabetic condition or pre-Diabetes, or from a pre-diabetic condition to pre-Diabetes or Diabetes. Risk evaluation can also comprise prediction of future glucose, HBA1c scores or other indices of Diabetes, either in absolute or relative terms in reference to a previously measured population. The methods of the present invention may be used to make continuous or categorical measurements of the risk of conversion to Type 2 Diabetes, thus diagnosing and defining the risk spectrum of a category of subjects defined as prediabetic. In the categorical scenario, the invention can be used to discriminate between normal and pre-Diabetes subject cohorts. In other embodiments, the present invention may be used so as to discriminate pre-Diabetes from Diabetes, or Diabetes from normal. Such differing use may require different biomarker combinations in individual panels, mathematical algorithm, and/or cut-off points, but be subject to the same aforementioned measurements of accuracy for the intended use.

A "sample" in the context of the present invention is a biological sample isolated from a subject and can include, by way of example and not limitation, whole blood, serum, plasma, blood cells, endothelial cells, tissue biopsies, lymphatic fluid, ascites fluid, interstitital fluid (also known as "extracellular fluid" and encompasses the fluid found in spaces between cells, including, inter alia, gingival crevicular fluid), bone marrow, cerebrospinal fluid (CSF), saliva, mucous, sputum, sweat, urine, or any other secretion, excretion, or other bodily fluids. "Blood sample" refers to whole blood or any fraction thereof, including blood cells, serum and plasma; serum is a preferred blood sample.

"Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of Diabetes Mellitus, pre-Diabetes, or pre-diabetic conditions. A subject can be male or female. A subject can be one who has been previously diagnosed or identified as having Diabetes, pre-Diabetes, or a pre-diabetic condition, and optionally has already undergone, or is undergoing, a therapeutic intervention for the Diabetes, pre-Diabetes, or prediabetic condition. Alternatively, a subject can also be one who has not been previously diagnosed as having Diabetes, pre-Diabetes, or a pre-diabetic condition. For example, a subject can be one who exhibits one or more risk factors for Diabetes, pre-Diabetes, or a pre-diabetic condition, or a subject who does not exhibit Diabetes risk factors, or a subject who is asymptomatic for Diabetes, pre-Diabetes, or pre-diabetic conditions. A subject can also be one who is suffering from or at risk of developing Diabetes, pre-Diabetes, or a pre-diabetic condition.

"TN" is true negative, which for a disease state test means classifying a non-disease or normal subject correctly.

"TP" is true positive, which for a disease state test means correctly classifying a disease subject.

"Traditional laboratory risk factors" or "TLRFs" correspond to biomarkers isolated or derived from subject samples and which are currently evaluated in the clinical laboratory and used in traditional global risk assessment algorithms, such as Stern, Framingham, Finland Diabetes Risk Score, ARIC Diabetes, and Archimedes. Traditional laboratory risk factors commonly tested from subject blood samples include, but are not limited to, total cholesterol (CHOL), LDL (LDL/LDLC), HDL (HDL/HDLC), VLDL (VLDLC), triglycerides (TRIG), glucose (including, without limitation, the fasting plasma glucose (Glucose) and the oral glucose tolerance test (OGTT)) and HBA1c (HBA1C) levels.

Again, where aspects or embodiments of the invention are described herein in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Quantitative Surrogate Markers for Diabetic Conditions

In some embodiments, the invention provides a method of assessing a diabetic condition. In some embodiments, the assessment of the diabetic condition comprises diagnosing, classifying, identifying, monitoring, determining the likelihood of risk of developing, determining the degree (or severity), and/or assessing the progression and/or regression of the diabetic condition. In some embodiments, the diabetic condition is a prediabetic condition. In some embodiments, the diabetic condition is insulin resistance. In some embodiments, the diabetic condition is impaired glucose tolerance. (The term "impaired glucose tolerance" is used interchangeably herein with "glucose intolerance.") In some embodiments, the diabetic condition is impaired fasting glucose. In some embodiments, the diabetic condition is prediabetes. In some embodiments, the diabetic condition is a form of diabetes.

In some embodiments, the invention provides testing methods that can be used to diagnose, classify, and/or monitor patients with diabetic conditions wherein the condition is selected from the group consisting of: diabetes, type 2 diabetes, insulin resistance, impaired glucose tolerance, impaired fasting glucose, prediabetes, metabolic syndrome, hepatic steatosis, insulin sensitivity, hyperinsulinemia, hepatic steatosis, muscle steatosis, hyperlipidemia, hypercholesterolemia. In some embodiments, the invention provides testing methods that can be used to diagnose, classify, and/or monitor patients with diabetic conditions wherein the condition is selected from the group consisting of: oral glucose intolerance, insulin resistance, insulin sensitivity, hepatic steatosis, type 2 diabetes, and gestational diabetes. In some embodiments, the invention provides testing methods that can be used to diagnose, classify, and/or monitor patients with diabetic conditions wherein the condition is oral glucose intolerance or insulin resistance. In some further embodiments, the invention provides testing methods that can be used to diagnose, classify, and/or monitor patients with diabetic conditions wherein the condition is selected from the group consisting of: non-alcoholic steatohepatitis (NASH), pediatric NASH, obesity, childhood obesity, metabolic syndrome, and polycystic ovary disease.

Diabetes and its related comorbidities and conditions are largely due to changes in the metabolism of lipids. The inventors have discovered that particular amounts of specific lipid metabolites in body fluids correlate with the diabetic condition.

In some aspects, the invention provides metabolic markers for oral glucose intolerance. Impaired glucose tolerance and impaired fasting glucose are known to be pre-diabetic states (Lin et al., Tohoku J. Exp. Med., 212:349-57 (2007)). Impaired oral glucose tolerance has been reported as being a predictor of non-alcoholic fatty liver disease in obese children (Sartorio et al., Eur. J. Clin. Nutr., 61:877-83 (2007)) and of steatoheptatitis and fibrosis in patients with non-alcoholic fatty liver disease (Haukeland et al., Scand. J. Gastroenterol. 40:1469-77 (2005)). The use of oral glucose tolerance testing (OGTT) for detection of gestational diabetes has also been reported (Lapolla et al., J. Clin. Endocrinol. Metab., 2007 Dec. 18 [Epub ahead of print]). In addition, oral glucose intolerance and insulin sensitivity have been linked to Polycystic Ovary Syndrome (Amato et al., Clin Endocrinol. (Oxf), 2007 Nov. 22 [Epub ahead of print]).

In some embodiments, the markers of the invention are used as a substitute for an existing test used to assess a diabetic condition (e.g. fasting blood glucose level or oral glucose tolerance test (OGTT)). In other embodiments, the markers of the invention are used in a test to identify or select a subject for further testing for the diabetic condition via another method including, but not limited to fasting blood glucose level or OGTT.

Diagnostic and Prognostic Indications of the Invention

The invention provides improved diagnosis and prognosis of Diabetes, pre-Diabetes, or a pre-diabetic condition. The risk of developing Diabetes, pre-Diabetes, or a pre-diabetic condition can be detected with a pre-determined level of predictability by measuring various biomarkers such as including, but not limited to, proteins, nucleic acids, polymorphisms, lipid metabolites, and other analytes in a test sample from a subject, and comparing the measured values to reference or index values, often utilizing mathematical algorithms or formula in order to combine information from results of multiple individual biomarkers and from non-analyte clinical parameters into a single measurement or index. Subjects identified as having an increased risk of Diabetes, pre-Diabetes, or a pre-diabetic condition can optionally be selected to receive treatment regimens, such as administration of prophylactic or therapeutic compounds such as "Diabetes-modulating agents" as defined herein, or implementation of exercise regimens or dietary supplements to prevent or delay the onset of Diabetes, pre-Diabetes, or a pre-diabetic condition.

The amount of the biomarker can be measured in a test sample and compared to the "normal control level", utilizing techniques such as reference limits, discrimination limits, or risk defining thresholds to define cutoff points and abnormal values for Diabetes, pre-Diabetes, and pre-diabetic conditions, all as described in Vasan, 2006. The normal control level means the level of one or more biomarkers or combined biomarker indices typically found in a subject not suffering from Diabetes, pre-Diabetes, or a pre-diabetic condition. Such normal control level and cutoff points may vary based on whether a biomarker is used alone or in a formula combining with other biomarkers into an index. Alternatively, the normal control level can be a database of biomarker patterns from previously tested subjects who did not convert to Diabetes over a clinically relevant time horizon.

The present invention may be used to make continuous or categorical measurements of the risk of conversion to Type 2 Diabetes, thus diagnosing and defining the risk spectrum of a category of subjects defined as pre-diabetic. In the categorical scenario, the methods of the present invention can be used to discriminate between normal and pre-Diabetes subject cohorts. In other embodiments, the present invention may be used so as to discriminate pre-Diabetes from Diabetes, or Diabetes from normal. Such differing use may require different biomarker combinations in individual panels, mathematical algorithms, and/or cut-off points, but subject to the same aforementioned measurements of accuracy for the intended use.

Identifying the pre-diabetic subject enables the selection and initiation of various therapeutic interventions or treatment regimens in order to delay, reduce or prevent that subject's conversion to a frank Diabetes disease state. Levels of an effective amount of biomarkers also allows for the course of treatment of Diabetes, pre-Diabetes or a pre-diabetic condition to be monitored. In this method, a biological sample can be provided from a subject undergoing treatment regimens or therapeutic interventions, e.g., drug treatments, for Diabetes. Such treatment regimens or therapeutic interventions can include, but are not limited to, exercise regimens, dietary modification, dietary supplementation, bariatric surgical intervention, administration of pharmaceuticals, and treatment with therapeutics or prophylactics used in subjects diagnosed or identified with Diabetes, pre-Diabetes, or a pre-diabetic condition. If desired, biological samples are obtained from the subject at various time points before, during, or after treatment.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life, or disability) may screen applicants in the process of determining coverage or pricing, or existing clients for possible intervention. Data collected in such population screens, particularly when tied to any clinical progression to conditions like Diabetes, pre-Diabetes, or a pre-diabetic condition, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein. Thus, in a health-related data management system, wherein risk of developing a diabetic condition for a subject or a population comprises analyzing Diabetes risk factors, the present invention provides an improvement comprising use of a data array encompassing the biomarker measurements as defined herein and/or the resulting evaluation of risk from those biomarker measurements.

A machine-readable storage medium can comprise a data storage material encoded with machine readable data or data arrays which, when using a machine programmed with instructions for using said data, is capable of use for a variety of purposes, such as, without limitation, subject information relating to Diabetes risk factors over time or in response to Diabetes-modulating drug therapies, drug discovery, and the like. Measurements of effective amounts of the biomarkers of the invention and/or the resulting evaluation of risk from those biomarkers can implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein. Levels of an effective amount of biomarkers can then be determined and compared to a reference value, e.g. a control subject or population whose diabetic state is known or an index value or baseline value. The reference sample or index value or baseline value may be taken or derived from one or more subjects who have been exposed to the treatment, or may be taken or derived from one or more subjects who are at low risk of developing Diabetes, pre-Diabetes, or a pre-diabetic condition, or may be taken or derived from subjects who have shown improvements in Diabetes risk factors (such as clinical parameters or traditional laboratory risk factors as defined herein) as a result of exposure to treatment. Alternatively, the reference sample or index value or baseline value may be taken or derived from one or more subjects who have not been exposed to the treatment. For example, samples may be collected from subjects who have received initial treatment for Diabetes, pre-Diabetes, or a pre-diabetic condition and subsequent treatment for Diabetes, pre-Diabetes, or a pre-diabetic condition to monitor the progress of the treatment. A reference value can also comprise a value derived from risk prediction algorithms or computed indices from population studies such as those disclosed herein.

Figure 6:
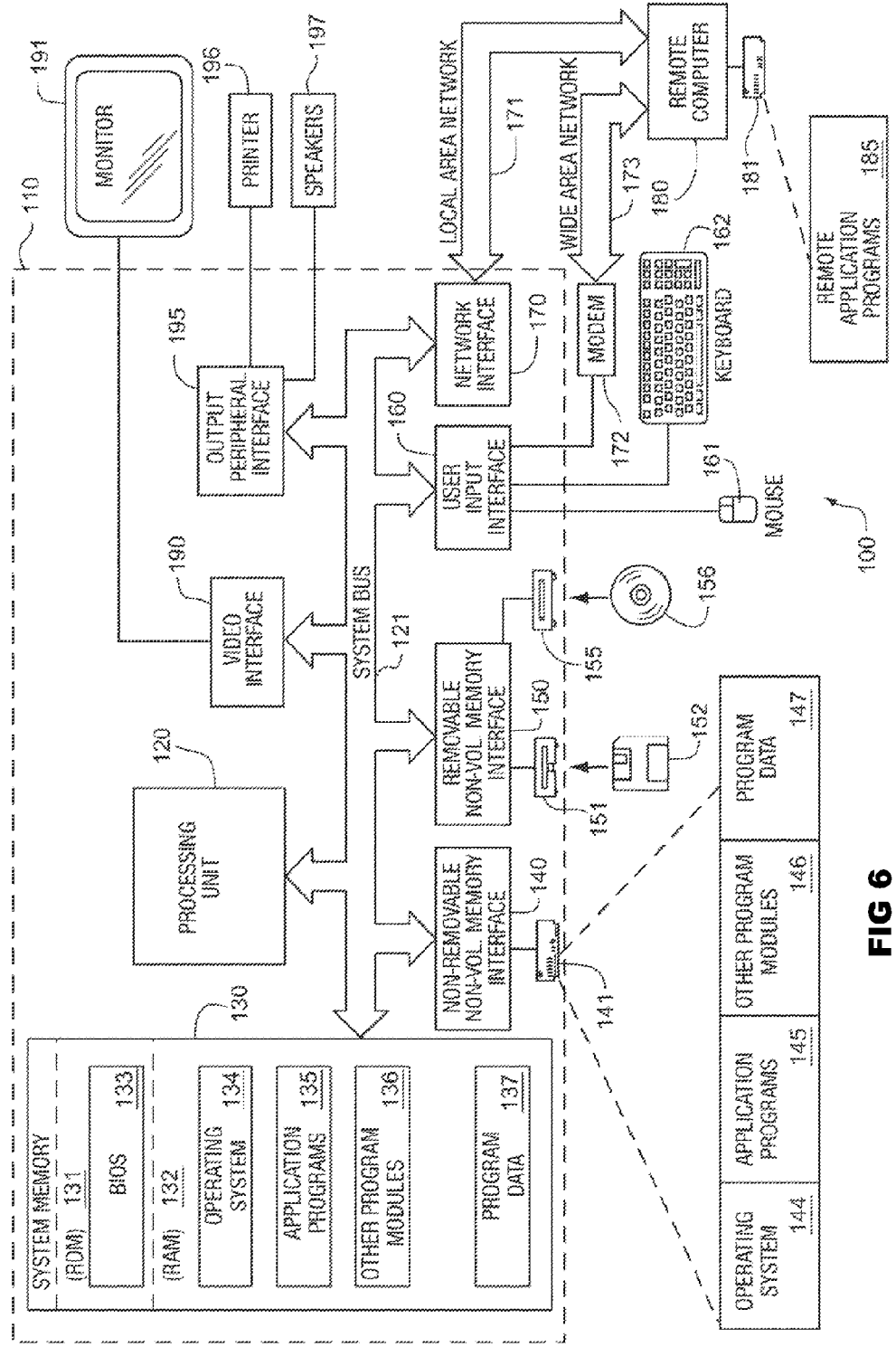
FIG. 6 illustrates an example of a suitable computing system environment 100 on which a system for the steps of the claimed method and apparatus may be implemented.

FIG. 6 illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method of apparatus of the claims. Neither should the computing environment 100 be interpreted as having any dependency or requirement relating to any one or combination of components illustrated in the exemplary operating environment 100.

The steps of the claimed method and system are operational with numerous other general purpose or special purpose computing system environments or configurations. Examples of well known computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like, including those systems, environments, configurations and means described elsewhere within this disclosure.

The steps of the claimed method and system may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In both integrated and distributed computing environments, program modules may be located in both local and remote computer storage media including memory storage devices.

With reference to FIG. 6, an exemplary system for implementing the steps of the claimed method and system includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 6 illustrates operating system 134, application programs 135, other program modules 136, and program data 137.

The computer 110 may also include other removable/non-removable, volatile/nonvolatile computer storage media. By way of example only, FIG. 6 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 6, provide storage of computer readable instructions, data structures, program modules and other data for the computer 110. In FIG. 6, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The biomarkers of the present invention can thus be used to generate a "reference biomarker profile" of those subjects who do not have Diabetes, pre-Diabetes, or a pre-diabetic condition such as impaired glucose tolerance, and would not be expected to develop Diabetes, pre-Diabetes, or a pre-diabetic condition. The biomarkers disclosed herein can also be used to generate a "subject biomarker profile" taken from subjects who have Diabetes, pre-Diabetes, or a pre-diabetic condition like impaired glucose tolerance. The subject biomarker profiles can be compared to a reference biomarker profile to diagnose or identify subjects at risk for developing Diabetes, pre-Diabetes or a pre-diabetic condition, to monitor the progression of disease, as well as the rate of progression of disease, and to monitor the effectiveness of Diabetes, pre-Diabetes or pre-diabetic condition treatment modalities. The reference and subject biomarker profiles of the present invention can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other Diabetes-risk algorithms and computed indices such as those described herein.

Differences in the genetic makeup of subjects can result in differences in their relative abilities to metabolize various drugs, which may modulate the symptoms or risk factors of Diabetes, pre-Diabetes or a pre-diabetic condition. Subjects that have Diabetes, pre-Diabetes, or a pre-diabetic condition, or at risk for developing Diabetes, pre-Diabetes, or a pre-diabetic condition can vary in age, ethnicity, body mass index (BMI), total cholesterol levels, blood glucose levels, blood pressure, LDL and HDL levels, and other parameters. Accordingly, use of the biomarkers disclosed herein, both alone and together in combination with known genetic factors for drug metabolism, allow for a pre-determined level of predictability that a putative therapeutic or prophylactic to be tested in a selected subject will be suitable for treating or preventing Diabetes, pre-Diabetes, or a pre-diabetic condition in the subject.

To identify therapeutics or drugs that are appropriate for a specific subject, a test sample from the subject can also be exposed to a therapeutic agent or a drug, and the level of one or more biomarkers can be determined. The level of one or more biomarkers can be compared to sample derived from the subject before and after treatment or exposure to a therapeutic agent or a drug, or can be compared to samples derived from one or more subjects who have shown improvements in Diabetes or pre-Diabetes risk factors (e.g., clinical parameters or traditional laboratory risk factors) as a result of such treatment or exposure.

Agents for reducing the risk of Diabetes, pre-Diabetes, pre-diabetic conditions, or diabetic complications include, without limitation of the following, insulin, hypoglycemic agents, anti-inflammatory agents, lipid reducing agents, anti-hypertensives such as calcium channel blockers, beta-adrenergic receptor blockers, cyclooxygenase-2 inhibitors, angiotensin system inhibitors, ACE inhibitors, rennin inhibitors, together with other common risk factor modifying agents (herein "Diabetes-modulating drugs").

The term "insulin (INS)" includes mature insulin (insulin-M), pro-insulin and soluble c-peptide (SCp). "Insulin" includes rapid acting forms, such as Insulin lispro rDNA origin: HUMALOG (1.5 mL, 10 mL, Eli Lilly and Company, Indianapolis, Ind.), Insulin Injection (Regular Insulin) form beef and pork (regular ILETIN I, Eli Lilly], human: rDNA: HUMULIN R (Eli Lilly), NOVOLIN R (Novo Nordisk, New York, N.Y.), Semisynthetic: VELOSULIN Human (Novo Nordisk), rDNA Human, Buffered: VELOSULIN BR, pork: regular Insulin (Novo Nordisk), purified pork: Pork Regular ILETIN II (Eli Lilly), Regular Purified Pork Insulin (Novo Nordisk), and Regular (Concentrated) ILETIN II U-500 (500 units/mL, Eli Lilly); intermediate-acting forms such as Insulin Zinc Suspension, beef and pork: LENTE ILETIN G I (Eli Lilly), Human, rDNA: HUMULIN L (Eli Lilly), NOVOLIN L (Novo Nordisk), purified pork: LENTE ILETIN II (Eli Lilly), Isophane Insulin Suspension (NPH): beef and pork: NPH ILETIN I (Eli Lilly), Human, rDNA: HUMULIN N (Eli Lilly), Novolin N (Novo Nordisk), purified pork: Pork NPH Iletin II (Eli Lilly), NPH-N (Novo Nordisk); and long-acting forms such as Insulin zinc suspension, extended (UL-TRALENTE, Eli Lilly), human, rDNA: HUMULIN U (Eli Lilly).

A subject cell (i.e., a cell isolated from a subject) can be incubated in the presence of a candidate agent and the pattern of biomarker expression in the test sample is measured and compared to a reference profile, e.g., a Diabetes reference expression profile or a non-Diabetes reference expression profile or an index value or baseline value. The test agent can be any compound or composition or combination thereof. For example, the test agents are agents frequently used in Diabetes treatment regimens and are described herein.

Additionally, any of the aforementioned methods can be used separately or in combination to assess if a subject has shown an "improvement in Diabetes risk factors" or moved within the risk spectrum of pre-Diabetes. Such improvements include, without limitation, a reduction in body mass index (BMI), a reduction in blood glucose levels, an increase in HDL levels, a reduction in systolic and/or diastolic blood pressure, an increase in insulin levels, or combinations thereof.

A subject suffering from or at risk of developing Diabetes or a pre-diabetic condition may also be suffering from or at risk of developing arteriovascular disease, hypertension, or obesity. Type 2 Diabetes in particular and arteriovascular disease have many risk factors in common, and many of these risk factors are highly correlated with one another. The relationship among these risk factors may be attributable to a small number of physiological phenomena, perhaps even a single phenomenon. Subjects suffering from or at risk of developing Diabetes, arteriovascular disease, hypertension or obesity are identified by methods known in the art.

Because of the interrelationship between Diabetes and arteriovascular disease, some or all of the individual biomarkers and biomarker panels of the present invention may overlap or be encompassed by biomarkers of arteriovascular disease, and indeed may be useful in the diagnosis of the risk of arteriovascular disease.

Mole Percentage Fatty Acid Compositions as Surrogates for Diabetic Conditions

A lipid metabolite that is a relative proportion of a triglyceride (or any other lipid class) can be measured in a body fluid, such as serum or plasma, as a quantitative measure of the relative proportion of that lipid metabolite in hepatic triglycerides (or other lipid class). If this relative proportion of lipid metabolite (or a collection of lipid metabolites) correlates with insulin resistance, it serves as a quantitative surrogate of the insulin resistance. Thus, the mole percentage of a particular fatty acid within a particular lipid class may be used as a quantitative surrogate for insulin resistance.

In one embodiment, the mole percentage of a single lipid metabolite may be used in the methods of the invention. In other embodiments, mole percentages of two or more lipid metabolites may be used in the methods of the invention, for example, 2, 3, 4, 5, 10, 15, 20, or more lipid metabolites.

According to the present invention, when analyzing the effects rendered by two or more lipid metabolites, one can either evaluate the effects of these lipid metabolites individually or obtain the net effect of these lipid metabolites, e.g., by using various mathematical formulas or models to quantify the effect of each lipid metabolite. A formula containing the levels of one or more lipid metabolites as variables includes any mathematical formula, model, equation, or expression established based on mathematic or statistical principles or methods using the values of one or more lipid metabolites as variables. As described herein, mathematical formulas or models can be used to evaluate and weigh the effects of lipid metabolism in combination with protein biomarkers and/or other factors.

In general, any suitable mathematic analyses can be used to analyze the net effect of two or more lipid metabolites (or one or more lipid metabolites in combination with protein biomarkers or other factors) with respect to projecting the diabetic condition of a subject. For example, methods such as multivariate analysis of variance, multivariate regression, multiple regression can be used to determine relationships between dependent variables, and independent variables. Clustering, including both hierarchical and nonhierarchical methods, as well as nonmetric Dimensional Scaling can be used to determine associations among variables and among changes in those variables.

In addition, principle component analysis is a common way of reducing the dimension of studies, and can be used to interpret the variance-covariance structure of a data set. Principle components may be used in such applications as multiple regression and cluster analysis. Factor analysis is used to describe the covariance by constructing "hidden" variables from the observed variables. Factor analysis may be considered an extension of principle component analysis, where principle component analysis is used as parameter estimation along with the maximum likelihood method. Furthermore, simple hypothesis such as equality of two vectors of means can be tested using Hotelling's T squared statistic.

In one embodiment, a formula containing one or more lipid metabolites (optionally in combination with one or more protein biomarkers or other factors) as variables is established by using regression analyses, e.g., multiple linear regressions. Examples of formulas developed include, without any limitation, the following:

$$k+k_1(FA_1)+k_2(FA_2)+k_3(FA_3) \quad \text{Formula I}$$

$$k-k_1(FA_1)+k_2(FA_2)+k_3(FA_3) \quad \text{Formula II}$$

$$k+k_1(FA_1)-k_2(FA_2)+k_3(FA_3) \quad \text{Formula III}$$

$$k+k_1(FA_1)+k_2(FA_2)-k_3(FA_3) \quad \text{Formula IV}$$

$$k-k_1(FA_1)-k_2(FA_2)+k_3(FA_3) \quad \text{Formula V}$$

$$k+k_1(FA_1)-k_2(FA_2)-k_3(FA_3) \quad \text{Formula VI}$$

$$k-k_1(FA_1)+k_2(FA_2)-k_3(FA_3) \quad \text{Formula VII}$$

$$k-k_1(FA_1)-k_2(FA_2)-k_3(FA_3) \quad \text{Formula VIII}$$

The formulas may use one or more lipid metabolites (optionally in combination with one or more protein biomarkers or other factors) as variables, such as 1, 2, 3, 4, 5, 10, 15, 20, or more lipid metabolites. The constants of these formulas can be established by using a set of data obtained from known diabetic conditions. Usually the levels of lipid metabolites used in these formulas can be either the levels at a time point or changes of levels over a period of time.

According to the invention, mathematic formulas established using lipid metabolites can be used to either qualitatively or quantitatively assess the diabetic condition of a subject over a period of time. For example, a formula having one or more lipid metabolites as variables can be used to directly calculate the diabetic condition of a subject. In addition, the net value of a formula containing one or more lipid metabolites can be compared to the standard value of such formula corresponding to a diabetic condition pattern, e.g. progression or regression of a diabetic condition, and the results of such comparison can be used to project diabetic condition development. Specifically, a subject having a net value of a formula similar to or within the range of the standard value of such formula that is assigned to or associated with a progression of a diabetic condition is likely to experience a progression over a period of time. Similarly, a subject having a net value of a formula similar to or within the range of the standard values of such formula that is assigned to or associated with a regression is likely to experience a regression of their diabetic condition over a period of time.

Additional Quantitative Surrogates for Diabetic Condition

Models of lipid metabolites other than mole percentage may be used as surrogate markers for a diabetic condition. For example see the list of additional biomarkers, e.g. eicosanoids.

Lipid Metabolites and Additional Biomarkers for Diabetic Conditions

In some embodiments, one or more lipid metabolites are used as metabolite markers for assessing diabetic conditions. In some other embodiments, the metabolite markers used comprise both lipid metabolites and additional biomarkers.

In one embodiment, lipid metabolites include a fatty acid present within a particular lipid class. In one embodiment, the lipid class is selected from the group consisting of neutral lipids, phospholipids, free fatty acids, total fatty acids, triglycerides, cholesterol esters, phosphatidylcholines, and phosphatidylethanolamines. In one embodiment, the lipid class is free fatty acids. In one embodiment, the lipid class is total fatty acids. In one embodiment, the lipid class is triglycerides. In one embodiment, the lipid class is cholesterol esters. In one embodiment, the lipid class is phosphatidylcholines. In one embodiment, the lipid class is phosphatidylethanolamines. In one embodiment, the lipid metabolite is selected from the fatty acids shown in Table 3. The method may involve measuring the amount of more than one lipid metabolite, such as 2, 3, 4, 5, 10, 15, 20, or more lipid metabolites. In one embodiment, two or more lipid metabolites in Table 3 are measured. In one embodiment, three or more lipid metabolites in Table 3 are measured.

In one embodiment, the lipid metabolite is positively correlated with a diabetic condition. In one embodiment, the lipid metabolite is negatively correlated with diabetic condition. In one embodiment, the lipid metabolite is measured as a relative amount within that particular lipid class. In one embodiment, the lipid metabolite is measured in a blood-based body fluid, such as blood, plasma, serum, or lipoprotein fractions.

TABLE 3

Blood-based Lipid Metabolite Markers of Diabetic Condition

| | | | | |
|---|---|---|---|---|
| CE14.0 | FA16.0 | PC14.0 | PE16.0 | TG20.2n6 |
| CE16.0 | FA16.1n7 | PC16.1n7 | PE20.0 | TG20.3n6 |
| CE20.0 | FA18.0 | PC18.0 | PE16.1n7 | TG20.3n9 |
| CE16:1n7 | FA18.1n9 | PC15.0 | PE18.1n9 | TG22.2n6 |
| CE18.1n7 | FA18.1n7 | PC18.1n7 | PE18:3n6 | TG22:4n6 |
| CE18.1n9 | FA18.2n6 | PC18.1n9 | PE20.0 | CETotal.LC |
| CE18.2n6 | FA20.4n6 | PC18.2n6 | PE20.1n9 | TGTotal.LC |
| CE18.3n6 | FA22.2n6 | PC18.3n6 | PE20:3n9 | DGTotal.LC |
| CE22:2n6 | FA22.4n6 | PC18.3n3 | PE20:3n6 | FSTotal.LC |
| CE20.3n9 | FA20.5n3 | PC20.1n9 | PE20.4n6 | AC6:0 |
| CE22.5n6 | FA22.6n3 | PC20:3n9 | PE20.5n3 | AC16:0 |
| DG16:0 | FA24.1n9 | PC20:4n3 | PEdm16.0 | AC14:0 |
| DG18.0 | LY18.0 | PC20.2n6 | PEdm18.0 | AC8:0 |
| DG18.2n6 | LY16.1n7 | PC20.4n6 | TG14.0 | AC10:0 |
| DG18.3n6 | LY18:1n7 | PC22.4n6 | TG14.1n5 | AC3:0 |
| DG20:0 | LY18.1n9 | PC22.5n3 | TG16.0 | AC12:0 |
| DG20.3n6 | LY20.3n9 | PCdm16.0 | TG20.0 | L-Carnitine |
| DG20.3n9 | LY18.2n6 | PCdm18.0 | TG16.1n7 | AC4:0 |
| DG22.1n9 | LY20:3n6 | PCdm18.1n9 | TG18.1n7 | CE20:3n6 |
| FA14.0 | LY22:4n6 | PCdm18:1n7 | TG18.1n9 | PE18:1n9 |
| FA15.0 | LY22:5n3 | PE14.0 | TG18.2n6 | TG18:0 |
| TG18:3n3 | TG18:3n3 | FA18:1n7 | PE22:0 | CE18:0 |
| CE20:4n3 | TGTL | DG18:1n9 | DG18:1n9 | DG18:3n3 |
| DGTL | FA16:0 | FA16:1n7 | | |

In some embodiments, the marker(s) for the diabetic condition(s) comprise one or more, two or more, three or more, four or more, five or more, or six or more markers selected from the group consisting of CE16:1n7, CE20:3n6, CE18:2n6, CE16:0, CE18:1n9, LY18:2n6, LY18:1n7 and LY18:1n9.

The following additional biomarkers may aid the diagnosis of diabetic conditions: (1) malonyl-CoA and malonylcarnitine; (2) free carnitine, and acylcarnitines listed in Table 4; and (3) sterols and bile acids listed in Table 5. Body fluid and cellular samples may be used to measure these additional biomarkers. Examples of cellular samples include, but are not limited to, lymphocytes and macrophages.

TABLE 4

List of Acylcarnitine Metabolites

| | | |
|---|---|---|
| L-Carnitine | Butyrobetaine | Acetyl carnitine |
| Propionyl carnitine | Butyryl carnitine | Hexanoyl carnitine |
| Valeryl carnitine | Octanoyl carnitine | Decanoyl carnitine |

TABLE 4-continued

List of Acylcarnitine Metabolites

| | | |
|---|---|---|
| Myristoyl carnitine | Palmitoyl carnitine | Stearoyl carnitine |
| Oleoyl carnitine | Linoleoyl carnitine | Arachidoyl carnitine |
| Dodecanoyl carnitine | | |

TABLE 5

List of Bile Acid and Sterol Metabolites

| | | |
|---|---|---|
| Cholic Acid | Chenodeoxycholic Acid | Deoxycholic Acid |
| Lithocholic Acid | Glycocholic Acid | Taurodeoxycholate |
| Glycochenodeoxycholate | Taurochenodeoxycholate | β-Muricholic Acid |
| Taurolithocholic acid | Ursodeoxycholic acid | Taurodeoxycholic acid |
| Taurocholic acid | Glycodesoxycholic acid | Glycolithocholic acid |
| Glycoursodeoxycholic acid | Cholesterol | Coprostanol |
| Cholestanol | Lanosterol | Lathosterol |
| Beta-Sitosterol | Desmosterol | Campesterol |
| Coprosterol | Lathosterol | Campesterol |
| Stigmasterol | 4-Cholesten-3-One | Fucosterol |

Additionally, the following additional biomarkers may aid in the diagnosis of a diabetic condition: (1) The sterols and bile acids listed in Table 5 (levels increase with increased cholesterol synthesis); (2) Eicosanoids including, but not limited to, those shown in Table 6; and/or (3) Cytokines and chemokines including, but not limited to, TNFα, IL-6, leptin, adiponectin. Body fluid and cellular samples may be used to measure the additional markers. Examples of cellular samples include, but are not limited to, lymphocytes and macrophages.

TABLE 6

List of Eicosanoid Metabolites

| | | |
|---|---|---|
| 13-14-dihydro-15-keto PGA2 | PGB2 | PGD2 |
| PGE2 | 6-keto PGF1a | PGF2a |
| 11b-PGF2a | 15-keto PGF2a | PGJ2 |
| 15-deoxy-o-12,14-PGJ2 | TXB2 | 11-dehydro TXB2 |
| 8-iso-PGF2a | 9-HODE | 13-HODE |
| 5-HETE | 8-HETE | 9-HETE |
| 11-HETE | 12-HETE | 15-HETE |
| 5(S)-HEPE | 12(S)-HEPE | 15(S)-HEPE |
| LTB4 | LTB5 | LTC4 |
| LTD4 | LTE4 | LTF4 |
| Lipoxin A4 | 20-HETE | 12(13)-DiHOME |
| 12(13)-EpOME | 9(10)-EpOME | 5(6)-EpETrE |
| 11(12)-EpETrE | 14(15)-EpETrE | 5,6-DiHETrE |
| 8,9-DiHETrE | 11,12-DiHETrE | 14,15-DiHETrE |
| 14,15-DiHETE | 17,18-DiHETE | 14(15)-EpETE |
| 17(18)-EpETE | 19(20)-DiHDPA | |

Measurements of the amounts of one or more of these additional biomarkers may be used in the methods of the invention, in addition to measurement of a lipid metabolite. In one embodiment, the amount of one of the biomarkers is measured in a sample from the subject. In one embodiment, the amounts of two of the biomarkers are measured in a sample from the subject. In other embodiments, 3, 4, 5, 6, 7, 8, 10, 12, 15, 20, or more of the biomarkers may be measured in a sample from the subject.

Diagnostic Cutoff Values for Selected Markers Associated with Oral Glucose Intolerance:

The concentration of AC6:0 expected to provide utility for diagnosing pre-diabetes and other diabetes-related conditions is between 0.44 and 0.70 nMoles per gram of plasma or serum. A higher value is associated with a more pronounced diabetic state or increased risk.

The concentration of AC8:0 expected to provide utility for diagnosing pre-diabetes and other diabetes-related conditions is between 0.119 and 0.260 nMoles per gram of plasma or serum. A higher value is associated with a more pronounced diabetic state or increased risk.

The concentration of AC10:0 expected to provide utility for diagnosing pre-diabetes and other diabetes-related conditions is between 0.123 and 0.315 nMoles per gram of plasma or serum. A higher value is associated with a more pronounced diabetic state or increased risk.

The concentration of PE20:4n6 expected to provide utility for diagnosing pre-diabetes and other diabetes-related conditions is between 21.30 and 24.15 mole percent of total phosphatidylethanolamine fatty acid composition in plasma or serum. A higher value is associated with a more pronounced diabetic state or increased risk.

The concentration of PC18:0 expected to provide utility for diagnosing pre-diabetes and other diabetes-related conditions is between 12.40 and 14.20 mole percent of total phosphatidylcholine fatty acid composition in plasma or serum. A higher value is associated with a more pronounced diabetic state or increased risk.

The concentration of TG14:0 expected to provide utility for diagnosing pre-diabetes and other diabetes-related conditions is between 0.07 and 0.04 mole percent of total triglyceride fatty acid composition in plasma or serum. A higher value is associated with a more pronounced diabetic state or increased risk.

Methods of Diagnosing and Monitoring

The methods of the invention may be used to diagnose a particular condition, for example diabetes, type 2 diabetes, insulin resistance, impaired glucose tolerance, impaired fasting glucose, prediabetes, metabolic syndrome, hepatic steatosis, insulin sensitivity, hyperinsulinemia, hepatic steatosis, muscle steatosis, hyperlipidemia, hypercholesterolemia. The methods may also be used to assess the severity of a diabetic condition, monitor a diabetic condition, assess the progression or regression of a diabetic condition, and/or monitor the response to a therapy.

For example, a method of diagnosis may comprise determining a relative amount of one or more fatty acids to total fatty acid content in the lipids of one or more lipid classes in a sample from a body fluid of the subject, and correlating that amount with the presence of a diabetic condition. In some embodiments, the method may further comprise the step of comparing the relative amount to a reference, wherein if the relative amount is greater than the reference, diabetes, type 2 diabetes, insulin resistance, impaired glucose tolerance, impaired fasting glucose, prediabetes, metabolic syndrome, hepatic steatosis, insulin sensitivity, hyperinsulinemia, hepatic steatosis, muscle steatosis, hyperlipidemia, hypercholesterolemia. is indicated. In some embodiments, the method may further comprise the step of comparing the relative amount to a reference, wherein if the relative amount is less than the reference, diabetes, type 2 diabetes, insulin resistance, impaired glucose tolerance, impaired fasting glucose, prediabetes, metabolic syndrome, hepatic steatosis, insulin sensitivity, hyperinsulinemia, hepatic steatosis, muscle steatosis, hyperlipidemia, hypercholesterolemia. is indicated.

Similarly, the severity of the diabetic condition may be measured, wherein the relative amount indicates the severity of the diabetic condition. Additionally, the relative amount indicates the current state of the condition, and thus a diabetic condition may be monitored and/or the progression or regression of the condition assessed. The relative amount may be measured at two or more time points. In some embodiments, the relative amount may be measured at 2, 3, 4, 5, 6, 7, 8, 10, 12, 15, 20, or more time points. Each time point may be separated by one or more hours, days, weeks, or months. By measuring the relative amount at more than one time point, the clinician may assess a subject's response to treatment.

Methods of Measurement of Lipid Metabolites and Biomarkers

Assays for lipid metabolite content may be performed on a body fluid or tissue sample. In one embodiment, the assays may be performed on whole blood, plasma, serum, or isolated lipoprotein fractions. Assays for the additional biomarkers may be performed on a body fluid or a cellular sample. These lipid metabolites and other biomarkers may readily be isolated and/or quantified by methods known to those of skill in the art, including, but not limited to, methods utilizing: mass spectrometry (MS), high performance liquid chromatography (HPLC), isocratic HPLC, gradient HPLC, normal phase chromatography, reverse phase HPLC, size exclusion chromatography, ion exchange chromatography, capillary electrophoresis, microfluidics, chromatography, gas chromatography (GC), thin-layer chromatography (TLC), immobilized metal ion affinity chromatography (IMAC), affinity chromatography, immunoassays, and/or colorimetric assays. In one embodiment, the methods of the invention utilize MS to determine lipid metabolite content. In one embodiment, the methods of the invention utilize an immunoassay to determine lipid metabolite content. In one embodiment, the methods of the invention utilize MS to determine the concentration of a biomarker. In one embodiment, the methods of the invention utilize an immunoassay to determine the concentration of a biomarker.

Various analytical methods are well known to those of skill in the art, and are further described in the following documents, which are herein incorporated by reference in their entirety:

Mass Spectrometry: Cyr et al., J Chromatogr B Analyt Technol Biomed Life Sci. 2006 Feb. 17; 832(1):24-9; Vogeser et al., Clin Chem Lab Med. 2003 February; 41(2):117-26.

HPLC: Khalil et al., J Chromatogr B Analyt Technol Biomed Life Sci. 2006 May 23; Fouassier et al., J Thromb Haemost. 2006 May; 4(5):1136-9; Badiou et al., Clin Lab. 2004; 50(3-4):153-8; Brunelli et al., Clin Lab. 2001; 47(7-8): 393-7.

Capillary electrophoresis: Zinellu et al., J Sep Sci. 2006 March; 29(5):704-8; Jabeen et al., Electrophoresis. 2006 May 23; Gao et al., Electrophoresis. 2006 May; 27(9):1784-9.

Microfluidics: Johannessen et al., IEEE Trans Nanobioscience. 2002 March; 1(1):29-36; Herrmann et al., Lab Chip. 2006 April; 6(4):555-60.; Yang et al., ASAIO J. 2005 September-October; 51(5):585-90; Dupuy et al., Clin Chem Lab Med. 2005; 43(12):1291-302.

Chromatography: Paterson et al., Addiction. 2005 December; 100(12):1832-9; Bottcher et al., J Anal Toxicol. 2005 November-December; 29(8):769-76; Julak, Prague Med Rep. 2005; 106(2):175-94; Boettcher et al., Clin Lab. 2000; 46(1-2):49-52.

Immunoassays: Westermann et al., Clin Lab. 2002; 48(1-2):61-71; Aoyagi et al., Clin Lab. 2001; 47(3-4):119-27; Hubl et al., Clin Lab. 2005; 51(11-12):641-5; Haller et al., J Anal Toxicol. 2006 March; 30(2):106-11; Bayer et al., Clin Lab. 2005; 51(9-10):495-504; Groche et al., Clin Lab. 2003; 49(11-12):657-61; Ivan et al., Clin Lab. 2005; 51(7-8):381-7.

Colorimetric assays: Kramer et al., Clin Chem. 2005 November; 51(11):2110-6; Groche et al., Clin Lab. 2003; 49(11-12):657-61; Wolf, Clin Chim Acta. 2006 Mar. 24.

The TrueMass® analytical platform may also be used for the methods of the invention. TrueMass® is an analytical platform that may be used to get quantitative data from serum or plasma on approximately 400 individual metabolites involved in structural and energetic lipid metabolism such as triglyceride, cholesterol ester and phospholipid metabolism. This platform is useful in profiling diseases as structural and energetic lipids are central components of metabolism and integrated into virtually every biological process in the body. A data set for a plasma or serum sample comprises the quantitative measurement of free cholesterol and the following fatty acids from phosphatidylcholines, phosphatidylethanolamines, lysophosphatidylcholines, triglycerides, diglycerides, free fatty acids, and cholesterol esters: 14:0, 15:0, 16:0, 18:0, 20:0, 22:0, 24:0, 14:1n5, 16:1n7, t16:1n7, 18:1n9, t18:1n9, 18:1n7, 18:2n6, t18:2n6, 18:3n6, 18:3n3, 18:4n3, 20:1n9, 20:2n6, 20:3n9, 20:3n6, 20:4n6, 20:3n3, 20:4n3, 20:5n3, 22:1n9, 22:2n6, 22:4n6, 22:5n3, 22:6n3, 24:1n9, 24:6n3 and plasmalogen derivatives of 16:0, 18:0, 18:1n9 and 18:1n7. Methods for using TrueMass® are known to those of skill in the art, and are also described in the following documents, which are herein incorporated by reference in their entirety: U.S. patent application Ser. No. 11/296,829 (filed Dec. 6, 2005; U.S. Patent Publication No. 2006/0084129); Mutch et al., FASEB J. 2005 April; 19(6):599-601.; Stone et al., J Biol Chem. 2004 Mar. 19; 279(12):11767-76; Watkins et al., J. Nutr. 2003 November; 133(11):3386-91; Watkins et al., Lipid Res. 2002 November; 43(11):1809-17.

Use of Metabolite Markers in Combination with Other Indicators/Tests

The invention further provides methods of assessing a diabetic condition that optionally comprise evaluating one or more risk indicators, measuring glucose levels, and/or performing another diagnostic test for a diabetic condition, in addition to measuring the level of one or more metabolite markers described herein. A variety of risk indicators for diabetes are known to those skilled in the art and can include, but are not limited to, the following: age, weight, body mass index (BMI), family history (e.g., relatives with diabetes), medical history (e.g., history of gestational diabetes), ethnic background, high blood pressure, cholesterol levels, and activity level. In some embodiments, glucose levels are measured by fasting plasma glucose (FPG). In some alternative embodiments, glucose levels are measured by oral glucose tolerance test (OGTT). In some embodiments, one or more of the metabolite markers used herein are used in combination with a test for glycosylated hemogoblin in the blood (e.g., HbA1c), to assess a diabetic condition.

In some embodiments, the methods, in addition to comprising measuring one or more metabolite markers such as lipid metabolites, further comprise (1) determining the presence or absence of one or more risk factors for the diabetic condition, and correlating the presence or absence of the risk factor with the presence, risk of developing, or severity of the diabetic condition; and/or (2) measuring the level of an additional biomarker, and correlating the level of the additional biomarker with the presence, risk of developing, or severity of the diabetic condition. In some embodiments, the one or more risk factors are selected from the group consisting of: age, weight, body mass index (BMI), family history, medical history, ethnic background, high blood pressure, cholesterol level, and activity level. In some embodiments, the additional biomarker is selected from the group consisting of blood glucose or glycosylated hemoglobin.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic or prognostic test, assay, or method concerns the ability of the test, assay, or method to distinguish between subjects having Diabetes, pre-Diabetes, or a pre-diabetic condition, or at risk for Diabetes, pre-Diabetes, or a pre-diabetic condition, is based on whether the subjects have an "effective amount" or a "significant alteration" in the levels of a biomarker. By "effective amount" or "significant alteration," it is meant that the measurement of the biomarker is different than the predetermined cut-off point (or threshold value) for that biomarker and therefore indicates that the subject has Diabetes, pre-Diabetes, or a pre-diabetic condition for which the biomarker is a determinant. The difference in the level of biomarker between normal and abnormal is preferably statistically significant and may be an increase in biomarker level or a decrease in biomarker level. As noted below, and without any limitation of the invention, achieving statistical significance, and thus the preferred analytical and clinical accuracy, generally but not always requires that combinations of several biomarkers be used together in panels and combined with mathematical algorithms in order to achieve a statistically significant biomarker index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

Using such statistics, an "acceptable degree of diagnostic accuracy", is herein defined as a test or assay (such as the test of the invention for determining the clinically significant presence of biomarkers, which thereby indicates the presence of Diabetes, pre-Diabetes, or a pre-diabetic condition) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.80, desirably at least 0.85, more desirably at least 0.875, preferably at least 0.90, more preferably at least 0.925, and most preferably at least 0.95.

The predictive value of any test depends both on the sensitivity and specificity of the test, and on the prevalence of the condition in the population being tested. This notion, based on Bayes' theorem, provides that the greater the likelihood that the condition being screened for is present in a subject or in the population (pre-test probability), the greater the validity of a positive test and the greater the likelihood that the result is a true positive. Thus, the problem with using any test in any population where there is a low likelihood of the condition being present is that a positive result has more limited value (i.e., a positive test is more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for developing Diabetes, pre-Diabetes, or a pre-diabetic condition and the bottom quartile comprising the group of subjects having the lowest relative risk for developing Diabetes, pre-Diabetes, or a pre-diabetic condition. Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy." Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future cardiovascular events. Often such lower diagnostic accuracy tests must be combined with additional parameters in order to derive meaningful clinical thresholds for therapeutic intervention, as is done with the aforementioned global risk assessment indices.

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category (such as pre-Diabetes) has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative concentration of what constitutes an effective amount of the biomarkers of the invention allows one of skill in the art to use the biomarkers to diagnose or identify subjects with a predetermined level of predictability and performance.

Calculation of the Diabetes Risk Score ("DRS")

After selection of a set of biomarkers (and other optional factors) as disclosed in the instant invention, well-known techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, or kernel principal components analysis algorithms, or other mathematical and statistical methods can be used to develop a DRS Formula for calculation of Diabetes risk score. A selected population of individuals is used, where historical information is available regarding the values of biomarkers in the population and their clinical outcomes. To calculate a Diabetes risk score for a given individual, biomarker values are obtained from one or more samples collected from the individual and used as input data (inputs into a DRS Formula fitted to the actual historical data obtained from the selected population of individuals.

Implementation of Biomarker Tests

Tests to measure biomarkers and biomarker panels can be implemented on a wide variety of diagnostic test systems. Diagnostic test systems are apparatuses that typically include means for obtaining test results from biological samples. Examples of such means include modules that automate the testing (e.g., biochemical, immunological, nucleic acid detection assays). Some diagnostic test systems are designed to handle multiple biological samples and can be programmed to run the same or different tests on each sample. Diagnostic test systems typically include means for collecting, storing and/or tracking test results for each sample, usually in a data structure or database. Examples include well-known physical and electronic data storage devices (e.g., hard drives, flash memory, magnetic tape, paper print-outs). It is also typical for diagnostic test systems to include means for reporting test results. Examples of reporting means include visible display, a link to a data structure or database, or a printer. The reporting means can be nothing more than a data link to send test results to an external device, such as a data structure, data base, visual display, or printer.

One embodiment of the present invention comprises a diagnostic test system that has been adapted to aide in the identification of individuals at risk of developing Diabetes. The test system employs means to apply a DRS Formula to inputs that include the levels of biomarkers measured from a biomarker panel in accordance with the description herein. Typically, test results from a biomarker panel of the present invention serve as inputs to a computer or microprocessor programmed with the DRS Formula. When the inputs include all the inputs for a Diabetes risk score, then the diagnostic test system can include the score in the reported test results. If some factors apart from the biomarkers tested in the system are used to calculate the final risk score, then these factors can be supplied to the diagnostic test system so that it can complete the risk score calculation, or the DRS Formula can produce an index score that will reported and externally combined with the other inputs to calculate a final risk score.

A number of diagnostic test systems are available for use in implementing the present invention and exemplify further means for carrying out the invention. One such device is the Abbott Architect® System, a high throughput, fully automated, clinical chemistry analyzer (ARCHITECT is a registered trademark of Abbott Laboratories, Abbott Park, Ill. 60064 United States of America, for data management and laboratory automation systems comprised of computer hardware and software for use in the field of medical diagnostics). The Architect® system is described at URL World-Wide-Web.abbottdiagnostics.com/pubs/2006/2006_AACC_Wilson_c16000.pdf (Wilson, C. et al., "Clinical Chemistry Analyzer Sub-System Level Performance," American Association for Clinical Chemistry Annual Meeting, Chicago, Ill., Jul. 23-27, 2006, and in Kisner H J, "Product development: the making of the Abbott ARCHITECT," Clin Lab Manage Rev. 1997 November-December; 11(6): 419-21; Ognibene A et al., "A new modular chemiluminescence immunoassay analyser evaluated," Clin Chem Lab Med. 2000 March; 38(3):251-60; Park J W et al., "Three-year experience in using total laboratory automation system," Southeast Asian J Trop Med Public Health. 2002; 33 Suppl 2:68-73; Pauli D et al., "The Abbott Architect c8000: analytical performance and productivity characteristics of a new analyzer applied to general chemistry testing," Clin Lab. 2005; 51(1-2):31-41. Another useful system is the Abbott AxSYM® and AxSYM® Plus systems, which is described, along with other Abbott systems, at URL World-Wide-Web.abbottdiagno stics.com/Products/Instruments_by_Platform/.

Other devices useful for implementation of the tests to measure biomarkers are the Johnson & Johnson Vitros® system (VITROS is a registered trademark of Johnson & Johnson Corp., New Brunswick, N.J., United States of America, for medical equipment, namely, chemistry analyzer apparatus used to generate diagnostic test results from blood and other body fluids by professionals in hospitals, laboratories, clinics and doctor's offices), see URL World-Wide-Web.jnjgateway.com/home.jhtml?loc=USENG&page=menu&nodekey=/Prod_Info/Specialty/Diagnostics/Laboratory_and_Transfusion_Medicine/Che mistry_Immunodiagnostics; and the Dade-Behring Dimension® system (DIMENSION is a registered trademark of Dade Behring Inc., Deerfield Ill., United States of America for medical diagnostic analyzers for the analysis of bodily fluids, and computer hardware and computer software for use in operating the analyzers and for use in analyzing the data generated by the analyzers), see URL diagnostics.siemens.com/webapp/wcs/stores/selet/PSGenericDisplay~q_catalogId~e_-111~a_langId~e_-111~a_pageId~e__94489~a_storeId~e__10001.htm.

The tests for the biomarker panels of the invention can be carried out by laboratories such as those which are certified under the Clinical Laboratory Improvement Amendments of the United States (42 U.S.C. §263(a)), or other federal, national, state, provincial, or other law of any country, state, or province governing the operation of laboratories which analyze samples for clinical purposes. Such laboratories include, for example, Laboratory Corporation of America, with headquarters at 358 South Main Street, Burlington, N.C. 27215, United States of America; Quest Diagnostics, with corporate headquarters at 3 Giralda Farms, Madison, N.J. 07940, United States of America; and hospital-based reference laboratories and clinical chemistry laboratories.

Selection of Biomarkers

Selection of lipid biomarkers is described in some detail above. This section emphasizes protein and other biomarkers and some other factors that can be used in combination with the lipid metabolites to provide enhanced predictive value.

The biomarkers and methods of the present invention allow one of skill in the art to identify, diagnose, or otherwise assess those subjects who do not exhibit any symptoms of Diabetes, pre-Diabetes, or a pre-diabetic condition, but who nonetheless may be at risk for developing Diabetes, pre-Diabetes, or experiencing symptoms characteristic of a pre-diabetic condition.

Two hundred and sixty-six (266) analyte-based biomarkers have been identified as being found to have altered or modified presence or concentration levels in subjects who have Diabetes, or who exhibit symptoms characteristic of a pre-diabetic condition, or have pre-Diabetes (as defined herein), including such subjects as are insulin resistant, have altered beta cell function or are at risk of developing Diabetes based upon known clinical parameters or traditional laboratory risk factors, such as family history of Diabetes, low activity level, poor diet, excess body weight (especially around the waist), age greater than 45 years, high blood pressure, high levels of triglycerides, HDL cholesterol of less than 35, previously identified impaired glucose tolerance, previous Diabetes during pregnancy (Gestational Diabetes Mellitus or GDM) or giving birth to a baby weighing more than nine pounds, and ethnicity Biomarkers can be selected from various groups as outlined in the instant specification to form a panel of n markers. For example, one embodiment of the invention embraces a method of evaluating the risk of developing Diabetes or another Diabetes-related condition, comprising measuring the levels of at least three biomarkers, where two biomarkers are selected from ADIPOQ; CRP; GLUCOSE; GPT; HBA1C; HSPA1B; IGFBP1; IGFBP2; INS; LEP; and TRIG; and one biomarker is selected from the ALLDBRISKS, CPs, and TLRFs of Table 7, Table 8 and Table 9 and using the measured levels of the biomarkers to evaluate the risk of developing Diabetes or a Diabetes-related condition. In this instance, n is 3. When selecting from different groups, unique biomarkers should be used; e.g., in the immediately preceding example, if ADIPOQ is selected from the group of ADIPOQ; CRP; GLUCOSE; GPT; HBA1C; HSPA1B; IGFBP1; IGFBP2; INS; LEP; and TRIG, then ADIPOQ should not also be selected from the markers of Table 7, Table 8, and Table 9. Diabetes-related conditions include Diabetes and the pre-diabetic conditions defined above.

Table 7 comprises several biomarkers, collectively referred to as ALLDBRISK, which are analyte-based or individual history-based biomarkers for use in the present invention. One skilled in the art will recognize that the ALLDBRISKS presented herein encompasses all forms and variants, including but not limited to, polymorphisms, isoforms, mutants, derivatives, precursors including nucleic acids and pro-proteins, cleavage products, receptors (including soluble and transmembrane receptors), ligands, protein-ligand complexes, and post-translationally modified variants (such as cross-linking or glycosylation), fragments, and degradation products, as well as any multi-unit nucleic acid, protein, and glycoprotein structures comprised of any of the ALLDBRISKS as constituent subunits of the fully assembled structure.

TABLE 7

| ALLDBRISK | Official Name | Common Name | Entrez Gene Link |
|---|---|---|---|
| 1 | ATP-binding cassette, sub-family C (CFTR/MRP), member 8 | sulfonylurea receptor (SUR1), HI; SUR; HHF1; MRP8; PHHI; SUR1; ABC36; HRINS | ABCC8 |
| 2 | ATP-binding cassette, sub-family C (CFTR/MRP), member 9 | sulfonylurea receptor (SUR2a), SUR2; ABC37; CMD1O; FLJ36852 | ABCC9 |
| 3 | angiotensin I converting enzyme (peptidyl-dipeptidase A) 1 | angiotensin-converting enzyme (ACE) - ACE1, CD143, DCP, DCP1, CD143 antigen; angiotensin I converting enzyme; angiotensin converting enzyme, somatic isoform; carboxycathepsin; dipeptidyl carboxypeptidase 1; kininase II; peptidase P; peptidyl-dipeptidase A; testicular ECA | ACE |
| 4 | adenylate cyclase activating polypeptide 1 (pituitary) | adenylate cyclase activating polypeptide | ADCYAP1 |
| 5 | adiponectin, C1Q and collagen domain containing | Adiponectin - ACDC, ACRP30, APM-1, APM1, GBP28, glycosylated adiponectin, adiponectin, adipocyte, C1Q and collagen domain containing; adipocyte, C1Q and collagen domain-containing; adiponectin; adipose most abundant gene transcript 1; gelatin-binding protein 28 | ADIPOQ |
| 6 | adiponectin receptor 1 | G Protein Coupled Receptor AdipoR1 - ACDCR1, CGI-45, PAQR1, TESBP1A | ADIPOR1 |
| 7 | adiponectin receptor 2 | G Protein Coupled Receptor AdipoR2 - ACDCR2, PAQR2 | ADIPOR2 |
| 8 | Adrenomedullin | adrenomedullin - AM, preproadrenomedullin | ADM |
| 9 | adrenergic, beta-2-, receptor, surface | G Protein-Coupled Beta-2 Adrenoceptor - ADRB2R, ADRBR, B2AR, BAR, BETA2AR, beta-2 adrenergic receptor; beta-2 adrenoceptor; catecholamine receptor | ADRB2 |

TABLE 7-continued

| ALLDBRISK | Official Name | Common Name | Entrez Gene Link |
|---|---|---|---|
| 10 | advanced glycosylation end product-specific receptor | RAGE - advanced glycosylation end product-specific receptor RAGE3; advanced glycosylation end product-specific receptor variant sRAGE1; advanced glycosylation end product-specific receptor variant sRAGE2; receptor for advanced glycosylation end-products; soluble receptor | AGER |
| 11 | agouti related protein homolog (mouse) | AGRT, ART, ASIP2, & Agouti-related transcript, mouse, homolog of; agouti (mouse) related protein; agouti related protein homolog | AGRP |
| 12 | angiotensinogen (serpin peptidase inhibitor, clade A, member 8) | angiotensin I; pre-angiotensinogen; angiotensin II precursor; angiotensinogen (serine (or cysteine) peptidase inhibitor, clade A, member 8); angiotensinogen (serine (or cysteine) proteinase inhibitor, clade A (alpha-1 antiproteinase, antitrypsin), member 8) | AGT |
| 13 | angiotensin II receptor, type 1 | G protein-Coupled Receptor AGTR1A - AG2S, AGTR1A, AGTR1B, AT1, AT1B, AT2R1, AT2R1A, AT2R1B, HAT1R, angiotensin receptor 1; angiotensin receptor 1B; type-1B angiotensin II receptor | AGTR1 |
| 14 | angiotensin II receptor-associated protein | angiotensin II - ATRAP, ATI receptor-associated protein; angiotensin II, type I receptor-associated protein | AGTRAP |
| 15 | alpha-2-HS-glycoprotein | A2HS, AHS, FETUA, HSGA, Alpha-2HS-glycoprotein; fetuin-A | AHSG |
| 16 | v-akt murine thymoma viral oncogene homolog 1 | Ser/Thr kinase Akt - PKB, PRKBA, RAC, RAC-ALPHA, RAC-alpha serine/threonine-protein kinase; murine thymoma viral (v-akt) oncogene homolog-1; protein kinase B; rac protein kinase alpha | AKT1 |
| 17 | v-akt murine thymoma viral oncogene homolog 2 | PKBBETA, PRKBB, RAC-BETA, Murine thymoma viral (v-akt) homolog-2; rac protein kinase beta | AKT2 |
| 18 | Albumin | Ischemia-modified albumin (IMA) - cell growth inhibiting protein 42; growth-inhibiting protein 20; serum albumin | ALB |
| 19 | Alstrom syndrome 1 | ALSS | ALMS1 |
| 20 | archidonate 12-lipoxygenase | LOG12, 12(S)-lipoxygenase; platelet-type 12-lipoxygenase/arachidonate 12-lipoxygenase | ALOX12 |
| 21 | Angiogenin, ribonuclease, RNase A family, 5 | Angiogenin, MGC71966, RNASE4, RNASE5, angiogenin, ribonuclease, RNase A family, 5 | ANG |
| 22 | ankyrin repeat domain 23 | DARP, MARP3, Diabetes related ankyrin repeat protein; muscle ankyrin repeat protein 3 | ANKRD23 |
| 23 | apelin, AGTRL 1 Ligand | XNPEP2, apelin, peptide ligand for APJ receptor | APLN |
| 24 | apolipoprotein A-I | apolipoproteins A-1 and B, amyloidosis; apolipoprotein A-I, preproprotein; apolipoprotein A1; preproapolipoprotein | APOA1 |
| 25 | apolipoprotein A-II | Apolipoprotein A-II | APOA2 |
| 26 | apolipoprotein B (including Ag(x) antigen) | apolipoproteins A-1 and B - Apolipoprotein B, FLDB, apoB-100; apoB-48; apolipoprotein B; apolipoprotein B48 | APOB |
| 27 | apolipoprotein E | APO E - AD2, apoprotein, Alzheimer disease 2 (APOE*E4-associated, late onset); apolipoprotein E precursor; apolipoprotein E3 | APOE |
| 28 | aryl hydrocarbon receptor nuclear translocator | dioxin receptor, nuclear translocator; hypoxia-inducible factor 1, beta subunit | ARNT |
| 29 | Aryl hydrocarbon receptor nuclear translocator-like | Bmal1, TIC; JAP3; MOP3; BMAL1; PASD3; BMAL1c; bHLH-PAS protein JAP3; member of PAS superfamily 3; ARNT-like protein 1, | ARNTL |

TABLE 7-continued

| ALLDBRISK | Official Name | Common Name | Entrez Gene Link |
|---|---|---|---|
| | | brain and muscle; basic-helix-loop-helix-PAS orphan MOP3 | |
| 30 | arrestin, beta 1 | beta arrestin - ARB1, ARR1, arrestin beta 1 | ARRB1 |
| 31 | arginine vasopressin (neurophysin II, antidiuretic hormone, Diabetes insipidus, neurohypophyseal) | copeptin - ADH, ARVP, AVP-NPII, AVRP, VP, arginine vasopressin-neurophysin II; vasopressin-neurophysin II-copeptin, vasopressin | AVP |
| 32 | bombesin receptor subtype 3 | G-protein coupled receptor; bombesin receptor subtype 3 | BRS3 |
| 33 | Betacellulin | betacellulin | BTC |
| 34 | benzodiazepine receptor (peripheral) | PBR - DBI, IBP, MBR, PBR, PKBS, PTBR, mDRC, pk18, benzodiazepine peripheral binding site; mitochondrial benzodiazepine receptor; peripheral benzodiazepine receptor; peripheral benzodiazepine receptor; peripheral-type benzodiazepine receptor | BZRP |
| 35 | complement component 3 | complement C3 - acylation-stimulating protein cleavage product; complement component C3, ASP; CPAMD1 | C3 |
| 36 | complement component 4A (Rodgers blood group) | complement C4 - C4A anaphylatoxin; Rodgers form of C4; acidic C4; c4 propeptide; complement component 4A; complement component C4B | C4A |
| 37 | complement component 4B (Childo blood group) | C4A, C4A13, C4A91, C4B1, C4B12, C4B2, C4B3, C4B5, C4F, CH, CO4, CPAMD3, C4 complement C4d region; Chido form of C4; basic C4; complement C4B; complement component 4B; complement component 4B, centromeric; complement component 4B, telomeric; complement component C4B | C4B |
| 38 | complement component 5 | anaphylatoxin C5a analog - CPAMD4 | C5 |
| 39 | Calpain-10 | calcium-activated neutral protease | CAPN10 |
| 40 | Cholecystokinin | cholecystokinin | CCK |
| 41 | cholecystokinin (CCK)-A receptor | CCK-A; CCK-A; CCKRA; CCK1-R; cholecystokinin-1 receptor; cholecystokinin type-A receptor | CCKAR |
| 42 | chemokine (C-C motif) ligand 2 | Monocyte chemoattractant protein-1 (MCP-1) - GDCF-2, GDCF-2 HC11, HC11, HSMCR30, MCAF, MCP-1, MCP1, SCYA2, SMC-CF, monocyte chemoattractant protein-1; monocyte chemotactic and activating factor; monocyte chemotactic protein 1, homologous to mouse Sig-je; monocyte secretory protein JE; small inducible cytokine A2; small inducible cytokine A2 (monocyte chemotactic protein 1, homologous to mouse Sig-je); small inducible cytokine subfamily A (Cys-Cys), member 2 | CCL2 |
| 43 | CD14 molecule | CD14 antigen - monocyte receptor | CD14 |
| 44 | CD163 molecule | CD163 - M130, MM130 - CD163 antigen; macrophage-associated antigen, macrophage-specific antigen | CD163 |
| 45 | CD36 molecule (thrombospondin receptor) | fatty acid translocase, FAT; GP4; GP3B; GPIV; PASIV; SCARB3, PAS-4 protein; collagen type I; glycoprotein IIIb; cluster determinant 36; fatty acid translocase; thrombospondin receptor; collagen type I receptor; platelet glycoprotein IV; platelet collagen receptor; scavenger receptor class B, member 3; leukocyte differentiation antigen CD36; CD36 antigen (collagen type I receptor, thrombospondin receptor) | CD36 |
| 46 | CD38 molecule | T10; CD38 antigen (p45); cyclic ADP-ribose hydrolase; ADP-ribosyl cyclase/cyclic ADP-ribose hydrolase | CD38 |
| 47 | CD3d molecule, delta (CD3-TCR complex) | CD3-DELTA, T3D, CD3D antigen, delta polypeptide; CD3d antigen, delta | CD3D |

TABLE 7-continued

| ALLDBRISK | Official Name | Common Name | Entrez Gene Link |
|---|---|---|---|
| 48 | CD3g molecule, gamma (CD3-TCR complex) | polypeptide (TiT3 complex); T-cell receptor T3 delta chain T3G; CD3-GAMMA, T3G, CD3G gamma; CD3g antigen, gamma polypeptide (TiT3 complex); T-cell antigen receptor complex, gamma subunit of T3; T-cell receptor T3 gamma chain; T-cell surface glycoprotein CD3 gamma chain precursor | CD3G |
| 49 | CD40 molecule, TNF receptor superfamily member 5 | Bp50, CDW40, TNFRSF5, p50, B cell surface antigen CD40; B cell-associated molecule; CD40 antigen; CD40 antigen (TNF receptor superfamily member 5); CD40 type II isoform; CD40L receptor; nerve growth factor receptor-related B-lymphocyte activation molecule; tumor necrosis factor receptor superfamily, member 5 | CD40 |
| 50 | CD40 ligand (TNF superfamily, member 5, hyper-IgM syndrome) | CD40 Ligand (CD40L) (also called soluble CD40L vs. platelet-bound CD40L), CD154, CD40L, HIGM1, IGM, IMD3, T-BAM, TNFSF5, TRAP, gp39, hCD40L, CD40 antigen ligand; CD40 ligand; T-B cell-activating molecule; TNF-related activation protein; tumor necrosis factor (ligand) superfamily member 5; tumor necrosis factor (ligand) superfamily, member 5 (hyper-IgM syndrome); tumor necrosis factor ligand superfamily member 5 | CD40LG |
| 51 | CD68 molecule | GP110; SCARD1; macrosialin; CD68 antigen; macrophage antigen CD68; scavenger receptor class D, member 1 | CD68 |
| 52 | cyclin-dependent kinase 5 | PSSALRE; cyclin-dependent kinase 5 | CDK5 |
| 53 | complement factor D (adipsin) | ADN, DF, PFD, C3 convertase activator; D component of complement (adipsin); adipsin; complement factor D; properdin factor D | CFD |
| 54 | CASP8 and FADD-like apoptosis regulator | FLIP - caspase 8 inhibitor, CASH; FLIP; MRIT; CLARP; FLAME; Casper; c-FLIP; FLAME-1; I-FLICE; USURPIN; c-FLIPL; c-FLIPR; c-FLIPS; CASP8AP1, usurpin beta; FADD-like anti-apoptotic molecule; Inhibitor of FLICE; Caspase-related inducer of apoptosis; Caspase homolog; Caspase-like apoptosis regulatory protein | CFLAR |
| 55 | Clock homolog (mouse) | clock protein; clock (mouse) homolog; circadian locomoter output cycles kaput protein | CLOCK |
| 56 | chymase 1, mast cell | chymase 1 - CYH, MCT1, chymase 1 preproprotein transcript E; chymase 1 preproprotein transcript I; chymase, heart; chymase, mast cell; mast cell protease I | CMA1 |
| 57 | cannabinoid receptor 1 (brain) | cannabinoid receptor 1 - CANN6, CB-R, CB1, CB1A, CB1K5, CNR, central cannabinoid receptor | CNR1 |
| 58 | cannabinoid receptor 2 (macrophage) | cannabinoid receptor 2 (macrophage), CB2, CX5 | CNR2 |
| 59 | Cortistatin | CST-14; CST-17; CST-29; cortistatin-14; cortistatin-17; cortistatin-29; preprocortistatin | CORT |
| 60 | carnitine palmitoyltransferase I | CPT1; CPT1-L; L-CPT1, carnitine palmitoyltransferase I; liver | CPT1A |
| 61 | carnitine palmitoyltransferase II | CPT1, CPTASE | CPT2 |
| 62 | complement component (3b/4b) receptor 1 | complement receptor CR1; KN; C3BR; CD35; CD35 antigen; C3b/C4b receptor; C3-binding protein; Knops blood group antigen; complement component receptor 1; complement component (3b/4b) | CR1 |

TABLE 7-continued

| ALLDBRISK | Official Name | Common Name | Entrez Gene Link |
|---|---|---|---|
| | | receptor 1, including Knops blood group system | |
| 63 | complement component (3d/Epstein Barr virus) receptor 2 | complement receptor CR2; C3DR; CD21 | CR2 |
| 64 | CREB binding protein (Rubinstein-Taybi syndrome) | Cbp; CBP; RTS; RSTS, CREB-binding protein | CREBBP |
| 65 | C-reactive protein, pentraxin-related | C-Reactive Protein, CRP, PTX1 | CRP |
| 66 | CREB regulated transcription coactivator 2 | Torc2 (transcriptional coactivator); transducer of regulated cAMP response element-binding protein (CREB) 2 | CRTC2 |
| 67 | colony stimulating factor 1 (macrophage) | M-CSF - colony stimulating factor 1; macrophage colony stimulating factor | CSF1 |
| 68 | cathepsin B | cathepsin B - procathepsin B, APPS; CPSB, APP secretase; amyloid precursor protein secretase; cathepsin B1; cysteine protease; preprocathepsin B | CTSB |
| 69 | cathepsin L | CATL, MEP, major excreted protein | CTSL |
| 70 | cytochrome P450, family 19, subfamily A, polypeptide 1 | ARO, ARO1, CPV1, CYAR, CYP19, P-450AROM, aromatase; cytochrome P450, family 19; cytochrome P450, subfamily XIX (aromatization of androgens); estrogen synthetase; flavoprotein-linked monooxygenase; microsomal monooxygenase | CYP19A1 |
| 71 | Dio-2, death inducer-obliterator 1 | death associated transcription factor 1; BYE1; DIO1; DATF1; DIDO2; DIDO3; DIO-1 | DIDO1 |
| 72 | dipeptidyl-peptidase 4 (CD26, adenosine deaminase complexing protein 2) | dipeptidylpeptidase IV - ADABP, ADCP2, CD26, DPPIV, TP103, T-cell activation antigen CD26; adenosine deaminase complexing protein 2; dipeptidylpeptidase IV; dipeptidylpeptidase IV (CD26, adenosine deaminase complexing protein 2) | DPP4 |
| 73 | epidermal growth factor (beta-urogastrone) | URG - urogastrone | EGF |
| 74 | early growth response 1 | zinc finger protein 225; transcription factor ETR103; early growth response protein 1; nerve growth factor-induced protein A | EGR1 |
| 75 | epididymal sperm binding protein 1 | E12, HE12, epididymal secretory protein | ELSPBP1 |
| 76 | ectonucleotide pyrophosphatase/phosphodiesterase 1 | ENPP1 - M6S1, NPP1, NPPS, PC-1, PCA1, PDNP1, Ly-41 antigen; alkaline phosphodiesterase 1; membrane component, chromosome 6, surface marker 1; phosphodiesterase I/nucleotide pyrophosphatase 1; plasma-cell membrane glycoprotein 1 | ENPP1 |
| 77 | E1A binding protein p300 | p300, E1A binding protein p300, E1A-binding protein, 300 kD; E1A-associated protein p300 | EP300 |
| 78 | coagulation factor XIII, A1 polypeptide | Coagulation Factor XIII - Coagulation factor XIII A chain; Coagulation factor XIII, A polypeptide; TGase; (coagulation factor XIII, A1 polypeptide); coagulation factor XIII A1 subunit; factor XIIIa, coagulation factor XIII A1 subunit | F13A1 |
| 79 | coagulation factor VIII, procoagulant component (hemophilia A) | Factor VIII, AHF, F8 protein, F8B, F8C, FVIII, HEMA, coagulation factor VIII; coagulation factor VIII, isoform b; coagulation factor VIIIc; factor VIII F8B; procoagulant component, isoform b | F8 |
| 80 | fatty acid binding protein 4, adipocyte | fatty acid binding protein 4, adipocyte - A-FABP | FABP4 |
| 81 | Fas (TNF receptor superfamily, member 6) | soluble Fas/APO-1 (sFas), ALPS1A, APO-1, APT1, Apo-1 Fas, CD95, FAS1, FASTM, TNFRSF6, APO-1 cell surface antigen; CD95 antigen; Fas antigen; apoptosis antigen 1; tumor necrosis factor receptor superfamily, member 6 | FAS |

TABLE 7-continued

| ALLDBRISK | Official Name | Common Name | Entrez Gene Link |
|---|---|---|---|
| 82 | Fas ligand (TNF superfamily, member 6) | Fas ligand (sFasL), APT1LG1, CD178, CD95L, FASL, TNFSF6, CD95 ligand; apoptosis (APO-1) antigen ligand 1; fas ligand; tumor necrosis factor (ligand) superfamily, member 6 | FASLG |
| 83 | free fatty acid receptor 1 | G protein-coupled receptor 40 - FFA1R, GPR40, G protein-coupled receptor 40 | FFAR1 |
| 84 | fibrinogen alpha chain | Fibrin, Fib2, fibrinogen, A alpha polypeptide; fibrinogen, alpha chain, isoform alpha preproprotein; fibrinogen, alpha polypeptide | FGA |
| 85 | forkhead box A2 | (Foxa2); HNF3B; TCF3B; hepatic nuclear factor-3-beta; hepatocyte nuclear factor 3, beta | FOXA2 |
| 86 | forkhead box O1A | FKH1; FKHR; FOXO1; forkhead (*Drosophila*) homolog 1 (rhabdomyosarcoma); forkhead, *Drosophila*, homolog of, in rhabdomyosarcoma | FOXO1A |
| 87 | Ferritin | FTH; PLIF; FTHL6; PIG15; apoferritin; placenta immunoregulatory factor; proliferation-inducing protein 15 | FTH1 |
| 88 | glutamate decarboxylase 2 | glutamic acid decarboxylase (GAD65) antibodies; Glutamate decarboxylase-2 (pancreas); glutamate decarboxylase 2 (pancreatic islets and brain, 65 kD) | GAD2 |
| 89 | Galanin | GALN; GLNN; galanin-related peptide | GAL |
| 90 | Gastrin | gastrin - GAS | GAST |
| 91 | glucagon | glucagon-like peptide-1, GLP-1, GLP2, GRPP, glicentin-related polypeptide; glucagon-like peptide 1; glucagon-like peptide 2 | GCG |
| 92 | Glucokinase | hexokinase 4, maturity to onset Diabetes of the young 2; GK; GLK; HK4; HHF3; HKIV; HXKP; MODY2 | GCK |
| 93 | gamma-glutamyltransferase 1 | GGT; GTG; CD224; glutamyl transpeptidase; gamma-glutamyl transpeptidase | GGT1 |
| 94 | growth hormone 1 | growth hormone - GH, GH-N, GHN, hGH-N, pituitary growth hormone | GH1 |
| 95 | ghrelin/obestatin preprohormone | ghrelin - MTLRP, ghrelin, obestatin, ghrelin; ghrelin precursor; ghrelin, growth hormone secretagogue receptor ligand; motilin-related peptide | GHRL |
| 96 | gastric inhibitory polypeptide | glucose-dependent insulinotropic peptide | GIP |
| 97 | gastric inhibitory polypeptide receptor | GIP Receptor | GIPR |
| 98 | glucagon-like peptide 1 receptor | glucagon-like peptide 1 receptor | GLP1R |
| 99 | guanine nucleotide binding protein (G protein), beta polypeptide 3 | G-protein beta-3 subunit - G protein, beta-3 subunit; GTP-binding regulatory protein beta-3 chain; guanine nucleotide-binding protein G(I)/G(S)/G(T) beta subunit 3; guanine nucleotide-binding protein, beta-3 subunit; hypertension associated protein; transducin beta chain 3 | GNB3 |
| 100 | glutamic-pyruvate transaminase (alanine aminotransferase) | glutamic-pyruvate transaminase (alanine aminotransferase), AAT1 ALT1, GPT1 | GPT |
| 101 | gastrin releasing peptide (bombesin) | bombesin; BN; GRP-10; proGRP; preproGRP; neuromedin C; pre-progastrin releasing peptide | GRP |
| 102 | gelsolin (amyloidosis, Finnish type) | Gelsolin | GSN |
| 103 | Hemoglobin | CD31; alpha-1 globin; alpha-1-globin; alpha-2 globin; alpha-2-globin; alpha one globin; hemoglobin alpha 2; hemoglobin alpha-2; hemoglobin alpha-1 chain; hemoglobin alpha 1 globin chain, glycosylated hemoglobin, HBA1c | HBA1 |

TABLE 7-continued

| ALLDBRISK | Official Name | Common Name | Entrez Gene Link |
|---|---|---|---|
| 104 | hemoglobin, beta | HBD, beta globin | HBB |
| 105 | hypocretin (orexin) neuropeptide precursor | orexin A; OX; PPDX | HCRT |
| 106 | hepatocyte growth factor (hepapoietin A; scatter factor) | Hepatocyte growth factor (HGF) - F-TCF, HGFB, HPTA, SF, fibroblast-derived tumor cytotoxic factor; hepatocyte growth factor; hepatopoietin A; lung fibroblast-derived mitogen; scatter factor | HGF |
| 107 | hepatocyte nuclear factor 4, alpha | hepatocyte nuclear factor 4 - HNF4, HNF4a7, HNF4a8, HNF4a9, MODY, MODY1, NR2A1, NR2A21, TCF, TCF14, HNF4-alpha; hepatic nuclear factor 4 alpha; hepatocyte nuclear factor 4 alpha; transcription factor-14 | HNF4A |
| 108 | haptoglobin | haptoglobin - hp2-alpha | HP |
| 109 | hydroxysteroid (11-beta) dehydrogenase 1 | Corticosteroid 11-beta-dehydrogenase, isozyme 1; HDL; 11-DH; HSD11; HSD11B; HSD11L; 11-beta-HSD1 | HSD11B1 |
| 110 | heat shock 70 kDa protein 1B | HSP70-2, heat shock 70 kD protein 1B | HSPA1B |
| 111 | islet amyloid polypeptide | Amylin - DAP, IAP, Islet amyloid polypeptide (Diabetes-associated peptide; amylin) | IAPP |
| 112 | intercellular adhesion molecule 1 (CD54), human rhinovirus receptor | soluble intercellular adhesion molecule-1, BB2, CD54, P3.58, 60 bp after segment 1; cell surface glycoprotein; cell surface glycoprotein P3.58; intercellular adhesion molecule 1 | ICAM1 |
| 113 | Intercellular adhesion molecule 3 (CD50), | CD50, CDW50, ICAM-R, intercellular adhesion molecule-3 | ICAM3 |
| 114 | interferon, gamma | IFNG: IFG; IFI | IFNG |
| 115 | insulin-like growth factor 1 (somatomedin C) | IGF-1: somatomedin C. insulin-like growth factor-1 | IGF1 |
| 116 | insulin-like growth factor 2 (somatomedin A) | IGF-II polymorphisms (somatomedin A) - C11orf43, INSIGF, pp9974, insulin-like growth factor 2; insulin-like growth factor II; insulin-like growth factor type 2; putative insulin-like growth factor II associated protein | IGF2 |
| 117 | insulin-like growth factor binding protein 1 | insulin-like growth factor binding protein-1 (IGFBP-1) - AFBP, IBP1, IGF-BP25, PP12, hIGFBP-1, IGF-binding protein 1; alpha-pregnancy-associated endometrial globulin; amniotic fluid binding protein; binding protein-25; binding protein-26; binding protein-28; growth hormone independent-binding protein; placental protein 12 | IGFBP1 |
| 118 | insulin-like growth factor binding protein 3 | insulin-like growth factor binding protein 3: IGF-binding protein 3 - BP-53, IBP3, IGF-binding protein 3; acid stable subunit of the 140 K IGF complex; binding protein 29; binding protein 53; growth hormone-dependent binding protein | IGFBP3 |
| 119 | inhibitor of kappa light polypeptide gene enhancer in B-cells, kinase beta | ikk-beta; IKK2; IKKB; NFKBIKB; IKK-beta; nuclear factor NF-kappa-B inhibitor kinase beta; inhibitor of nuclear factor kappa B kinase beta subunit | IKBKB |
| 120 | interleukin 10 | IL-10, CSIF, IL-10, IL10A, TGIF, cytokine synthesis inhibitory factor | IL10 |
| 121 | interleukin 18 (interferon-gamma-inducing factor) | IL-18 - IGIF, IL-18, IL-1g, IL1F4, IL-1 gamma; interferon-gamma-inducing factor; interleukin 18; interleukin-1 gamma; interleukin-18 | IL18 |
| 122 | interleukin 1, alpha | IL 1 - IL-1A, IL1, IL1-ALPHA, IL1F1, IL1A (IL1F1); hematopoietin-1; preinterleukin 1 alpha; pro-interleukin-1-alpha | IL1A |
| 123 | interleukin 1, beta | interleukin-1 beta (IL-1 beta) - IL-1, IL1-BETA, IL1F2, catabolin; preinterleukin 1 beta; pro-interleukin-1-beta | IL1B |
| 124 | interleukin 1 receptor antagonist | interleukin-1 receptor antagonist (IL-1Ra) - ICIL-1RA, IL-1ra3, IL1F3, | IL1RN |

TABLE 7-continued

| ALLDBRISK | Official Name | Common Name | Entrez Gene Link |
|---|---|---|---|
| | | IL1RA, IRAP, IL1RN (IL1F3); intracellular IL-1 receptor antagonist type II; intracellular interleukin-1 receptor antagonist (icIL-1ra); type II interleukin-1 receptor antagonist | |
| 125 | interleukin 2 | interleukin-2 (IL-2) - IL-2, TCGF, lymphokine, T cell growth factor; aldesleukin; interleukin-2; involved in regulation of T-cell clonal expansion | IL2 |
| 126 | interleukin 2 receptor, alpha | Interleukin-2 receptor; IL-2RA; IL2RA; RP11-536K7.1; CD25; IDDM10; IL2R; TCGFR; interleukin 2 receptor alpha chain | IL2RA |
| 127 | interleukin 6 (interferon, beta 2) | Interleukin-6 (IL-6), BSF2, HGF, HSF, IFNB2, IL-6 | IL6 |
| 128 | interleukin 6 receptor | interleukin-6 receptor, soluble (sIL-6R) - CD126, IL-6R-1, IL-6R-alpha, IL6RA, CD126 antigen; interleukin 6 receptor alpha subunit | IL6R |
| 129 | interleukin 6 signal transducer (gp130, oncostatin M receptor) | CD130, CDw130, GP130, GP130-RAPS, IL6R-beta; CD130 antigen; IL6ST nirs variant 3; gp130 of the rheumatoid arthritis antigenic peptide-bearing soluble form; gp130 transducer chain; interleukin 6 signal transducer; interleukin receptor beta chain; membrane glycoprotein gp130; oncostatin M receptor | Il6ST |
| 130 | interleukin 8 | Interleukin-8 (IL-8), 3-10C, AMCF-I, CXCL8, GCP-1, GCP1, IL-8, K60, LECT, LUCT, LYNAP, MDNCF, MONAP, NAF, NAP-1, NAP1, SCYB8, TSG-1, b-ENAP, CXC chemokine ligand 8; LUCT/interleukin-8; T cell chemotactic factor; beta-thromboglobulin-like protein; chemokine (C—X—C motif) ligand 8; emoctakin; granulocyte chemotactic protein 1; lymphocyte-derived neutrophil-activating factor; monocyte derived neutrophil-activating protein; monocyte-derived neutrophil chemotactic factor; neutrophil-activating factor; neutrophil-activating peptide 1; neutrophil-activating protein 1; protein 3-10C; small inducible cytokine subfamily B, member 8 | IL8 |
| 131 | inhibin, beta A (activin A, activin AB alpha polypeptide) | activin A - EDF, FRP, Inhibin, beta-1; inhibin beta A | INHBA |
| 132 | insulin | Insulin (mature polypeptide) | INSULIN-M |
| 133 | insulin receptor | CD220, HHF5 | INSR |
| 134 | insulin promoter factor-1 | IPF-1, PDX-1 (pancreatic and duodenal homeobox factor-1) | IPF1 |
| 135 | insulin receptor substrate 1 | HIRS-1 | IRS1 |
| 136 | insulin receptor substrate-2 | IRS2 | IRS2 |
| 137 | potassium inwardly-rectifying channel, subfamily J, member 11 | ATP gated K+ channels, Kir 6.2; BIR; HHF2; PHHI; IKATP; KIR6.2 | KCNJ11 |
| 138 | potassium inwardly-rectifying channel, subfamily J, member 8 | ATP gated K+ channels, Kir 6.1 | KCNJ8 |
| 139 | klotho | klotho | KL |
| 140 | kallikrein B, plasma (Fletcher factor) 1 | kallikrein 3 - KLK3 - Kallikrein, plasma; kallikrein 3, plasma; kallikrein B plasma; kininogenin; plasma kallikrein B1 | KLKB1 |
| 141 | leptin (obesity homolog, mouse) | leptin - OB, OBS, leptin; leptin (murine obesity homolog); obesity; obesity (murine homolog, leptin) | LEP |
| 142 | leptin receptor | leptin receptor, soluble - CD295, OBR, OB receptor | LEPR |
| 143 | legumain | putative cysteine protease 1 - AEP, LGMN1, PRSC1, asparaginyl endopeptidase; cysteine protease 1; protease, cysteine, 1 (legumain) | LGMN |
| 144 | lipoprotein, Lp(a) | lipoprotein (a) [Lp(a)], AK38, APOA, LP, Apolipoprotein Lp(a); | LPA |

TABLE 7-continued

| ALLDBRISK | Official Name | Common Name | Entrez Gene Link |
|---|---|---|---|
| | | antiangiogenic AK38 protein; apolipoprotein(a) | |
| 145 | lipoprotein lipase | LPL - LIPD | LPL |
| 146 | v-maf musculoaponeurotic fibrosarcoma oncogene homolog A (avian) | MafA (transcription factor) - RIPE3b1, hMafA, v-maf musculoaponeurotic fibrosarcoma oncogene homolog A | MAFA |
| 147 | mitogen-activated protein kinase 8 interacting protein 1 | IB1, JIP-1, JIP1, PRKM8IP, JNK-interacting protein 1; PRKM8 interacting protein; islet-brain 1 | MAPK8IP1 |
| 148 | mannose-binding lectin (protein C) 2, soluble (opsonic defect) | COLEC1, HSMBPC, MBL, MBP, MBP1, Mannose-binding lectin 2, soluble (opsonic defect); mannan-binding lectin; mannan-binding protein; mannose binding protein; mannose-binding protein C; soluble mannose-binding lectin | MBL2 |
| 149 | melanocortin 4 receptor | G protein coupled receptor MC4 | MC4R |
| 150 | melanin-concentrating hormone receptor 1 | G Protein-Coupled Receptor 24 - GPR24, MCH1R, SLC1, G protein-coupled receptor 24; G-protein coupled receptor 24 isoform 1, GPCR24 | MCHR1 |
| 151 | matrix metallopeptidase 12 (macrophage elastase) | Matrix Metalloproteinases (MMP), HME, MME, macrophage elastase; macrophage metalloelastase; matrix metalloproteinase 12; matrix metalloproteinase 12 (macrophage elastase) | MMP12 |
| 152 | matrix metallopeptidase 14 (membrane-inserted) | Matrix Metalloproteinases (MMP), MMP-X1, MT1-MMP, MTMMP1, matrix metalloproteinase 14; matrix metalloproteinase 14 (membrane-inserted); membrane type 1 metalloprotease; membrane-type matrix metalloproteinase 1; membrane-type-1 matrix metalloproteinase | MMP14 |
| 153 | matrix metallopeptidase 2 (gelatinase A, 72 kDa gelatinase, 72 kDa type IV collagenase) | Matrix Metalloproteinases (MMP), MMP-2, CLG4, CLG4A, MMP-II, MONA, TBE-1, 72 kD type IV collagenase; collagenase type IV-A; matrix metalloproteinase 2; matrix metalloproteinase 2 (gelatinase A, 72 kD gelatinase, 72 kD type IV collagenase); matrix metalloproteinase 2 (gelatinase A, 72 kDa gelatinase, 72 kDa type IV collagenase); matrix metalloproteinase-II; neutrophil gelatinase | MMP2 |
| 154 | matrix metallopeptidase 9 (gelatinase B, 92 kDa gelatinase, 92 kDa type IV collagenase) | Matrix Metalloproteinases (MMP), MMP-9, CLG4B, GELB, 92 kD type IV collagenase; gelatinase B; macrophage gelatinase; matrix metalloproteinase 9; matrix metalloproteinase 9 (gelatinase B, 92 kD gelatinase, 92 kD type IV collagenase); matrix metalloproteinase 9 (gelatinase B, 92 kDa gelatinase, 92 kDa type IV collagenase); type V collagenase | MMP9 |
| 155 | nuclear receptor co-repressor 1 | NCoR; thyroid hormone- and retinoic acid receptor-associated corepressor 1 | NCOR1 |
| 156 | neurogenic differentiation 1 | neuroD (transcription factor) - BETA2, BHF-1, NEUROD | NEUROD1 |
| 157 | nuclear factor of kappa light polypeptide gene enhancer in B-cells 1(p105) | nuclear factor, kappa B (NFKB); DNA binding factor KBF1; nuclear factor NF-kappa-B p50 subunit; nuclear factor kappa-B DNA binding subunit | NFKB1 |
| 158 | nerve growth factor, beta polypeptide | B-type neurotrophic growth factor (BNGF) - beta-nerve growth factor; nerve growth factor, beta subunit | NGFB |
| 159 | non-insulin-dependent Diabetes Mellitus (common, type 2) 1 | NIDDM1 | NIDDM1 |
| 160 | non-insulin-dependent Diabetes Mellitus (common, type 2) 2 | NIDDM2 | NIDDM2 |

TABLE 7-continued

| ALLDBRISK | Official Name | Common Name | Entrez Gene Link |
|---|---|---|---|
| 161 | Noninsulin-dependent Diabetes Mellitus 3 | NIDDM3 | NIDDM3 |
| 162 | nischarin (imidazoline receptor) | imidazoline receptor; IRAS; I-1 receptor candidate protein; imidazoline receptor candidate; imidazoline receptor antisera selected | NISCH |
| 163 | NF-kappaB repressing factor | NRF; ITBA4 gene; transcription factor NRF; NF-kappa B repressing factor; NF-kappa B-repressing factor | NKRF |
| 164 | neuronatin | Peg5 | NNAT |
| 165 | nitric oxide synthase 2A | NOS, type II; nitric oxide synthase, macrophage | NOS2A |
| 166 | Niemann-Pick disease, type C2 | epididymal secreting protein 1 - HE1, NP-C2, epididymal secretory protein; epididymal secretory protein E1; tissue-specific secretory protein | NPC2 |
| 167 | natriuretic peptide precursor B | B-type Natriuretic Peptide (BNP), BNP, brain type natriuretic peptide, pro-BNP?, NPPB | NPPB |
| 168 | nuclear receptor subfamily 1, group D, member 1 | Human Nuclear Receptor NR1D1 - EAR1, THRA1, THRAL, ear-1, hRev, Rev-erb-alpha; thyroid hormone receptor, alpha-like | NR1D1 |
| 169 | nuclear respiratory factor 1 | NRF1; ALPHA-PAL; alpha palindromic-binding protein | NRF1 |
| 170 | oxytocin, prepro - (neurophysin I) | oxytocin - OT, OT-NPI, oxytocin-neurophysin I; oxytocin-neurophysin I, preproprotein | OXT |
| 171 | purinergic receptor P2Y, G-protein coupled, 10 | G Protein Coupled Receptor P2Y10 - P2Y10, G-protein coupled purinergic receptor P2Y10; P2Y purinoceptor 10; P2Y-like receptor | P2RY10 |
| 172 | purinergic receptor P2Y, G-protein coupled, 12 | G Protein-Coupled Receptor P2Y12 - ADPG-R, HORK3, P2T(AC), P2Y(AC), P2Y(ADP), P2Y(cyc), P2Y12, SP1999, ADP-glucose receptor; G-protein coupled receptor SP1999; Gi-coupled ADP receptor HORK3; P2Y purinoceptor 12; platelet ADP receptor; purinergic receptor P2RY12; purinergic receptor P2Y, G-protein coupled 12; purinergic receptor P2Y12; putative G-protein coupled receptor | P2RY12 |
| 173 | purinergic receptor P2Y, G-protein coupled, 2 | Purinoceptor 2 Type Y (P2Y2) - HP2U, P2RU1, P2U, P2U1, P2UR, P2Y2, P2Y2R, ATP receptor; P2U nucleotide receptor; P2U purinoceptor 1; P2Y purinoceptor 2; purinergic receptor P2Y2; purinoceptor P2Y2 | P2RY2 |
| 174 | progestagen-associated endometrial protein (placental protein 14, pregnancy-associated endometrial alpha-2-globulin, alpha uterine protein) | glycodelin-A; glycodelin-F; glycodelin-S; progesterone-associated endometrial protein | PAEP |
| 175 | paired box gene 4 | Pax4 (transcription factor) - paired domain gene 4 | PAX4 |
| 176 | pre-B-cell colony enhancing factor 1 | visfatin; nicotinamide phosphoribosyltransferase | PBEF1 |
| 177 | phosphoenolpyruvate carboxykinase 1 (PEPCK1) | PEPCK1; PEP carboxykinase; phosphopyruvate carboxylase; phosphoenolpyruvate carboxylase | PCK1 |
| 178 | proprotein convertase subtilisin/kexin type 1 | proprotein convertase 1 (PC1, PC3, PCSK1, cleaves pro-insulin) | PCSK1 |
| 179 | placental growth factor, vascular endothelial growth factor-related protein | placental growth factor - PLGF, PlGF-2 | PGF |
| 180 | phosphoinositide-3-kinase, catalytic, alpha polypeptide | PI3K, p110-alpha, PI3-kinase p110 subunit alpha; PtdIns-3-kinase p110; phosphatidylinositol 3-kinase, catalytic, 110-KD, alpha; phosphatidylinositol 3-kinase, catalytic, alpha polypeptide; phosphatidylinositol-4,5-bisphosphate 3-kinase catalytic subunit, alpha isoform | PIK3CA |
| 181 | phosphoinositide-3-kinase, regulatory subunit 1 (p85 alpha) | phophatidylinositol 3-kinase; phosphatidylinositol 3-kinase, | PIK3R1 |

TABLE 7-continued

| ALLDBRISK | Official Name | Common Name | Entrez Gene Link |
|---|---|---|---|
| | | regulatory, 1; phosphatidylinositol 3-kinase-associated p-85 alpha; phosphoinositide-3-kinase, regulatory subunit, polypeptide 1 (p85 alpha); phosphatidylinositol 3-kinase, regulatory subunit, polypeptide 1 (p85 alpha) | |
| 182 | phospholipase A2, group XIIA | PLA2G12, group XII secreted phospholipase A2; group XIIA secreted phospholipase A2 | PLA2G12A |
| 183 | phospholipase A2, group IID | phospholipase A2, secretory - SPLASH, sPLA2S, secretory phospholipase A2s | PLA2G2D |
| 184 | plasminogen activator, tissue | tissue Plasminogen Activator (tPA), T-PA, TPA, alteplase; plasminogen activator, tissue type; reteplase; t-plasminogen activator; tissue plasminogen activator (t-PA) | PLAT |
| 185 | patatin-like phospholipase domain containing 2 | Adipose tissue lipase, ATGL - ATGL, TTS-2.2, adipose triglyceride lipase; desnutrin; transport-secretion protein 2.2; triglyceride hydrolase | PNPLA2 |
| 186 | proopiomelanocortin (adrenocorticotropin/beta-lipotropin/ alpha-melanocyte stimulating hormone/ beta-melanocyte stimulating hormone/ beta-endorphin) | proopiomelanocortin - beta-LPH; beta-MSH; alpha-MSH; gamma-LPH; gamma-MSH; corticotropin; beta-endorphin; met-enkephalin; lipotropin beta; lipotropin gamma; melanotropin beta; N-terminal peptide; melanotropin alpha; melanotropin gamma; pro-ACTH-endorphin; adrenocorticotropin; pro-opiomelanocortin; corticotropin-lipotrophin; adrenocorticotropic hormone; alpha-melanocyte-stimulating hormone; corticotropin-like intermediary peptide | POMC |
| 187 | paraoxonase 1 ESA, PON, Paraoxonase | paraoxonase - ESA, PON, Paraoxonase | PON1 |
| 188 | peroxisome proliferative activated receptor, alpha | Peroxisome proliferator-activated receptor (PPAR), NR1C1, PPAR, hPPAR, PPAR alpha | PPARA |
| 189 | peroxisome proliferative activated receptor, delta | Peroxisome proliferator-activated receptor (PPAR), FAAR, NR1C2, NUC1, NUCI, NUCII, PPAR-beta, PPARB, nuclear hormone receptor 1, PPAR Delta | PPARD |
| 190 | peroxisome proliferative activated receptor, gamma | Peroxisome proliferator-activated receptor (PPAR), HUMPPARG, NR1C3, PPARG1, PPARG2, PPAR gamma; peroxisome proliferative activated receptor gamma; peroxisome proliferator activated-receptor gamma; peroxisome proliferator-activated receptor gamma 1; ppar gamma2 | PPARG |
| 191 | peroxisome proliferative activated receptor, gamma, coactivator 1 | Pgc1 alpha; PPAR gamma coactivator-1; ligand effect modulator-6; PPAR gamma coactivator variant form3 | PPARGC1A |
| 192 | protein phosphatase 1, regulatory (inhibitor) subunit 3A (glycogen and sarcoplasmic reticulum binding subunit, skeletal muscle) | PP1G, PPP1R3, protein phosphatase 1 glycogen-associated regulatory subunit; protein phosphatase 1 glycogen-binding regulatory subunit 3; protein phosphatase type-1 glycogen targeting subunit; serine/threonine specific protein phosphatase; type-1 protein phosphatase skeletal muscle glycogen targeting subunit | PPP1R3A |
| 193 | protein phosphatase 2A, regulatory subunit B' (PR 53) | protein phosphatase 2A - PP2A, PR53, PTPA, PP2A, subunit B'; phosphotyrosyl phosphatase activator; protein phosphatase 2A, regulatory subunit B' | PPP2R4 |
| 194 | protein kinase, AMP-activated, beta 1 non-catalytic subunit | on list as adenosine monophosphate kinase? - AMPK, HAMPKb, 5'-AMP-activated protein kinase beta-1 subunit; AMP-activated protein kinase | PRKAB1 |

TABLE 7-continued

| ALLDBRISK | Official Name | Common Name | Entrez Gene Link |
|---|---|---|---|
| | | beta 1 non-catalytic subunit; AMP-activated protein kinase beta subunit; AMPK beta-1 chain; AMPK beta 1; protein kinase, AMP-activated, noncatalytic, beta-1 | |
| 195 | protein kinase, cAMP-dependent, catalytic, alpha | PKA (kinase) - PKACA, PKA C-alpha; cAMP-dependent protein kinase catalytic subunit alpha; cAMP-dependent protein kinase catalytic subunit alpha, isoform 1; protein kinase A catalytic subunit | PRKACA |
| 196 | protein kinase C, epsilon | PKC-epsilon - PKCE, nPKC-epsilon | PRKCE |
| 197 | proteasome (prosome, macropain) 26S subunit, non-ATPase, 9 (Bridge-1) | Bridge-1; homolog of rat Bridge 1; 26S proteasome regulatory subunit p27; proteasome 26S non-ATPase regulatory subunit 9 | PSMD9 |
| 198 | prostaglandin E synthase | mPGES - MGST-IV, MGST1-L1, MGST1L1, PGES, PIG12, PP102, PP1294, TP53I12<br>Other Designations: MGST1-like 1; glutathione S-transferase 1-like 1; microsomal glutathione S-transferase 1-like 1; p53-induced apoptosis protein 12; p53-induced gene 12; tumor protein p53 inducible protein 12 | PTGES |
| 199 | prostaglandin-endoperoxide synthase 2 (prostaglandin G/H synthase and cyclooxygenase) | Cyclo-oxygenase-2 (COX-2) - COX-2, COX2, PGG/HS, PGHS-2, PHS-2, hCox-2, cyclooxygenase 2b; prostaglandin G/H synthase and cyclooxygenase; prostaglandin-endoperoxide synthase 2 | PTGS2 |
| 200 | protein tyrosine phosphatase, mitochondrial 1 | PTPMT1 - PLIP, PNAS-129, NB4 apoptosis/differentiation related protein; PTEN-like phosphatase | PTPMT1 |
| 201 | Peptide YY | PYY1 | PYY |
| 202 | retinol binding protein 4, plasma (RBP4) | RBP4; retinol-binding protein 4, plasma; retinol-binding protein 4, interstitial | RBP4 |
| 203 | regenerating islet-derived 1 alpha (pancreatic stone protein, pancreatic thread protein) | regenerating gene product (Reg); protein-X; lithostathine 1 alpha; pancreatic thread protein; regenerating protein I alpha; islet cells regeneration factor; pancreatic stone protein, secretory; islet of langerhans regenerating protein | REG1A |
| 204 | resistin | resistin - ADSF, FIZZ3, RETN1, RSTN, XCP1, C/EBP-epsilon regulated myeloid-specific secreted cysteine-rich protein precursor 1; found in inflammatory zone 3 | RETN |
| 205 | ribosomal protein S6 kinase, 90 kDa, polypeptide 1 | S6-kinase 1 - HU-1, RSK, RSK1, S6K-alpha 1, (ribosomal protein S6 kinase, 90 kD, polypeptide 1); p90-RSK 1; ribosomal protein S6 kinase alpha 1; ribosomal protein S6 kinase, 90 kD, 1; ribosomal protein S6 kinase, 90 kD, polypeptide 1 | RPS6KA1 |
| 206 | Ras-related associated with Diabetes | RAD, RAD1, REM3, RAS (RAD and GEM) like GTP binding 3 | RRAD |
| 207 | serum amyloid A1 | Serum Amyloid A (SAA), PIG4, SAA, TP53I4, tumor protein p53 inducible protein 4 | SAA1 |
| 208 | selectin E (endothelial adhesion molecule 1) | E-selectin, CD62E, ELAM, ELAM1, ESEL, LECAM2, leukocyte endothelial cell adhesion molecule 2; selectin E, endothelial adhesion molecule 1 | SELE |
| 209 | selectin P (granule membrane protein 140 kDa, antigen CD62) | CD62, CD62P, FLJ45155, GMP140, GRMP, PADGEM, PSEL; antigen CD62; granulocyte membrane protein; selectin P; selectin P (granule membrane protein 140 kD, antigen CD62) | SELP |
| 210 | serpin peptidase inhibitor, clade A (alpha-1 antiproteinase, antitrypsin), member 6 | corticosteroid-binding globulin; transcortin; corticosteroid binding globulin; serine (or cysteine) | SERPINA6 |

TABLE 7-continued

| ALLDBRISK | Official Name | Common Name | Entrez Gene Link |
|---|---|---|---|
| 211 | serpin peptidase inhibitor, clade E (nexin, plasminogen activator inhibitor type 1), member 1 | proteinase inhibitor, clade A (alpha-1 antiproteinase, antitrypsin), member 6 plasminogen activator inhibitor-1 - PAI, PAI-1, PAI1, PLANH1, plasminogen activator inhibitor, type I; plasminogen activator inhibitor-1; serine (or cysteine) proteinase inhibitor, clade E (nexin, plasminogen activator inhibitor type 1), member 1 | SERPINE1 |
| 212 | serum/glucocorticoid regulated kinase | Serum/Glucocorticoid Regulated Kinase 1 - SGK1, serine/threonine protein kinase SGK; serum and glucocorticoid regulated kinase | SGK |
| 213 | sex hormone-binding globulin | sex hormone-binding globulin (SHBG) - ABP, Sex hormone-binding globulin (androgen binding protein) | SHBG |
| 214 | thioredoxin interacting protein | Sirt1; SIR2alpha; sir2-like 1; sirtuin type 1; sirtuin (silent mating type information regulation 2, S. cerevisiae, homolog) 1 | SIRT1 |
| 215 | solute carrier family 2, member 10 | glucose transporter 10 (GLUT10); ATS | SLC2A10 |
| 216 | solute carrier family 2, member 2 | glucose transporter 2 (GLUT2) | SLC2A2 |
| 217 | solute carrier family 2, member 4 | glucose transporter 4 (GLUT4) | SLC2A4 |
| 218 | solute carrier family 7 (cationic amino acid transporter, y+ system), member 1(ERR) | ERR - ATRC1, CAT-1, ERR, HCAT1, REC1L, amino acid transporter, cationic 1; ecotropic retroviral receptor | SLC7A1 |
| 219 | SNF1-like kinase 2 | Sik2; salt-inducible kinase 2; salt-inducible serine/threonine kinase 2 | SNF1LK2 |
| 220 | suppressor of cytokine signaling 3 | CIS3, Cish3, SOCS-3, SSI-3, SSI3, STAT induced STAT inhibitor 3; cytokine-induced SH2 protein 3 | SOCS3 |
| 221 | v-src sarcoma (Schmidt-Ruppin A-2) viral oncogene homolog (avian) | ASV, SRC1, c-SRC, p60-Src, proto-oncogene tyrosine-protein kinase SRC; protooncogene SRC, Rous sarcoma; tyrosine kinase pp60c-src; tyrosine-protein kinase SRC-1 | SRC |
| 222 | sterol regulatory element binding transcription factor 1 | sterol regulatory element-binding protein 1c (SREBP-1c) | SREBF1 |
| 223 | solute carrier family 2, member 4 | SMST, somatostatin-14, somatostatin-28 | SST |
| 224 | somatostatin receptor 2 | somatostatin receptor subtype 2 | SSTR2 |
| 225 | somatostatin receptor 5 | somatostatin receptor 5 - somatostatin receptor subtype 5 | SSTR5 |
| 226 | transcription factor 1, hepatic; LF-B1, hepatic nuclear factor (HNF1) | HNF1α; albumin proximal factor; hepatic nuclear factor 1; maturity onset Diabetes of the young 3; Interferon production regulator factor (HNF1) | TCF1 |
| 227 | transcription factor 2, hepatic; LF-B3; variant hepatic nuclear factor | hepatocyte nuclear factor 2 - FJHN, HNF1B, HNF1beta, HNF2, LFB3, MODY5, VHNF1, transcription factor 2 | TCF2 |
| 228 | transcription factor 7-like 2 (T-cell specific, HMG-box) | TCF7L2 - TCF-4, TCF4 | TCF7L2 |
| 229 | transforming growth factor, beta 1 (Camurati-Engelmann disease) | TGF-beta: TGF-beta 1 protein; diaphyseal dysplasia 1, progressive; transforming growth factor beta 1; transforming growth factor, beta 1; transforming growth factor-beta 1, CED, DPD1, TGFB | TGFB1 |
| 230 | transglutaminase 2 (C polypeptide, protein-glutamine-gamma-glutamyltransferase) | TG2, TGC, C polypeptide; TGase C; TGase-H; protein-glutamine-gamma-glutamyltransferase; tissue transglutaminase; transglutaminase 2; transglutaminase C | TGM2 |
| 231 | thrombospondin 1 | thrombospondin - THBS, TSP, TSP1, thrombospondin-1p180 | THBS1 |
| 232 | thrombospondin, type I, domain containing 1 | TMTSP, UNQ3010, thrombospondin type I domain-containing 1; thrombospondin, type I, domain 1; transmembrane molecule with thrombospondin module | THSD1 |
| 233 | TIMP metallopeptidase inhibitor | CSC-21K; tissue inhibitor of metalloproteinase 2; tissue inhibitor of metalloproteinase 2 precursor; tissue inhibitor of metalloproteinases 2 | TIMP2 |

TABLE 7-continued

| ALLDBRISK | Official Name | Common Name | Entrez Gene Link |
|---|---|---|---|
| 234 | tumor necrosis factor (TNF superfamily, member 2) | TNF-alpha (tumour necrosis factor-alpha) - DIF, TNF-alpha, TNFA, TNFSF2, APC1 protein; TNF superfamily, member 2; TNF, macrophage-derived; TNF, monocyte-derived; cachectin; tumor necrosis factor alpha | TNF |
| 235 | tumor necrosis factor receptor superfamily, member 11b (osteoprotegerin) | MGC29565, OCIF, OPG, TR1; osteoclastogenesis inhibitory factor; osteoprotegerin | TNFRSF11B |
| 236 | tumor necrosis factor receptor superfamily, member 1A | tumor necrosis factor receptor 1 gene R92Q polymorphism - CD120a, FPF, TBP1, TNF-R, TNF-R-I, TNF-R55, TNFAR, TNFR1, TNFR55, TNFR60, p55, p55-R, p60, tumor necrosis factor binding protein 1; tumor necrosis factor receptor 1; tumor necrosis factor receptor type 1; tumor necrosis factor-alpha receptor | TNFRSF1A |
| 237 | tumor necrosis factor receptor superfamily, member 1B | soluble necrosis factor receptor - CD120b, TBPII, TNF-R-II, TNF-R75, TNFBR, TNFR2, TNFR80, p75, p75TNFR, p75 TNF receptor; tumor necrosis factor beta receptor; tumor necrosis factor binding protein 2; tumor necrosis factor receptor 2 | TNFRSF1B |
| 238 | tryptophan hydroxylase 2 | enzyme synthesizing serotonin; neuronal tryptophan hydroxylase, NTPH | TPH2 |
| 239 | thyrotropin-releasing hormone | thyrotropin-releasing hormone | TRH |
| 240 | transient receptor potential cation channel, subfamily V, member 1 | vanilloid receptor 1 - VR1, capsaicin receptor; transient receptor potential vanilloid 1a; transient receptor potential vanilloid 1b; vanilloid receptor subtype 1, capsaicin receptor; transient receptor potential vanilloid subfamily 1 (TRPV1) | TRPV1 |
| 241 | thioredoxin interacting protein | thioredoxin binding protein 2; upregulated by 1,25-dihydroxyvitamin D-3 | TXNIP |
| 242 | thioredoxin reductase 2 | TR; TR3; SELZ; TRXR2; TR-BETA; selenoprotein Z; thioredoxin reductase 3; thioredoxin reductase beta | TXNRD2 |
| 243 | urocortin 3 (stresscopin) | archipelin, urocortin III, SCP, SPC, UCNIII, stresscopin; urocortin 3 | UCN3 |
| 244 | uncoupling protein 2 (mitochondrial, proton carrier) | UCPH, uncoupling protein 2; uncoupling protein-2 | UCP2 |
| 245 | upstream transcription factor 1 | major late transcription factor 1 | USF1 |
| 246 | urotensin 2 | PRO1068, U-II, UCN2, UII | UTS2 |
| 247 | vascular cell adhesion molecule 1 | (soluble) vascular cell adhesion molecule-1, CD106, INCAM-100, CD106 antigen, VCAM-1 | VCAM1 |
| 248 | vascular endothelial growth factor | VEGF - VEGFA, VPF, vascular endothelial growth factor A; vascular permeability factor | VEGF |
| 249 | vimentin | vimentin | VIM |
| 250 | vasoactive intestinal peptide | vasoactive intestinal peptide - PHM27 | VIP |
| 251 | vasoactive intestinal peptide receptor 1 | vasoactive intestinal peptide receptor 1 - HVR1, II, PACAP-R-2, RCD1, RDC1, VIPR, VIRG, VPAC1, PACAP type II receptor; VIP receptor, type I; pituitary adenylate cyclase activating polypeptide receptor, type II | VIPR1 |
| 252 | vasoactive intestinal peptide receptor 2 | Vasoactive Intestinal Peptide Receptor 2 - VPAC2 | VIPR2 |
| 253 | von Willebrand factor | von Willebrand factor, F8VWF, VWD, coagulation factor VIII VWF | VWF |
| 254 | Wolfram syndrome 1 (wolframin) | DFNA14, DFNA38, DFNA6, DIDMOAD, WFRS, WFS, WOLFRAMIN | WFS1 |
| 255 | X-ray repair complementing defective repair in Chinese hamster cells 6 | Ku autoantigen, 70 kDa; Ku autoantigen p70 subunit; thyroid-lupus autoantigen p70; CTC box binding factor 75 kDa subunit; thyroid autoantigen 70 kD (Ku antigen); | XRCC6 |

TABLE 7-continued

| ALLDBRISK | Official Name | Common Name | Entrez Gene Link |
|---|---|---|---|
| | | thyroid autoantigen 70 kDa (Ku antigen); ATP-dependent DNA helicase II, 70 kDa subunit | |
| 256 | c-peptide | c-peptide, soluble c-peptide | SCp |
| 257 | cortisol | cortisol - hydrocortisone is the synthetic form | |
| 258 | vitamin D3 | vitamin D3 | |
| 259 | estrogen | estrogen | |
| 260 | estradiol | estradiol | |
| 261 | digitalis-like factor | digitalis-like factor | |
| 262 | oxyntomodulin | oxyntomodulin | |
| 263 | dehydroepiandrosterone sulfate (DHEAS) | dehydroepiandrosterone sulfate (DHEAS) | |
| 264 | serotonin (5-hydroxytryptamine) | serotonin (5-hydroxytryptamine) | |
| 265 | anti-CD38 autoantibodies | anti-CD38 autoantibodies | |
| 266 | gad65 autoantibody | gad65 autoantibody epitopes | |
| 267 | Proinsulin | | PROINS |
| 268 | endoglin | END; ORW; HHT1; ORW1; CD105; FLJ41744; RP11-228B15.2 | ENG |
| 269 | interleukin 2 receptor, beta | CD122; P70-75; CD122 antigen; OTTHUMP00000028799; high affinity IL-2 receptor beta subunit | IL2RB |
| 270 | insulin-like growth factor binding protein 2 | IBP2; IGF-BP53 | IGFBP2 |
| 271 | insulin-like growth factor 1 receptor | CD221, IGFIR, JTK13, MGC142170, MGC142172, MGC18216 | IGF1R |
| 272 | fructosamine | | |

TABLE 8

| # | Clinical Parameter ("CPs") |
|---|---|
| 272 | Age (AGE) |
| 273 | Body Mass Index (BMI) |
| 274 | Diastolic Blood Pressure (DBP) |
| 275 | Family History (FHX) (or FHX1—one parent with Diabetes; and FHX2—two parents with Diabetes) |
| 276 | Gestational Diabetes Mellitus (GDM), Past |
| 277 | Height (HT) |
| 278 | Hip Circumference (Hip) |
| 279 | Race (RACE) |
| 280 | Sex (SEX) |
| 281 | Systolic Blood Pressure (SBP) |
| 282 | Waist Circumference (Waist) |
| 283 | Weight (WT) |

(and other combinations thereof, including Waist to Hip Ratio (WHr)).

TABLE 9

| # | Traditional Laboratory Risk Factors ("TLRFs") |
|---|---|
| 284 | Cholesterol (CHOL) |
| 285 | Glucose (fasting plasma glucose (FPG/Glucose) or with oral glucose tolerance test (OGTT)) |
| 286 | HBA1c (Glycosylated Hemoglobin (HBA1/HBA1C) |
| 287 | High Density Lipoprotein (HDL/HDLC) |
| 288 | Low Density Lipoprotein (LDL/LDLC) |
| 289 | Very Low Density Lipoprotein (VLDLC) |
| 290 | Triglycerides (TRIG) |

One skilled in the art will note that the above listed ALLDBRISK markers ("ALLDBRISKS") come from a diverse set of physiological and biological pathways, including many which are not commonly accepted to be related to Diabetes. These groupings of different ALLDBRISK markers, even within those high significance segments, may presage differing signals of the stage or rate of the progression of the disease. Such distinct groupings of ALLDBRISK markers may allow a more biologically detailed and clinically useful signal from the ALLDBRISK markers as well as opportunities for pattern recognition within the ALLDBRISK algorithms combining the multiple ALLDBRISK signals.

The present invention concerns, in one aspect, a subset of ALLDBRISK markers; other ALLDBRISKS and even biomarkers which are not listed in the above Table 7, but related to these physiological and biological pathways, may prove to be useful given the signal and information provided from these studies. To the extent that other biomarker pathway participants (i.e., other biomarker participants in common pathways with those biomarkers contained within the list of ALLDBRISKS in the above Table 7) are also relevant pathway participants in pre-Diabetes, Diabetes, or a pre-diabetic condition, they may be functional equivalents to the biomarkers thus far disclosed in Table 7.

These other pathway participants are also considered ALLDBRISKS in the context of the present invention, provided they additionally share certain defined characteristics of a good biomarker, which would include both involvement in the herein disclosed biological processes and also analytically important characteristics such as the bioavailability of said biomarkers at a useful signal to noise ratio, and in a useful sample matrix such as blood serum. Such requirements typically limit the diagnostic usefulness of many members of a biological pathway, and frequently occurs only in pathway members that constitute secretory substances, those accessible on the plasma membranes of cells, as well as those that are released into the serum upon cell death, due to apoptosis or for other reasons such as endothelial remodeling or other cell turnover or cell necrotic processes, whether or not they are related to the disease progression of pre-Diabetes, a pre-diabetic condition, and Diabetes. However, the remaining and future biomarkers that meet this high standard for ALLDBRISKS are likely to be quite valuable.

Furthermore, other unlisted biomarkers will be very highly correlated with the biomarkers listed as ALLDBRISKS in Table 7 (for the purpose of this application, any two variables will be considered to be "very highly correlated" when they have a correlation (R) of 0.4 or greater). The present invention encompasses such functional and statistical equivalents to the aforementioned ALLDBRISKS. Furthermore, the statistical utility of such additional ALLDBRISKS is substantially dependent on the cross-correlation between multiple biomarkers and any new biomarkers will often be required to operate within a panel in order to elaborate the meaning of the underlying biology.

One or more, preferably two or more of the listed ALLDBRISKS can be detected in the practice of the present invention. For example, two (2), three (3), four (4), five (5), ten (10), fifteen (15), twenty (20), forty (40), fifty (50), seventy-five (75), one hundred (100), one hundred and twenty five (125), one hundred and fifty (150), one hundred and seventy-five (175), two hundred (200), two hundred and ten (210), two hundred and twenty (220), two hundred and thirty (230), two hundred and forty (240), two hundred and fifty (250), two hundred and sixty (260) or more ALLDBRISKS can be detected. In some aspects, all ALLDBRISKS listed herein can be detected. Preferred ranges from which the number of ALLDBRISKS can be detected include ranges bounded by any minimum selected from between one and all known ALLDBRISKS, particularly up to two, five, ten, twenty, twenty-five, thirty, forty, fifty, seventy-five, one hundred, one hundred and twenty five, one hundred and fifty, one hundred and seventy-five, two hundred, two hundred and ten, two hundred and twenty, two hundred and thirty, two hundred and forty, two hundred and fifty, paired with any maximum up to the total known ALLDBRISKS, particularly up to five, ten, twenty, fifty, and seventy-five. Particularly preferred ranges include two to five (2-5), two to ten (2-10), two to fifty (2-50), two to seventy-five (2-75), two to one hundred (2-100), five to ten (5-10), five to twenty (5-20), five to fifty (5-50), five to seventy-five (5-75), five to one hundred (5-100), ten to twenty (10-20), ten to fifty (10-50), ten to seventy-five (10-75), ten to one hundred (10-100), twenty to fifty (20-50), twenty to seventy-five (20-75), twenty to one hundred (20-100), fifty to seventy-five (50-75), fifty to one hundred (50-100), one hundred to one hundred and twenty-five (100-125), one hundred and twenty-five to one hundred and fifty (125-150), one hundred and fifty to one hundred and seventy five (150-175), one hundred and seventy-five to two hundred (175-200), two hundred to two hundred and ten (200-210), two hundred and ten to two hundred and twenty (210-220), two hundred and twenty to two hundred and thirty (220-230), two hundred and thirty to two hundred and forty (230-240), two hundred and forty to two hundred and fifty (240-250), two hundred and fifty to two hundred and sixty (250-260), and two hundred and sixty to more than two hundred and sixty (260+).

In some variation of the invention, any integer number of ALLDBRISK from 1 to 20 is combined with an integer number of lipid metabolite biomarker from 1 to 20, as well as any integer number from 1 to 10 of other factors described herein, including glucose, clinical parameters and traditional risk factors.

Construction of Clinical Algorithms

Any formula may be used to combine ALLDBRISK results, lipid metabolites, traditional risk factors, glucose and other parameters described herein, into indices useful in the practice of the invention. As indicated above, and without limitation, such indices may indicate, among the various other indications, the probability, likelihood, absolute or relative risk, time to or rate of conversion from one to another disease states, or make predictions of future biomarkers measurements of Diabetes such as Glucose or HBA1c used for Diabetes in the diagnosis of the frank disease. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from ALLDBRISK, lipid metabolites and other results in the relevant training population. Amongst other uses, such formula may be intended to map the feature space derived from one or more ALLDBRISK, lipid metabolites and other inputs to a set of subject classes (e.g. useful in predicting class membership of subjects as normal, pre-Diabetes, Diabetes), to derive an estimation of a probability function of risk using a Bayesian approach (e.g. the risk of Diabetes), or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual ALLDBRISK, lipid metabolite, and other measurements into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on Clinical Parameters such as age, gender, race, or sex, where specific formula are used solely on subjects within a class or continuously combining a Clinical Parameter as an input. In other cases, analyte-based biomarkers can be combined into calculated variables (much as BMI is a calculation using Height and Weight) which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al. (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves; and Vasan, R. S., 2006 regarding biomarkers of cardiovascular disease.

Finally, the numeric result of a classifier formula itself may be transformed post-processing by its reference to an actual clinical population and study results and observed endpoints, in order to calibrate to absolute risk and provide confidence intervals for varying numeric results of the classifier or risk formula. An example of this is the presentation of absolute risk, and confidence intervals for that risk, derivied using an actual clinical study, chosen with reference to the output of the recurrence score formula in the Oncotype Dx product of Genomic Health, Inc. (Redwood City, Calif.). A further modification is to adjust for smaller sub-populations of the study based on the output of the classifier or risk formula and defined and selected by their Clinical Parameters, such as age or sex.

Summary of Algorithm Development Process and Application of Algorithms

FIG. 7 is a flow diagram of an example method 200 for developing a model which may be used to evaluate a risk of a person, or group of people, for developing a diabetic condition. The method 200 may be implemented using the example computing system environment 100 of FIG. 6 and will be used to explain the operation of the environment 100. However, it should be recognized that the method 200 could be implemented by a system different than the computing system environment 100. At a block 202, biomarker data from a representative population, as has been described herein, is obtained from a data storage device, such as the system memory 130, an internal or external database, or other computer storage media. The biomarker data may be initially derived through a variety of means, including prospective (longitudinal) studies to involving observations of the representative population over a period of time, retrospective studies of samples of a representative population that queries the samples and/or from a retrospective epidemiological data storage containing the results from previous studies, such as an NIH database. The biomarker data may be derived from a single study or multiple studies, and generally includes data pertaining to the desired indication and endpoint of the representative population, including values of the biomarkers described herein, clinical annotations (which may include endpoints), and most particularly the desired endpoints for training an algorithm for use in the invention, across many subjects.

At a block 204, the representative population data set is prepared as needed to meet the requirements of the model or analysis that will be used for biomarker selection, as described below. For example, data set preparation may include preparing the biomarker values from each subject within the representative population, or a chosen subset thereof. However, the raw biomarker data alone may not be entirely useful for the purposes of model training. As such, various data preparation methods may be used to prepare the data, such as gap fill techniques (e.g., nearest neighbor interpolation or other pattern recognition), quality checks, data combination using of various formulae (e.g., statistical classification algorithms), normalization and/or transformations, such as logarithmic functions to change the distribution of data to meet model requirements (e.g., base 10, natural log, etc.). Again, the particular data preparation procedures are dependent upon the model or models that will be trained using the representative population data. The particular data preparation techniques for various different model types are known, and need not be described further.

At a block 206, the particular biomarkers are selected to be subsequently used in the training of the model used to evaluate a risk of developing a diabetic condition. Biomarker selection may involve utilizing a selection model to validate the representative population data set and selecting the biomarker data from the data set that provides the most reproducible results. Examples of data set validation may include, but are not limited to, cross-validation and bootstrapping. From the marker selection, the model to be used in evaluating a risk of developing a diabetic condition may be determined and selected. However, it is noted that not all models provide the same results with the same data set. For example, different models may utilize different numbers of biomarkers and produce different results, thereby adding significance to the combination of biomarkers on the selected model. Accordingly, multiple selection models may be chosen and utilized with the representative population data set, or subsets of the data set, in order to identify the optimal model for risk evaluation. Examples of the particular models, including statistical models, algorithms, etc., which may be used for selecting the biomarkers have been described above.

For each selection model used with the data set, or subset thereof, the biomarkers are selected based on each biomarker's statistical significance in the model. When input to each model, the biomarkers are selected based on various criteria for statistical significance, and may further involve cumulative voting and weighting. Tests for statistical significance may include exit-tests and analysis of variance (ANOVA). The model may include classification models (e.g., LDA, logistic regression, SVM, RF, tree models, etc.) and survival models (e.g., cox), many examples of which have been described above.

It is noted that while biomarkers may be applied individually to each selection model to identify the statistically significant biomarkers, in some instances individual biomarkers alone may not be fully indicative of a risk for a diabetic condition, in which case combinations of biomarkers may be applied to the selection model. For example, rather than utilizing univariate biomarker selection, multivariate biomarker selection may be utilized. That is, a biomarker may not be a good indicator when used as a univariate input to the selection model, but may be a good indicator when used in combination with other biomarkers (i.e., a multivariate input to the model), because each marker may bring additional information to the combination that would not be indicative if taken alone.

At a block 208, the model to be used for evaluating risk is selected, trained and validated. In particular, leading candidate models may be selected based on one or more performance criteria, examples of which have been described above. For example, from using the data set, or data subsets, with various models, not only are the models used to determine statistically significant biomarkers, but the results may be used to select the optimal models along with the biomarkers. As such, the evaluation model used to evaluate risk may include one of those used as a selection model, including classification models and survival models. Combinations of models markers, including marker subsets, may be compared and validated in subsets and individual data sets. The comparison and validation may be repeated many times to train and validate the model and to choose an appropriate model, which is then used as an evaluation model for evaluating risk of a diabetic condition.

FIG. 8 is a flow diagram of an example method 250 for using a model to evaluate a risk of a subject (e.g., a person, or group of people) developing a diabetic condition. At a block 252, biomarker data from the subject is obtained from a data storage device, which may be the same as, or different from, the data storage device discussed above with reference to FIG. 7. The subject biomarker data may be initially derived through a variety of means, including self-reports, physical examination, laboratory testing and existing medical records, charts or databases. As with the representative population biomarker data at block 204 of FIG. 7, the subject biomarker data at block 254 may be prepared using transforms, logs, combinations, normalization, etc. as needed according to the model type selected and trained in FIG. 7. Once the data has been prepared, at a block 256, the subject biomarker data is input into the evaluation model, and at a block 258 the evaluation model outputs an index value (e.g., risk score, relative risk, time to conversion, etc.). Many examples have been provided herein as to how a model may be used to evaluate the subject biomarkers and output an index value, e.g. see Example 1.

Modifications for Therapeutic Intervention Panels

A panel of ALLDBRISK, lipid metabolites, glucose and optionally other parameters can be constructed and formula derived specifically to enhance performance for use also in subjects undergoing therapeutic interventions, or a separate panel and formula may alternatively be used solely in such patient populations. An aspect of the invention is the use of specific known characteristics of these biomarkers and other parameters and their changes in such subjects for such panel construction and formula derivation. Such modifications may enhance the performance of various indications noted above in Diabetes prevention, and diagnosis, therapy, monitoring, and prognosis of Diabetes and pre-Diabetes.

Several of the ALLDBRISKS and other biomarkers and parameters disclosed herein are known to those skilled in the art to vary predictably under therapeutic intervention, whether lifestyle (e.g. diet and exercise), surgical (e.g. bariatric surgery) or pharmaceutical (e.g., one of the various classes of drugs mentioned herein or known to modify common risk factors or risk of Diabetes) intervention. For example, a PubMed search using the terms "Adiponectin drug," will return over 700 references, many with respect to the changes or non-changes in the levels of adiponectin (ADIPOQ) in subjects treated with various individual Diabetes-modulating agents. Similar evidence of variance under therapeutic intervention is widely available for many of the biomarkers listed in Table 7, such as CRP, FGA, INS, LEP, among others. Certain of the biomarkers listed, most particularly the Clinical Parameters and the Traditional Laboratory Risk Factors, (and including such biomarkers as GLUCOSE, SBP, DBP, CHOL, HDL, and HBA1c), are traditionally used as surrogate or primary endpoint markers of efficacy for entire classes of Diabetes-modulating agents, thus most certainly changing in a statistically significant way.

Still others, including genetic biomarkers, such as those polymorphisms known in the PPARG and INSR (and generally all genetic biomarkers absent somatic mutation), are similarly known not to vary in their measurement under particular therapeutic interventions. Such variation may or may not impact the general validity of a given panel, but will often impact the index values reported, and may require different marker selection, the formula to be re-optimized or other changes to the practice of the invention. Alternative model calibrations may also be practiced in order to adjust the normally reported results under a therapeutic intervention, including the use of manual table lookups and adjustment factors.

Such properties of the individual ALLDBRISKS and other parameters can thus be anticipated and exploited to select, guide, and monitor therapeutic interventions. For example, specific ALLDBRISKS and other parameters may be added to, or subtracted from, the set under consideration in the construction of the ALLDBRISK panels, based on whether they are known to vary, or not to vary, under therapeutic intervention. Alternatively, such ALLDBRISKS and other parameters may be individually normalized or formula recalibrated to adjust for such effects according to the above and other means well known to those skilled in the art.

Combination with Clinical Parameters

Any of the aforementioned Clinical Parameters, ALLDBRISK biomarkers, lipid metabolite other factors, may be used in the practice of the invention as an input to a formula or as a pre-selection criteria defining a relevant population to be measured using a particular panel and formula. As noted above, Clinical Parameters may also be useful in the biomarker normalization and pre-processing, or in biomarker selection, panel construction, formula type selection and derivation, and formula result post-processing.

Endpoints of the Invention

One embodiment of the invention is to tailor panels and formulas to the population and end point or use that is intended. For example, the panels and formulas may used for assessment of subjects for primary prevention and diagnosis and for secondary prevention and management. For the primary assessment, the panels and formulas may be used for prediction and risk stratification for conditions, for the diagnosis of diabetic conditions, for the prognosis of glucose level and rate of change and for indication for future diagnosis. For secondary prevention and management, the panels and formulas may be used for prognosis, risk stratification for Diabetes complications. The panels and formulas may be used for clinical decision support, such as determining whether to defer intervention to next visit, to recommend normal preventive check-ups, to recommend increased visit frequency, to recommend increased testing and to recommend therapeutic intervention. The panels and formulas may also be useful for intervention in subjects with diabetic conditions, such as therapeutic selection and response, adjustment and dosing of therapy, monitoring ongoing therapeutic efficiency and indication for change in therapeutic intervention.

The disease endpoints of the invention include type I and type II Diabetes Mellitus and other diabetic conditions and pre-diabetic conditions. The panels and formulas may be used to evaluate the current status of the disease endpoints by aiding in the diagnosis of latent type II Diabetes Mellitus, and aiding in the determination of severity of the type II Diabetes Mellitus and determination of the subclass of type II Diabetes Mellitus. The panels and formulas are also useful for determining the future status of intervention such as determining the prognosis of future type II Diabetes Mellitus with therapy, intervention and drug therapy. The invention may be tailored to a specific intervention, drug class, therapeutic class or therapy or drug therapy or a combination thereof.

The surrogate endpoints of the invention include measuring HBA1c, glucose (FPG and OGTT), and glucose class (normal glucose tolerance (NGT), IGT, IFG AND T2DM). The panels and formulas are useful for determining the current status of the surrogate endpoints by diagnosing glucose class with or without fasting. The future status of surrogate endpoints may be determined using the panels and formulas of the invention such as determination of the prognosis of future glucose class. The panels and formulas are also useful for determining the future status of intervention such as determination of prognosis of future glucose class with drug therapy.

The complication endpoints of diabetic conditions include eye retinopathy, microvascular damage, liver damage, limb amputation and cardiovascular complications to name a few. The panels and formulas may be used to evaluate the current status of the disease endpoints by aiding in the diagnosis of liver damage. The future status of complication endpoints may be determined using the panels and formulas such as determination of the prognosis of future retinopathy. The panels and formulas are also useful for determining the future status of intervention such as determining the prognosis of future retinopathy with therapy or drug therapy.

Measurement of ALLDBRISKS and Other Biomarkers and Parameters

Biomarkers may be measured in using several techniques designed to achieve more predictable subject and analytical variability. On subject variability, many of the above ALLDBRISKS and other biomarkers and parameters are commonly measured in a fasting state, and most commonly in the morning, providing a reduced level of subject variability due to both food consumption and metabolism and diurnal variation. The invention hereby claims all fasting and temporal-based sampling procedures using the ALLDBRISKS and other biomarkers and parameters described herein. Pre-processing adjustments of ALLDBRISK and other biomarker and parameter results may also be intended to reduce this effect.

The actual measurement of levels of the ALLDBRISKS can be determined at the protein or nucleic acid level using any method known in the art. For example, at the nucleic acid level, Northern and Southern hybridization analysis, as well as ribonuclease protection assays using probes which specifically recognize one or more of these sequences can be used to determine gene expression. Alternatively, levels of ALLDBRISKS can be measured using reverse-transcription-based PCR assays (RT-PCR), e.g., using primers specific for the differentially expressed sequence of genes. Levels of ALLDBRISKS can also be determined at the protein level, e.g., by measuring the levels of peptides encoded by the gene products described herein, or activities thereof. Such methods are well known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the biomarker genes according to the activity of each protein analyzed.

The ALLDBRISK proteins, polypeptides, mutations, and polymorphisms thereof can be detected in any suitable manner, but is typically detected by contacting a sample from the subject with an antibody which binds the ALLDBRISK protein, polypeptide, mutation, or polymorphism and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological fluid as described above, and may be the same sample of biological fluid used to conduct the method described above.

Immunoassays carried out in accordance with the present invention may be homogeneous assays or heterogeneous assays. In a homogeneous assay the immunological reaction usually involves the specific antibody (e.g., anti-ALLDBRISK protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include, but are not limited to oligonucleotides, immunoblotting, immunoprecipitation, immunofluorescence methods, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogeneous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of ALLDBRISK proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51).

For ALLDBRISK proteins, polypeptides, mutations, and polymorphisms known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Using sequence information provided by the database entries for the ALLDBRISK sequences, expression of the ALLDBRISK sequences can be detected (if present) and measured using techniques well known to one of ordinary skill in the art. For example, sequences within the sequence database entries corresponding to ALLDBRISK sequences, or within the sequences disclosed herein, can be used to construct probes for detecting ALLDBRISK RNA sequences in, e.g., Northern blot hybridization analyses or methods which specifically, and, preferably, quantitatively amplify specific nucleic acid sequences. As another example, the sequences can be used to construct primers for specifically amplifying the ALLDBRISK sequences in, e.g., amplification-based detection methods such as reverse-transcription based polymerase chain reaction (RT-PCR). When alterations in gene expression are associated with gene amplification, deletion, polymorphisms, and mutations, sequence comparisons in test and reference populations can be made by comparing relative amounts of the examined DNA sequences in the test and reference cell populations.

Expression of the genes disclosed herein can be measured at the RNA level using any method known in the art. For example, Northern hybridization analysis using probes which specifically recognize one or more of these sequences can be used to determine gene expression. Alternatively, expression can be measured using reverse-transcription-based PCR assays (RT-PCR), e.g., using primers specific for the differentially expressed sequences. RNA can also be quantified using, for example, other target amplification methods (e.g., TMA, SDA, NASBA), or signal amplification methods (e.g., bDNA), and the like.

Alternatively, ALLDBRISK protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. (See, WO 04/056456 and WO 04/088309, each of which are hereby incorporated by reference in their entireties) In this regard, other ALLDBRISK analytes can be measured using the above-mentioned detection methods, or other methods known to the skilled artisan. For example, circulating calcium ions (Ca2+) can be detected in a sample using fluorescent dyes such as the Fluo series, Fura-2A, Rhod-2, among others. Other ALLDBRISK metabolites can be similarly detected using reagents that specifically designed or tailored to detect such metabolites.

Kits

Kits for practicing the methods of the invention are provided. The kits include (a) one or more reagents for measuring the amount of one or more lipid metabolites (and/or additional biomarkers); and (b) instructions for use. A kit may provide 1, 2, 3, 4, 5, 10, 15, 20, or more reagents for measuring the amount of 1, 2, 3, 4, 5, 10, 15, 20, or more lipid metabolites. The kit may further provide one or more reagents for measuring one or more additional biomarkers, such as those disclosed above, and in Tables X-X. In one embodiment, the kit includes one or more reagents for use in an immunoassay. In one embodiment, the kit includes one or more reagents for use in an MS assay. The invention is further illustrated by the following nonlimiting examples.

The invention also includes a ALLDBRISK-detection reagent, e.g., nucleic acids that specifically identify one or more ALLDBRISK nucleic acids by having homologous nucleic acid sequences, such as oligonucleotide sequences or aptamers, complementary to a portion of the ALLDBRISK nucleic acids or antibodies to proteins encoded by the ALLDBRISK nucleic acids packaged together in the form of a kit. The oligonucleotides can be fragments of the ALLDBRISK genes. For example the oligonucleotides can be 200, 150, 100, 50, 25, 10 or less nucleotides in length. The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or a sandwich ELISA as known in the art.

For example, ALLDBRISK detection reagents can be immobilized on a solid matrix such as a porous strip to form at least one ALLDBRISK detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, e.g., a higher amount in the first detection site and lesser amounts in subsequent sites. Upon the addition of test sample, the number of sites displaying a detectable signal provides a quantitative indication of the amount of ALLDBRISKS present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences represented by ALLDBRISKS1-271. In various embodiments, the expression of 2, 3, 4, 5, 6, 7, 8, 9, 10, 15, 20, 25, 40, 50, 100, 125, 150, 175, 200, 210, 220, 230, 240, 250, 260 or more of the sequences represented by ALLD-BRISKS1-271 can be identified by virtue of binding to the array. The substrate array can be on, e.g., a solid substrate, e.g., a "chip" as described in U.S. Pat. No. 5,744,305. Alternatively, the substrate array can be a solution array, e.g., xMAP (Luminex, Austin, Tex.), Cyvera (Illumina, San Diego, Calif.), CellCard (Vitra Bioscience, Mountain View, Calif.) and Quantum Dots' Mosaic (Invitrogen, Carlsbad, Calif.).

Suitable sources for antibodies for the detection of ALL-DBRISK include commercially available sources such as, for example, Abazyme, Abnova, Affinity Biologicals, Antibody-Shop, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, nucleic acid probes, e.g., oligonucleotides, aptamers, siRNAs, antisense oligonucleotides, against any of the ALLDBRISK in Table 7.

EXAMPLES

Example 1

This is an description of calculating Risk using the algorithm LDA and the formula set out as (DRS=exp(D)/[1+exp(D)]) in order to select some of the preferred protein biomarkers of Table 1.

Marker Selection

An exemplary data set collected from human subjects included 632 observations in this data set and 65 potential blood-borne biomarkers (Inputs). To reduce the number of Inputs, three broad marker selection algorithms were used: Univariate marker selection, exhaustive small model searches, and bootstrap replicates of common heuristic marker selection techniques. The bootstrap marker selection process included forward, backward, and stepwise selection based on Akaike's information criteria (AIC) and Hoetelling's $T^2$, Analysis of variance based filters, random forest filters and Eigengene-based linear discriminant analysis. These selection techniques were used on 100 bootstrap replicates and the marker counts were tabulated and averaged. To control for model size, marker counts were weighted by 1/k where k is the size of the model. Markers were selected for modeling based on a permutation test as follows: Algorithm outputs were permuted and the 100 bootstrap replicates were used to calculate weighted marker count averages of the six selection techniques. This process was repeated 20 times and the 95 percentile of the weighted marker count averages was used as a cutoff to identify markers that were selected significantly more than random. Similar permutation techniques were used to identify univariate features and exhaustive searches that were different from random.

Algorithm Construction

The markers selected as described above were then combined to calculate coefficients that result in a functioning model. Logistic regression and/or linear discriminant analysis were used to estimate coefficients based on maximum likelihood and least-squares means, respectively. Initially, individual markers were evaluated for linearity using decile plots and transformations were attempted if strong departures are noted. Models including all markers were then constructed and the coefficients were examined to determine if all were necessary. The ability to reduce the marker number is evaluated using regression models of principle components of the Inputs, backward selection, and bootstrapping methods. The remaining parameters were used to produce an algorithm is that is a linear model constructed at a prior probability of 50% group membership for the each of the two model outputs. This weighting is useful in balancing sensitivity and specificity of the resulting model when the number of cases and controls (also known as converters and non-converters, respectively) are imbalanced. Cases refer to the samples that were being analyzed to determine if different than the control.

For illustrative purposes, exemplary coefficients for selected biomarkers with the resulting intercept for analysis are set out in Table 10 below. The transformed values for the biomarkers are also set out under subject 20311 (1) and 77884 (0).

TABLE 10

|  | LDA.BWD | LDA.SWS | LDA.KW10 | LDA.RF10 | LDA.ELDA3 | LDA.ELDA2 | 20311 (1) | 77884 (0) |
| --- | --- | --- | --- | --- | --- | --- | --- | --- |
| Intercept | −26.4567 | −27.9154 | −25.1138 | −25.4264 | −5.96578 | −13.1593 |  |  |
| ADIPOQ | −0.66724 | −0.74205 |  | −0.13523 |  | −0.47984 | 3.837386 | 3.59833 |
| CHOL | −2.66393 |  |  |  |  |  | 0.90309 | 0.690196 |
| CRP | 0.70821 | 0.717325 | 0.603214 |  | 0.514556 | 0.6277 | 4.136395 | 2.709206 |
| DPP4 |  |  |  | 0.078344 |  |  | 2.624639 | 2.55854 |
| ENG | −1.12999 | −1.14016 |  |  |  |  | 0.433883 | −0.025635 |
| FTH1 | 0.711809 | 0.706316 | 0.473219 | 0.389999 | 0.620951 | 0.586941 | 3.600816 | 3.079284 |

TABLE 10-continued

| | LDA.BWD | LDA.SWS | LDA.KW10 | LDA.RF10 | LDA.ELDA3 | LDA.ELDA2 | 20311 (1) | 77884 (0) |
|---|---|---|---|---|---|---|---|---|
| GH1 | | | | | −0.23073 | −0.04613 | −0.331038 | −0.607982 |
| GLUCOSE | 17.46311 | 17.41075 | 17.37771 | 16.54193 | | 19.69818 | 0.812913 | 0.653213 |
| GPT | 1.087745 | 1.021178 | | | | 0.788968 | 0.325215 | 0.441237 |
| HBA1C | 12.05816 | 11.23972 | 9.050276 | 10.31996 | | | 0.770852 | 0.755875 |
| HDL | | | 0.390531 | | | | 0.269513 | 0.093422 |
| HGF | | | 0.026509 | | | −0.10911 | −0.201097 | −0.417961 |
| HSPA1B | | | | | | 0.789939 | 1.238439 | 0.348427 |
| IGFBP1 | | | | | | 0.045342 | 0.294254 | 0.918387 |
| IGFBP2 | | | | | −0.00518 | −0.01889 | 20.68154 | 14.95522 |
| IL18 | | | 0.759557 | 1.049944 | 0.808142 | 0.820012 | −0.702241 | −0.627808 |
| IL2RA | | | 0.60912 | | | 0.74837 | −0.787264 | −0.301986 |
| INSULIN | 0.665954 | 0.882926 | 1.194011 | 1.36753 | 1.576526 | 1.103641 | 1.869232 | 0.954243 |
| LEP | 0.696587 | 0.69285 | | | | 0.658789 | 1.016614 | 0.35699 |
| PLAT | −0.99971 | −0.94709 | | | | | 1.024778 | 0.885599 |
| SELE | | | | | | −0.51067 | 1.978515 | 2.085064 |
| SELP | | | | | | −0.2501 | 2.539756 | 2.537585 |
| SERPINE1 | | | | | 0.019556 | −0.08744 | 7.794406 | 4.859024 |
| SGK | | | | | | −0.39277 | 3.019246 | 3.989198 |
| SHBG | | | | | | −0.39018 | 4.185424 | 3.527613 |
| TRIG | 0.846546 | | 0.591921 | 0.495268 | 0.848019 | 0.171855 | 0.079181 | −0.09691 |
| VCAM1 | 0.995924 | 1.073903 | | 0.497995 | | | 2.726349 | 2.497237 |
| VEGF | | | | | | 0.653159 | −0.53022 | −1.569929 |
| VWF | | | | 0.226829 | | −0.08 | 4.484484 | 3.835305 |

Calculation of Risk

The algorithm produced a linear predictor, lp, that is related to group membership of a sample (e.g. case or controls), assuming a 50% prior probability of belonging to a group of converters being a case. This lp can be converted to a convenient score for an individual subject (DRS) on a 0-10 scale using the following equation:

$$DRS = 10 * e^{lp}/(1+e^{lp})$$

This score correlates with the absolute risk of conversion at a specified prior probability (assuming a specified probability of 50%). Changing the prior probability that was used to construct the algorithm to a probability that reflects the actual percentage of "cases" in the population (based on epidemiology data of that population) effectively shifts the linear model by changing the intercept term, $\alpha$, as follows:

$$\alpha' = \alpha + \ln(\pi_1/\pi_0)$$

Where $\alpha'$ is the new intercept, $\alpha$ is the intercept assuming a 50% prior, $\pi_1$ is the prior probability of being a case and $\pi_0$ is the prior probability of being a control. The remaining coefficients stay the same and a new linear predictor, lp', is computed. From this Risk (is computed as follows:

$$Risk = e^{lp'}/(1+e^{lp'})$$

The Risk is the probability that a subject would become a case (a converter). For example, a risk of 25% indicates that 25% of the people with a similar DRS will convert to a diabetic within 5 years.

Example Calculation of Risk

To calculate risk for algorithm LDA.BWD in Table 10, the following biomarker value coefficients and intercept were used: intercept 26.4567, ADIPOQ coefficient −0.66724, CHOL coefficient −2.66393, CRP coefficient 0.70821, ENG coefficient −1.12999, FTH1 coefficient 0.711809, GLUCOSE coefficient 17.46311, GPT coefficient 1.087745, HBA1C coefficient 12.05816, INSULIN coefficient 665954, LEP coefficient 0.696587, PLAT coefficient −0.99971, TRIG coefficient 0.846546, and VCAM1 coefficient 0.995924.

For two subjects the transformed biomarker values (concentration measured) as indicated in Table 10 the lp and score were calculated as follows and set out in Table 11.

$$lp = (ADIPOQ * -0.66724) + (CHOL * -2.66393) +$$
$$(CRP * 0.70821) + (ENG * -1.12999) + (FTH1 * 0.711809) +$$
$$(GLUCOSE * 17.46311) + (GPT * 1.087745) + (HBA1C * 12.05816) +$$
$$(INSULIN * 665954) + (LEP * 0.696587) + (PLAT * -0.99971) +$$
$$(TRIG * 0.846546) + (VCAM1 * 0.995924) + -26.4567$$

$$DRS = 10 * e^{lp}/(1+e^{lp})$$

TABLE 11

| Subjects | Group | lp | DRS |
|---|---|---|---|
| 77884 | 0 | 1.426083 | 8.062902 |
| 20311 | 1 | −2.41455 | 0.820701 |

To calculate Risk the prior predictability is shifted in view of the epidemiology data of the population that the subject being analyzed is a member. In this example the prior predictability is shifted to 12.5%, and using the following equation the resulting new intercept ($\alpha'$) is −28.4026

$$\alpha' = \alpha + \ln(\pi_1/\pi_0)$$

Using the new intercept the adjusted linear predictor (lp') and Risk is calculated using the following equations. The risk scores are set out in Table 12.

$$lp = (ADIPOQ * -0.66724) + (CHOL * -2.66393) +$$
$$(CRP * 0.70821) + (ENG * -1.12999) + (FTH1 * 0.711809) +$$
$$(GLUCOSE * 17.46311) + (GPT * 1.087745) + (HBA1C * 12.05816) +$$
$$(INSULIN * 665954) + (LEP * 0.696587) + (PLAT * -0.99971) +$$
$$(TRIG * 0.846546) + (VCAM1 * 0.995924) + -24.5108$$

$$Risk = e^{lp'}/(1+e^{lp'})$$

TABLE 12

| Subjects | Group | lp' | Score | Risk |
|---|---|---|---|---|
| 77884 | 0 | −0.51983 | 8.062902 | 0.372893 |
| 20311 | 1 | −4.36046 | 0.820701 | 0.012611 |

Example 2

Selection of Protein Biomarkers Using the Inter99 Cohort

This is a discussion of an exemplary method to select some of the preferred protein biomarkers of the invention.

Study Population

The Inter99 cohort consists of 61,301 subjects aged 30-60 years from the Danish Civil Registration System. Although this was a lifestyle intervention trial for cardiovascular disease, registered at ClinicalTrials.gov, Identifier NCT00289237 (14), the 5-year rate of progression to type 2 diabetes observed in this study (3.4%) was similar to other estimates of progression for this age group (16). A sample of 13,016 was randomly selected, 12,934 were eligible and invited for an examination, and 6784 (52.5%) attended the investigation (17). Eligible individuals (n=6536) were re-invited after five years and 4511 (69%) attended. Fasting blood samples, lifestyle data, blood pressure, waist circumference, plasma lipids, and OGTT results were collected at baseline and 5-year time points. An "at-risk" sub-population was defined as those with BMI≥25 kg/m$^2$, age≥39 years and free of diabetes at baseline. Among these individuals, 174 progressed to type 2 diabetes during the 5-year follow-up (converters), and baseline samples were available for 160, while 2872 did not progress (non-converters). Diagnosis of type 2 diabetes was defined by 2 hour plasma glucose of ≥11.1 mmol/l in an OGTT, or ≥7.0 mmol/L for FPG. Non-converters (n=472) were randomly selected in an approximately 3:1 ratio to converters.

Clinical and Standard Laboratory Measurements

Anthropometric measurements, blood pressure, routine laboratory measures (FPG, insulin, lipids), and the OGTT were performed as previously described (17). Serum was stored at −19° C.

Candidate Biomarker Selection

Potential biomarkers were identified by searching the PubMed database using search terms relevant to the development of diabetes. Of 260 candidate biomarkers identified as involved in pathways associated with metabolic or cardiovascular disorders, obesity, cell death, or inflammatory response, assay reagents were obtained for 89 of these biomarkers. Data from 58 candidates met our quality control criteria, which required that results from ≥66% of the samples fell within the assay's linear dynamic range.

Molecular Assays

Sandwich immunoassays developed for the 58 proteins typically used a monoclonal capture antibody and a fluorescently-labeled detection antibody. Biomarker candidates were measured using an ultrasensitive molecular counting technology (MCT) platform (Singulex, St. Louis, Mo.). Details regarding assay reagents have been previously described (18). Briefly, detection of labeled antibodies was performed on the ZeptX™ System, where liquid from each well is pumped through an interrogation space within a capillary flow cell. Laser light (wavelength ~650 nm) is directed into the interrogation space, and the resulting emission from each labeled antibody (wavelength 668 nm) is measured via a confocal microscope with a photon detector.

For biomarkers in the model, reagents were obtained from R&D Systems (Minneapolis, Minn.) individually (monomeric adiponectin (ADIPOQ)) or as DuoSet Kits (interleukin 2 receptor A (IL2RA)), and United States Biological (Swampscott, Mass.) (C-reactive protein (CRP), ferritin heavy chain 1 (FTH1)). Detection antibodies for ADIPOQ, CRP, and FTH1, were conjugated with Alexa Fluor® 647 (Invitrogen, Carlsbad, Calif.) according to manufacturer's instructions, and purified by ultrafiltration with Microcon YM-30 from Millipore (Billerica, Mass.). Analytes detected using DuoSet Kits utilized biotinylated detection antibodies and Alexa Fluor® 647-conjugated streptavidin (Invitrogen).

One biomarker was measured per 384 microwell plate, using an average of 1.3 µl serum in a total assay volume of 10 µl per well. Biomarker concentrations were calculated as the mean of three replicates. Assays had dynamic ranges of $10^2$ to $10^3$, intra-plate CVs of ≤5%, and an average lower limit of detection of 10 pg/ml.

Model Development Process

A model development process was devised which applied multiple statistical approaches in which a limited number of the most informative markers would be selected for inclusion. Sixty-four candidate biomarkers were evaluated for inclusion in multi-marker models: six routine laboratory measures (FPG, fasting serum insulin, triglycerides, total cholesterol, HDL-cholesterol, and LDL-cholesterol), and 58 serum proteins. Biomarker candidates were selected for inclusion in the model based on frequency of selection in four statistical-learning approaches. The four approaches were referred to as U (univariate logistic regression analyses), E (exhaustive enumeration of small (≤6) multivariate logistic models), H (six different heuristic model building methods, including forward, backward, and stepwise selection, Kruskal-Wallis test, random forest, and Eigengene-based linear discriminant analysis with three different statistical learning algorithms, including logistic regression, linear discriminant analysis, and support vector machines), and B (frequency of selection within 100 bootstrap replicates using the same basic heuristic model building methods).

Permutation testing was used to establish a threshold of selection frequency for inclusion of a biomarker in the model. For the permutation testing, the entire selection procedure was repeated using a dataset with randomly-assigned outcomes. To be included in the model, a biomarker's selection frequency in the dataset with non-permuted (true) outcomes had to fall outside the 95% confidence interval of its selection frequency using the dataset with randomly assigned outcomes. To make the model more parsimonious, the selected biomarkers were subjected to backwards selection, sequentially removing biomarkers until all remaining biomarkers were significant at the 90% confidence level.

Results

Baseline characteristics of converter and non-converter groups are summarized in Table 13.

|  | Converters | Non-Converters | p |
|---|---|---|---|
| Participants | 160 | 472 |  |
| Male | 110 (68.8%) | 279 (59.1%) | 0.031 |
| NFG and NGT | 12 (7.6%) | 226 (49.7%) | <0.0001 |
| IFG only | 46 (29.1%) | 174 (38.2%) | 0.0433 |
| IGT only | 25 (15.8%) | 19 (4.2%) | <0.0001 |
| Both IFG and IGT | 75 (47.5%) | 36 (7.9%) | <0.0001 |
| Family history | 48 (30%) | 98 (20.8%) | 0.0223 |
| Age (yrs) | 50.2 (45.2-55.0) | 49.8 (44.8-54.8) | <0.0001 |

-continued

|  | Converters | Non-Converters | p |
|---|---|---|---|
| Height (cm) | 172 (166-179) | 172 (166-179) | 0.9277 |
| Weight (kg) | 89 (80-100) | 84 (77-93) | 0.0001 |
| BMI (kg/m$^2$) | 29.7 (27.5-32.9) | 27.6 (26.1-30.1) | <0.0001 |
| Waist (cm) | 97 (91-109) | 93 (86-99) | <0.0001 |
| Hip (cm) | 106 (102-113) | 104 (100-109) | 0.004 |
| Systolic blood pressure (mmHg) | 140 (130-150) | 130 (120-144) | <0.0001 |
| Diastolic blood pressure (mmHg) | 90 (80-96) | 85 (80-90) | 0.0008 |
| Fasting serum total cholesterol (mmol/l) | 5.8 (5.1-6.5) | 5.7 (5.0-6.4) | 0.2513 |
| Fasting serum HDL cholesterol (mmol/l) | 1.2 (1.0-1.4) | 1.3 (1.1-1.6) | 0.0013 |
| Fasting serum LDL cholesterol (mmol/l) | 3.6 (3.1-4.4) | 3.6 (3.1-4.3) | 0.6898 |
| Fasting serum triglycerides (mmol/l) | 1.6 (1.3-2.2) | 1.3 (0.9-1.8) | <0.0001 |
| Fasting serum insulin (pmol/l) | 58 (37-81) | 40 (27-59) | <0.0001 |
| 2-h serum insulin (pmol/l) | 325 (210-486) | 186 (100-298) | <0.0001 |
| Fasting plasma glucose (mmol/l) | 6.1 (5.7-6.5) | 5.6 (5.3-6.0) | <0.0001 |
| 2-h plasma glucose (mmol/l) | 8.4 (7.1-9.5) | 6.1 (5.1-7.0) | <0.0001 |
| HbA1c (%) | 6.1 (5.8-6.4) | 5.9 (5.6-6.1) | <0.0001 |
| Adiponectin (μg/ml) | 19.5 (9.3-39.6) | 22.2 (12.9-42.6) | 0.0345 |
| CRP (μg/ml) | 3.2 (1.5-7.9) | 2.0 (0.8-5.3) | <0.0001 |
| Ferritin (ng/ml) | 867 (290-1749) | 483 (168-1045) | <0.0001 |
| IL2RA (pg/ml) | 290 (230-400) | 270 (200-350) | 0.0049 |

Applying the model development process to all 64 candidate biomarkers (58 serum proteins and six routine laboratory measures), CRP, FTH1, glucose, alanine aminotransferase, and insulin were selected by all four approaches (U, E, H, B), insulin-like growth factor binding protein 2 (IGFBP2), IL2RA and heat shock 70 kDa protein 1B (HSPA1B) were selected by three approaches (E, H, B), leptin and interleukin 18 (IL18) were selected by two approaches (U, E), and ADIPOQ was selected by one approach (E). After backwards selection, the resulting DRS model included six biomarkers (ADIPOQ, CRP, FTH1, glucose, IL2RA, and insulin). The performance of this model was estimated using the bootstrap re-sampling approach. FIG. 1 compares the area under the ROC curves for the fitted performance of this DRS model to assess 5-year type 2 diabetes risk in the dataset (AUC=0.78) to that of this DRS model using bootstrap re-sampling of the dataset (AUC=0.76). The similarity of the AUCs suggests that this model is not over-fit and is likely to be robust when used to assess risk in a different population. The similarity in performance between the bootstrap estimate of performance on the training set and performance on a sequestered validation dataset validates using the bootstrap approach to estimate model performance.

Figure 2:
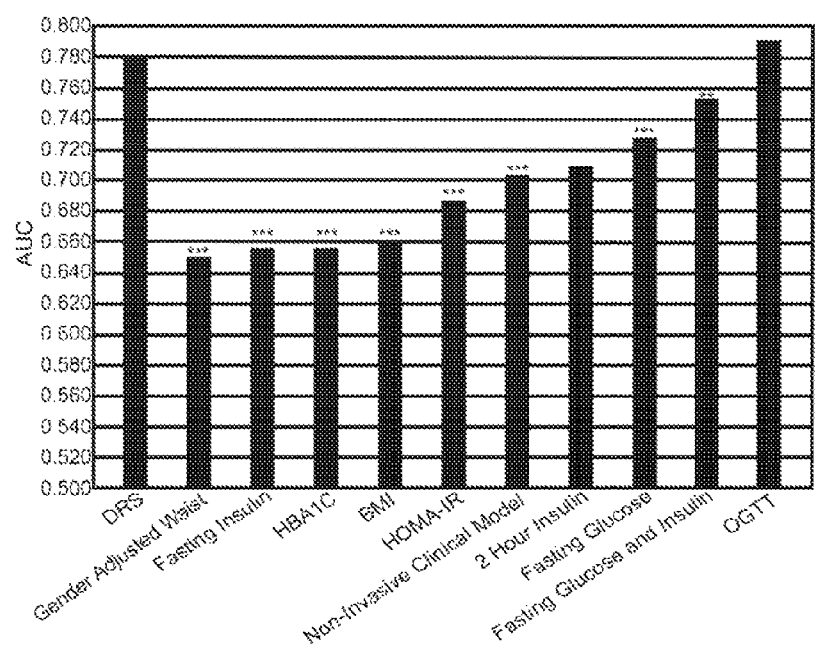
FIG. 2 depicts the ROC analyses for 11 methods of assessing 5-year risk for type 2 diabetes. DRS, diabetes risk score developed in the present study; HOMA-IR, homeostasis model assessment insulin resistance (fasting serum insulin× fasting plasma glucose)/22.5); non-invasive clinical model (a non-invasive clinical algorithm using age, BMI, waist circumference, and family history in a first degree relative); OGTT, 2-hour oral glucose tolerance test. Significance codes: $0<*<0.001<<0.01<*<0.05<<1$.

FIG. 2 compares the AUC of this DRS model to that of several routine laboratory measures (HbA1c, FPG, fasting serum insulin, 2-hour serum insulin and 2-hour plasma glucose from the OGTT), two clinical variables (BMI and gender-adjusted waist), a model using fasting glucose and insulin, and a non-invasive clinical model (age, BMI, waist circumference, and family history of type 2 diabetes in first-degree relatives). The AUC of this DRS model is statistically significantly different from that of single marker measures from fasting blood samples, a model using fasting glucose and insulin, anthropometric measures, and a clinical index, while it is equivalent to 2-hour glucose (from OGTT) and 2-hour insulin (p=0.18, p=0.70, respectively). Adding family history, age, BMI and waist circumference components of the non-invasive model to this DRS model improved the fit slightly (p=0.0067, likelihood ratio test), but produced only a marginal performance gain (AUC 0.792 vs. 0.780, p=0.059). It should also be noted that the DRS average for females is 1.35 lower than males (p<0.0001). However, this gender difference accurately reflects the difference in risk of developing diabetes and the performance of the DRS is equivalent in both sexes (AUC=0.770 and 0.783 for females and males, respectively; p=0.7908).

In order to extrapolate results from this nested case-control study to the entire at-risk population within the Inter99 cohort, and to provide a way to convert a DRS to the absolute risk of developing diabetes for an individual, Bayes' Law was applied to adjust for the observed 5.7% 5-year rate of conversion to diabetes for the population with BMI≥25 kg/m2 and age≥39 years.

Figure 3:
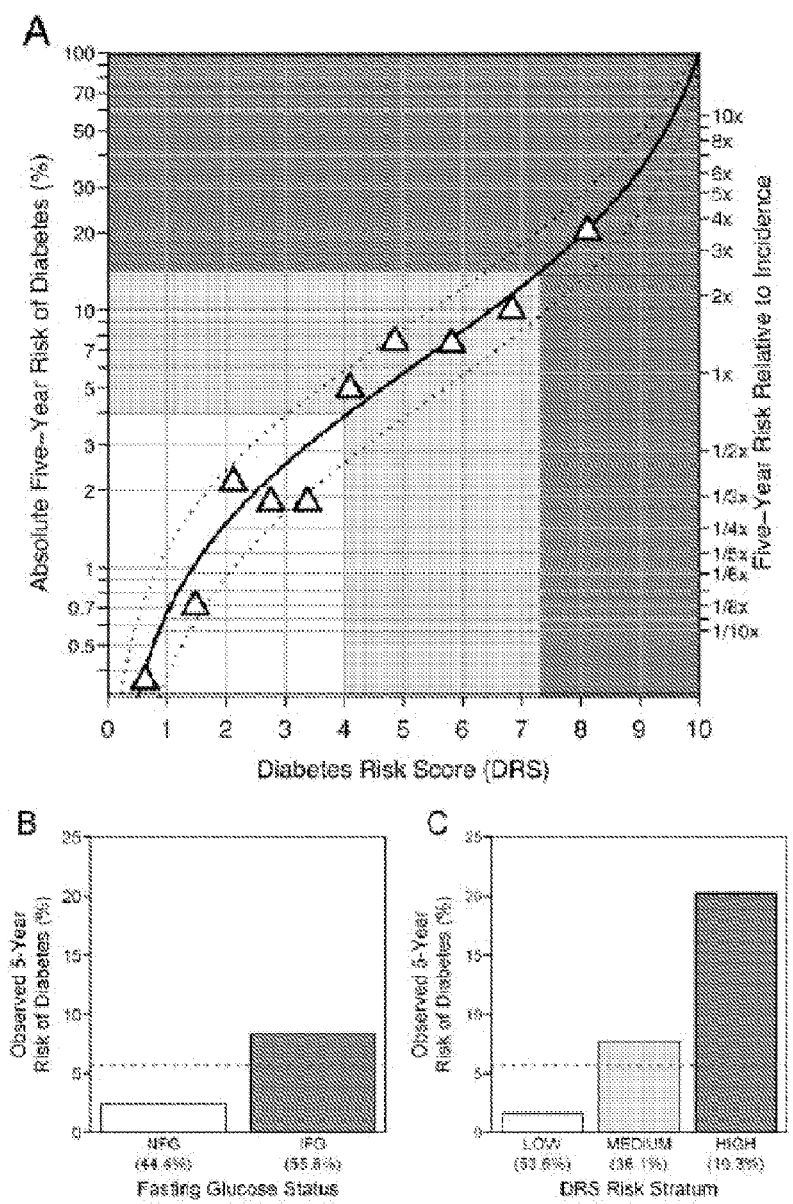
FIG. 3 depicts the performance of the Diabetes Risk Score and fasting plasma glucose in the at-risk Inter99 subpopulation defined by BMI≥25 kg/m² and age≥39 years. The white, light gray and dark gray regions correspond to the low-, medium- and high-risk strata, respectively. The results from the study were adjusted using Bayes' rule to reflect the observed five-year incidence of 5.7% among the 3032 at-risk individuals in Inter99 (A). On the left axis, absolute risk is indicated, while relative risk is shown on the right axis. The solid black line represents the relationship between risk and DRS prediction. The dashed curves indicate mean upper and lower 95% confidence intervals on the risk, as estimated from the standard error of the individual risk predictions in the study. The triangles represent deciles of the adjusted study population; the mean observed fraction that converted is plotted vs. mean DRS. Details of the development of this risk curve are presented in Online Appendix C. Stratification of the at-risk Inter99 subpopulation by fasting plasma glucose status (B), and by DRS risk stratum (C). NFG, normal fasting glucose (≤100 mg/dl); IFG, impaired fasting glucose (>100 mg/dl).

FIG. 3 compares the stratification of risk achieved by measuring FPG and 2-hour glucose to that achieved using this DRS model. FIG. 3A shows that the DRS provides a continuous measure of risk of progressing to type 2 diabetes in the at-risk population. FIG. 3B illustrates the risk level by FPG class, using the threshold of 100 mg/dL for IFG. The IFG group has a 5-year conversion risk which is 1.4-fold higher than the pre-test probability, and comprises 56% of the at-risk population. FIG. 3C illustrates the level of risk in each stratum when using this DRS to stratify the individuals into low-, medium-, and high-risk groups. Individuals in the high-risk group have 3.5-fold increased risk over the pre-test probability and comprise 10% of the population. Individuals in the low-risk group have a 3.5-fold lower risk and comprise 54% of the population, and the remaining medium-risk group has a 1.3-fold increased risk and comprises 36% of the population. As might be expected from the AUC comparison, the risk of developing diabetes in subjects with IGT (which is 14.6% of the population) is 24.5%, which is similar to the risk in the high-risk DRS group. Yet, the low-risk group identified by DRS has a 1.6% risk of developing diabetes, which is lower than subjects with either NFG (2.4%) or NGT (2.5%) in this study.

FIG. 3

Analysis of Biomarkers and Lipid Metabolites

In order to identify this panel of biomarkers, over 90 protein biomarkers in two European cohorts (Botnia and Inter99) (Lyssenko et al., Diabetes 54:166-174, 2005: Jorgensen et al., Eur. J. Cardiovasc Prev. Rehabil, 10:377-386, 2000) using a molecular counting technology highly sensitive for measuring proteins in serum. The algorithms developed from these two studies produced receiver operator curves (ROC) with area under the curve (AUC) of approximately 0.75 in a population age≥39 and BMI≥25.

With respect to performance assessment, two orthogonal sets of criteria were used in marker selection. The first criteria picked markers based on outcome studies of Diabetic Converters in 2 separate population cohorts. A stepwise procedure of marker prioritization involved a filtering of markers based on 1) consistency of univariate performance between cohorts; 2) dimensionality reduction via shrinkage and stepwise selection techniques, and 3) relative rankings using leave-one-out (LOO) and backward elimination procedures. The results of this analysis were used to prioritize clinical, protein and lipid markers according to the ability of resulting models to discriminate among outcomes (as assessed by bootstrap AUC (bsAUC)) and the relative strength of marker contribution in a multivariate algorithm as assessed by measures of model fit, such as the likelihood ratio test (LRT).

A second set of criteria additionally assessed lipid markers based on their univariate performance in a meta-analysis of several treatment-based studies. Lipid markers were selected based on the consistency of their univariate performance across multiple studies of drug intervention and lifestyle modifications that relate to diabetes treatment.

Marker lists from both sets of selection criteria were combined and resubmitted for dimensionality reduction using a shrinkage technique and reprioritized based on their relative performance in LOO and BWD elimination procedures as measured by the LRT using a single outcome-based study. This "performance-based" list of markers were then interrogated using an Exhaustive Search technique, in which all combinations of markers were used to build multiple models—each of which were comparatively assessed on a single outcome-based study using cross-validated AUCs. The relative importance of markers were assessed by p-values of the coefficients within these models and the frequency of selection of markers in multiple iterations of resampling.

The subset of lipid markers in the "performance-based" list was then vetted based on considerations of analytical stability, limitations of measurement, and the ability to develop assays within prescribed timelines. Some lipids not passing this vetting procedure, were replaced with alternative biological analogues and derivatives that also showed good univariate performance, good signal-to-noise characteristics and did not have limitations related to distinguishing between mass-isomers.

The resulting list of protein, clinical measures, and vetted lipid metabolites were again subjected to an Exhaustive Search technique. The resulting relative performance of example models as well as the relative marker performance is noted in the attached supplementary materials. The performance of an example model relative to OGTT is also included.

Table 14 shows 14 markers identified to be highly predictive and includes several different classes of molecules associated with diabetes development including growth factors, cytokines, hormones, lipids from the cholesterol ester and lysophosphatidyl choline classes, and specific molecules of glucose metabolism.

TABLE 14

Informative Biomarkers in Algorithms Predicting
Risk of Diabetes within 5 years

Adiponectin
C-reactive protein
ferritin
glucose
hemoglobin A1c (HbA1c)
insulin
interleukin-2 receptor, alpha (IL2RA)
Cholesteryl palmitoleate (CE 16:1n7)
Cholesteryl homo gamma linoleate (CE 20:3n6)
Cholesteryl linoleate (CE 18:2n6)
Cholesteryl palmitate (CE 16:0)
Cholesteryl petroselinate (CE 18:1n9)
1-Linoleoyl-2-hydroxy-sn-glycero-3-phosphocholine (LY 18:2n6)
1-Oleoyl-2-hydroxy-sn-glycero-3-phosphocholine (LY18:1n7 and LY18:1n9)

Figure 4:
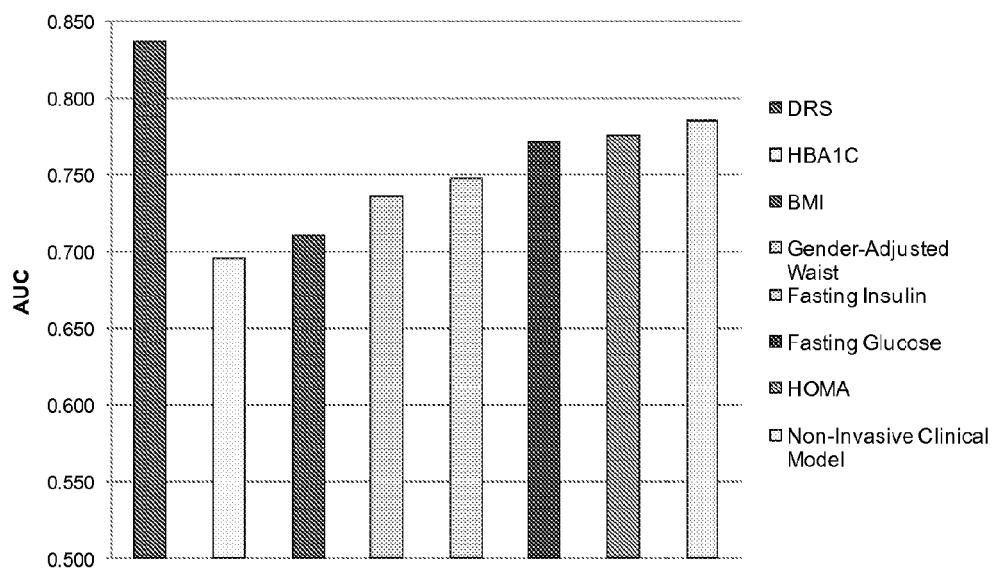
FIG. 4 depicts the AUC of DRS, HbA1c, BMI, Gender-adjusted Waist, Fasting Insulin and Fasting Glucose, HOMA IR and a Non-invasive Clinical Model FIG. 5 displays the pathways associated with progression to diabetes.

Results of additional testing were generated using validated assays in the CLIA certified Tethys Clinical Laboratory in subjects between 30 and 60 yrs. The AUC in this study was 0.84 (see FIG. 4). Preliminary results incorporating specific lipid molecules into a multi-marker model showed a significant increase in the AUC.

Figure 5:
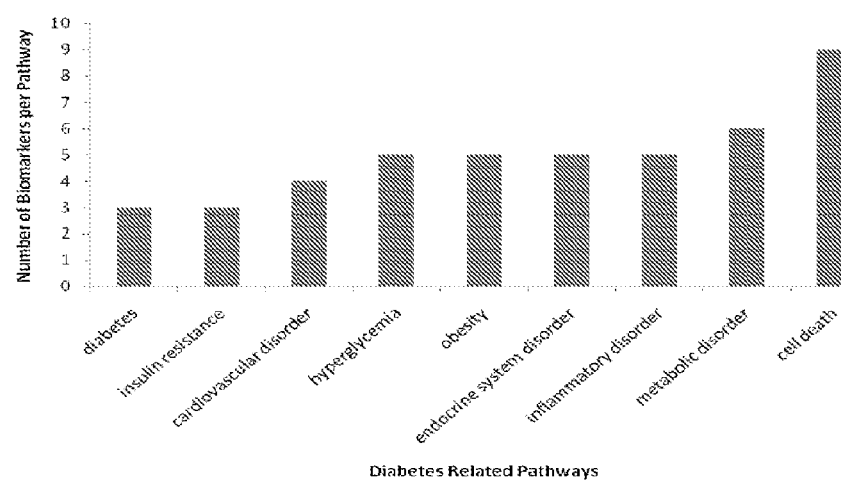

These biomarkers span many pathways associated with progression to diabetes such as insulin resistance, obesity, endocrine disorders, and hyperglycemia. FIG. 5 shows the number of markers in each pathway that were shown to be informative for the prediction of diabetes in one or more algorithms developed from the Botnia and Inter99 studies. Some markers overlap the various pathways.

Example 2

Validated Lipid Assays

Biological Samples were prepared via a simple internal standard spike and protein precipitation as follows. The internal standard mix (3 odd chain analogs: CE 15:1, CE 17:0, LY 17:0) was added to 20 μL serum sample. The sample was then vortexed for at least 3 seconds. To precipitate the proteins, 1 mL of 50/50 MeOH/CHCl3 was added to the sample followed by vortexing for at least 3 seconds. The samples were then centrifuged for 10 minutes at 17000×G. Subsequently, the supernatant was transferred to a 2 mL glass vial and loaded into the autosampler of the Waters ACQUITY HPLC system. The autosampler was maintained at 10° C. The samples were injected (2 uL per sample) onto a Waters HPLC BEH C18 column (2.1×30 mm, 1.7 um) with a Waters Vangaurd BEH C18 precolumn (2.1×5 mm, 1.7 um). The column compartment was heated to 80° C. Solvent A was 5 mM NH4HCO2 in water. Solvent B was 5 mM NH4HCO2 in MeOH. From 0-1 min, the column was maintained at 80% solvent B, then ramped to 100% B in 1 minute and held at 100% B for 1.7 minutes. The column was immediately returned to 80% and allowed to re-equilibrate for 1.2 minutes. The flow rate was 1 mL/min. The Waters ACQUITY HPLC was coupled to a Waters Xevo TQD mass spectrometer. The analytes were ionized via positive electrospray and the mass spectrometer was operated in tandem MS mode with argon as the collision gas. Waters MassLynx software was used to automatically integrate all analyte and internal standard chromatographic peaks. Peak area ratios (analyte/internal standard) were then calculated and then converted to absolute analyte concentrations using external calibration curves.

What is claimed:

1. A method of evaluating risk for developing a diabetic condition, the method comprising:
   (a) obtaining biomarker measurement data for an individual from at least one biological sample of the individual; wherein the biomarkers comprise: (i) glucose, (ii) protein biomarkers adiponectin, ferritin, and insulin, and (iii) at least one lipid metabolite selected from the lipid metabolites in Table 2; and
   (b) evaluating the individual's risk for developing a diabetic condition based on an output from a model, wherein the model is executed based on an input of the biomarker measurement data; or
   wherein the model comprises the measurements of biomarkers by fitting data from a longitudinal study of a population of individuals and the fitted data comprises levels of the biomarkers and conversion to Diabetes in the longitudinal study of the population of individuals.

2. The method of claim 1, wherein the individual has not been previously diagnosed as having Diabetes, pre-Diabetes, or a pre-diabetic condition.

3. The method of claim 1, wherein the individual has a pre-diabetic condition, and the method evaluates the individual's risk for developing Diabetes.

4. The method of claim 1, wherein the individual is pregnant.

5. The method of claim 1, wherein the diabetic condition is selected from the group consisting of Type 2 Diabetes, pre-Diabetes, Metabolic Syndrome, Impaired Glucose Tolerance, and Impaired Fasting Glycemia.

6. The method according to claim 1, wherein the method has an area under the ROC curve, reflecting the degree of diagnostic accuracy for predicting development of the diabetic condition, of at least 0.02, 0.03, 0.04, 0.05, 0.06, 0.07, 0.08, 0.09, 0.10, 0.11, 0.12, 0.13, 0.14, or 0.15 greater than a corresponding method using only glucose and the protein biomarkers but not the lipid metabolites as the biomarkers.

7. A kit comprising reagents for measuring a group of biomarkers, wherein the biomarkers comprise:
(i) glucose,
(ii) protein biomarkers adiponectin, ferritin, and insulin, and
(iii) at least one lipid metabolite selected from the lipid metabolites in Table 2.

8. A computer readable medium having computer executable instructions for evaluating an individual's risk for developing a diabetic condition, the computer readable medium comprising: a routine, stored on the computer readable medium and adapted to be executed by a processor, to store biomarker measurement data representing measurements of at least the following: (i) glucose, (ii) protein biomarkers adiponectin, ferritin, and insulin, and (iii) at least one lipid metabolite selected from the lipid metabolites in Table 2; and
a routine stored on the computer readable medium and adapted to be executed by a processor to analyze the biomarker measurement data of the individual to evaluate a risk for developing a diabetic condition.

9. A medical diagnostic test system for evaluating risk for developing a diabetic condition, the system comprising:
a data collection tool adapted to collect biomarker measurement data representative of measurements of biomarkers in at least one biological sample from the individual, wherein the biomarkers comprise: (i) glucose, (ii) protein biomarkers adiponectin, ferritin, and insulin, and (iii) at least one lipid metabolite selected from the lipid metabolites in Table 2; and
an analysis tool comprising a statistical analysis engine adapted to generate a representation of a correlation between a risk for developing a diabetic condition and measurements of the biomarkers, wherein the representation of the correlation is adapted to be executed to generate a result; and
an index computation tool adapted to analyze the result to determine the individual's risk for developing a diabetic condition and represent the result as an index value.

10. A method of developing a model for evaluating an individual's risk for developing a diabetic condition, the method comprising:
obtaining biomarker measurement data, wherein the biomarker measurement data is representative of measurements of biomarkers from a population and includes endpoints of the population; wherein the biomarkers for which measurement data is obtained comprise: (i) glucose, (ii) protein biomarkers adiponectin, ferritin, and insulin, and (iii) at least one lipid metabolite selected from the lipid metabolites in Table 2;
inputting the biomarker measurement data of at least a subset of the population into a model; and
training the model for endpoints using the inputted biomarker measurement data to derive a representation of a correlation between a risk of developing a diabetic condition and measurements of biomarkers in at least one biological sample from the individual.

11. A method of evaluating an individual's current diabetic condition, the method comprising:
obtaining biomarker measurement data from at least one biological sample of the individual, wherein the biomarkers comprise: (i) glucose, (ii) protein biomarkers adiponectin, ferritin, and insulin, and (iii) at least one lipid metabolite selected from the lipid metabolites in Table 2; and
evaluating the current diabetic condition of the individual based on an output from a model, wherein the model is executed based on an input of the biomarker measurement data.

12. A method of evaluating a diabetic disease surrogate endpoint for an individual, the method comprising:
obtaining biomarker measurement data from at least one biological sample of the individual; wherein the biomarkers comprise: (i) glucose, (ii) protein biomarkers adiponectin, ferritin, and insulin, and (iii) at least one lipid metabolite selected from the lipid metabolites in Table 2; and
evaluating a diabetic disease surrogate endpoint in the individual based on an output from a model, wherein the model is executed based on an input of the biomarker measurement data.

13. The method of claim 1, wherein the protein biomarkers further comprise one or more of: C-reactive protein (CRP), and IL2RA.

14. The method of claim 1, wherein the at least one lipid metabolite is selected from the group consisting of: CE18:2n6, CE16:1n7, CE18:2n6, CE20:3n6, CE16:0, LY18:2n6, LY18:1n7, and LY18:1n9.

15. The method of claim 1, wherein the biomarkers comprise at least two, at least three, at least four, at least five, at least six, at least seven, at least eight, at least nine, or at least ten lipid metabolites from Table 2.

16. A method of evaluating an individual's current diabetic condition comprising:
obtaining biomarker measurement data from at least one biological sample of the individual, wherein the biomarkers comprise: (i) glucose, (ii) protein biomarkers adiponectin, ferritin, and insulin, and (iii) at least one lipid metabolite selected from the lipid metabolites in Table 2; and
evaluating the current status of a diabetic condition in the individual based on an output from a model, wherein the model is executed based on an input of the biomarker measurement data.

17. A method of prophylaxis for Diabetes comprising:
evaluating an individual's risk for developing a diabetic condition according to the method of claim 1; and
treating the individual, wherein the individual is at an elevated risk for a diabetic condition, with a treatment regimen to delay or prevent the onset of Diabetes.

18. A method of ranking or grouping a population of individuals, comprising:
calculating a risk for developing a diabetic condition according to the method of claim 1 for individuals comprised within the population; and
ranking individuals within the population relative to the remaining individuals in the population or dividing the population into at least two groups, based on factors comprising the risk for developing a diabetic condition.

19. The method of claim 18, further comprising using ranking data representing the ranking or grouping of the population of individuals for one or more of the following purposes:

to determine an individual's eligibility for health insurance;
to determine an individual's premium for health insurance;
to determine an individual's premium for membership in a health care plan, health maintenance organization, or preferred provider organization; and
to assign health care practitioners to an individual in a health care plan, health maintenance organization, or preferred provider organization.

20. A method of prophylaxis for Diabetes comprising:
obtaining a Diabetes risk score for an individual, wherein the Diabetes risk score is computed according to the method of claim 16 for calculating a risk of developing a diabetic condition; and
generating prescription treatment data representing a prescription for a treatment regimen to delay or prevent the onset of Diabetes to an individual identified by the Diabetes risk score as being at elevated risk for Diabetes.

* * * * *